US012724343B2

(12) United States Patent
Komuro et al.

(10) Patent No.: US 12,724,343 B2
(45) **Date of Patent: *Sep. 1, 2026**

(54) SALT, QUENCHER, RESIST COMPOSITION AND METHOD FOR PRODUCING RESIST PATTERN

(71) Applicant: SUMITOMO CHEMICAL COMPANY, LIMITED, Tokyo (JP)

(72) Inventors: Katsuhiro Komuro, Osaka (JP); Yuki Takahashi, Osaka (JP); Koji Ichikawa, Osaka (JP)

(73) Assignee: SUMITOMO CHEMICAL COMPANY, LIMITED, Tokyo (JP)

( * ) Notice: Subject to any disclaimer, the term of this patent is extended or adjusted under 35 U.S.C. 154(b) by 114 days.

This patent is subject to a terminal disclaimer.

(21) Appl. No.: 17/004,437

(22) Filed: Aug. 27, 2020

(65) Prior Publication Data

US 2021/0063875 A1 Mar. 4, 2021

(30) Foreign Application Priority Data

Aug. 29, 2019 (JP) ................................ 2019-156973

(51) Int. Cl.

*G03F 7/004* (2006.01)
*C07C 381/12* (2006.01)
*C07D 333/76* (2006.01)
*C07D 335/16* (2006.01)
*G03F 7/038* (2006.01)
*G03F 7/039* (2006.01)

(52) U.S. Cl.

CPC .......... *G03F 7/0045* (2013.01); *C07C 381/12* (2013.01); *C07D 333/76* (2013.01); *C07D 335/16* (2013.01); *G03F 7/038* (2013.01); *G03F 7/039* (2013.01)

(58) Field of Classification Search

CPC ... G03F 7/0045; C07C 381/12; C07C 323/62; C07D 333/76; C07D 335/16

See application file for complete search history.

(56) References Cited

U.S. PATENT DOCUMENTS 11,385,542 B2* 7/2022 Komuro ................ G03F 7/0045
11,550,219 B2* 1/2023 Komuro .................... G03F 7/38
12,105,419 B2* 10/2024 Komuro ............... C07D 339/08
2010/0015555 A1* 1/2010 Utsumi ................ C07C 381/12 430/286.1
2010/0239978 A1* 9/2010 Wada ................... C07D 493/14 430/322
2010/0304294 A1* 12/2010 Ichikawa ............. G03F 7/0397 549/322
2013/0224658 A1 8/2013 Komuro et al.
2016/0200702 A1* 7/2016 Sakamoto ............. G03F 7/0046 549/14
2017/0329223 A1 11/2017 Masuyama et al.
2017/0329227 A1* 11/2017 Ohashi .................. G03F 7/0397
2018/0039175 A1* 2/2018 Masunaga ............. G03F 7/0045
2018/0039177 A1* 2/2018 Masunaga ............. G03F 7/0046
2018/0095364 A1 4/2018 LaBeaume et al.
2020/0159116 A1* 5/2020 Komuro ................ G03F 7/0382
2020/0363720 A1* 11/2020 Komuro .................. G03F 7/039
2020/0385343 A1* 12/2020 Komuro ................ C07C 381/12
2020/0387069 A1* 12/2020 Komuro .................. G03F 7/322

FOREIGN PATENT DOCUMENTS

JP 2007178858 A * 7/2007
JP 2013200560 A 10/2013
JP 2017-202993 A 11/2017

(Continued)

OTHER PUBLICATIONS

English translation of WO2019123895. (Year: 2019).*
English translation of JP2007178858. (Year: 2007).*
Search Report (Form PCT/ISA 201 A) and Written Opinion (Form BE237) issued Mar. 9, 2021, by Belgian Patent Office in corresponding Belgian Patent Application No. BE202005595 and an English translation of the Written Opinion. (16 pages).
Office Action issued Apr. 29, 2024, by the Taiwan Patent Office in corresponding Taiwan Application No. 109129019, and an English translation of the Office Action.

(Continued)

*Primary Examiner* — Mark F. Huff
*Assistant Examiner* — Anna Malloy
(74) *Attorney, Agent, or Firm* — Panitch Schwarze Belisario & Nadel LLP

(57) ABSTRACT

A salt represented by formula (I), a quencher, and a resist composition including the same:

(I)

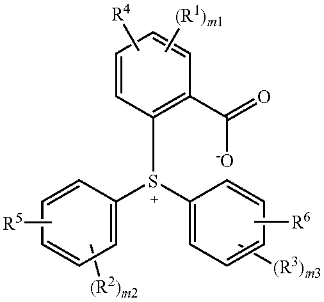

wherein at least one of $R^4$, $R^5$ and $R^6$ represents-$X^2$—$R^7$, $X^2$ represents *—CO—O—, *—O—CO—or ——O—CO—O—, and * represents a bonding site to the benzene ring, and $R^7$ represents a hydrocarbon group including a cyclic hydrocarbon group having 3 to 18 carbon atoms which may have a substituent, and —$CH_2$-included in the hydrocarbon group may be replaced by —O—, —S—, —$SO_2$— or —CO—.

19 Claims, No Drawings

(56) References Cited

FOREIGN PATENT DOCUMENTS

| | | | | | |
|---|---|---|---|---|---|
| JP | 2017207741 | A | | 11/2017 | |
| JP | 2018022103 | A | | 2/2018 | |
| JP | 2018025778 | A | | 2/2018 | |
| JP | 2018-066985 | A | | 4/2018 | |
| JP | 2020083880 | A | | 6/2020 | |
| JP | 2020094319 | A | | 6/2020 | |
| JP | 2020189830 | A | | 11/2020 | |
| JP | 2020200311 | A | | 12/2020 | |
| TW | 201808894 | A | | 3/2018 | |
| WO | WO-2019123895 | A1 | * | 6/2019 | ............. G03F 7/004 |

OTHER PUBLICATIONS

Office Action issued Jul. 24, 2024, by the Japan Patent Office in corresponding Japanese Application No. 2020-142032, and an English translation of the Office Action.

* cited by examiner

SALT, QUENCHER, RESIST COMPOSITION AND METHOD FOR PRODUCING RESIST PATTERN

TECHNICAL FIELD

The present invention relates to a salt, a quencher including the salt and a resist composition, and a method for producing a resist pattern using the resist composition.

BACKGROUND ART

Patent Document 1 mentions a resist composition comprising a salt of the following structural formula, a resin including a structural unit having an acid-labile group, and an acid generator.

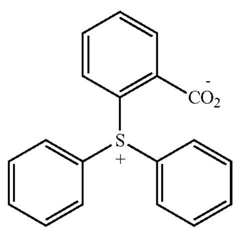

Patent Document 2 mentions a resist composition comprising a salt of the following structural formula, a resin including a structural unit having an acid-labile group, and an acid generator.

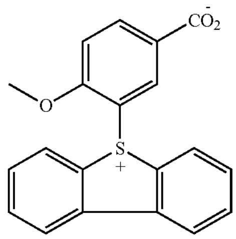

PRIOR ART DOCUMENT

Patent Document

Patent Document 1: JP 2017-202993 A

Patent Document 2: JP 2018-066985 A

DISCLOSURE OF THE INVENTION

Problems to be Solved by the Invention

An object of the present invention is to provide a salt capable of producing a resist pattern with mask error factor (MEF) which is better than that of a resist pattern formed from the resist composition including the above-mentioned salts.

Means for Solving the Problems

The present invention includes the following inventions.

[1] A salt represented by formula (I):

(I)

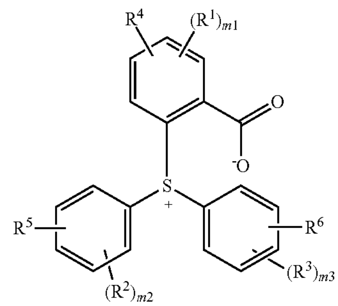

wherein, in formula (I), $R^1$ represents a halogen atom, an alkyl fluoride group having 1 to 6 carbon atoms or a hydrocarbon group having 1 to 18 carbon atoms, and $-CH_2-$ included in the hydrocarbon group may be replaced by $-O-$ or $-CO-$, $R^2$ and $R^3$ each independently represent a halogen atom, an alkyl fluoride group having 1 to 6 carbon atoms or a hydrocarbon group having 1 to 18 carbon atoms, $-CH_2-$ included in the hydrocarbon group may be replaced by $-O-$ or $-CO-$, or $R^2$ and $R^3$ may be bonded to each other to form a single bond or an alkanediyl bridge having 1 to 6 carbon atoms together with carbon atoms to which $R^2$ and $R^3$ are bonded, and $-CH_2-$ included in the alkanediyl bridge may be replaced by $-O-$, $-S-$, $-CO-$, $-SO-$ or $-SO_2-$, m1 represents an integer of 0 to 3, and when m1 is 2 or more, a plurality of $R^1$ may be the same or different from each other, m2 represents an integer of 0 to 4, and when m2 is 2 or more, a plurality of $R^2$ may be the same or different from each other, m3 represents an integer of 0 to 4, and when m3 is 2 or more, a plurality of $R^3$ may be the same or different from each other, $R^4$, $R^5$ and $R^6$ each independently represent a hydrogen atom or $-X^2-R^7$, in which at least one of $R^4$, $R^5$ and $R^6$ represents $-X^2-R^7$, $X^2$ represents $*-CO-O-$, $*-O-CO-$ or $*-O-CO-O-$, and * represents a bonding site to the benzene ring, and $R^7$ represents a hydrocarbon group including a cyclic hydrocarbon group having 3 to 18 carbon atoms (the cyclic hydrocarbon group may have a substituent), and $-CH_2-$ included in the hydrocarbon group may be replaced by $-O-$, $-S-$, $-SO_2-$ or $-CO-$.

[2] The salt according to [1], wherein $R^4$ is $-X^2-R^7$.

[3] A quencher comprising the salt according to [1] or [2].

[4] A resist composition comprising the quencher according to [3], a resin including a structural unit having an acid-labile group, and an acid generator.

[5] The resist composition according to [4], wherein the resin including a structural unit having an acid-labile group includes at least one selected from the group consisting of a structural unit represented by formula (a1-1) and a structural unit represented by formula (a1-2):

(a1-1)

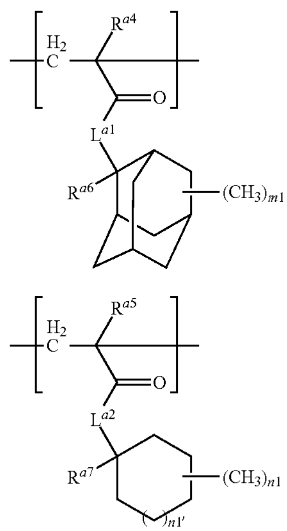

(a1-2)

wherein, in formula (a1-1) and formula (a1-2), $L^{a1}$ and $L^{a2}$ each independently represent —O— or *—O—$(CH_2)_{k1}$—CO—O—, k1 represents an integer of 1 to 7, and * represents a bonding site to —CO—, $R^{a4}$ and $R^{a5}$ each independently represent a hydrogen atom or a methyl group, $R^{a6}$ and $R^{a7}$ each independently represent an alkyl group having 1 to 8 carbon atoms, an alicyclic hydrocarbon group having 3 to 18 carbon atoms, or a group obtained by combining these groups, m1 represents an integer of 0 to 14, n1 represents an integer of 0 to 10, and n1' represents an integer of 0 to 3.

[6] The resist composition according to [4] or [5], wherein the acid generator includes a salt represented by formula (B1):

(B1)

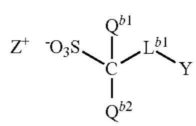

wherein, in formula (B1), $Q^{b1}$ and $Q^{b2}$ each independently represent a fluorine atom or a perfluoroalkyl group having 1 to 6 carbon atoms, $L^{b1}$ represents a divalent saturated hydrocarbon group having 1 to 24 carbon atoms, —$CH_2$— included in the divalent saturated hydrocarbon group may be replaced by —O— or —CO—, and the hydrogen atom included in the divalent saturated hydrocarbon group may be substituted with a fluorine atom or a hydroxy group, Y represents a methyl group which may have a substituent or an alicyclic hydrocarbon group having 3 to 24 carbon atoms which may have a substituent, and —$CH_2$— included in the alicyclic hydrocarbon group may be replaced by —O—, —$S(O)_2$— or —CO—, and $Z^+$ represents an organic cation.

[7] The resist composition according to any one of [4] to [6], further comprising a salt generating an acid having an acidity lower than that of an acid generated from the acid generator.

[8] The resist composition according to any one of [4] to [7], further comprising a resin including a structural unit having a fluorine atom.

[9] A method for producing a resist pattern, which comprises:

(1) a step of applying the resist composition according to any one of [4] to [8] on a substrate, (2) a step of drying the applied composition to form a composition layer, (3) a step of exposing the composition layer, (4) a step of heating the exposed composition layer, and (5) a step of developing the heated composition layer.

Effects of the Invention

It is possible to produce a resist pattern with satisfactory mask error factor (MEF) by using a resist composition including a salt of the present invention.

MODE FOR CARRYING OUT THE INVENTION

As used herein, "(meth)acrylate" means "at least one of acrylate and methacrylate". The terms such as "(meth) acrylic acid" and "(meth)acryloyl" have the same meanings.

Unless otherwise specified, regarding groups capable of having linear, branched and/or ring structures such as "aliphatic hydrocarbon group" include any one of them. "Combined group" means a group obtained by bonding two or more exemplified groups, and a valence of the group may appropriately vary depending on the bonding state. "derived" or "induced" means that a polymerizable C═C bond included in the molecule becomes a —C—C— group by the polymerization. When stereoisomers exist, all stereoisomers are included.

As used herein, "solid component of resist composition" means the total of components excluding the below-mentioned solvent (E) from the total amount of the resist composition.

[Salt Represented by Formula (I)]

The salt of the present invention relates to a salt represented by formula (I) (hereinafter sometimes referred to as "salt (I)"):

(I)

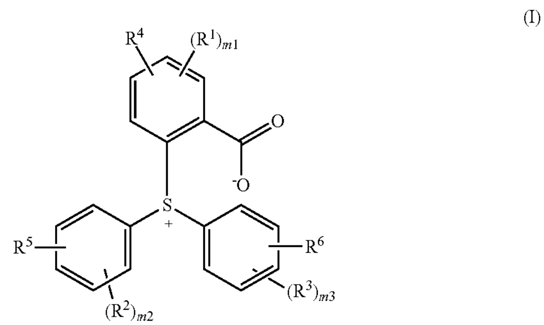

wherein, in formula (I), all symbols are the same as defined above.

In formula (I), examples of the halogen atom in $R^1$, $R^2$ and $R^3$ include a fluorine atom, a chlorine atom, a bromine atom and an iodine atom.

Examples of the alkyl fluoride group having 1 to 6 carbon atoms in $R^1$, $R^2$ and $R^3$ include alkyl fluoride groups such as a trifluoromethyl group, a difluoromethyl group, a perfluoroethyl group, a 2,2,2-trifluoroethyl group, a 1,1,2,2-tetrafluoroethyl group, a perfluoropropyl group, a 2,2,3,3,3-pentafluoropropyl group, a perfluorobutyl group, a 1,1,2,2,3,3,4,4-octafluorobutyl group, a perfluoropentyl group, a 2,2,3,3,4,4,5,5,5-nonafluoropentyl group and a perfluorohexyl group. The number of carbon atoms of the alkyl fluoride group is preferably 1 to 4, and more preferably 1 to 3.

Examples of the hydrocarbon group having 1 to 18 carbon atoms in $R^1$, $R^2$ and $R^3$ include a chain hydrocarbon group such as an alkyl group, an alicyclic hydrocarbon group, an aromatic hydrocarbon group, and a group obtained by combining these groups.

Examples of the alkyl group include alkyl groups such as a methyl group, an ethyl group, a propyl group, an isopropyl group, a butyl group, an isobutyl group, a tert-butyl group, a pentyl group, a hexyl group, an octyl group and a nonyl group. The number of carbon atoms of the alkyl group is preferably 1 to 12, more preferably 1 to 9, still more preferably 1 to 6, yet more preferably 1 to 4, and further preferably 1 to 3.

The alicyclic hydrocarbon group may be either monocyclic, polycyclic or spiro ring, or may be either saturated or unsaturated. Examples of the alicyclic hydrocarbon group include monocyclic cycloalkyl groups such as a cyclopropyl group, a cyclobutyl group, a cyclopentyl group, a cyclohexyl group, a cyclooctyl group, a cyclononyl group, a cyclodecyl group and a cyclododecyl group; and polycyclic cycloalkyl groups such as a norbornyl group and an adamantyl group. The number of carbon atoms of the alicyclic hydrocarbon group is preferably 3 to 16, more preferably 3 to 12, and still more preferably 3 to 10.

Specific examples of the alicyclic hydrocarbon group include the following groups and the like. The bonding site can be any position.

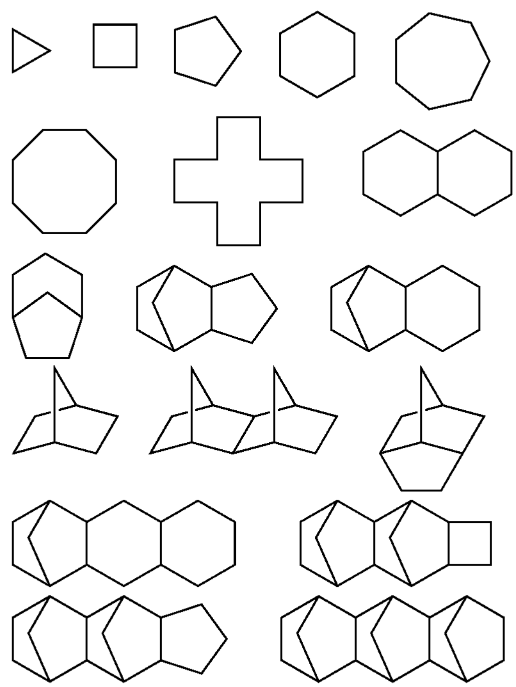

-continued

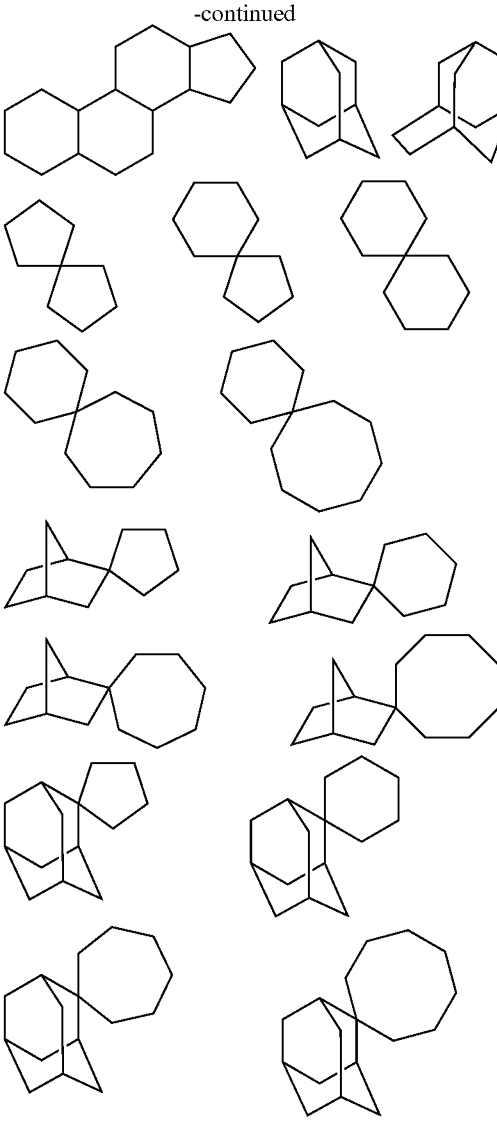

Examples of the aromatic hydrocarbon group include aryl groups such as a phenyl group, a naphthyl group, a biphenyl group, an anthryl group and a phenanthryl group. The number of carbon atoms of the aromatic hydrocarbon group is preferably 6 to 14, and more preferably 6 to 10.

Examples of the group combined include a group obtained by combining the above-mentioned alkyl group and an alicyclic hydrocarbon group (a cycloalkylalkyl group, etc.), an aralkyl group (benzyl group, etc.), an aromatic hydrocarbon group having an alkyl group (a p-methylphenyl group, a p-tert-butylphenyl group, a tolyl group, a xylyl group, a cumenyl group, a mesityl group, a 2,6-diethylphenyl group, a 2-methyl-6-ethylphenyl group, etc.), an aromatic hydrocarbon group having an alicyclic hydrocarbon group (a p-cyclohexylphenyl group, a p-adamantylphenyl group, etc.), an aryl-cycloalkyl group (a phenylcyclohexyl group, etc.) and the like.

When $—CH_2—$ included in the hydrocarbon group in $R^1$, $R^2$ and $R^3$ is replaced by —O— or —CO—, the number of carbon atoms before replacement is taken as the number of carbon atoms of the hydrocarbon group.

Examples of the group replaced include a hydroxy group (group in which $—CH_2—$ included in a methyl group is replaced by —O—), a carboxy group (group in which —$CH_2$—$CH_2$— included in an ethyl group is replaced by —O—CO—), an alkoxy group (a group in which —$CH_2$— at any position included in an alkyl group is replaced by —O—), an alkoxycarbonyl group (group in which —$CH_2$—$CH_2$— at any position included in an alkyl group is replaced by —O—CO—), an alkylcarbonyl group (group in which —$CH_2$— at any position included in an alkyl group is replaced by —CO—), an alkylcarbonyloxy group (group in which —$CH_2$—$CH_2$— at any position included in an alkyl group is replaced by —CO—O—) and the like.

Examples of the alkoxy group include a methoxy group, an ethoxy group, a propoxy group, a butoxy group, a pentyloxy group, a hexyloxy group, a heptyloxy group, an octyloxy group, a nonyloxy group, a decyloxy group, an undecyloxy group and a dodecyloxy group. The number of carbon atoms of the alkoxy group is preferably 1 to 12, more preferably 1 to 9, still more preferably 1 to 6, yet more preferably 1 to 4, and further preferably 1 to 3.

Examples of the alkoxycarbonyl group include a methoxycarbonyl group, an ethoxycarbonyl group, a propoxycarbonyl group and a butoxycarbonyl group. The number of carbon atoms of the alkoxycarbonyl group is preferably 2 to 13, more preferably 2 to 10, still more preferably 2 to 7, and yet more preferably 2 to 5.

Examples of the alkylcarbonyl group include an acetyl group, a propionyl group and a butyryl group. The number of carbon atoms of the alkylcarbonyl group is preferably 2 to 13, more preferably 2 to 10, still more preferably 2 to 7, and yet more preferably 2 to 5.

Examples of the alkylcarbonyloxy group include a methylcarbonyloxy group, an ethylcarbonyloxy group, a propylcarbonyloxy group and a butylcarbonyloxy group. The number of carbon atoms of the alkylcarbonyloxy group is preferably 2 to 13, more preferably 2 to 10, still more preferably 2 to 7, and yet more preferably 2 to 5.

Examples of the group in which —$CH_2$— included in an alicyclic hydrocarbon group is replaced by —O— or —CO— include the following groups. The bonding site can be any position.

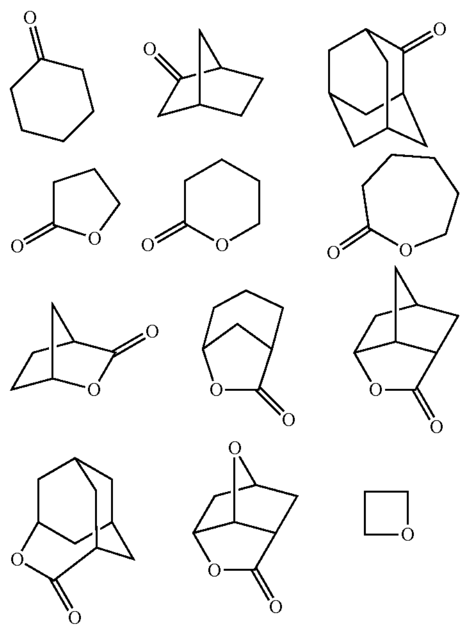

-continued

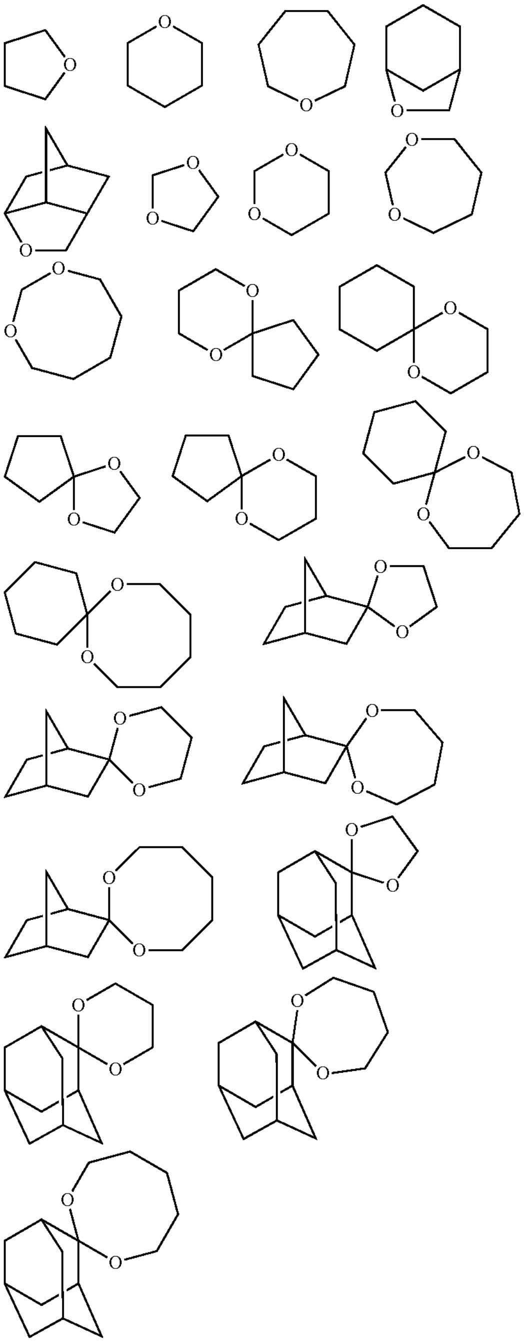

m1 is preferably an integer of 0 to 2, more preferably 1 or 2, and still more preferably 2.

m2 and m3 each independently represent preferably an integer of 0 to 3, more preferably an integer of 0 to 2, and still more preferably 1 or 2.

$R^1$ is preferably a fluorine atom, an alkyl fluoride group having 1 to 4 carbon atoms, an alkyl group having 1 to 6 carbon atoms or an alicyclic hydrocarbon group having 3 to 10 carbon atoms (—$CH_2$— included in the alkyl group and the alicyclic hydrocarbon group may be replaced by —O— or —CO—), more preferably a fluorine atom, an alkyl group having 1 to 6 carbon atoms or an alicyclic hydrocarbon group having 3 to 10 carbon atoms (—$CH_2$— included in the alkyl group and the alicyclic hydrocarbon group may be replaced by —O— or —CO—), still more preferably a fluorine atom or an alkyl group having 1 to 4 carbon atoms (—$CH_2$— included in the alkyl group may be replaced by —O— or —CO—), and yet more preferably an alkyl group having 1 to 3 carbon atoms (—$CH_2$— included in the alkyl group may be replaced by —O— or —CO—).

$R^2$ and $R^3$ each independently represent preferably a fluorine atom, an alkyl fluoride group having 1 to 4 carbon atoms, an alkyl group having 1 to 6 carbon atoms or an alicyclic hydrocarbon group having 3 to 10 carbon atoms (—$CH_2$— included in the alkyl group and the alicyclic hydrocarbon group may be replaced by —O— or —CO—), or $R^2$ and $R^3$ are bonded to each other to form a single bond or an alkanediyl bridge having 1 to 6 carbon atoms together with carbon atoms to which $R^2$ and $R^3$ are bonded (—$CH_2$— included in the alkanediyl bridge may be replaced by —O—, —S—, —CO—, —SO— or —$SO_2$—), more preferably, a fluorine atom, an alkyl fluoride group having 1 to 3 carbon atoms, an alkyl group having 1 to 6 carbon atoms or an alicyclic hydrocarbon group having 3 to 10 carbon atoms (—$CH_2$— included in the alkyl group and the alicyclic hydrocarbon group may be replaced by —O— or —CO—), or $R^2$ and $R^3$ are bonded to each other to form a single bond or an alkanediyl bridge having 1 to 6 carbon atoms together with carbon atoms to which $R^2$ and $R^3$ are bonded (—$CH_2$— included in the alkanediyl bridge may be replaced by —O—, —S—, —CO—, —SO— or —$SO_2$—), still more preferably, a fluorine atom, an alkyl fluoride group having 1 to 2 carbon atoms or an alkyl group having 1 to 4 carbon atoms (—$CH_2$— included in the alkyl group may be replaced by —O— or —CO—), or $R^2$ and $R^3$ are bonded to each other to form a single bond or an alkanediyl bridge having 1 to 3 carbon atoms together with carbon atoms to which $R^2$ and $R^3$ are bonded (—$CH_2$— included in the alkanediyl bridge may be replaced by —O—, —S—, —CO—, —SO— or —$SO_2$—), and yet more preferably an alkyl group having 1 to 4 carbon atoms (—$CH_2$— included in the alkyl group may be replaced by —O— or —CO—), or $R^2$ and $R^3$ are bonded to each other to form a single bond or an alkanediyl bridge having 1 to 3 carbon atoms together with carbon atoms to which $R^2$ and $R^3$ are bonded (—$CH_2$— included in the alkanediyl bridge may be replaced by —O—, —S—, —CO—, —SO— or —$SO_2$—).

Particularly, when $R^2$ and $R^3$ are bonded to each other to form a single bond or an alkanediyl bridge having 1 to 6 carbon atoms together with carbon atoms to which $R^2$ and $R^3$ are bonded (—$CH_2$— included in the alkanediyl bridge may be replaced by —O—, —S—, —CO—, —SO— or —$SO_2$—), $R^2$ and $R^3$ are bonded to each other to form more preferably a single bond or an alkanediyl bridge having 1 to 3 carbon atoms together with carbon atoms to which $R^2$ and $R^3$ are bonded (—$CH_2$— included in the alkanediyl bridge may be replaced by —O—, —S—, —CO—, —SO— or —$SO_2$—), and still more preferably a single bond or an alkanediyl bridge having 1 to 3 carbon atoms (—$CH_2$— included in the alkanediyl bridge may be replaced by —O— or —CO—).

When $R^2$ and $R^3$ are bonded to each other to form a single bond or an alkanediyl bridge having 1 to 6 carbon atoms together with carbon atoms to which $R^2$ and $R^3$ are bonded (—$CH_2$— included in the alkanediyl bridge may be replaced by —O—, —S—, —CO—, —SO— or —$SO_2$—), $R^2$ and $R^3$ may be bonded to any position of the benzene ring, preferably carbon atoms adjacent to the carbon atoms to which $S^+$ is bonded, of carbon atoms of the benzene ring.

Examples of the hydrocarbon group including a cyclic hydrocarbon group in $R^7$ in formula (I) include cyclic hydrocarbon groups such as a monocyclic or polycyclic alicyclic hydrocarbon group having 3 to 18 carbon atoms and an aromatic hydrocarbon group having 6 to 18 carbon atoms, or a group obtained by combining these groups, groups obtained by optionally combining a cyclic hydrocarbon group such as a monocyclic or polycyclic alicyclic hydrocarbon group having 3 to 18 carbon atoms and an aromatic hydrocarbon group having 6 to 18 carbon atoms with a chain hydrocarbon group having 1 to 6 carbon atoms (alkyl group, alkenyl group, alkynyl group) and the like.

The alicyclic hydrocarbon group may be either monocyclic, polycyclic or spiro ring, or may be either saturated or unsaturated. Examples of the alicyclic hydrocarbon group include monocyclic cycloalkyl groups such as a cyclopropyl group, a cyclobutyl group, a cyclopentyl group, a cyclohexyl group, a cycloheptyl group, a cyclooctyl group, a cyclononyl group, a cyclodecyl group and a cyclododecyl group; and polycyclic cycloalkyl groups such as a decahydronaphthyl group, a norbornyl group and an adamantyl group. The number of carbon atoms of the alicyclic hydrocarbon group is preferably 3 to 16, more preferably 5 to 16, and still more preferably 6 to 16.

Specific examples of the alicyclic hydrocarbon group include the following groups and the like. The bonding site can be any position.

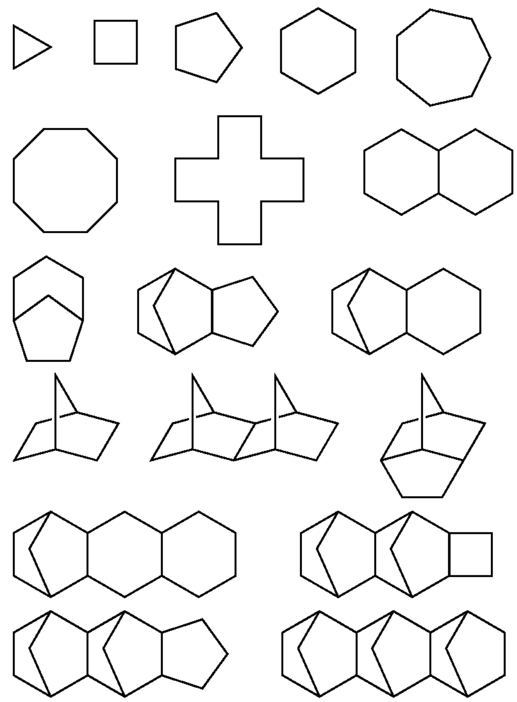

-continued

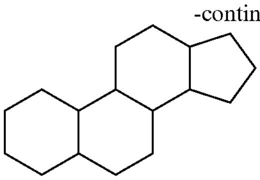
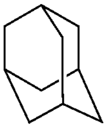
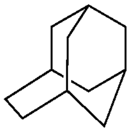

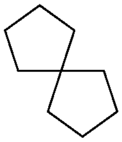
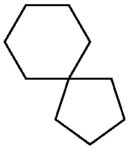
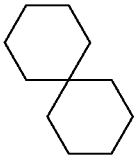

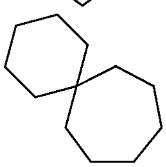
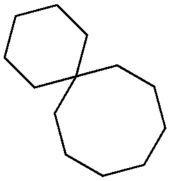

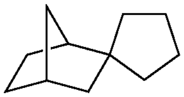
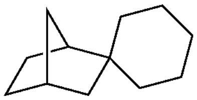

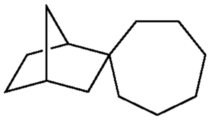
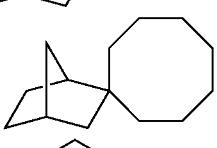

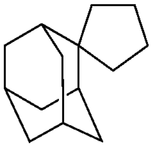
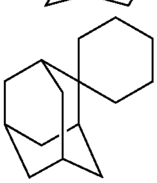

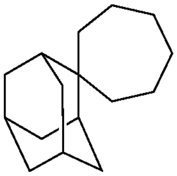
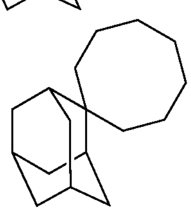

Examples of the aromatic hydrocarbon group include aryl groups such as a phenyl group, a naphthyl group, a biphenyl group, an anthryl group, a phenanthryl group and a binaphthyl group. The number of carbon atoms of the aromatic hydrocarbon group is preferably 6 to 14, and more preferably 6 to 10.

Examples of the alkyl group include alkyl groups such as a methyl group, an ethyl group, a propyl group, an isopropyl group, a butyl group, an isobutyl group, a tert-butyl group, a pentyl group, a hexyl group, a heptyl group, an octyl group, a nonyl group, a decyl group, an undecyl group and a dodecyl group. The number of carbon atoms of the alkyl group is preferably 1 to 12, more preferably 1 to 9, still more preferably 1 to 6, and yet more preferably 1 to 4.

Examples of the alkenyl group include an ethenyl group, a propenyl group, an isopropenyl group, a butenyl group, an isobutenyl group, a tert-butenyl group, a pentenyl group, a hexenyl group, a heptenyl group, an octynyl group, an isooctynyl group, a nonenyl group and the like.

Examples of the alkynyl group include an ethynyl group, a propynyl group, an isopropynyl group, a butynyl group, an isobutynyl group, a tert-butynyl group, a pentynyl group, a hexynyl group, an octynyl group, a nonynyl group and the like.

Examples of the combined group include:

A group obtained by combining an alicyclic hydrocarbon group with an aromatic hydrocarbon group (—$CH_2$— included in the combined group may be replaced by —O—, —S—, —CO— or —$SO_2$—), a group obtained by combining an alicyclic hydrocarbon group with a chain hydrocarbon group (alkyl group, alkenyl group, alkynyl group) (—$CH_2$— included in the combined group may be replaced by —O—, —S—, —CO— or —$SO_2$—) and a group obtained by combining an aromatic hydrocarbon group with a chain hydrocarbon group (alkyl group, alkenyl group, alkynyl group) (—$CH_2$— included in the combined group may be replaced by —O—, —S—, —CO— or —$SO_2$—).

In combination, two or more of alicyclic hydrocarbon groups, aromatic hydrocarbon groups and chain hydrocarbon groups (alkyl group, alkenyl group, alkynyl group, etc.) may be used in combination. Any group may be bonded to $X^2$. In the above-mentioned groups, groups having different valences (alkanediyl group, alkanetriyl group, cycloalkanediyl group, cycloalkanetriyl group, etc.) may be included. The total number of carbon atoms of the hydrocarbon group including the cyclic hydrocarbon group in $R^7$ is, for example, 3 to 24 and is preferably 4 to 18, and more preferably 5 to 16.

Specific examples of the combined group include:

alicyclic hydrocarbon group-chain hydrocarbon group-* (—$CH_2$— included in the chain hydrocarbon group and the alicyclic hydrocarbon group may be replaced by —O—, —S—, —CO— or —$SO_2$—) such as an adamantylmethyl group, an adamantylethyl group, a cyclohexylmethyl group and a cyclohexylethyl group, chain hydrocarbon group-alicyclic hydrocarbon group-* (—$CH_2$— included in the chain hydrocarbon group and the alicyclic hydrocarbon group may be replaced by —O—, —S—, —CO— or —$SO_2$—) such as a methyladamantyl group, a methylcyclohexyl group and a dimethylcyclohexyl group, chain hydrocarbon group-aromatic hydrocarbon group-* (—$CH_2$— included in the chain hydrocarbon group may be replaced by —O—, —S—, —CO— or —$SO_2$—) such as a tolyl group and a xylyl group, chain hydrocarbon group-alicyclic hydrocarbon group-chain hydrocarbon group-* (—$CH_2$— included in the chain hydrocarbon group and the alicyclic hydrocarbon group may be replaced by —O—, —S—, —CO— or —$SO_2$—) such as a methylcyclohexylmethyl group, aromatic hydrocarbon group-chain hydrocarbon group-* (—$CH_2$— included in the chain hydrocarbon group may be replaced by —O—, —S—, —CO— or —$SO_2$—) such as a benzyl group and a phenethyl group, chain hydrocarbon group-aromatic hydrocarbon group-chain hydrocarbon group-* (—$CH_2$— included in the chain hydrocarbon group may be replaced by —O—, —S—, —CO— or —$SO_2$—), such as a tolylmethyl group, aromatic hydrocarbon group-alicyclic hydrocarbon group-* (—$CH_2$— included in the alicyclic hydrocarbon group may be replaced by —O—, —S—, —CO— or —$SO_2$—) such as a phenyladamantyl group, and alicyclic hydrocarbon group-aromatic hydrocarbon group-* (—$CH_2$— included in the alicyclic hydrocarbon group may be replaced by —O—, —S—, —CO— or —$SO_2$—) such as a cyclohexylphenyl group and an adamantylphenyl group. * represents a bonding site to $X^2$.

When $—CH_2—$ included in the hydrocarbon group in $R^7$ is replaced by —O—, —S—, —CO— or $—SO_2—$, the number of carbon atoms before replacement is the total number of carbon atoms of the hydrocarbon group. The number may be 1, or 2 or more.

Examples of the group in which $—CH_2—$ included in a hydrocarbon group is replaced by —O— or —CO— include a hydroxy group, a carboxy group, alkoxy groups such as a methoxy group, an ethoxy group and a butoxy group, cycloalkoxy groups such as a cyclohexyloxy group, cycloalkylalkoxy groups such as a cyclohexylmethoxy group, alkylcarbonyl groups such as an acetyl group, alkoxycarbonyl groups such as a methoxycarbonyl group, alkylcarbonyloxy groups such as an acetyloxy group, alkoxycarbonyloxy groups such as a butoxycarbonyloxy group, and aromatic hydrocarbon group-carbonyloxy groups such as a benzoyloxy group.

Examples of the group in which $—CH_2—$ included in the alicyclic hydrocarbon group is replaced by —O—, —CO— or $—SO_2—$ include the following groups. The bonding site can be any position.

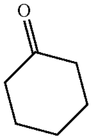 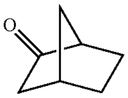 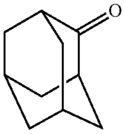

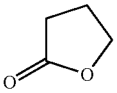 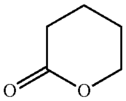 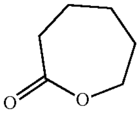

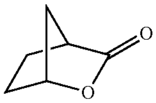 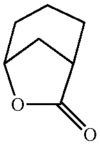 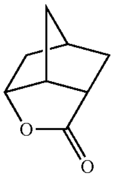

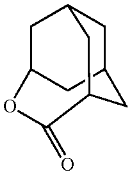 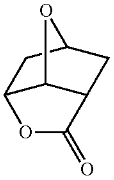 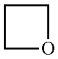

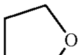 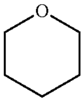 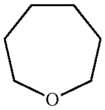 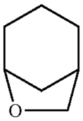

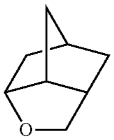 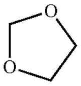 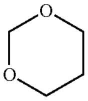 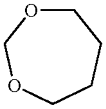

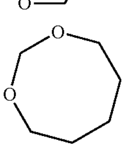 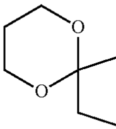 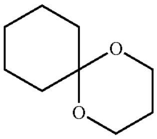

-continued

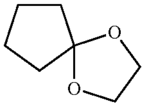 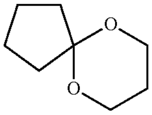 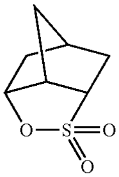

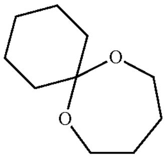 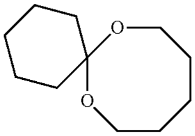 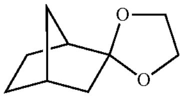

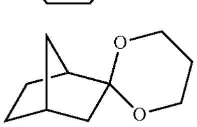 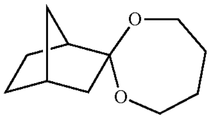

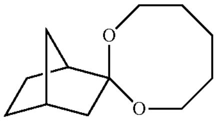 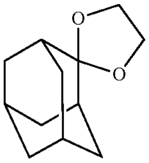

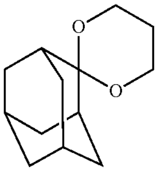 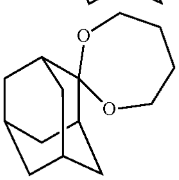

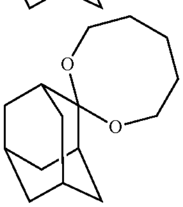

Examples of the substituent which may be possessed by the cyclic hydrocarbon group include a halogen atom, a cyano group and an alkyl group having 1 to 12 carbon atoms ($—CH_2—$ included in the alkyl group may be replaced by —O—, —S—, —CO— or $—SO_2—$).

Examples of the halogen atom include a fluorine atom, a chlorine atom, a bromine atom and an iodine atom.

Examples of the alkyl group having 1 to 12 carbon atoms include a methyl group, an ethyl group, a propyl group, an isopropyl group, a butyl group, an isobutyl group, a tert-butyl group, a pentyl group, a hexyl group, an octyl group, a nonyl group and the like. The number of carbon atoms of the alkyl group is preferably 1 to 9, more preferably 1 to 6, and still more preferably 1 to 4.

When $—CH_2—$ included in the alkyl group as the substituent is replaced by —O— or —CO—, the number of carbon atoms before replacement is the total number of carbon atoms of the alkyl group. Examples of the group replaced include a hydroxy group (group in which $—CH_2—$ included in the methyl group is replaced by —O—), a carboxy group (group in which $—CH_2—CH_2—$ included in an ethyl group is replaced by —O—CO—), an alkoxy group (group in which $—CH_2—$ at any position included in an alkyl group is replaced by —O—), an alkoxycarbonyl group (group in which $—CH_2—CH_2—$ at any position included in an alkyl group is replaced by —O—CO—), an alkylcarbonyl group (group in which $—CH_2—$ at any position included in an alkyl group is replaced by —CO—), an alkylcarbonyloxy group (group in which —$CH_2$—$CH_2$— at any position included in an alkyl group is replaced by —CO—O—) and the like.

Examples of the alkoxy group include alkoxy groups having 1 to 11 carbon atoms, for example, a methoxy group, an ethoxy group, a propoxy group, a butoxy group, a pentyloxy group, a hexyloxy group, an octyloxy group, a 2-ethylhexyloxy group, a nonyloxy group, a decyloxy group, an undecyloxy group and the like.

The alkoxycarbonyl group, the alkylcarbonyl group and the alkylcarbonyloxy group represent a group in which a carbonyl group or a carbonyloxy group is bonded to the above-mentioned alkyl group or alkoxy group.

Examples of the alkoxycarbonyl group include alkoxycarbonyl groups having 2 to 11 carbon atoms, for example, a methoxycarbonyl group, an ethoxycarbonyl group, a butoxycarbonyl group and the like. Examples of the alkylcarbonyl group include alkylcarbonyl groups having 2 to 12 carbon atoms, for example, an acetyl group, a propionyl group and a butyryl group. Examples of the alkylcarbonyloxy group include alkylcarbonyloxy groups having 2 to 11 carbon atoms, for example, an acetyloxy group, a propionyloxy group and a butyryloxy group.

The cyclic hydrocarbon group may have one substituent or a plurality of substituents.

The cyclic hydrocarbon group having 3 to 18 carbon atoms (the cyclic hydrocarbon group may have a substituent, and —$CH_2$— included in the cyclic hydrocarbon group may be replaced by —O—, —S—, —$SO_2$— or —CO—) is:

preferably an alicyclic hydrocarbon group having 3 to 18 carbon atoms (the alicyclic hydrocarbon group may have a substituent, and —$CH_2$— included in the alicyclic hydrocarbon group may be replaced by —O—, —S—, —$SO_2$— or —CO—), or an aromatic hydrocarbon group having 6 to 18 carbon atoms (the aromatic hydrocarbon group may have a substituent), more preferably an alicyclic hydrocarbon group having 3 to 18 carbon atoms (the alicyclic hydrocarbon group may have at least one selected from the group consisting of an alkyl group having 1 to 4 carbon atoms, a hydroxy group and a fluorine atom, and —$CH_2$— included in the alicyclic hydrocarbon group may be replaced by —O—, —S—, —$SO_2$— or —CO—), or an aromatic hydrocarbon group having 6 to 18 carbon atoms (the aromatic hydrocarbon group may have at least one selected from the group consisting of an alkyl group having 1 to 4 carbon atoms, a hydroxy group and a fluorine atom), and still more preferably a polycyclic alicyclic hydrocarbon group having 6 to 16 carbon atoms (the alicyclic hydrocarbon group may have at least one selected from the group consisting of an alkyl group having 1 to 4 carbon atoms, a hydroxy group and a fluorine atom, and —$CH_2$— included in the alicyclic hydrocarbon group may be replaced by —O—, —S—, —$SO_2$— or —CO—).

The hydrocarbon group including a cyclic hydrocarbon group having 3 to 18 carbon atoms in $R^7$ (the cyclic hydrocarbon group may have a substituent and —$CH_2$-included in the hydrocarbon group may be replaced by —O—, —S—, —$SO_2$— or —CO—) is:

preferably a hydrocarbon group including an alicyclic hydrocarbon group having 3 to 18 carbon atoms (the alicyclic hydrocarbon group may have a substituent, and —$CH_2$-included in the hydrocarbon group may be replaced by —O—, —S—, —$SO_2$— or —CO—), or a hydrocarbon group including an aromatic hydrocarbon group having 6 to 18 carbon atoms (the aromatic hydrocarbon group may have a substituent, and —$CH_2$-included in the hydrocarbon group may be replaced by —O—, —S—, —$SO_2$—or —CO—), more preferably a hydrocarbon group including an alicyclic hydrocarbon group having 3 to 18 carbon atoms (the alicyclic hydrocarbon group may have at least one selected from the group consisting of an alkyl group having 1 to 4 carbon atoms, a hydroxy group and a fluorine atom, and —$CH_2$-included in the hydrocarbon group may be replaced by —O—, —S—, —$SO_2$—or —CO—), or a hydrocarbon group including an aromatic hydrocarbon group having 6 to 18 carbon atoms (the aromatic hydrocarbon group may have at least one selected from the group consisting of an alkyl group having 1 to 4 carbon atoms, a hydroxy group and a fluorine atom, and —$CH_2$-included in the hydrocarbon group may be replaced by —O—, —S—, —$SO_2$—or —CO—), still more preferably an alicyclic hydrocarbon group having 3 to 18 carbon atoms (the alicyclic hydrocarbon group may have at least one selected from the group consisting of an alkyl group having 1 to 4 carbon atoms, a hydroxy group and a fluorine atom, and —$CH_2$-included in the alicyclic hydrocarbon group may be replaced by —O—, —S—, —$SO_2$—or —CO—), a group obtained by combining an alicyclic hydrocarbon group having 3 to 18 carbon atoms with a chain hydrocarbon group having 1 to 6 carbon atoms (the alicyclic hydrocarbon group may have at least one selected from the group consisting of an alkyl group having 1 to 4 carbon atoms, a hydroxy group and a fluorine atom, and —$CH_2$-included in the combined group may be replaced by —O—, —S—, —$SO_2$—or —CO—), an aromatic hydrocarbon group having 6 to 18 carbon atoms (the aromatic hydrocarbon group may have at least one selected from the group consisting of an alkyl group having 1 to 4 carbon atoms, a hydroxy group and a fluorine atom), or a group obtained by combining an aromatic hydrocarbon group having 6 to 18 carbon atoms with a chain hydrocarbon group having 1 to 6 carbon atoms (the aromatic hydrocarbon group may have at least one selected from the group consisting of an alkyl group having 1 to 4 carbon atoms, a hydroxy group and a fluorine atom, and —$CH_2$-included in the combined group may be replaced by —O—, —S—, —$SO_2$—or —CO—), and yet more preferably a polycyclic alicyclic hydrocarbon group having 6 to 16 carbon atoms (the alicyclic hydrocarbon group may have at least one selected from the group consisting of an alkyl group having 1 to 4 carbon atoms, a hydroxy group and a fluorine atom, and —$CH_2$-included in the alicyclic hydrocarbon group may be replaced by —O—, —S—, —$SO_2$—or —CO—), or a group obtained by combining a polycyclic alicyclic hydrocarbon group having 6 to 16 carbon atoms with a chain hydrocarbon group having 1 to 4 carbon atoms (the alicyclic hydrocarbon group may have at least one selected from the group consisting of an alkyl group having 1 to 4 carbon atoms, a hydroxy group and a fluorine atom, and —$CH_2$-included in the combined group may be replaced by —O—, —S—, —$SO_2$—or —CO—).

When, in formula (I), $R^2$ and $R^3$ are bonded to each other to form a single bond or an alkanediyl bridge having 1 to 6 carbon atoms together with carbon atoms to which $R^2$ and $R^3$ are bonded (—$CH_2$-included in the alkanediyl bridge may be replaced by —O—, —S—, —CO—, —SO—or —$SO_2$—), examples of the salt represented by formula (I) include a salt represented by formula (IB):

(IB)

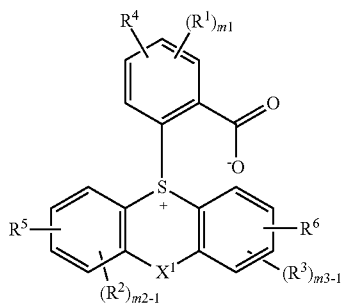

wherein, in formula (IB), $R^1$, $R^2$, $R^3$, $R^4$, $R^5$, $R^6$, $X^2$ and $R^7$ are as defined above in formula (I), m2 and m3 each independently represent an integer of 1 to 4, and $X^1$ represents a single bond, —$CH_2$—, —O—, —S—, —CO—, —SO—or —$SO_2$—.

Examples of the salt (I) include salts represented by the following formulas.

(I-1)

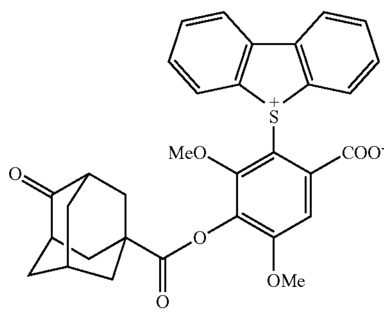

(I-2)

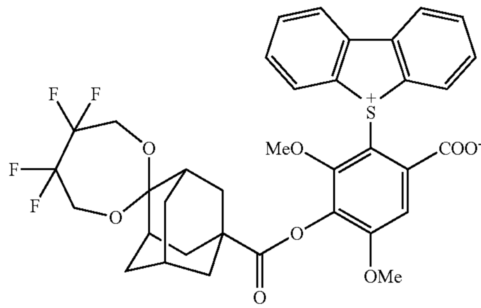

-continued (I-3)

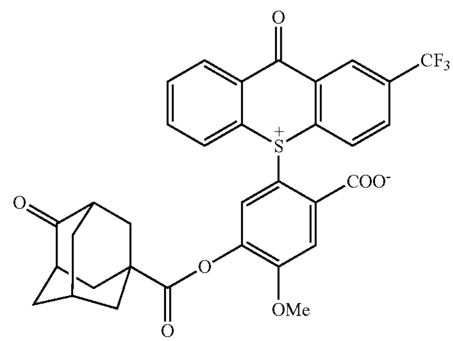

(I-4)

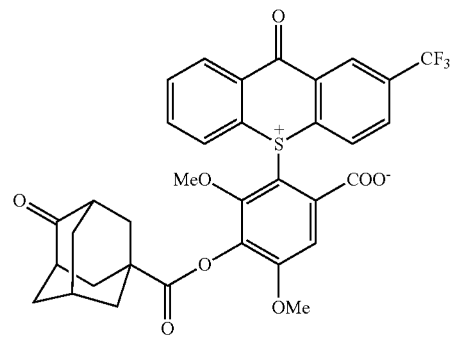

(I-5)

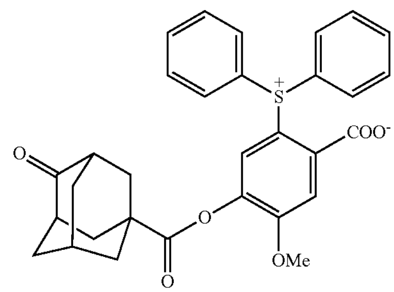

(I-6)

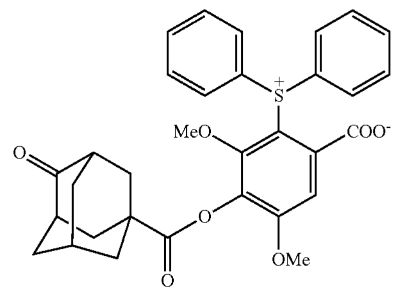

(I-7)

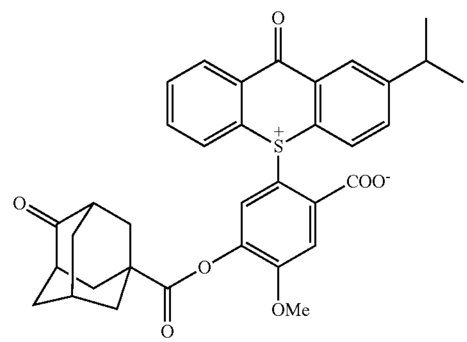

-continued
(I-8)
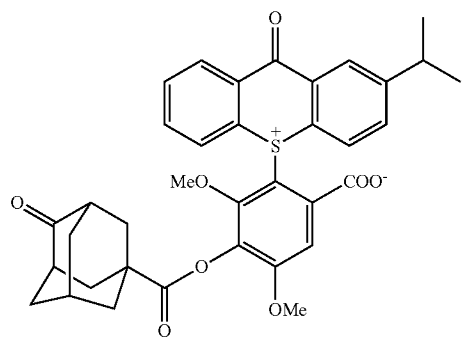
(I-9)
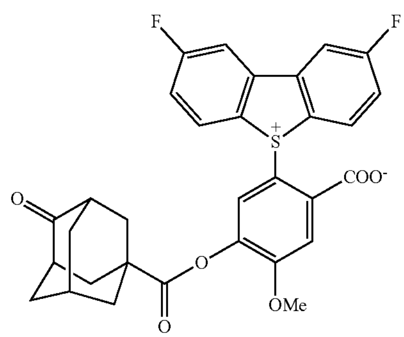
(I-10)
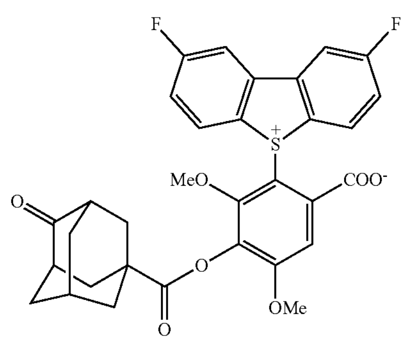
(I-11)
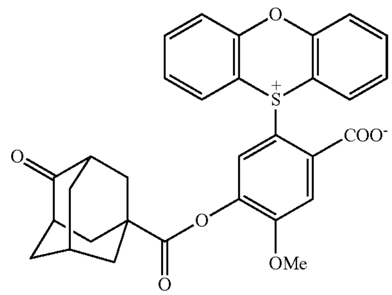
(I-12)
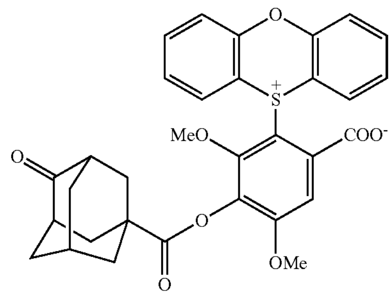
-continued
(I-13)
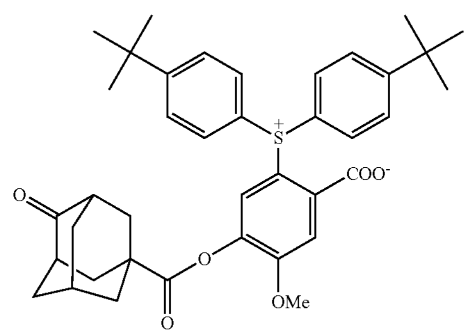
(I-14)
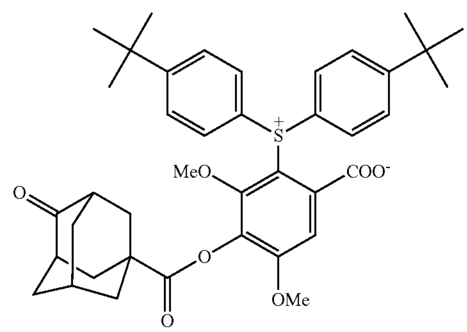
(I-15)
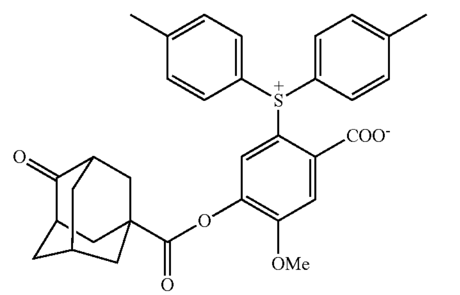
(I-16)
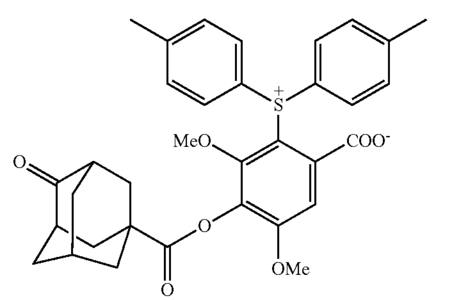
(I-17)
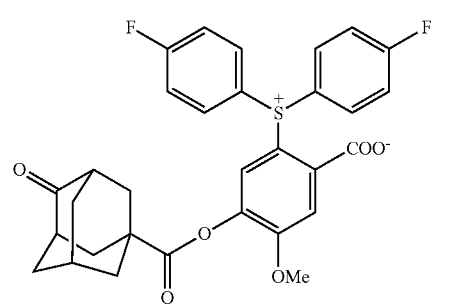

-continued
(I-18)
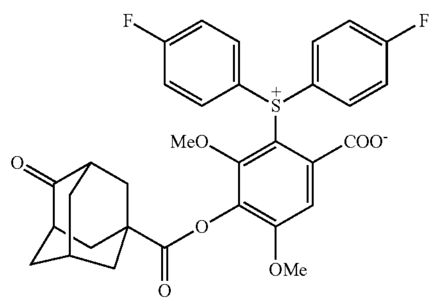
(I-19)
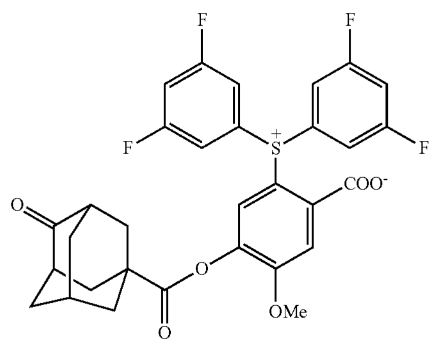
(I-20)
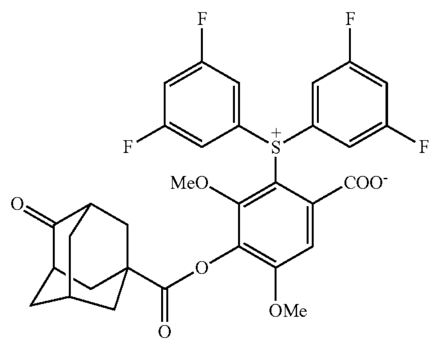
(I-21)
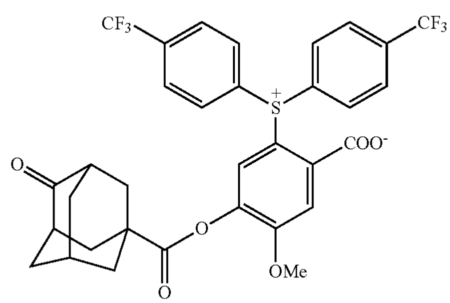
(I-22)
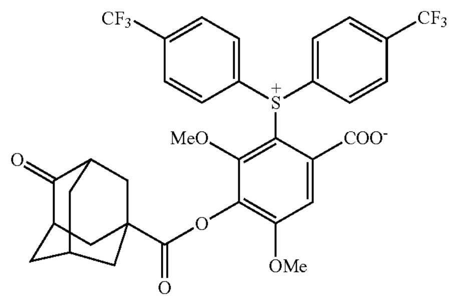
-continued
(I-23)
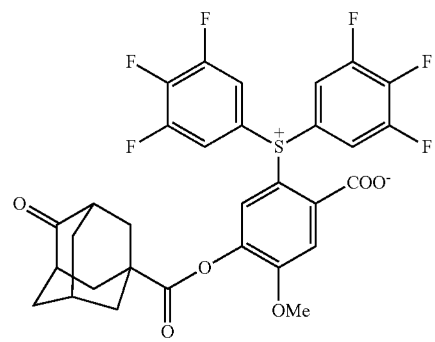
(I-24)
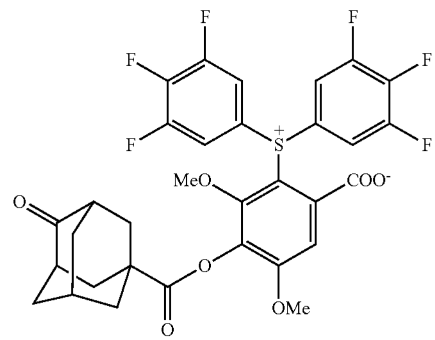
(I-25)
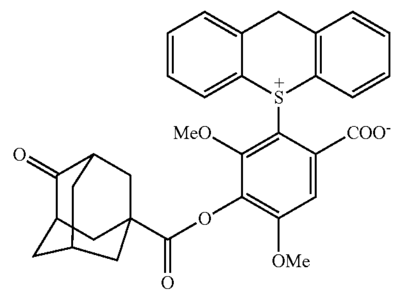
(I-26)
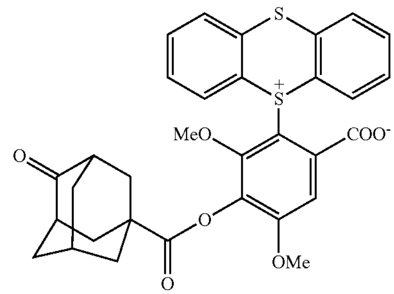
(I-27)
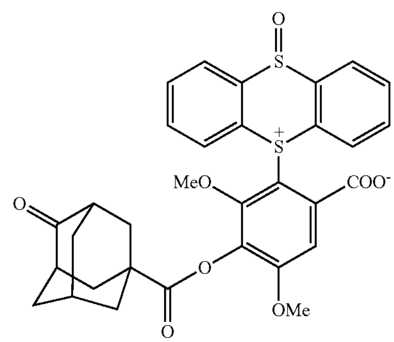

-continued
(I-28)
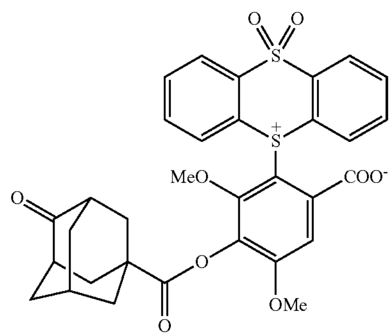
(I-29)
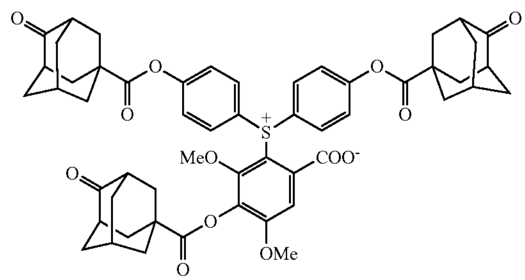
(I-30)
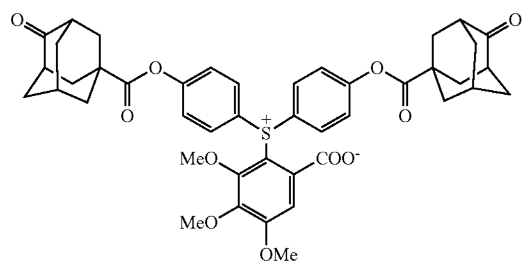
(I-31)
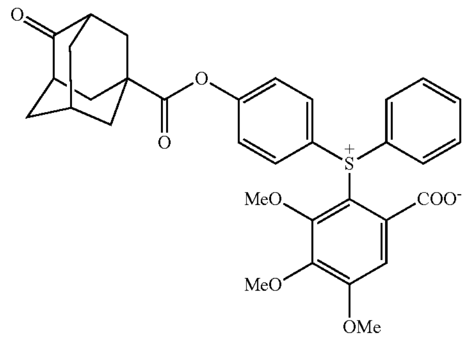
(I-32)
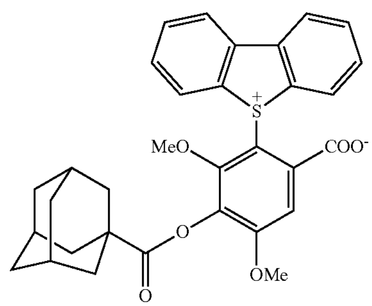
-continued
(I-33)
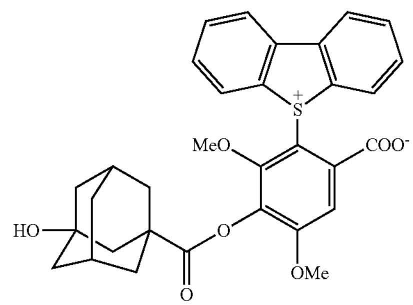
(I-34)
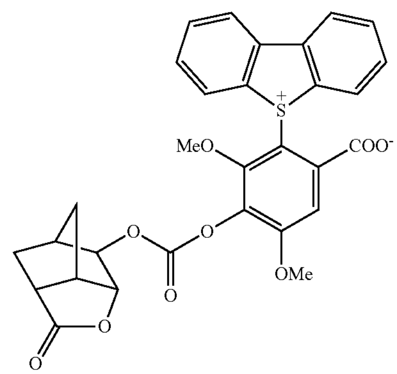
(I-35)
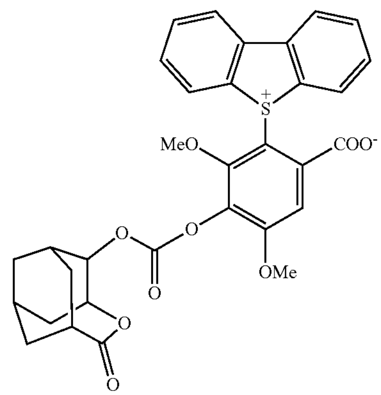
(I-36)
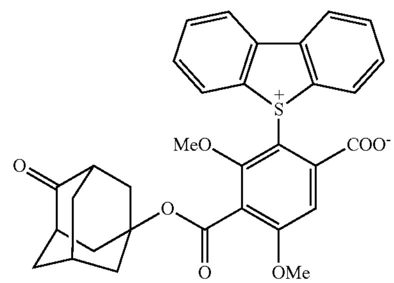

-continued (I-37)

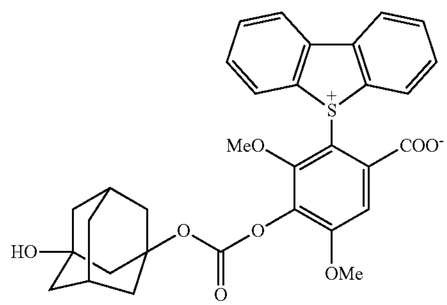

(I-38)

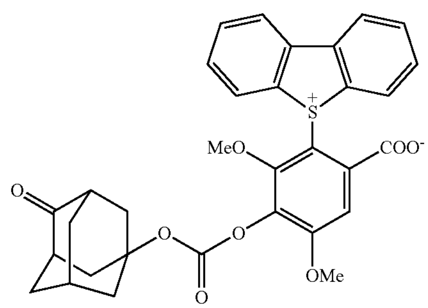

(I-39)

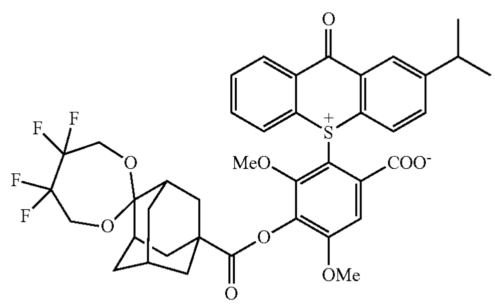

(I-40)

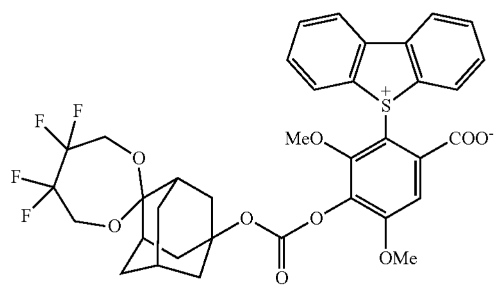

<Method for Producing Salt (I)>

The salt (I) can be produced by mixing a salt represented by formula (I-a) under a base catalyst in a solvent:

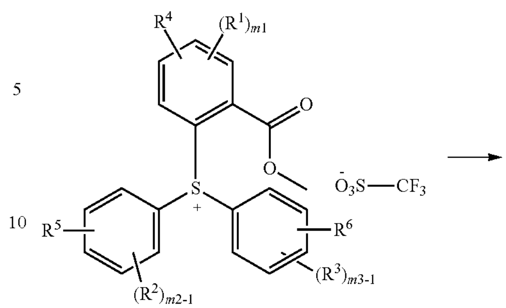

(I-a)

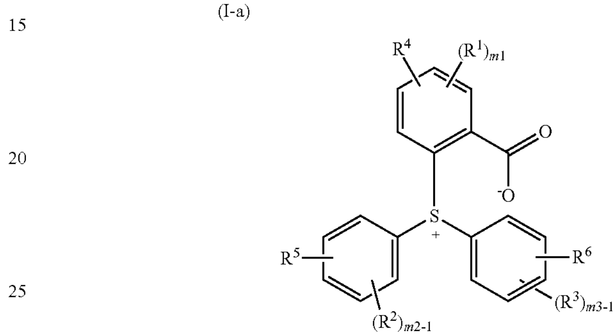

(I)

wherein all symbols are as defined above.

Examples of the base include sodium hydroxide, potassium hydroxide and the like.

Examples of the solvent include chloroform and the like.

The reaction is usually performed at a temperature in a range of 0 to 80° C. for 0.5 to 24 hours.

The salt represented by formula (I-a) can be produced by reacting a compound represented by formula (I-b) with a compound represented by formula (I-c) in the presence of trifluoromethanesulfonic acid and trifluoroacetic anhydride in a solvent:

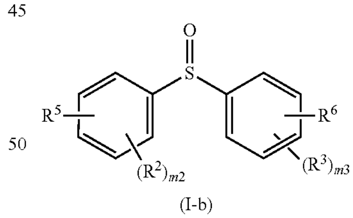

(I-b)

+

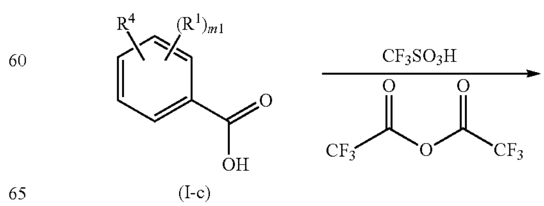

(I-c)

-continued

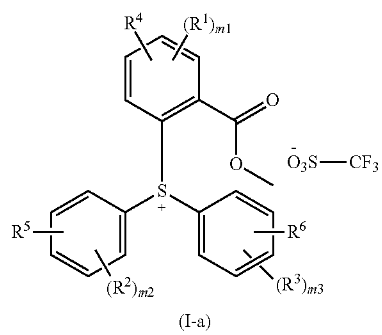

(I-a)

wherein all symbols are as defined above.

Examples of the solvent include chloroform, acetonitrile and the like.

The reaction is usually performed at a temperature in a range of 0 to 60° C. for 0.5 to 24 hours.

Examples of the compound represented by formula (I-b) include compounds represented by the following formulas, which are easily available on the market, and can also be easily produced by a known production method.

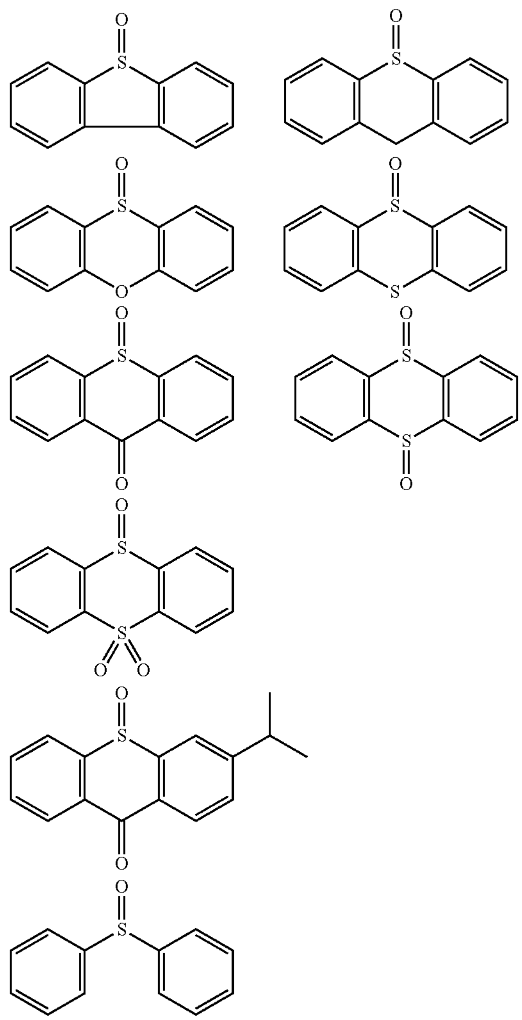

-continued

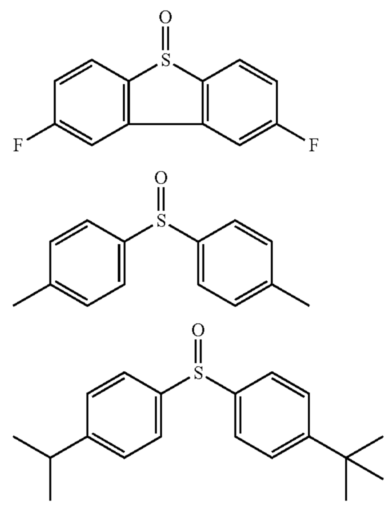

Examples of the compound represented by formula (I-c) include compounds represented by the following formulas, which are easily available on the market, and can also be easily produced by a known production method.

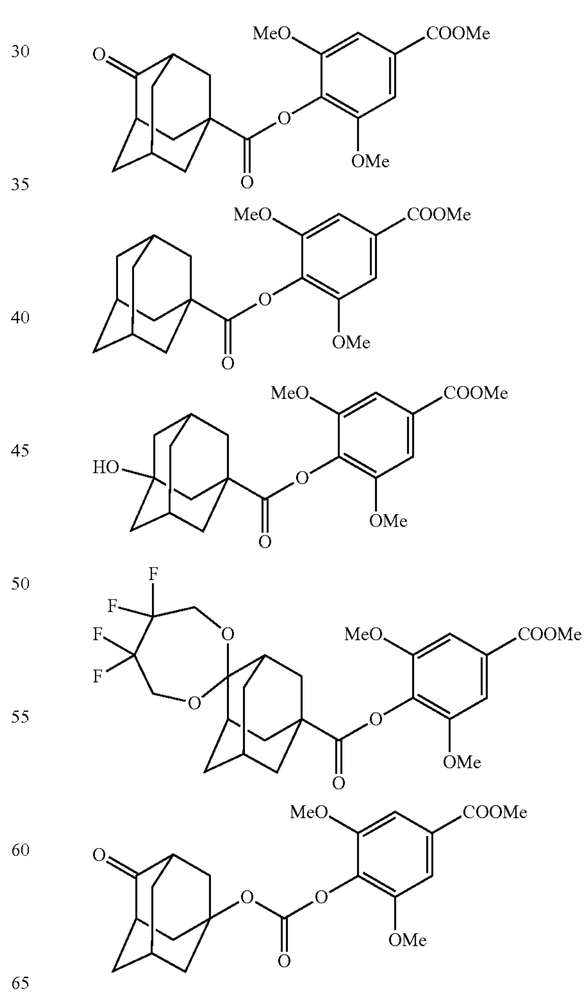

-continued

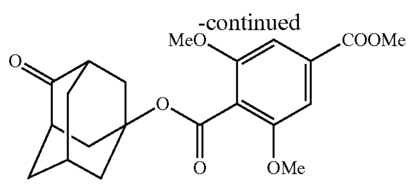

[Quencher]

The quencher of the present invention includes a salt (I). The quencher may contain one salt (I), or two or more salts (I).

The quencher of the present invention may include, in addition to the salt (I), a quencher known in the resist field (hereinafter sometimes referred to as "quencher (C)"). The quencher (C) may be used alone, or two or more quenchers may be used in combination.

<Quencher (C)>

Examples of the quencher (C) include a basic nitrogen-containing organic compound and a salt generating an acid having an acidity lower than that of an acid generated from an acid generator (B) mentioned below (excluding a salt represented by formula (I)). It is particularly preferable to include a salt generating a carboxylic acid having an acidity lower than that of an acid generated from the acid generator (B) such as a weak acid inner salt (hereinafter sometimes referred to as "weak acid inner salt (D)").

Examples of the basic nitrogen-containing organic compound include an amine and an ammonium salt. Examples of the amine include an aliphatic amine and an aromatic amine. Examples of the aliphatic amine include a primary amine, a secondary amine and a tertiary amine.

Examples of the amine include 1-naphthylamine, 2-naphthylamine, aniline, diisopropylaniline, 2-, 3- or 4-methylaniline, 4-nitroaniline, N-methylaniline, N,N-dimethylaniline, diphenylamine, hexylamine, heptylamine, octylamine, nonylamine, decylamine, dibutylamine, dipentylamine, dihexylamine, diheptylamine, dioctylamine, dinonylamine, didecylamine, triethylamine, trimethylamine, tripropylamine, tributylamine, tripentylamine, trihexylamine, triheptylamine, trioctylamine, trinonylamine, tridecylamine, methyldibutylamine, methyldipentylamine, methyldihexylamine, methyldicyclohexylamine, methyldiheptylamine, methyldioctylamine, methyldinonylamine, methyldidecylamine, ethyldibutylamine, ethyldipentylamine, ethyldihexylamine, ethyldiheptylamine, ethyldioctylamine, ethyldinonylamine, ethyldidecylamine, dicyclohexylmethylamine, tris[2-(2-methoxyethoxy)ethyl]amine, triisopropanolamine, ethylenediamine, tetramethylenediamine, hexamethylenediamine, 4,4'-diamino-1,2-diphenylethane, 4,4'-diamino-3,3'-dimethyldiphenylmethane, 4,4'-diamino-3,3'-diethyldiphenylmethane, 2,2'-methylenebisaniline, imidazole, 4-methylimidazole, pyridine, 4-methylpyridine, 1,2-di(2-pyridyl)ethane, 1,2-di(4-pyridyl)ethane, 1,2-di(2-pyridyl)ethene, 1,2-di(4-pyridyl)ethene, 1,3-di(4-pyridyl) propane, 1,2-di(4-pyridyloxy)ethane, di(2-pyridyl)ketone, 4,4'-dipyridyl sulfide, 4,4'-dipyridyl disulfide, 2,2'-dipyridylamine, 2,2'-dipicolylamine, bipyridine and the like, preferably diisopropylaniline, and more preferably 2,6-diisopropylaniline.

Examples of the ammonium salt include tetramethylammonium hydroxide, tetraisopropylammonium hydroxide, tetrabutylammonium hydroxide, tetrahexylammonium hydroxide, tetraoctylammonium hydroxide, phenyltrimethylammonium hydroxide, 3-(trifluoromethyl)phenyltrimethylammonium hydroxide, tetra-n-butylammonium salicylate and choline.

The acidity in a salt generating an acid having an acidity lower than that of an acid generated from the acid generator (B) is indicated by the acid dissociation constant (pKa). Regarding the salt generating an acid having an acidity lower than that of an acid generated from the acid generator (B), the acid dissociation constant of an acid generated from the salt usually meets the following inequality: $-3<pKa$, preferably $-1<pKa<7$, and more preferably $0<pKa<5$.

Examples of the salt generating an acid having an acidity lower than that of an acid generated from the acid generator (B) include salts represented by the following formulas, a salt represented by formula (D) mentioned in JP 2015-147926 A (hereinafter sometimes referred to as "weak acid inner salt (D)", and salts mentioned in JP 2012-229206 A, JP 2012-6908 A, JP 2012-72109 A, JP 2011-39502 A and JP 2011-191745 A. The salt generating an acid having an acidity lower than that of an acid generated from the acid generator (B) is preferably a salt generating a carboxylic acid having an acidity lower than that of an acid generated from the acid generator (B) (salt having a carboxylic acid anion), and more preferably a weak acid inner salt (D).

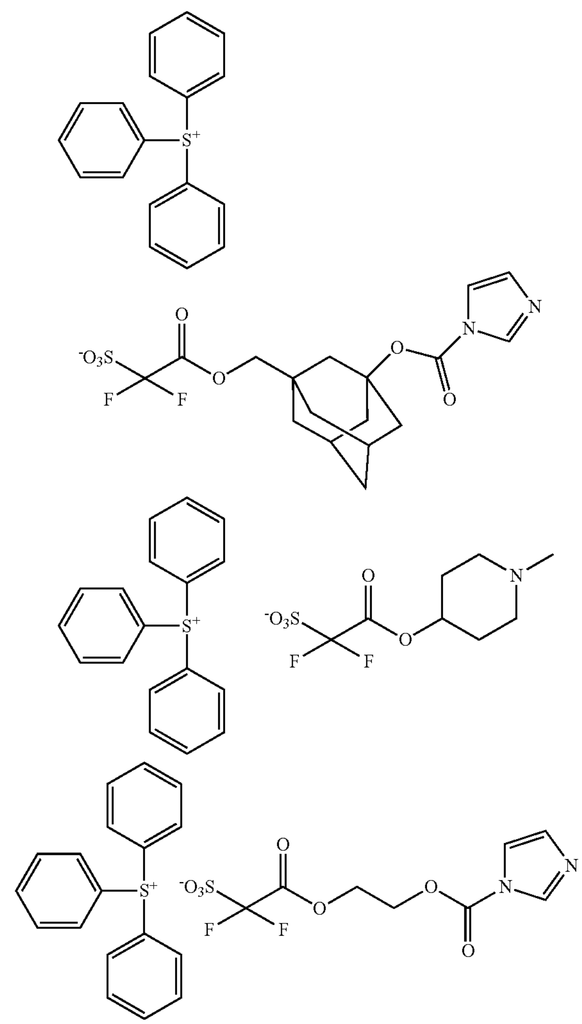

-continued
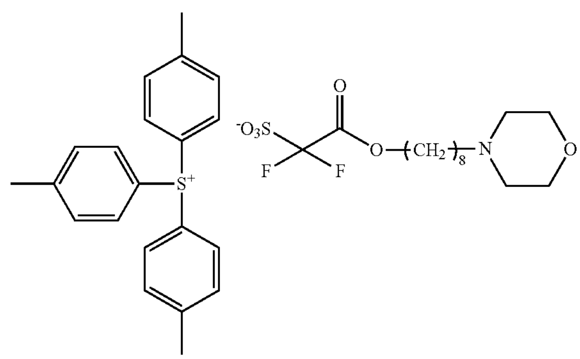
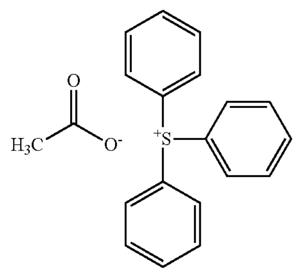
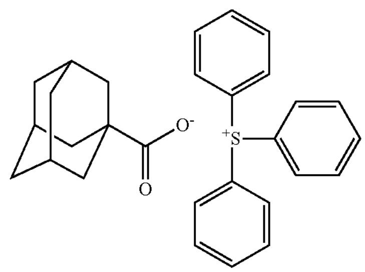
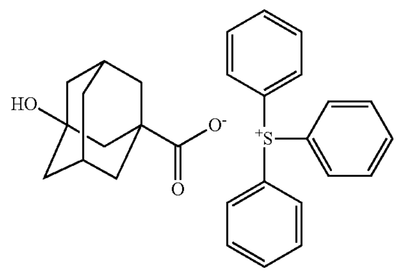
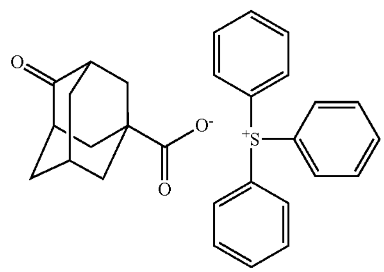
-continued
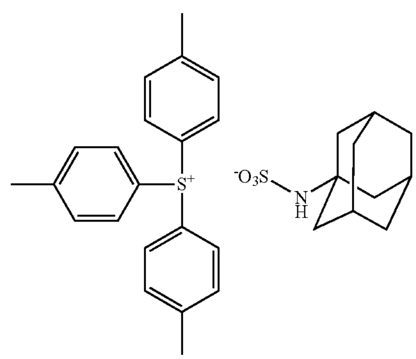
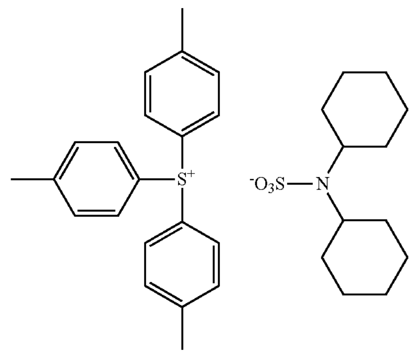
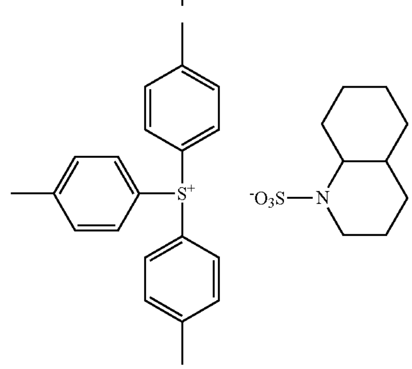
Examples of the weak acid inner salt (D) include the following salts.
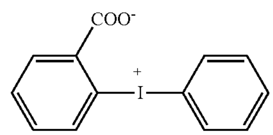
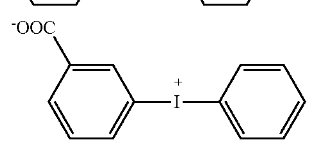
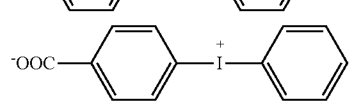
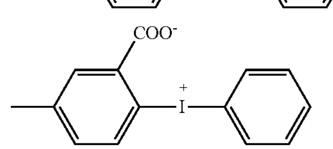

-continued

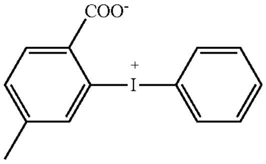

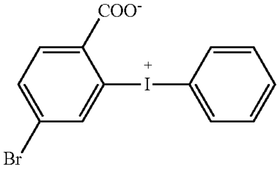

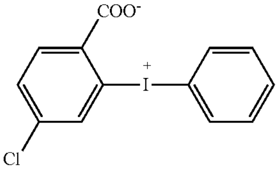

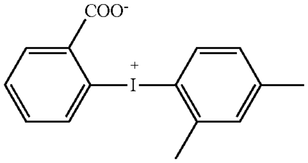

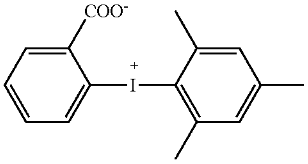

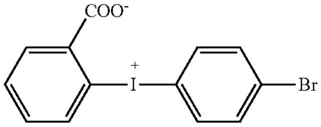

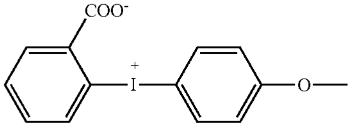

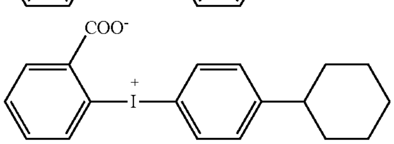

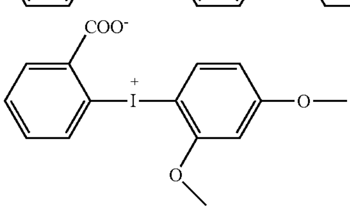

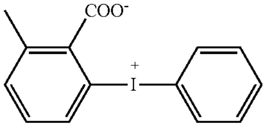

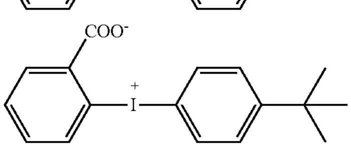

-continued

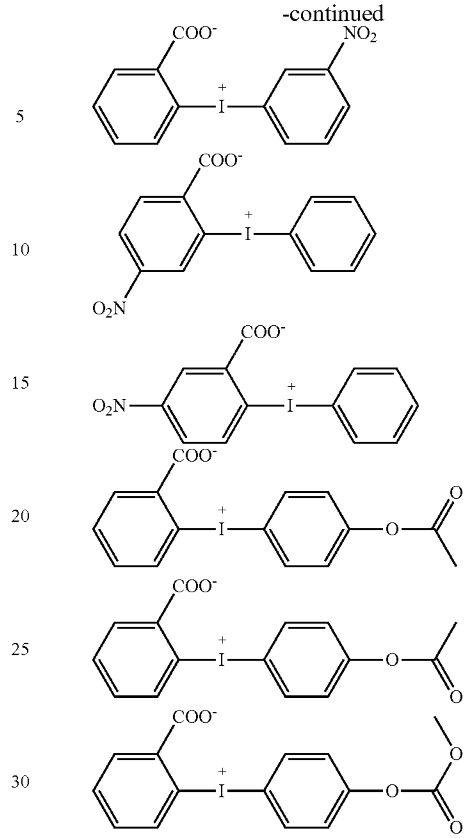

When including, as the quencher, a salt (I) and a quencher (C), a ratio of the salt (I) to the quencher (C) (mass ratio; salt (I):quencher (C)) is usually 1:99 to 99:1, preferably 2:98 to 98:2, more preferably 5:95 to 95:5, still more preferably 10:90 to 90:10, and particularly preferably 15:85 to 85:15.

[Resist Composition]

The resist composition of the present invention includes a quencher including a salt (I), a resin including a structural unit having an acid-labile group (hereinafter sometimes referred to as "resin (A)") and an acid generator (hereinafter sometimes referred to as "acid generator (B)"). The "acid-labile group" means a group having a leaving group which is eliminated by contact with an acid, thus forming a hydrophilic group (e.g. a hydroxy group or a carboxy group).

The resist composition of the present invention preferably includes a solvent (hereinafter sometimes referred to as "solvent (E)").

<Quencher>

In the resist composition of the present invention, the content of the salt (I) is usually 0.001 to 20% by mass, preferably 0.005 to 15% by mass, and more preferably 0.01 to 10% by mass, based on the solid content of the resist composition. When the quencher includes the quencher (C), the content of the quencher (C) is preferably 0.01 to 20% by mass, more preferably 0.01 to 15% by mass, still more preferably 0.01 to 10% by mass, yet more preferably 0.01 to 5% by mass, and further preferably 0.01 to 3% by mass, based on the solid content of the resist composition.

<Resin (A)>

The resin (A) includes a structural unit having an acid-labile group (hereinafter sometimes referred to as "structural unit (a1)"). It is preferable that the resin (A) further includes a structural unit other than the structural unit (a1). Examples of the structural unit other than the structural unit (a1) include a structural unit having no acid-labile group (hereinafter sometimes referred to as "structural unit (s)"), a structural unit other than the structural unit (a1) and the structural unit (s) (e.g. a structural unit having a halogen atom mentioned later (hereinafter sometimes referred to as "structural unit (a4)"), a structural unit having a non-leaving hydrocarbon group mentioned later (hereinafter sometimes referred to as "structural unit (a5)) and other structural units derived from monomers known in the art.

<Structural Unit (a1)>

The structural unit (a1) is derived from a monomer having an acid-labile group (hereinafter sometimes referred to as "monomer (a1)").

The acid-labile group contained in the resin (A) is preferably a group represented by formula (1) (hereinafter also referred to as group (1)) and/or a group represented by formula (2) (hereinafter also referred to as group (2)):

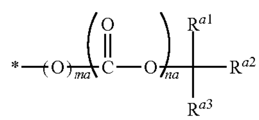

(1)

wherein, in formula (1), $R^{a1}$, $R^{a2}$ and $R^{a3}$ each independently represent an alkyl group having 1 to 8 carbon atoms, an alicyclic hydrocarbon group having 3 to 20 carbon atoms or groups obtained by combining these groups, or $R^{a1}$ and $R^{a2}$ are bonded to each other to form an alicyclic hydrocarbon group having 3 to 20 carbon atoms together with carbon atoms to which $R^{a1}$ and $R^{a2}$ are bonded, ma and na each independently represent 0 or 1, and at least one of ma and na represents 1, and represents a bonding site:

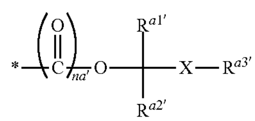

(2)

wherein, in formula (2), $R^{a1'}$ and $R^{a2'}$ each independently represent a hydrogen atom or a hydrocarbon group having 1 to 12 carbon atoms, $R^{a3'}$ represents a hydrocarbon group having 1 to 20 carbon atoms, or $R^{a2'}$ and $R^{a3'}$ are bonded to each other to form a heterocyclic group having 3 to 20 carbon atoms together with carbon atoms and X to which $R^{a2'}$ and $R^{a3'}$ are bonded, and $—CH_2—$ included in the hydrocarbon group and the heterocyclic group may be replaced by —O— or —S—, X represents an oxygen atom or a sulfur atom, na' represents 0 or 1, and represents a bonding site.

Examples of the alkyl group in $R^{a1}$, $R^{a2}$ and $R^{a3}$ include a methyl group, an ethyl group, a propyl group, a butyl group, a pentyl group, a hexyl group, a heptyl group, an octyl group and the like.

The alicyclic hydrocarbon group in $R^{a1}$, $R^{a2}$ and $R^{a3}$ may be either monocyclic or polycyclic. Examples of the monocyclic alicyclic hydrocarbon group include cycloalkyl groups such as a cyclopentyl group, a cyclohexyl group, a cycloheptyl group and a cyclooctyl group. Examples of the polycyclic alicyclic hydrocarbon group include a decahydronaphthyl group, an adamantyl group, a norbornyl group and the following groups (* represents a bonding site). The number of carbon atoms of the alicyclic hydrocarbon group of $R^{a1}$, $R^{a2}$ and $R^{a}$ is preferably 3 to 16.

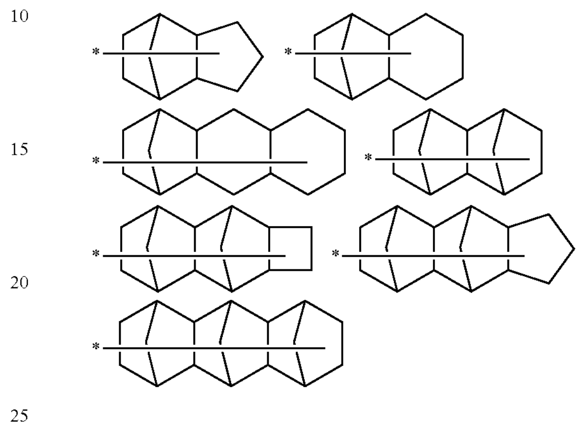

The group obtained by combining an alkyl group with an alicyclic hydrocarbon group includes, for example, a methylcyclohexyl group, a dimethylcyclohexyl group, a methylnorbornyl group, a cyclohexylmethyl group, an adamantylmethyl group, an adamantyldimethyl group, a norbornylethyl group and the like.

Preferably, ma is 0 and na is 1.

When $R^{a1}$ and $R^{a2}$ are bonded to each other to form an alicyclic hydrocarbon group, examples of $—C(R^{a1})(R^{a2})(R^{a3})$ include the following groups. The alicyclic hydrocarbon group preferably has 3 to 12 carbon atoms. * represents a bonding site to —O—.

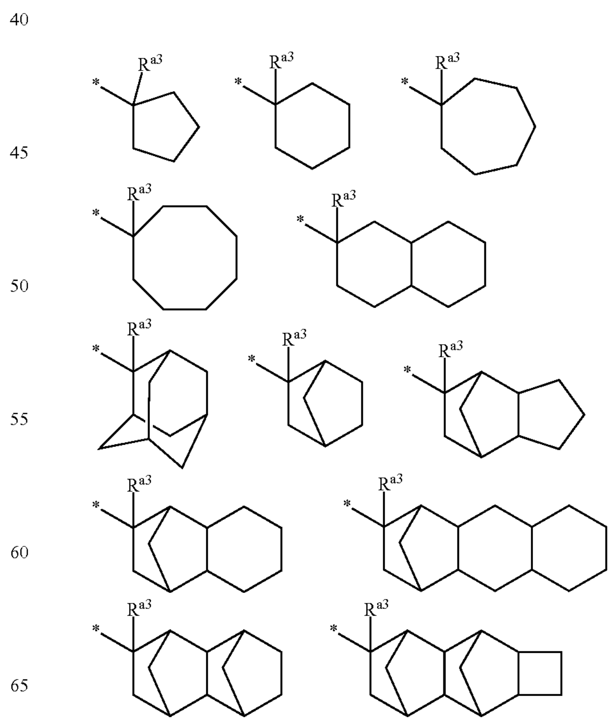

-continued

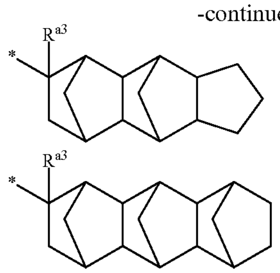

Examples of the hydrocarbon group in $R^{a1'}$, $R^{a2'}$ and $R^{a3'}$ include an alkyl group, an alicyclic hydrocarbon group, an aromatic hydrocarbon group, and groups obtained by combining these groups.

Examples of the alkyl group and the alicyclic hydrocarbon group include those which are the same as mentioned in $R^{a1}$, $R^{a2}$ and $R^{a3}$.

Examples of the aromatic hydrocarbon group include aryl groups such as a phenyl group, a naphthyl group, an anthryl group, a biphenyl group and a phenanthryl group.

Examples of the group combined include a group obtained by combining the above-mentioned alkyl group and alicyclic hydrocarbon group (a cycloalkylalkyl group, etc.), an aralkyl group such as a benzyl group, an aromatic hydrocarbon group having an alkyl group (a p-methylphenyl group, a p-tert-butylphenyl group, a tolyl group, a xylyl group, a cumenyl group, a mesityl group, a 2,6-diethylphenyl group, a 2-methyl-6-ethylphenyl group, etc.), an aromatic hydrocarbon group having an alicyclic hydrocarbon group (a p-cyclohexylphenyl group, a p-adamantylphenyl group, etc.), an aryl-cycloalkyl group (a phenylcyclohexyl group, etc.), and the like.

When $R^{a2'}$ and $R^{a3'}$ are bonded to each other together with carbon atoms and X to which $R^{a2'}$ and $R^{a3'}$ are bonded to form a heterocyclic group, examples of $—C(R^{a1'})(R^{a2'})—X—R^{a3'}$ include the following groups. * represents a bonding site.

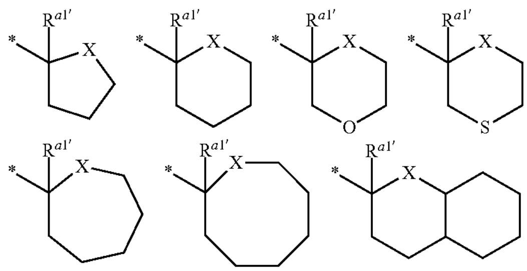

Of $R^{a1'}$ and $R^{a2'}$, at least one is preferably a hydrogen atom.

na' is preferably 0.

Examples of the group (1) include the following groups.

A group wherein, in formula (1), $R^{a1}$, $R^{a2}$ and $R^{a3}$ are alkyl groups, ma=0 and na=1. The group is preferably a tert-butoxycarbonyl group.

A group wherein, in formula (1), $R^{a1}$ and $R^{a2}$ are bonded to each other to form an adamantyl group together with carbon atoms to which $R^{a1}$ and $R^{a2}$ are bonded, $R^{a3}$ is an alkyl group, ma=0 and na=1.

A group wherein, in formula (1), $R^{a1}$ and $R^{a2}$ are each independently an alkyl group, $R^{a3}$ is an adamantyl group, ma=0 and na=1.

Specific examples of the group (1) include the following groups. * represents a bonding site.

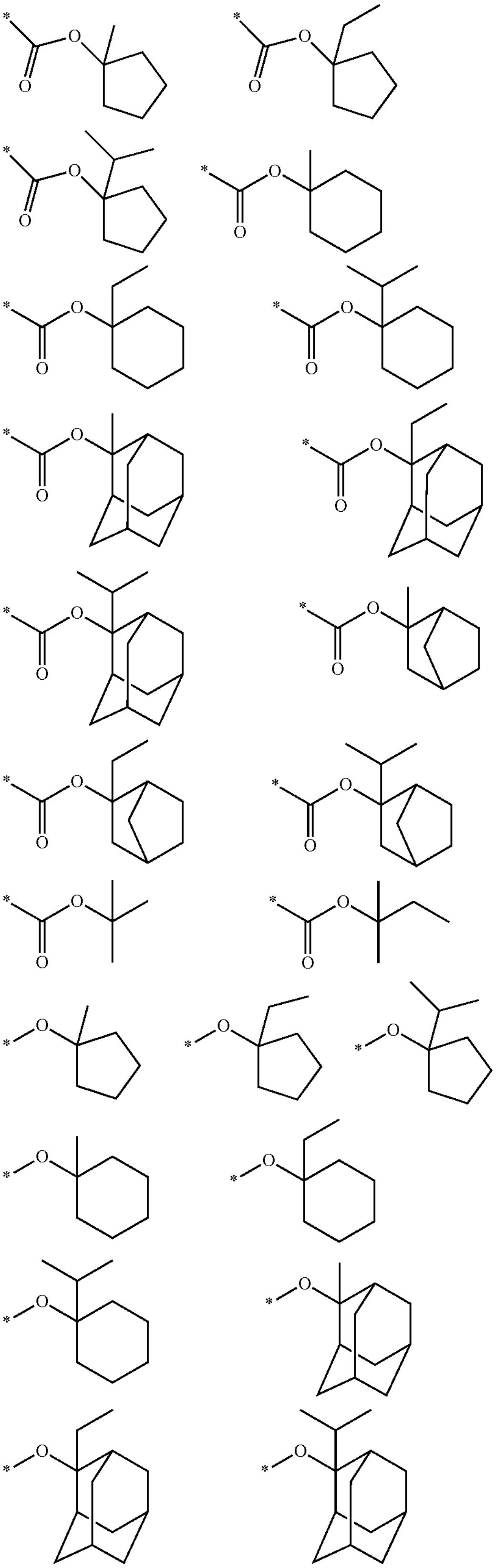

-continued
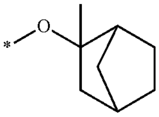
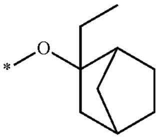
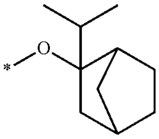
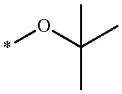
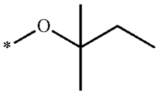
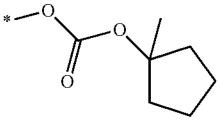
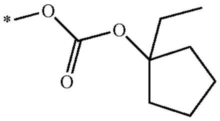
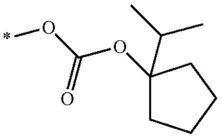
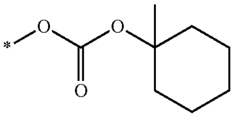
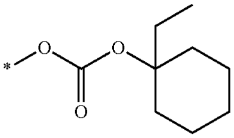
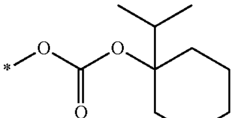
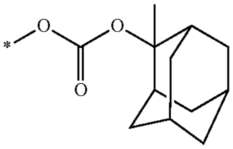
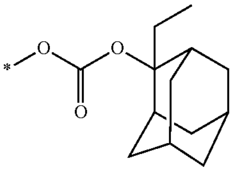
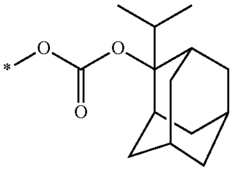
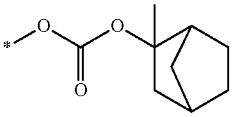
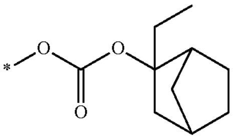
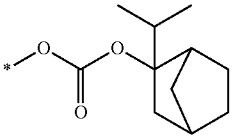
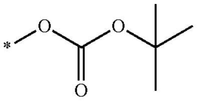
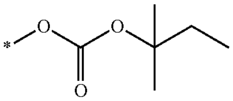
Specific examples of the group (2) include the following groups. * represents a bonding site.
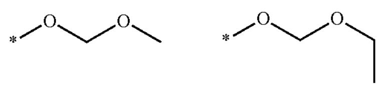
-continued
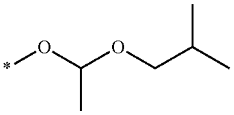
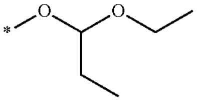
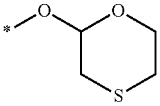
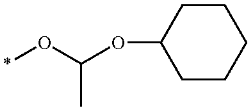
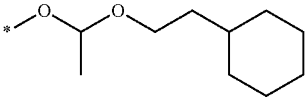
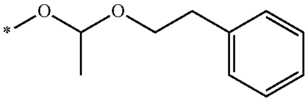
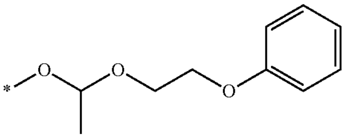
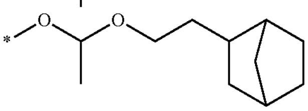
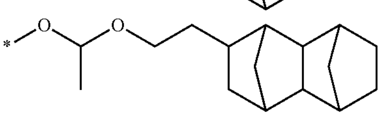
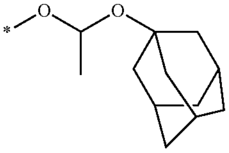
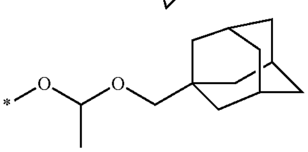
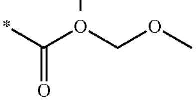
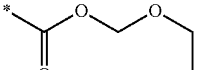
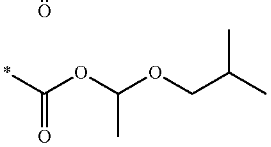
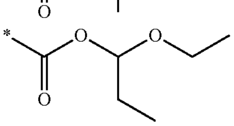
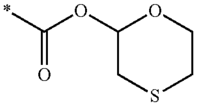
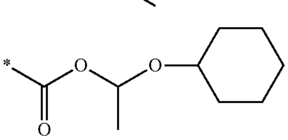
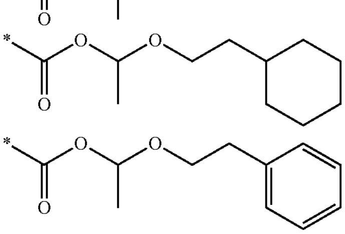

-continued

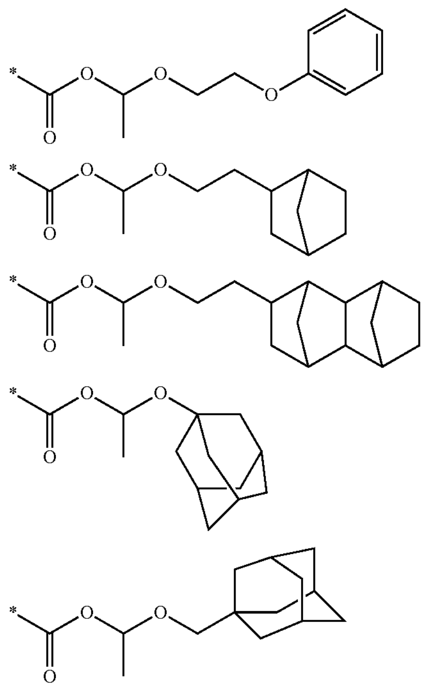

The monomer (a1) is preferably a monomer having an acid-labile group and an ethylenic unsaturated bond, and more preferably a (meth)acrylic monomer having an acid-labile group.

Of the (meth)acrylic monomers having an acid-labile group, those having an alicyclic hydrocarbon group having 5 to 20 carbon atoms are preferably exemplified. When a resin (A) including a structural unit derived from a monomer (a1) having a bulky structure such as an alicyclic hydrocarbon group is used in a resist composition, it is possible to improve the resolution of a resist pattern.

The structural unit derived from a (meth)acrylic monomer having a group (1) is a structural unit represented by formula (a1-0) (hereinafter sometimes referred to as structural unit (a1-0)), a structural unit represented by formula (a1-1) (hereinafter sometimes referred to as structural unit (a1-1)) or a structural unit represented by formula (a1-2) (hereinafter sometimes referred to as structural unit (a1-2)). The structural unit is preferably at least one structural unit selected from the group consisting of a structural unit (a1-1) and a structural unit (a1-2). These structural units may be used alone, or two or more structural units may be used in combination.

(a1-0)

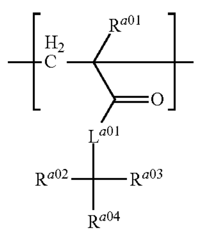

-continued (a1-1)

(a1-2)

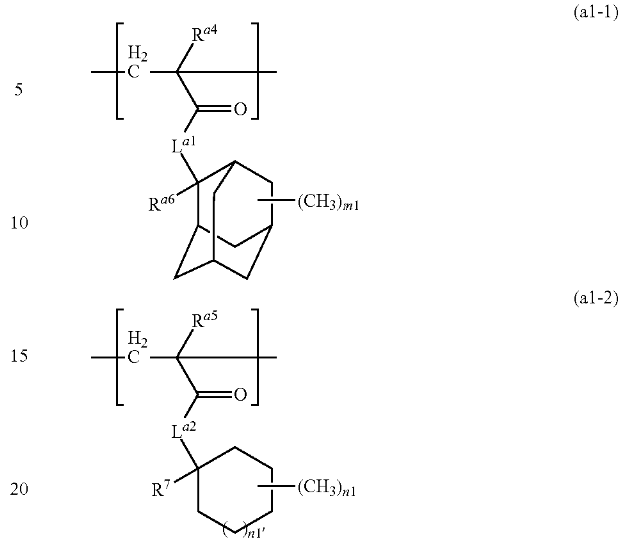

In formula (a1-0), formula (a1-1) and formula (a1-2), $L^{a01}$, $L^{a1}$ and $L^{a2}$ each independently represent —O— or *—O—$(CH_2)_{k1}$—CO—O—, k1 represents an integer of 1 to 7, and * represents a bonding site to —CO—, $R^{a01}$, $R^{a4}$ and $R^{a5}$ each independently represent a hydrogen atom or a methyl group, $R^{a02}$, $R^{a03}$ and $R^{a04}$ each independently represent an alkyl group having 1 to 8 carbon atoms, an alicyclic hydrocarbon group having 3 to 18 carbon atoms or groups obtained by combining these groups, $R^{a6}$ and $R^{a7}$ each independently represent an alkyl group having 1 to 8 carbon atoms, an alicyclic hydrocarbon group having 3 to 18 carbon atoms or groups obtained by combining these groups, m1 represents an integer of 0 to 14, n1 represents an integer of 0 to 10, and n1' represents an integer of 0 to 3.

$R^{a01}$, $R^{a4}$ and $R^{a5}$ are preferably a methyl group.

$L^{a01}$, $L^{a1}$ and $L^{a2}$ are preferably an oxygen atom or *—O—$(CH_2)_{k01}$—CO—O— (in which k01 is preferably an integer of 1 to 4, and more preferably 1), and more preferably an oxygen atom.

Examples of the alkyl group, the alicyclic hydrocarbon group and groups obtained by combining these groups in $R^{a02}$, $R^{a03}$, $R^{a04}$, $R^{a6}$ and $R^{a7}$ include the same groups as mentioned for $R^{a1}$, $R^{a2}$ and $R^{a3}$ of formula (1).

The alkyl group in $R^{a02}$, $R^{a03}$, and $R^{a04}$ is preferably an alkyl group having 1 to 6 carbon atoms, more preferably a methyl group or an ethyl group, and still more preferably a methyl group.

The alkyl group in $R^{a6}$ and $R^{a7}$ is preferably an alkyl group having 1 to 6 carbon atoms, more preferably a methyl group, an ethyl group or an isopropyl group, and still more preferably an ethyl group or an isopropyl group.

The number of carbon atoms of the alicyclic hydrocarbon group of $R^{a02}$, $R^{a03}$, $R^{a04}$, $R^{a6}$ and $R^{a7}$ is preferably 5 to 12, and more preferably 5 to 10.

The total number of carbon atoms of the group obtained by combining the alkyl group with the alicyclic hydrocarbon group is preferably 18 or less.

$R^{a02}$ and $R^{a03}$ are preferably an alkyl group having 1 to 6 carbon atoms, and more preferably a methyl group or an ethyl group.

$R^{a04}$ is preferably an alkyl group having 1 to 6 carbon atoms or an alicyclic hydrocarbon group having 5 to 12 carbon atoms, and more preferably a methyl group, an ethyl group, a cyclohexyl group or an adamantyl group.

Preferably, $R^{a6}$ and $R^{a7}$ are each independently an alkyl group having 1 to 6 carbon atoms, more preferably a methyl group, an ethyl group or an isopropyl group, and still more preferably an ethyl group or an isopropyl group.

m1 is preferably an integer of 0 to 3, and more preferably 0 or 1.

n1 is preferably an integer of 0 to 3, and more preferably 0 or 1.

n1' is preferably 0 or 1.

The structural unit (a1-0) includes, for example, a structural unit represented by any one of formula (a1-0-1) to formula (a1-0-12) and a structural unit in which a methyl group corresponding to $R^{a01}$ in the structural unit (a1-0) is substituted with a hydrogen atom and is preferably a structural unit represented by any one of formula (a1-0-1) to formula (a1-0-10).

(a1-0-1)

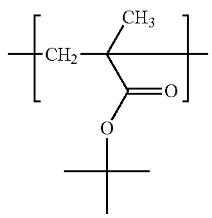

(a1-0-2)

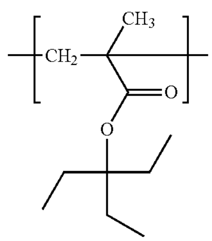

(a1-0-3)

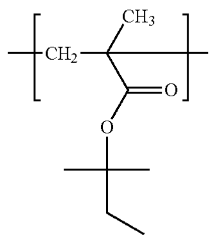

(a1-0-4)

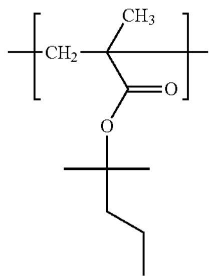

-continued (a1-0-5)

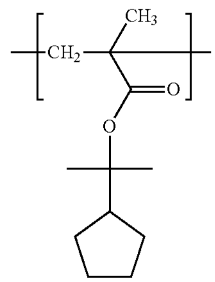

(a1-0-6)

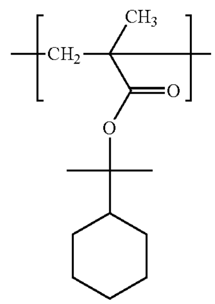

(a1-0-7)

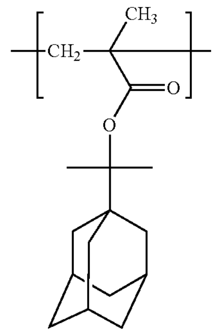

(a1-0-8)

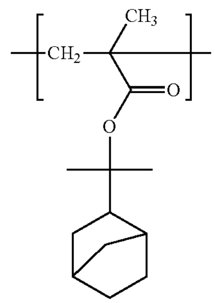

(a1-0-9)

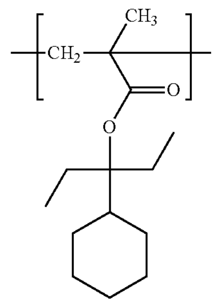

-continued (a1-0-10)

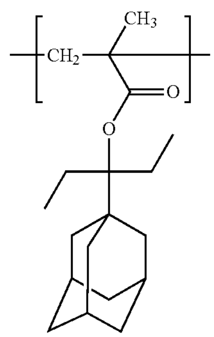

(a1-0-11)

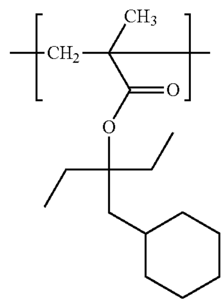

(a1-0-12)

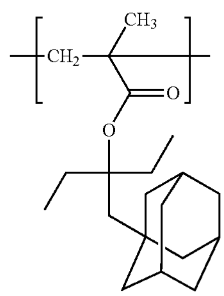

The structural unit (a1-1) includes, for example, structural units derived from the monomers mentioned in JP 2010-204646 A. Of these structural units, a structural unit represented by any one of formula (a1-1-1) to formula (a1-1-4) and a structural unit in which a methyl group corresponding to $R^{a4}$ in the structural unit (a1-1) is substituted with a hydrogen atom are preferable, and a structural unit represented by any one of formula (a1-1-1) to formula (a1-1-4) is more preferable.

(a1-1-1)

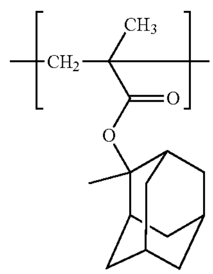

-continued (a1-1-2)

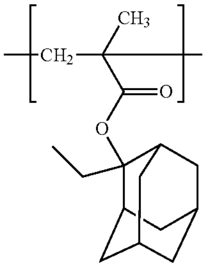

(a1-1-3)

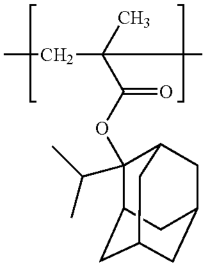

(a1-1-4)

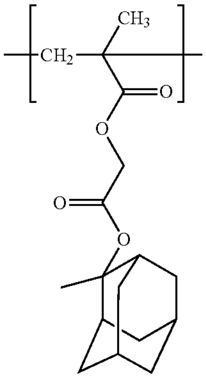

Examples of the structural unit (a1-2) include a structural unit represented by any one of formula (a1-2-1) to formula (a1-2-6) and a structural unit in which a methyl group corresponding to $R^{a5}$ in the structural unit (a1-2) is substituted with a hydrogen atom, and a structural unit represented by any one of formula (a1-2-2), formula (a1-2-5) and formula (a1-2-6) is preferable.

(a1-2-1)

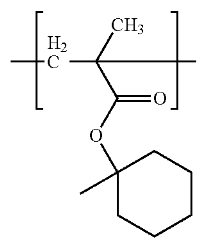

-continued (a1-2-2)

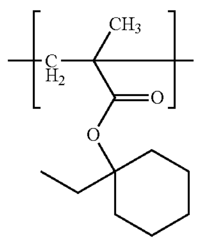

(a1-2-3)

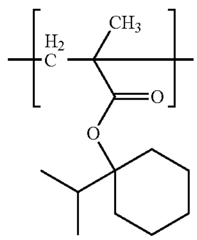

(a1-2-4)

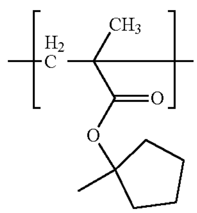

(a1-2-5)

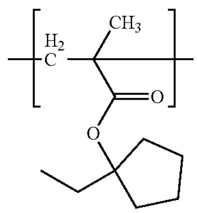

(a1-2-6)

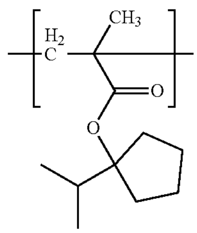

When the resin (A) includes a structural unit (a1-0), the content thereof is usually 5 to 60 mol %, preferably 5 to 50 mol %, and more preferably 10 to 40 mol %, based on all structural units of the resin (A).

When the resin (A) includes a structural unit (a1-1) and/or a structural unit (a1-2), the total content thereof is usually 10 to 95 mol %, preferably 15 to 90 mol %, more preferably 20 to 85 mol %, still more preferably 25 to 75 mol %, and yet more preferably 30 to 70 mol %, based on all structural units of the resin (A).

In the structural unit (a1), examples of the structural unit having a group (2) include a structural unit represented by formula (a1-4) (hereinafter sometimes referred to as "structural unit (a1-4)"):

(a1-4)

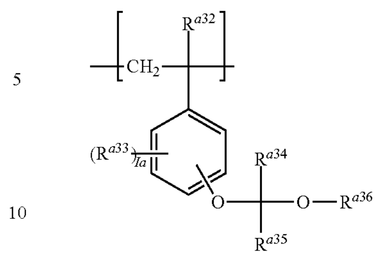

wherein, in formula (a1-4), $R^{a32}$ represents a hydrogen atom, a halogen atom or an alkyl group having 1 to 6 carbon atoms which may have a halogen atom, $R^{a33}$ represents a halogen atom, a hydroxy group, an alkyl group having 1 to 6 carbon atoms, an alkoxy group having 1 to 6 carbon atoms, an alkylcarbonyl group having 2 to 4 carbon atoms, an alkylcarbonyloxy group having 2 to 4 carbon atoms, an acryloyloxy group or a methacryloyloxy group, la represents an integer of 0 to 4, and when la is 2 or more, a plurality of $R^{a33}$ may be the same or different from each other, and $R^{a34}$ and $R^{a35}$ each independently represent a hydrogen atom or a hydrocarbon group having 1 to 12 carbon atoms, $R^{a36}$ represents a hydrocarbon group having 1 to 20 carbon atoms, or $R^{a35}$ and $R^{a36}$ are bonded to each other to form a divalent hydrocarbon group having 2 to 20 carbon atoms together with —C—O— to which $R^{a35}$ and $R^{a36}$ are bonded, and —$CH_2$— included in the hydrocarbon group and the divalent hydrocarbon group may be replaced by —O— or —S—.

Examples of the alkyl group in $R^{a32}$ and $R^{a33}$ include a methyl group, an ethyl group, a propyl group, an isopropyl group, a butyl group, a pentyl group and a hexyl group. The alkyl group is preferably an alkyl group having 1 to 4 carbon atoms, more preferably a methyl group or an ethyl group, and still more preferably a methyl group.

Examples of the halogen atom in $R^{a32}$ and $R^{a33}$ include a fluorine atom, a chlorine atom and a bromine atom.

Examples of the alkyl group having 1 to 6 carbon atoms which may have a halogen atom include a trifluoromethyl group, a difluoromethyl group, a methyl group, a perfluoroethyl group, a 2,2,2-trifluoroethyl group, a 1,1,2,2-tetrafluoroethyl group, an ethyl group, a perfluoropropyl group, a 2,2,3,3,3-pentafluoropropyl group, a propyl group, a perfluorobutyl group, a 1,1,2,2,3,3,4,4-octafluorobutyl group, a butyl group, a perfluoropentyl group, a 2,2,3,3,4,4,5,5,5-nonafluoropentyl group, a pentyl group, a hexyl group, a perfluorohexyl group and the like.

Examples of the alkoxy group include a methoxy group, an ethoxy group, a propoxy group, a butoxy group, a pentyloxy group and a hexyloxy group. Of these groups, an alkoxy group having 1 to 4 carbon atoms is preferable, a methoxy group or an ethoxy group are more preferable, and a methoxy group is still more preferable.

Examples of the alkylcarbonyl group include an acetyl group, a propionyl group and a butyryl group.

Examples of the alkylcarbonyloxy group include an acetyloxy group, a propionyloxy group, a butyryloxy group and the like.

Examples of the hydrocarbon group in $R^{a34}$, $R^{a35}$ and $R^{a36}$ include an alkyl group, an alicyclic hydrocarbon group, an aromatic hydrocarbon group, and groups obtained by combining these groups.

Examples of the alkyl group include a methyl group, an ethyl group, a propyl group, a butyl group, a pentyl group, a hexyl group, a heptyl group, an octyl group and the like.

The alicyclic hydrocarbon group may be either monocyclic or polycyclic, and examples of the monocyclic alicyclic hydrocarbon group include cycloalkyl groups such as a cyclopentyl group, a cyclohexyl group, a cycloheptyl group and a cyclooctyl group. Examples of the polycyclic alicyclic hydrocarbon group include a decahydronaphthyl group, an adamantyl group, a norbornyl group and the following groups (* represents a bonding site).

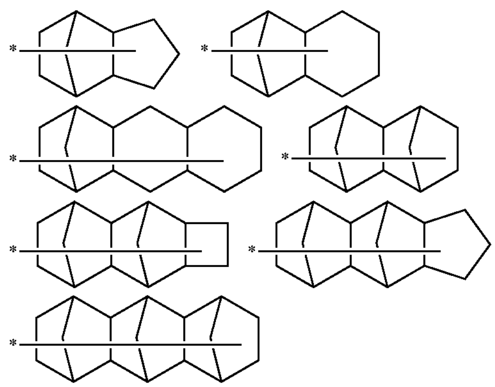

Examples of the aromatic hydrocarbon group include aryl groups such as a phenyl group, a naphthyl group, an anthryl group, a biphenyl group and a phenanthryl group.

Examples of the group combined include a group obtained by combining the above-mentioned alkyl group and alicyclic hydrocarbon group (e.g., a cycloalkylalkyl group), an aralkyl group such as a benzyl group, an aromatic hydrocarbon group having an alkyl group (a p-methylphenyl group, a p-tert-butylphenyl group, a tolyl group, a xylyl group, a cumenyl group, a mesityl group, a 2,6-diethylphenyl group, a 2-methyl-6-ethylphenyl group, etc.), an aromatic hydrocarbon group having an alicyclic hydrocarbon group (a p-cyclohexylphenyl group, a p-adamantylphenyl group, etc.), an aryl-cycloalkyl group such as a phenylcyclohexyl group and the like. Particularly, examples of $R^{a36}$ include an alkyl group having 1 to 18 carbon atoms, an alicyclic hydrocarbon group having 3 to 18 carbon atoms, an aromatic hydrocarbon group having 6 to 18 carbon atoms or groups obtained by combining these groups.

In formula (a1-4), $R^{a32}$ is preferably a hydrogen atom, $R^{a33}$ is preferably an alkoxy group having 1 to 4 carbon atoms, more preferably a methoxy group and an ethoxy group, and still more preferably a methoxy group, la is preferably 0 or 1, and more preferably 0, $R^{a34}$ is preferably a hydrogen atom, and $R^{a35}$ is preferably an alkyl group having 1 to 12 carbon atoms or an alicyclic hydrocarbon group, and more preferably a methyl group or an ethyl group.

The hydrocarbon group of $R^{a36}$ is preferably an alkyl group having 1 to 18 carbon atoms, an alicyclic hydrocarbon group having 3 to 18 carbon atoms, an aromatic hydrocarbon group having 6 to 18 carbon atoms or groups formed by combining these groups, and more preferably an alkyl group having 1 to 18 carbon atoms, an alicyclic aliphatic hydrocarbon group having 3 to 18 carbon atoms or an aralkyl group having 7 to 18 carbon atoms. The alkyl group and the alicyclic hydrocarbon group in $R^{a36}$ are preferably unsubstituted. The aromatic hydrocarbon group in $R^{a36}$ is preferably an aromatic ring having an aryloxy group having 6 to 10 carbon atoms.

$—OC(R^{a34})(R^{a35})—O—R^{a36}$ in the structural unit (a1-4) is eliminated by contacting with an acid (e.g., p-toluenesulfonic acid) to form a hydroxy group.

The structural unit (a1-4) includes, for example, structural units derived from the monomers mentioned in JP 2010-204646 A. The structural unit preferably includes structural units represented by formula (a1-4-1) to formula (a1-4-12) and a structural unit in which a hydrogen atom corresponding to $R^{a32}$ in the structural unit (a1-4) is substituted with a methyl group, and more preferably structural units represented by formula (a1-4-1) to formula (a1-4-5) and formula (a1-4-10).

(a1-4-1)

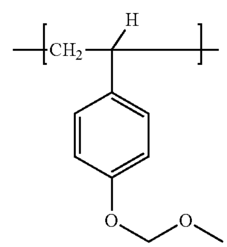

(a1-4-2)

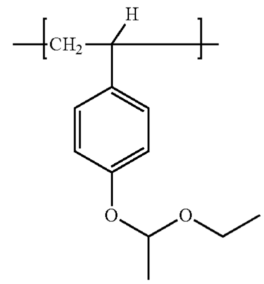

(a1-4-3)

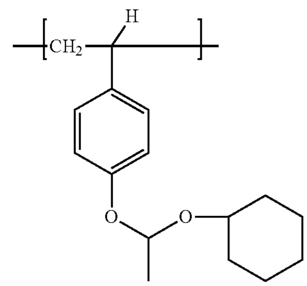

(a1-4-4)

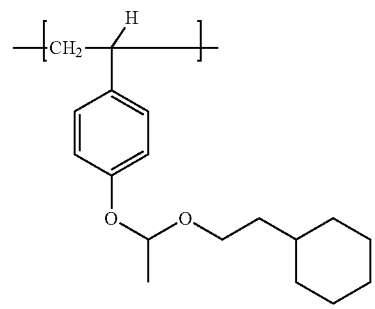

-continued (a1-4-5)

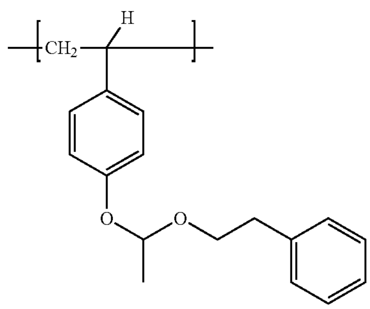

(a1-4-6)

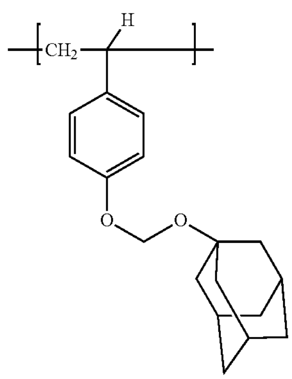

(a1-4-7)

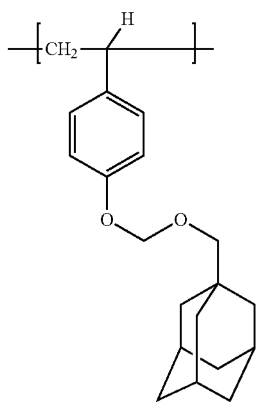

(a1-4-8)

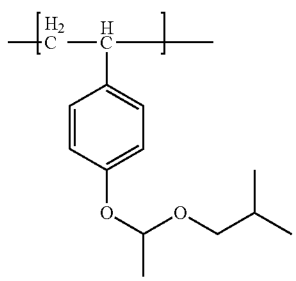

(a1-4-9)

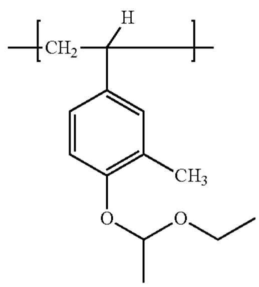

-continued (a1-4-10)

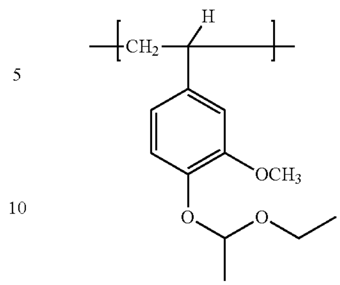

(a1-4-11)

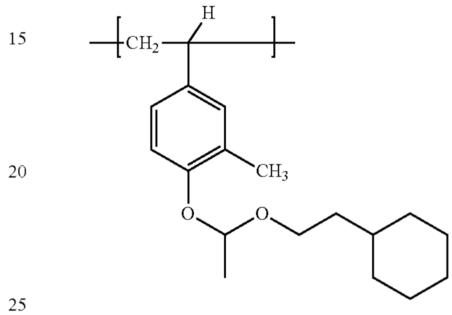

(a1-4-12)

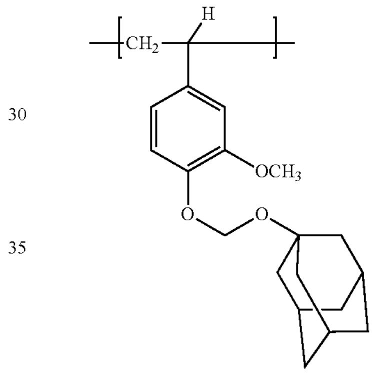

When the resin (A) includes the structural unit (a1-4), the content is preferably 10 to 95 mol %, more preferably 15 to 90 mol %, still more preferably 20 to 85 mol %, yet more preferably 20 to 70 mol %, and particularly preferably 20 to 60 mol %, based on the total of all structural units of the resin (A).

The structural unit derived from a (meth)acrylic monomer having a group (2) also includes a structural unit represented by formula (a1-5) (hereinafter sometimes referred to as "structural unit (a1-5)").

(a1-5)

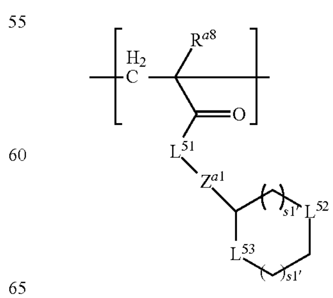

In formula (a1-5), $R^{a8}$ represents an alkyl group having 1 to 6 carbon atoms which may have a halogen atom, a hydrogen atom or a halogen atom, $Z^{a1}$ represents a single bond or $*-(CH_2)_{h3}-CO-L^{54}-$, h3 represents an integer of 1 to 4, and * represents a bonding site to $L^{51}$, $L^{51}$, $L^{52}$, $L^{53}$ and $L^{54}$ each independently represent —O— or —S—, s1 represents an integer of 1 to 3, and s1' represents an integer of 0 to 3.

The halogen atom includes a fluorine atom and a chlorine atom and is preferably a fluorine atom. Examples of the alkyl group having 1 to 6 carbon atoms which may have a halogen atom include a methyl group, an ethyl group, a propyl group, a butyl group, a pentyl group, a hexyl group, a heptyl group, an octyl group, a fluoromethyl group and a trifluoromethyl group.

In formula (a1-5), $R^{a8}$ is preferably a hydrogen atom, a methyl group or a trifluoromethyl group, $L^{51}$ is preferably an oxygen atom, one of $L^{52}$ and $L^{53}$ is preferably —O— and the other one is preferably —S—, s1 is preferably 1, s1' is preferably an integer of 0 to 2, and $Z^{a1}$ is preferably a single bond or $*-CH_2-CO-O-$.

The structural unit (a1-5) includes, for example, structural units derived from the monomers mentioned in JP 2010-61117 A. Of these structural units, structural units represented by formula (a1-5-1) to formula (a1-5-4) are preferable, and structural units represented by formula (a1-5-1) or formula (a1-5-2) are more preferable.

(a1-5-1)

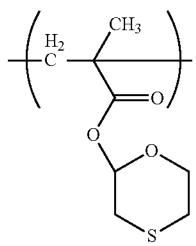

(a1-5-2)

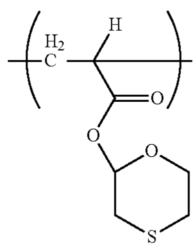

(a1-5-3)

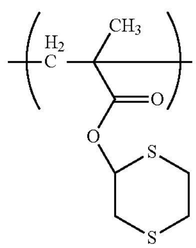

-continued (a1-5-4)

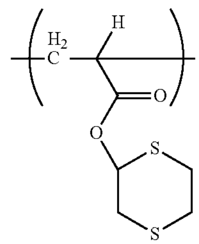

When the resin (A) includes the structural unit (a1-5), the content is preferably 1 to 50 mol %, more preferably 3 to 45 mol %, still more preferably 5 to 40 mol %, and yet more preferably 5 to 30 mol %, based on all structural units of the resin (A).

The structural unit (a1) also includes the following structural units.

(a1-3-1)

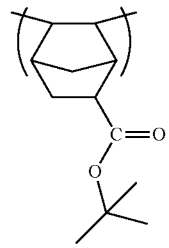

(a1-3-2)

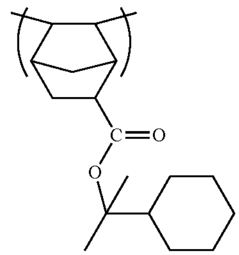

(a1-3-3)

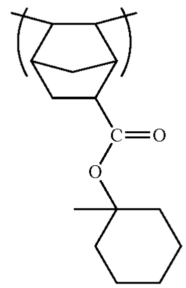

(a1-3-4)

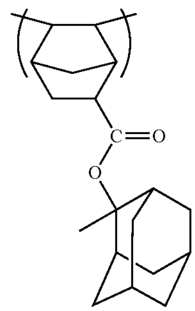

-continued (a1-3-5)

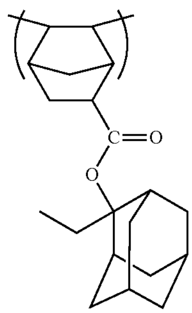

(a1-3-6)

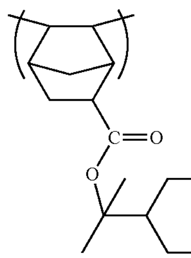

(a1-3-7)

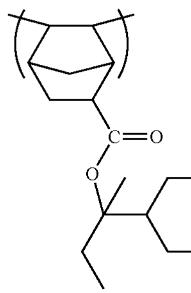

When the resin (A) includes the above-mentioned structural units such as (a1-3-1) to (a1-3-7), the content is preferably 10 to 95 mol %, more preferably 15 to 90 mol %, still more preferably 20 to 85 mol %, yet more preferably 20 to 70 mol %, and particularly preferably 20 to 60 mol %, based on all structural units of the resin (A).

<Structural Unit (s)>

The structural unit (s) is derived from a monomer having no acid-labile group (hereinafter sometimes referred to as "monomer (s)"). It is possible to use, as the monomer from which the structural unit (s) is derived, a monomer having no acid-labile group known in the resist field.

The structural unit (s) preferably has a hydroxy group or a lactone ring. When a resin including a structural unit having a hydroxy group and having no acid-labile group (hereinafter sometimes referred to as "structural unit (a2)") and/or a structural unit having a lactone ring and having no acid-labile group (hereinafter sometimes referred to as "structural unit (a3)") is used in the resist composition of the present invention, it is possible to improve the resolution of a resist pattern and the adhesion to a substrate.

<Structural Unit (a2)>

The hydroxy group possessed by the structural unit (a2) may be either an alcoholic hydroxy group or a phenolic hydroxy group.

When a resist pattern is produced from the resist composition of the present invention, in the case of using, as an exposure source, high energy rays such as KrF excimer laser (248 nm), electron beam or extreme ultraviolet light (EUV), a structural unit (a2) having a phenolic hydroxy group is preferably used as the structural unit (a2), and a structural unit (a2-A) mentioned below is more preferably used. When using ArF excimer laser (193 nm) or the like, a structural unit (a2) having an alcoholic hydroxy group is preferably used as the structural unit (a2), and the below-mentioned structural unit (a2-1) is more preferably used. The structural unit (a2) may be included alone, or two or more structural units may be included.

In the structural unit (a2), examples of the structural unit having a phenolic hydroxy group include a structural unit represented by formula (a2-A) (hereinafter sometimes referred to as "structural unit (a2-A)")

(a2-A)

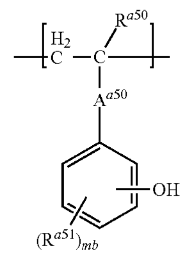

wherein, in formula (a2-A), $R^{a50}$ represents a hydrogen atom, a halogen atom or an alkyl group having 1 to 6 carbon atoms which may have a halogen atom, $R^{a51}$ represents a halogen atom, a hydroxy group, an alkyl group having 1 to 6 carbon atoms, an alkoxy group having 1 to 6 carbon atoms, an alkylcarbonyl group having 2 to 4 carbon atoms, an alkylcarbonyloxy group having 2 to 4 carbon atoms, an acryloyloxy group or a methacryloyloxy group, $A^{a50}$ represents a single bond or $*—X^{a51}-(A^{a52}-X^{a32})_{nb}—$, and * represents a bonding site to carbon atoms to which $—R^{a50}$ is bonded, $A^{a52}$ represents an alkanediyl group having 1 to 6 carbon atoms, $X^{a51}$ and $X^{a52}$ each independently represent —O—, —CO—O— or —O—CO—, nb represents 0 or 1, and mb represents an integer of 0 to 4, and when mb is an integer of 2 or more, a plurality of $R^{a51}$ may be the same or different from each other.

Examples of the halogen atom in $R^{a50}$ include a fluorine atom, a chlorine atom and a bromine atom.

Examples of the alkyl group having 1 to 6 carbon atoms which may have a halogen atom in $R^{a50}$ include a trifluoromethyl group, a difluoromethyl group, a methyl group, a perfluoroethyl group, a 2,2,2-trifluoroethyl group, a 1,1,2,2-tetrafluoroethyl group, an ethyl group, a perfluoropropyl group, a 2,2,3,3,3-pentafluoropropyl group, a propyl group, a perfluorobutyl group, a 1,1,2,2,3,3,4,4-octafluorobutyl group, a butyl group, a perfluoropentyl group, a 2,2,3,3,4,4,5,5,5-nonafluoropentyl group, a pentyl group, a hexyl group and a perfluorohexyl group.

$R^{a50}$ is preferably a hydrogen atom or an alkyl group having 1 to 4 carbon atoms, more preferably a hydrogen atom, a methyl group or an ethyl group, and still more preferably a hydrogen atom or a methyl group.

Examples of the alkyl group in $R^{a51}$ include a methyl group, an ethyl group, a propyl group, an isopropyl group, a butyl group, a sec-butyl group, a tert-butyl group, a pentyl group and a hexyl group.

Examples of the alkoxy group in $R^{a51}$ include a methoxy group, an ethoxy group, a propoxy group, an isopropoxy group, a butoxy group, a sec-butoxy group and a tert-butoxy group. An alkoxy group having 1 to 4 carbon atoms is preferable, a methoxy group or an ethoxy group is more preferable, and a methoxy group is still more preferable.

Examples of the alkylcarbonyl group in $R^{a51}$ include an acetyl group, a propionyl group and a butyryl group.

Examples of the alkylcarbonyloxy group in $R^{a51}$ include an acetyloxy group, a propionyloxy group and a butyryloxy group.

$R^{a51}$ is preferably a methyl group.

Examples of $*—X^{a51}-(A^{a52}-X^{a52})_{nb}—$ include *—O—, *—CO—O—, *—O—CO—, $*—CO—O-A^{a52}-CO—O—$, $*—O—CO-A^{a52}-O—$, $*—O-A^{a52}-CO—O—$, $*—CO—O-A^{a52}-O—CO—$ and $*—O—CO-A^{a52}-O—CO—$. Of these, *—CO—O—, $*—CO—O-A^{a52}-CO—O—$ or $*—O-A^{a52}-CO—O—$ is preferable.

Examples of the alkanediyl group include a methylene group, an ethylene group, a propane-1,3-diyl group, a propane-1,2-diyl group, a butane-1,4-diyl group, a pentane-1,5-diyl group, a hexane-1,6-diyl group, a butane-1,3-diyl group, a 2-methylpropane-1,3-diyl group, a 2-methylpropane-1,2-diyl group, a pentane-1,4-diyl group and a 2-methylbutane-1,4-diyl group.

$A^{a52}$ is preferably a methylene group or an ethylene group.

$A^{a50}$ is preferably a single bond, *—CO—O— or $*—CO—O-A^{a52}-CO—O—$, more preferably a single bond, *—CO—O— or $*—CO—O—CH_2—CO—O—$, and still more preferably a single bond or *—CO—O—.

mb is preferably 0, 1 or 2, more preferably 0 or 1, and particularly preferably 0.

The hydroxy group is preferably bonded to the ortho-position or the para-position of a benzene ring, and more preferably the para-position.

Examples of the structural unit (a2-A) include structural units derived from the monomers mentioned in JP 2010-204634 A and JP 2012-12577 A.

Examples of the structural unit (a2-A) include structural units represented by formula (a2-2-1) to formula (a2-2-6), and a structural unit in which a methyl group corresponding to $R^{a50}$ in the structural unit (a2-A) is substituted with a hydrogen atom in structural units represented by formula (a2-2-1) to formula (a2-2-6). The structural unit (a2-A) is preferably a structural unit represented by formula (a2-2-1), a structural unit represented formula (a2-2-3), a structural unit represented by formula (a2-2-6), and a structural unit in which a methyl group corresponding to $R^{a50}$ in the structural unit (a2-A) is substituted with a hydrogen atom in the structural unit represented by formula (a2-2-1), the structural unit represented by formula (a2-2-3) or the structural unit represented by formula (a2-2-6).

(a2-2-1)

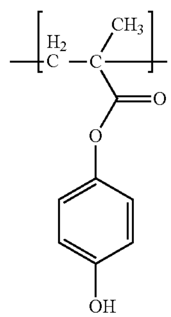

-continued (a2-2-2)

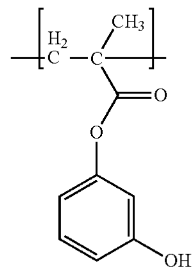

(a2-2-3)

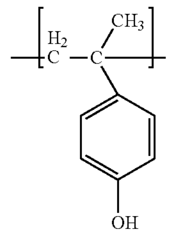

(a2-2-4)

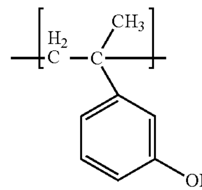

(a2-2-5)

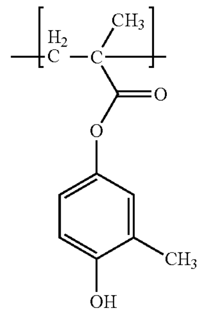

(a2-2-6)

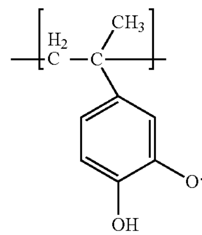

When the structural unit (a2-A) is included in the resin (A), the content of the structural unit (a2-A) is preferably 5 to 80 mol %, more preferably 10 to 70 mol %, still more preferably 15 to 65 mol %, and yet more preferably 20 to 65 mol %, based on all structural units.

The structural unit (a2-A) can be included in a resin (A) by treating a resin including a structural unit (a1-4) with an acid such as p-toluenesulfonic acid. The structural unit (a2-A) can also be included in the resin (A) by polymerizing with acetoxystyrene and treating with an alkali such as tetramethylammonium hydroxide.

Examples of the structural unit having an alcoholic hydroxy group in the structural unit (a2) include a structural unit represented by formula (a2-1) (hereinafter sometimes referred to as "structural unit (a2-1)").

(a2-1)

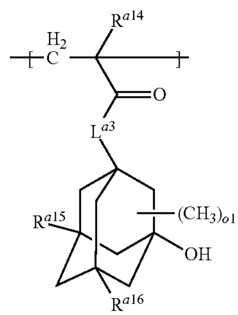

In formula (a2-1), $L^{a3}$ represents —O— or *—O—$(CH_2)_{k2}$—CO—O—, k2 represents an integer of 1 to 7, and * represents a bonding site to —CO—, $R^{a14}$ represents a hydrogen atom or a methyl group, $R^{a15}$ and $R^{a16}$ each independently represent a hydrogen atom, a methyl group or a hydroxy group, and o1 represents an integer of 0 to 10.

In formula (a2-1), $L^{a3}$ is preferably —O— or —O—$(CH_2)_{f1}$—CO—O— (f1 represents an integer of 1 to 4), and more preferably —O—, $R^{a14}$ is preferably a methyl group, $R^{a15}$ is preferably a hydrogen atom, $R^{a16}$ is preferably a hydrogen atom or a hydroxy group, and o1 is preferably an integer of 0 to 3, and more preferably 0 or 1.

The structural unit (a2-1) includes, for example, structural units derived from the monomers mentioned in JP 2010-204646 A. A structural unit represented by any one of formula (a2-1-1) to formula (a2-1-6) is preferable, a structural unit represented by any one of formula (a2-1-1) to formula (a2-1-4) is more preferable, and a structural unit represented by formula (a2-1-1) or formula (a2-1-3) is still more preferable.

(a2-1-1)

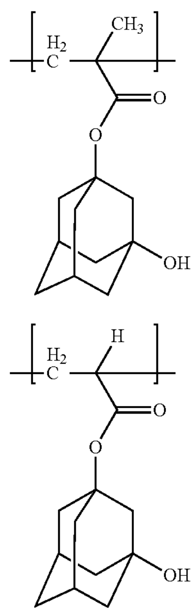

(a2-1-2)

-continued (a2-1-3)

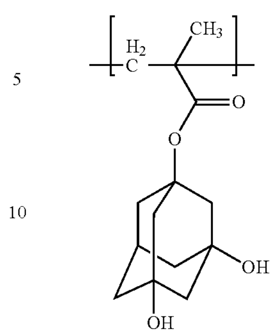

(a2-1-4)

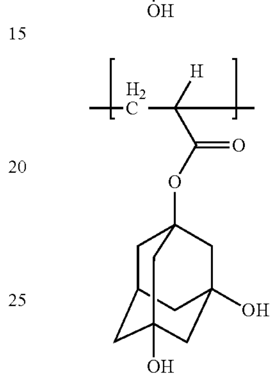

(a2-1-5)

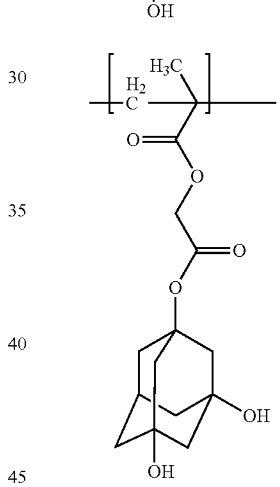

(a2-1-6)

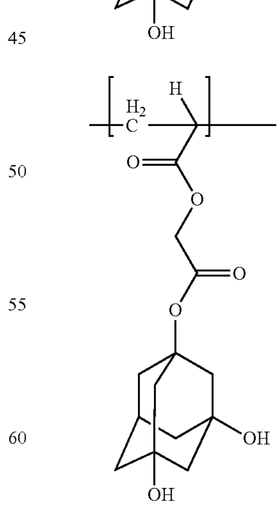

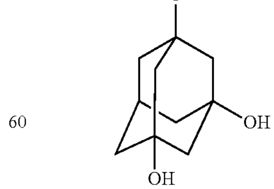

When the resin (A) includes the structural unit (a2-1), the content is usually 1 to 45 mol %, preferably 1 to 40 mol %, more preferably 1 to 35 mol %, still more preferably 1 to 20 mol %, and yet more preferably 1 to 10 mol %, based on all structural units of the resin (A).

<Structural Unit (a3)>

The lactone ring possessed by the structural unit (a3) may be a monocyclic ring such as a β-propiolactone ring, a γ-butyrolactone ring or a δ-valerolactone ring, or a condensed ring of a monocyclic lactone ring and the other ring. Preferably, a γ-butyrolactone ring, an adamantanelactone ring or a bridged ring including a γ-butyrolactone ring structure (e.g. a structural unit represented by the following formula (a3-2)) is exemplified.

The structural unit (a3) is preferably a structural unit represented by formula (a3-1), formula (a3-2), formula (a3-3) or formula (a3-4). These structural units may be included alone, or two or more structural units may be included:

(a3-1)

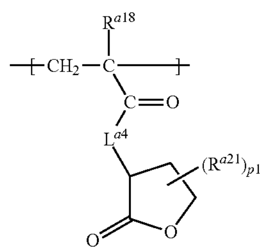

(a3-2)

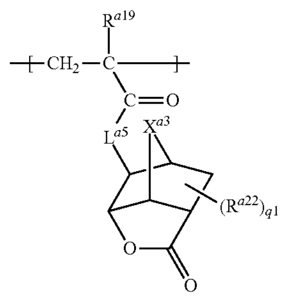

(a3-3)

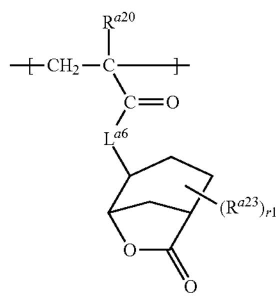

(a3-4)

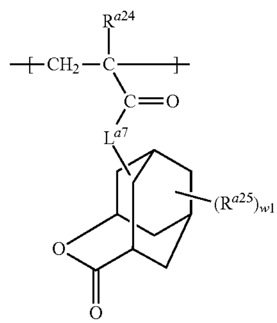

wherein, in formula (a3-1), formula (a3-2), formula (a3-3) and formula (a3-4), $L^{a4}$, $L^{a5}$ and $L^{a6}$ each independently represent —O— or a group represented by *—O—$(CH_2)_{k3}$—CO—O— (k3 represents an integer of 1 to 7), $L^{a7}$ represents —O—, *—O-$L^{a8}$-O—, *—O-$L^{a8}$-CO—O—, *—O-$L^{a8}$-CO—O-$L^{a9}$-CO—O— or *—O-$L^{a8}$-O—CO-$L^{a9}$-O—, $L^{a8}$ and $L^{a9}$ each independently represent an alkanediyl group having 1 to 6 carbon atoms, represents a bonding site to a carbonyl group, $R^{a18}$, $R^{a19}$ and $R^{a20}$ each independently represent a hydrogen atom or a methyl group, $R^{a24}$ represents an alkyl group having 1 to 6 carbon atoms which may have a halogen atom, a hydrogen atom or a halogen atom, $X^{a3}$ represents —$CH_2$— or an oxygen atom, $R^{a21}$ represents an aliphatic hydrocarbon group having 1 to 4 carbon atoms, $R^{a22}$, $R^{a23}$ and $R^{a25}$ each independently represent a carboxy group, a cyano group or an aliphatic hydrocarbon group having 1 to 4 carbon atoms, p1 represents an integer of 0 to 5, q1 represents an integer of 0 to 3, r1 represents an integer of 0 to 3, w1 represents an integer of 0 to 8, and when p1, q1, r1 and/or w1 is/are 2 or more, a plurality of $R^{a21}$, $R^{a22}$, $R^{a23}$ and/or $R^{a25}$ may be the same or different from each other.

Examples of the aliphatic hydrocarbon group in $R^{a21}$, $R^{a22}$, $R^{a23}$ and $R^{a25}$ include alkyl groups such as a methyl group, an ethyl group, a propyl group, an isopropyl group, a butyl group, a sec-butyl group and a tert-butyl group.

Examples of the halogen atom in $R^{a24}$ include a fluorine atom, a chlorine atom, a bromine atom and an iodine atom.

Examples of the alkyl group in $R^{a24}$ include a methyl group, an ethyl group, a propyl group, an isopropyl group, a butyl group, a sec-butyl group, a tert-butyl group, a pentyl group and a hexyl group, and the alkyl group is preferably an alkyl group having 1 to 4 carbon atoms, and more preferably a methyl group or an ethyl group.

Examples of the alkyl group having a halogen atom in $R^{a24}$ include a trifluoromethyl group, a perfluoroethyl group, a perfluoropropyl group, a perfluoroisopropyl group, a perfluorobutyl group, a perfluorosec-butyl group, a perfluoro-tert-butyl group, a perfluoropentyl group, a perfluorohexyl group, a trichloromethyl group, a tribromomethyl group, a triiodomethyl group and the like.

Examples of the alkanediyl group in $L^{a8}$ and $L^{a9}$ include a methylene group, an ethylene group, a propane-1,3-diyl group, a propane-1,2-diyl group, a butane-1,4-diyl group, a pentane-1,5-diyl group, a hexane-1,6-diyl group, a butane-1,3-diyl group, a 2-methylpropane-1,3-diyl group, a 2-methylpropane-1,2-diyl group, a pentane-1,4-diyl group and a 2-methylbutane-1,4-diyl group.

In formula (a3-1) to formula (a3-3), $L^{a4}$, $L^{a5}$ and $L^{a6}$ are each independently preferably —O— or a group in which k3 is an integer of 1 to 4 in *—O—$(CH_2)_{k3}$—CO—O—, more preferably —O— and *—O—$CH_2$—CO—O—, and still more preferably an oxygen atom, $R^{a18}$, $R^{a19}$, $R^{a20}$ and $R^{a21}$ are each independently preferably a methyl group, preferably, $R^{a22}$ and $R^{a23}$ are each independently a carboxy group, a cyano group or a methyl group, and preferably, p1, q1 and r1 are each independently an integer of 0 to 2, and more preferably 0 or 1.

In formula (a3-4), $R^{a24}$ is preferably a hydrogen atom or an alkyl group having 1 to 4 carbon atoms, more preferably a hydrogen atom, a methyl group or an ethyl group, and still more preferably a hydrogen atom or a methyl group, $R^{a25}$ is preferably a carboxy group, a cyano group or a methyl group, $L^{a7}$ is preferably —O— or *—O-$L^{a8}$-CO—O—, and more preferably —O—, —O—$CH_2$—CO—O— or —O—$C_2H_4$—CO—O—, and w1 is preferably an integer of 0 to 2, and more preferably 0 or 1.

Particularly, formula (a3-4) is preferably formula (a3-4)':

(a3-4)'

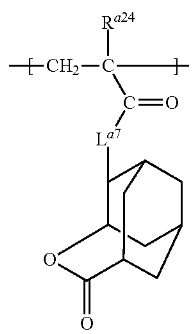

wherein $R^{a24}$ and $L^{a7}$ are the same as defined above.

Examples of the structural unit (a3) include structural units derived from the monomers mentioned in JP 2010-204646 A, the monomers mentioned in JP 2000-122294 A and the monomers mentioned in JP 2012-41274 A. The structural unit (a3) is preferably a structural unit represented by any one of formula (a3-1-1), formula (a3-1-2), formula (a3-2-1), formula (a3-2-2), formula (a3-3-1), formula (a3-3-2) and formula (a3-4-1) to formula (a3-4-12), and structural units in which methyl groups corresponding to $R^{a18}$, $R^{a19}$, $R^{a20}$ and $R^{a24}$ in formula (a3-1) to formula (a3-4) are substituted with hydrogen atoms in the above structural units.

(a3-1-1)

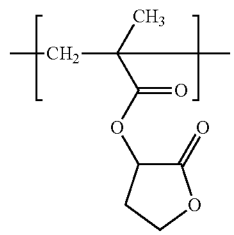

(a3-1-2)

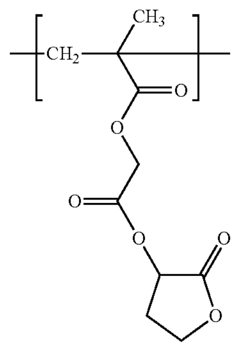

-continued (a3-2-1)

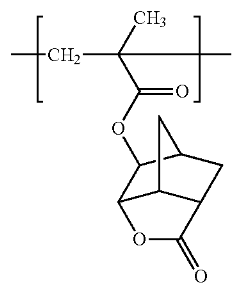

(a3-2-2)

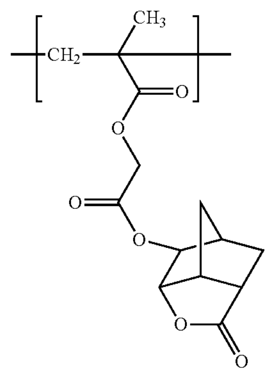

(a3-2x-1)

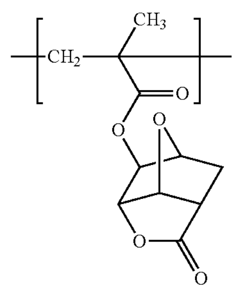

(a3-2x-2)

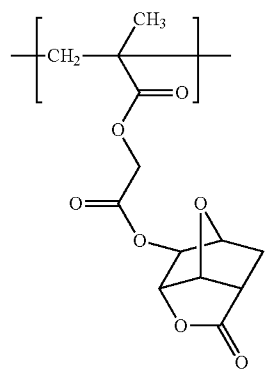

(a3-3-1)

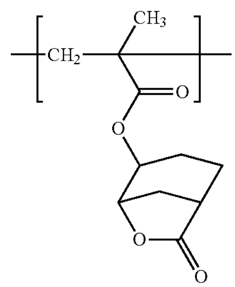

-continued
(a3-3-2)
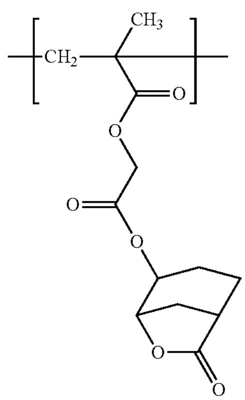
(a3-4-1)
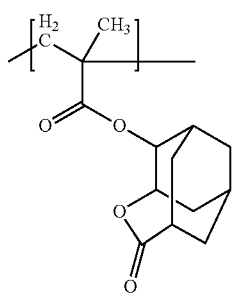
(a3-4-2)
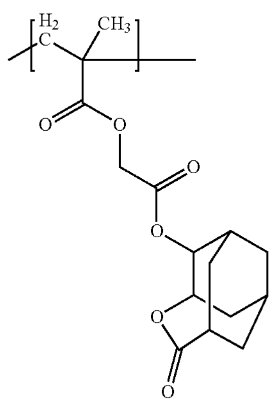
(a3-4-3)
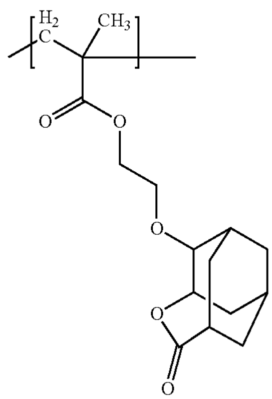
-continued
(a3-4-4)
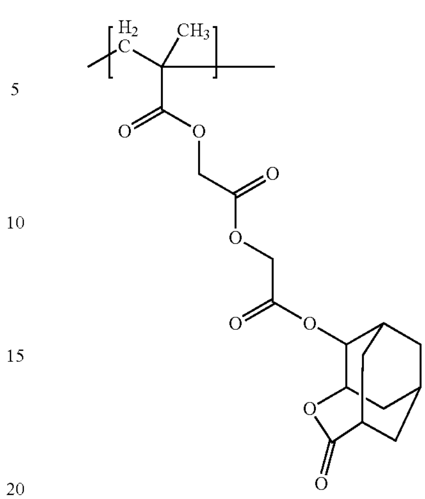
(a3-4-5)
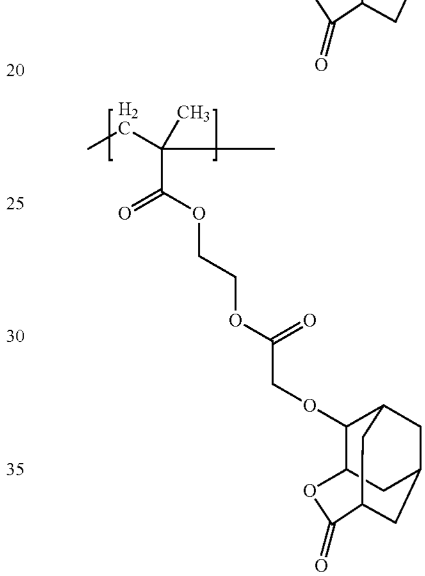
(a3-4-6)
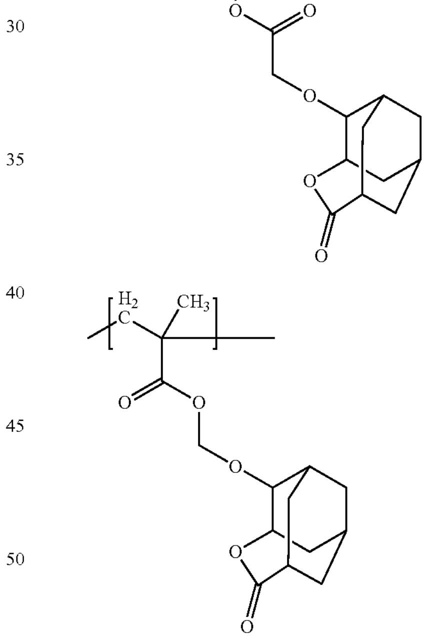
(a3-4-7)
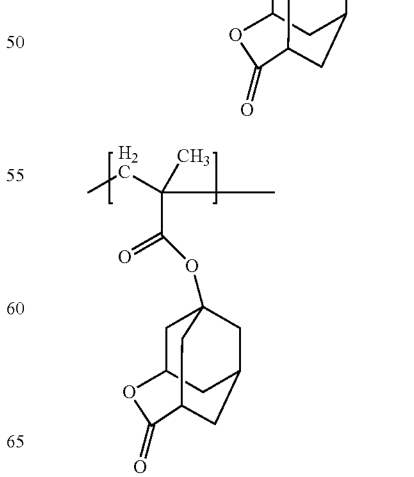

-continued (a3-4-8)

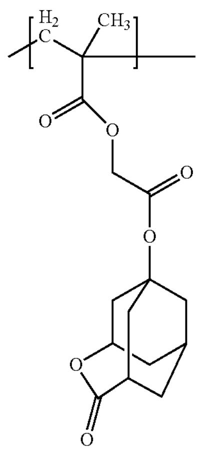

(a3-4-9)

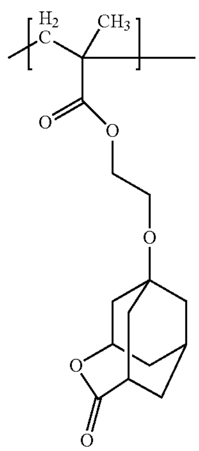

(a3-4-10)

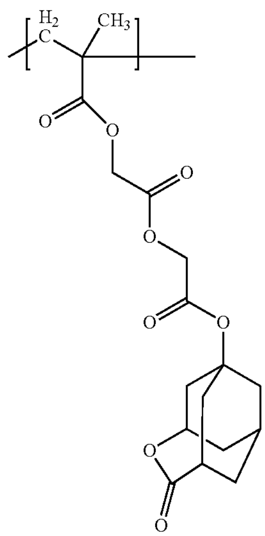

-continued (a3-4-11)

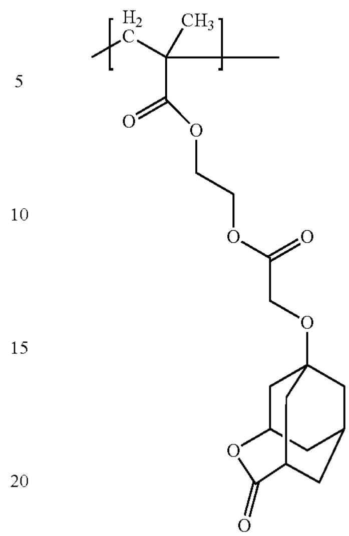

(a3-4-12)

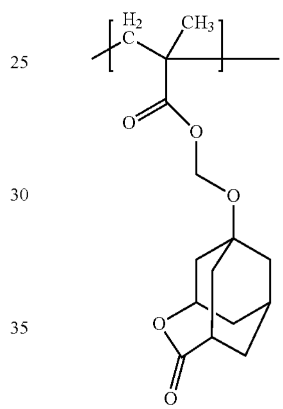

When the resin (A) includes the structural unit (a3), the total content is usually 5 to 70 mol %, preferably 10 to 65 mol %, and more preferably 10 to 60 mol %, based on all structural units of the resin (A).

Each content of the structural unit (a3-1), the structural unit (a3-2), the structural unit (a3-3) or the structural unit (a3-4) is preferably 5 to 60 mol %, more preferably 5 to 50 mol %, and still more preferably 10 to 50 mol %, based on all structural units of the resin (A).

<Structural Unit (a4)>

Examples of the structural unit (a4) include the following structural units:

(a4)

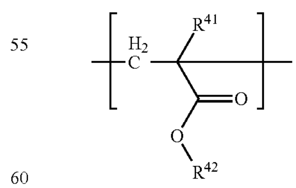

wherein, in formula (a4), $R^{41}$ represents a hydrogen atom or a methyl group, and $R^{42}$ represents a saturated hydrocarbon group having 1 to 24 carbon atoms which has a fluorine atom, and —$CH_2$— included in the saturated hydrocarbon group may be replaced by —O— or —CO.

Examples of the saturated hydrocarbon group represented by $R^{42}$ include a chain hydrocarbon group and a monocyclic or polycyclic alicyclic hydrocarbon group, and groups formed by combining these groups.

Examples of the chain hydrocarbon group include a methyl group, an ethyl group, a propyl group, a butyl group, a pentyl group, a hexyl group, a heptyl group, an octyl group, a decyl group, a dodecyl group, a pentadecyl group, a hexadecyl group, a heptadecyl group and an octadecyl group. Examples of the monocyclic or polycyclic alicyclic hydrocarbon group include cycloalkyl groups such as a cyclopentyl group, a cyclohexyl group, a cycloheptyl group and a cyclooctyl group; and polycyclic alicyclic saturated hydrocarbon groups such as a decahydronaphthyl group, an adamantyl group, a norbornyl group and the following groups (* represents a bonding site).

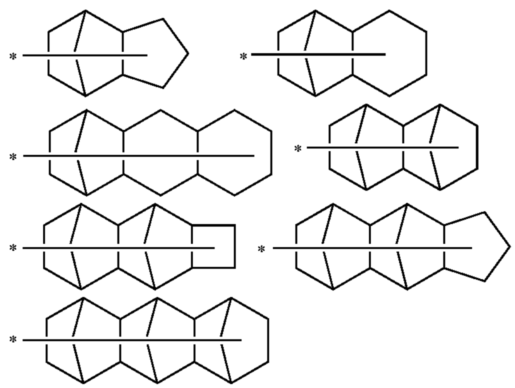

Examples of the group formed by combination include groups formed by combining one or more alkyl groups or one or more alkanediyl groups with one or more alicyclic hydrocarbon groups, and include an alkanediyl group-alicyclic hydrocarbon group, an alicyclic hydrocarbon group-alkyl group, an alkanediyl group-alicyclic hydrocarbon group-alkyl group and the like.

Examples of the structural unit (a4) include a structural unit represented by at least one selected from the group consisting of formula (a4-0), formula (a4-1), formula (a4-2), formula (a4-3) and formula (a4-4):

(a4-0)

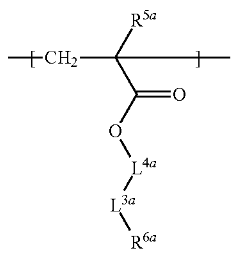

wherein, in formula (a4-0), $R^{5a}$ represents a hydrogen atom or a methyl group, $L^{4a}$ represents a single bond or a divalent aliphatic saturated hydrocarbon group having 1 to 4 carbon atoms, $L^{3a}$ represents a perfluoroalkanediyl group having 1 to 8 carbon atoms or a perfluorocycloalkanediyl group having 3 to 12 carbon atoms, and $R^{6a}$ represents a hydrogen atom or a fluorine atom.

Examples of the divalent aliphatic saturated hydrocarbon group in $L^{4a}$ include linear alkanediyl groups such as a methylene group, an ethylene group, a propane-1,3-diyl group and a butane-1,4-diyl group; and branched alkanediyl groups such as an ethane-1,1-diyl group, a propane-1,2-diyl group, a butane-1,3-diyl group, a 2-methylpropane-1,3-diyl group and a 2-methylpropane-1,2-diyl group.

Examples of the perfluoroalkanediyl group in $L^{3a}$ include a difluoromethylene group, a perfluoroethylene group, a perfluoropropane-1,1-diyl group, a perfluoropropane-1,3-diyl group, a perfluoropropane-1,2-diyl group, a perfluoropropane-2,2-diyl group, a perfluorobutane-1,4-diyl group, a perfluorobutane-2,2-diyl group, a perfluorobutane-1,2-diyl group, a perfluoropentane-1,5-diyl group, a perfluoropentane-2,2-diyl group, a perfluoropentane-3,3-diyl group, a perfluorohexane-1,6-diyl group, a perfluorohexane-2,2-diyl group, a perfluorohexane-3,3-diyl group, a perfluoroheptane-1,7-diyl group, a perfluoroheptane-2,2-diyl group, a perfluoroheptane-3,4-diyl group, a perfluoroheptane-4,4-diyl group, a perfluorooctane-1,8-diyl group, a perfluorooctane-2,2-diyl group, a perfluorooctane-3,3-diyl group, a perfluorooctane-4,4-diyl group and the like.

Examples of the perfluorocycloalkanediyl group in $L^{3}a$ include a perfluorocyclohexanediyl group, a perfluorocyclopentanediyl group, a perfluorocycloheptanediyl group, a perfluoroadamantanediyl group and the like.

$L^{4a}$ is preferably a single bond, a methylene group or an ethylene group, and more preferably a single bond or a methylene group.

$L^{3a}$ is preferably a perfluoroalkanediyl group having 1 to 6 carbon atoms, and more preferably a perfluoroalkanediyl group having 1 to 3 carbon atoms.

Examples of the structural unit (a4-0) include the following structural units, and structural units in which a methyl group corresponding to $R^{5a}$ in the structural unit (a4-0) in the following structural units is substituted with a hydrogen atom:

(a4-0-1)

(a4-0-2)

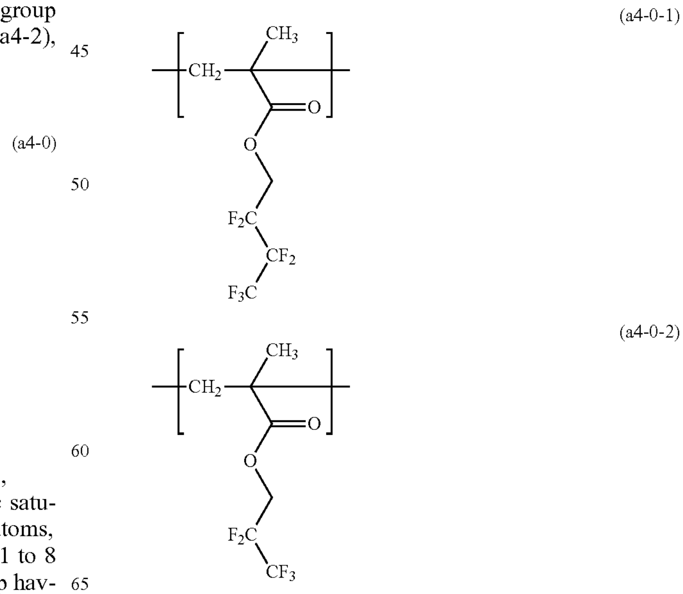

-continued
(a4-0-3)
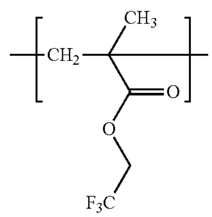
(a4-0-4)
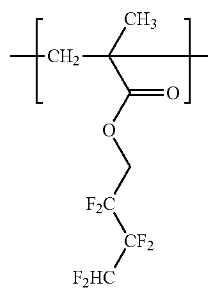
(a4-0-5)
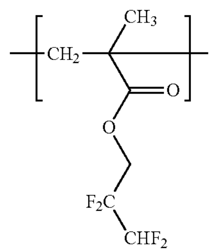
(a4-0-6)
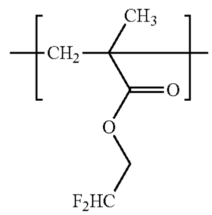
(a4-0-7)
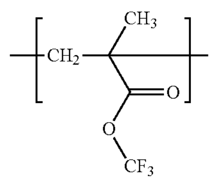
(a4-0-8)
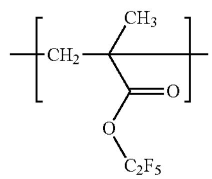
(a4-0-9)
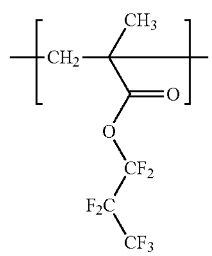
-continued
(a4-0-10)
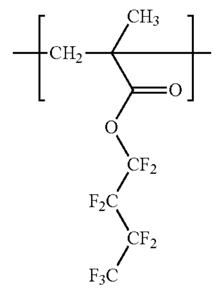
(a4-0-11)
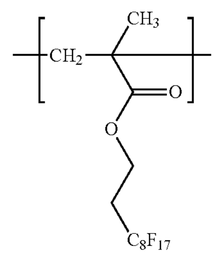
(a4-0-12)
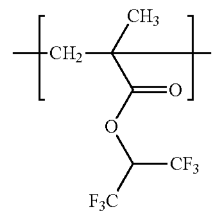
(a4-0-13)
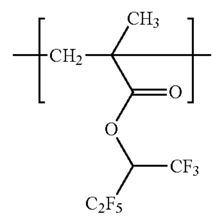
(a4-0-14)
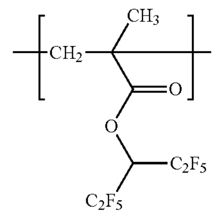
(a4-0-15)
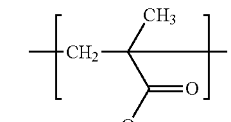
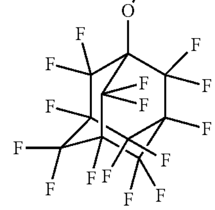

-continued (a4-0-16)

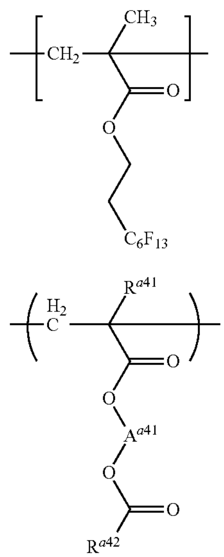

(a4-1)

wherein, in formula (a4-1), $R^{a41}$ represents a hydrogen atom or a methyl group, $R^{a42}$ represents a hydrocarbon group having 1 to 20 carbon atoms which may have a substituent, and —$CH_2$— included in the saturated hydrocarbon group may be replaced by —O— or —CO—, $A^{a41}$ represents an alkanediyl group having 1 to 6 carbon atoms which may have a substituent or a group represented by formula (a-g1), in which at least one of $A^{a41}$ and $R^{a42}$ has, as a substituent, a halogen atom (preferably a fluorine atom):

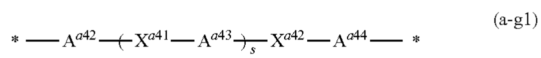

(a-g1)

[in which, in formula (a-g1), s represents 0 or 1, $A^{a42}$ and $A^{a44}$ each independently represent a divalent saturated hydrocarbon group having 1 to 5 carbon atoms which may have a substituent, $A^{a43}$ represents a single bond or a divalent aliphatic hydrocarbon group having 1 to 5 carbon atoms which may have a substituent, $X^{a41}$ and $X^{a42}$ each independently represent —O—, —CO—, —CO—O— or —O—CO—, in which the total number of carbon atoms of $A^{a42}$, $A^{a43}$, $A^{a44}$, $X^{a41}$ and $X^{a42}$ is 7 or less], and is a bonding site and * at the right side is a bonding site to —O—CO—$R^{a42}$.

Examples of the saturated hydrocarbon group in $R^{a42}$ include a chain saturated hydrocarbon group and a monocyclic or polycyclic alicyclic saturated hydrocarbon group, and groups formed by combining these groups.

Examples of the chain saturated hydrocarbon group include a methyl group, an ethyl group, a propyl group, a butyl group, a pentyl group, a hexyl group, a heptyl group, an octyl group, a decyl group, a dodecyl group, a pentadecyl group, a hexadecyl group, a heptadecyl group and an octadecyl group.

Examples of the monocyclic or polycyclic alicyclic saturated hydrocarbon group include cycloalkyl groups such as a cyclopentyl group, a cyclohexyl group, a cycloheptyl group and a cyclooctyl group; and polycyclic alicyclic saturated hydrocarbon groups such as a decahydronaphthyl group, an adamantyl group, a norbornyl group and the following groups (* represents a bonding site).

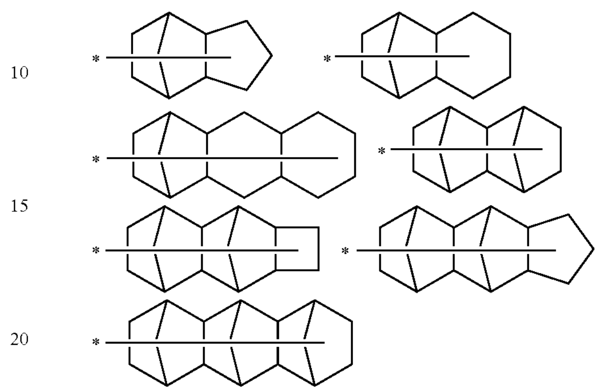

Examples of the group formed by combination include groups formed by combining one or more alkyl groups or one or more alkanediyl groups with one or more alicyclic saturated hydrocarbon groups, and include an alkanediyl group-alicyclic saturated hydrocarbon group, an alicyclic saturated hydrocarbon group-alkyl group, an alkanediyl group-alicyclic saturated hydrocarbon group-alkyl group and the like.

Examples of the substituent possessed by $R^{a42}$ include at least one selected from the group consisting of a halogen atom and a group represented by formula (a-g3). Examples of the halogen atom include a fluorine atom, a chlorine atom, a bromine atom and an iodine atom, and a fluorine atom is preferred:

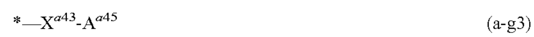

(a-g3)

wherein, in formula (a-g3), $X^{a43}$ represents an oxygen atom, a carbonyl group, *—O—CO— or *—CO—O—, $A^{a45}$ represents an aliphatic hydrocarbon group having 1 to 17 carbon atoms which may have a halogen atom, and represents a bonding site to $R^{a42}$.

In $R^{a42}$—$X^{a43}$-$A^{a45}$, when $R^{a42}$ has no halogen atom, $A^{a45}$ represents an aliphatic hydrocarbon group having 1 to 17 carbon atoms having at least one halogen atom.

Examples of the aliphatic hydrocarbon group in $A^{a45}$ include alkyl groups such as a methyl group, an ethyl group, a propyl group, a butyl group, a pentyl group, a hexyl group, a heptyl group, an octyl group, a decyl group, a dodecyl group, a pentadecyl group, a hexadecyl group, a heptadecyl group and an octadecyl group; monocyclic alicyclic hydrocarbon groups such as a cyclopentyl group, a cyclohexyl group, a cycloheptyl group and a cyclooctyl group; and polycyclic alicyclic hydrocarbon groups such as a decahydronaphthyl group, an adamantyl group, a norbornyl group and the following groups (* represents a bonding site):

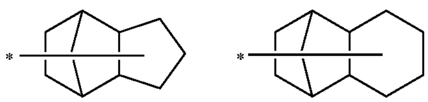

-continued

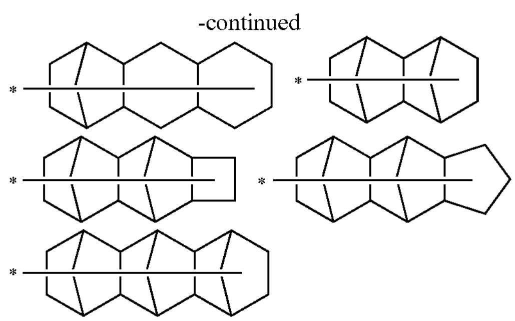

Examples of the group formed by combination include a group obtained by combining one or more alkyl groups or one or more alkanediyl groups with one or more alicyclic hydrocarbon groups, and include an -alkanediyl group-alicyclic hydrocarbon group, an -alicyclic hydrocarbon group-alkyl group, an -alkanediyl group-alicyclic hydrocarbon group-alkyl group and the like.

$R^{a42}$ is preferably an aliphatic hydrocarbon group which may have a halogen atom, and more preferably an alkyl group having a halogen atom and/or an aliphatic hydrocarbon group having a group represented by formula (a-g3).

When $R^{a42}$ is an aliphatic hydrocarbon group having a halogen atom, an aliphatic hydrocarbon group having a fluorine atom is preferred, a perfluoroalkyl group or a perfluorocycloalkyl group is more preferred, a perfluoroalkyl group having 1 to 6 carbon atoms is still more preferred, and a perfluoroalkyl group having 1 to 3 carbon atoms is particularly preferred. Examples of the perfluoroalkyl group include a perfluoromethyl group, a perfluoroethyl group, a perfluoropropyl group, a perfluorobutyl group, a perfluoropentyl group, a perfluorohexyl group, a perfluoroheptyl group and a perfluorooctyl group. Examples of the perfluorocycloalkyl group include a perfluorocyclohexyl group and the like.

When $R^{a42}$ is an aliphatic hydrocarbon group having a group represented by formula (a-g3), the total number of carbon atoms of $R^{a42}$ is preferably 15 or less, and more preferably 12 or less, including the number of carbon atoms included in the group represented by formula (a-g3). When having the group represented by formula (a-g3) as the substituent, the number thereof is preferably 1.

When $R^{a42}$ is an aliphatic hydrocarbon group having the group represented by formula (a-g3), $R^{a42}$ is still more preferably a group represented by formula (a-g2):

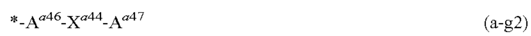

$$*\text{-}A^{a46}\text{-}X^{a44}\text{-}A^{a47} \quad \text{(a-g2)}$$

wherein, in formula (a-g2), $A^{a46}$ represents a divalent aliphatic hydrocarbon group having 1 to 17 carbon atoms which may have a halogen atom, $X^{a44}$ represents —O—CO— or —CO—O— (** represents a bonding site to $A^{a46}$), $A^{a47}$ represents an aliphatic hydrocarbon group having 1 to 17 carbon atoms which may have a halogen atom, the total number of carbon atoms of $A^{a46}$, $A^{a47}$ and $X^{a44}$ is 18 or less, and at least one of $A^{a46}$ and $A^{a47}$ has at least one halogen atom, and represents a bonding site to a carbonyl group.

The number of carbon atoms of the aliphatic hydrocarbon group of $A^{a46}$ is preferably 1 to 6, and more preferably 1 to 3.

The number of carbon atoms of the aliphatic hydrocarbon group of $A^{a47}$ is preferably 4 to 15, and more preferably 5 to 12, and $A^{a47}$ is still more preferably a cyclohexyl group or an adamantyl group.

Preferred structure of the group represented by formula (a-g2) is the following structure (* represents a bonding site to a carbonyl group).

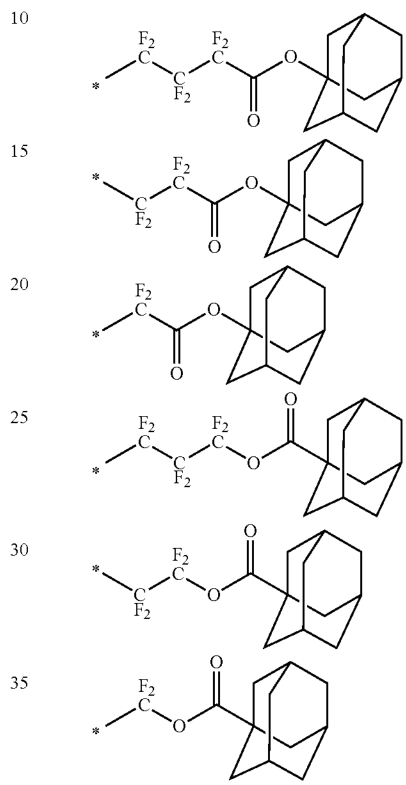

Examples of the alkanediyl group in $A^{a41}$ include linear alkanediyl groups such as a methylene group, an ethylene group, a propane-1,3-diyl group, a butane-1,4-diyl group, a pentane-1,5-diyl group and a hexane-1,6-diyl group; and branched alkanediyl groups such as a propane-1,2-diyl group, a butane-1,3-diyl group, a 2-methylpropane-1,2-diyl group, a 1-methylbutane-1,4-diyl group and a 2-methylbutane-1,4-diyl group.

Examples of the substituent in the alkanediyl group represented by $A^{a41}$ include a hydroxy group and an alkoxy group having 1 to 6 carbon atoms.

$A^{a41}$ is preferably an alkanediyl group having 1 to 4 carbon atoms, more preferably an alkanediyl group having 2 to 4 carbon atoms, and still more preferably an ethylene group.

Examples of the divalent saturated hydrocarbon group represented by $A^{a42}$, $A^{a43}$ and $A^{a44}$ in the group represented by formula (a-g1) include a linear or branched alkanediyl group and a monocyclic divalent alicyclic hydrocarbon group, and groups formed by combining an alkanediyl group and a divalent alicyclic hydrocarbon group. Specific examples thereof include a methylene group, an ethylene group, a propane-1,3-diyl group, a propane-1,2-diyl group, a butane-1,4-diyl group, a 1-methylpropane-1,3-diyl group, a 2-methylpropane-1,3-diyl group, a 2-methylpropane-1,2-diyl group and the like.

Examples of the substituent of the divalent saturated hydrocarbon group represented by $A^{a42}$, $A^{a43}$ and $A^{a44}$ include a hydroxy group and an alkoxy group having 1 to 6 carbon atoms.

s is preferably 0.

In the group represented by formula (a-g1), examples of the group in which $X^{a42}$ is —O—, —CO—, —CO—O— or —O—CO— include the following groups. In the following exemplification, * and  each represent a bonding site, and  represents a bonding site to —O—CO—$R^{a42}$.

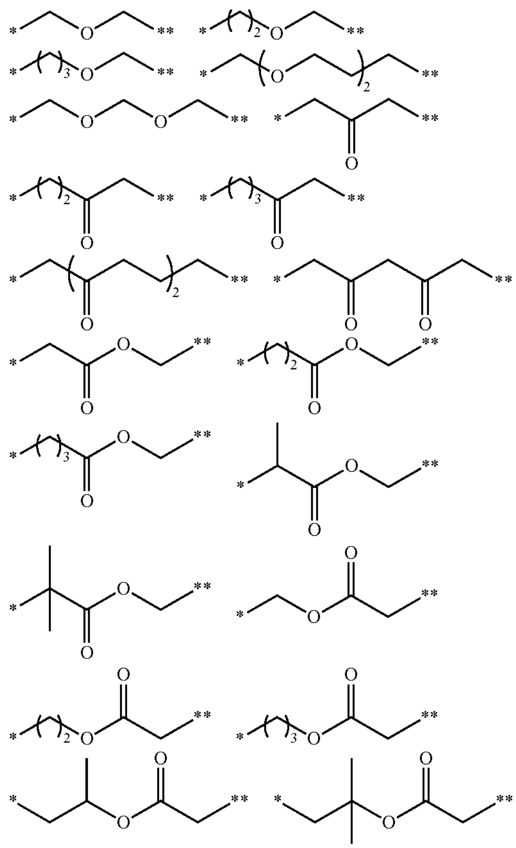

Examples of the structural unit represented by formula (a4-1) include the following structural units, and structural units in which a methyl group corresponding to $A^{a41}$ in the structural unit represented by formula (a4-1) in the following structural units is substituted with a hydrogen atom.

(a4-1-1)

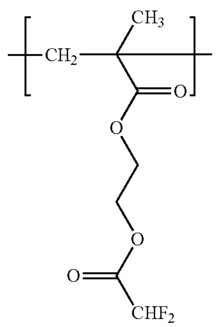

-continued (a4-1-2)

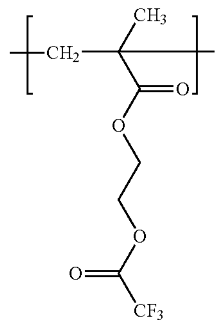

(a4-1-3)

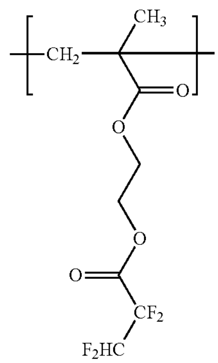

(a4-1-4)

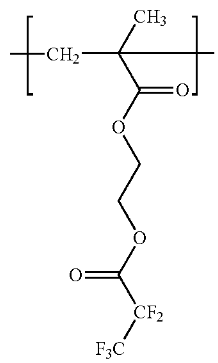

(a4-1-5)

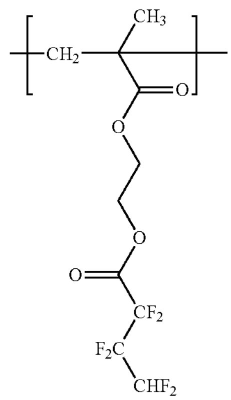

-continued
(a4-1-6)
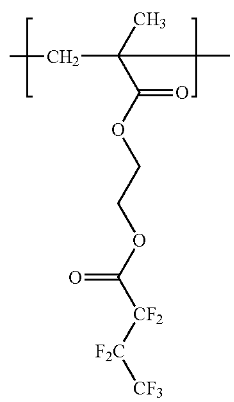
(a4-1-7)
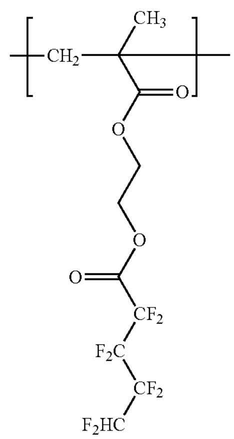
(a4-1-8)
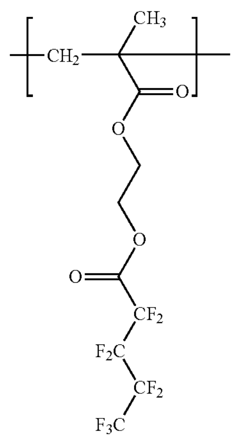
-continued
(a4-1-9)
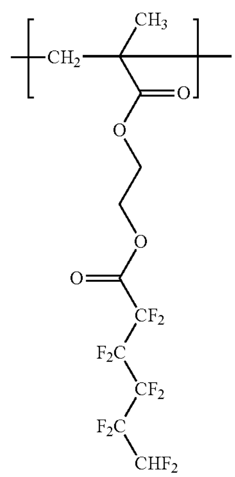
(a4-1-10)
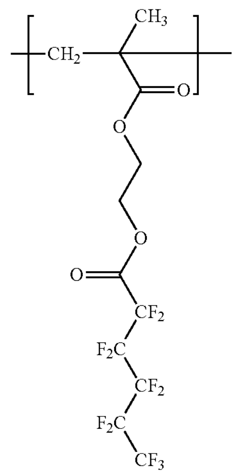
(a4-1-11)
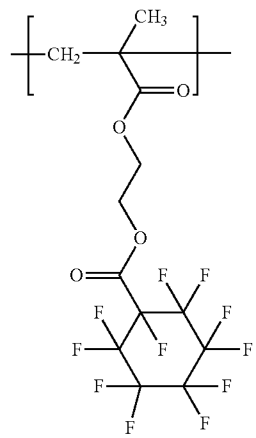

-continued
(a4-1′-1)
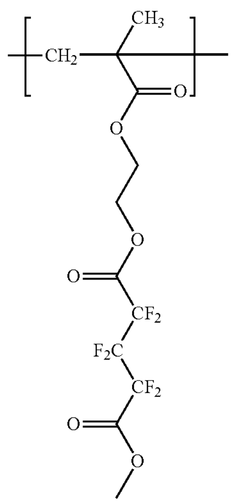
(a4-1′-2)
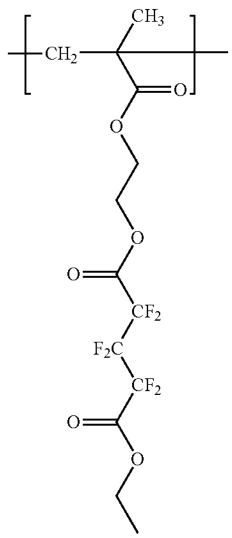
(a4-1′-3)
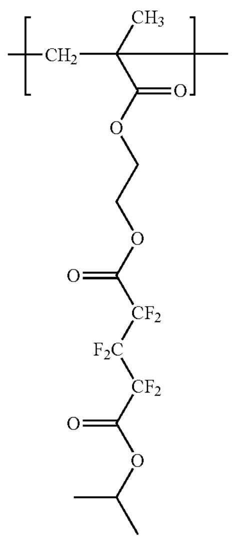
-continued
(a4-1′-4)
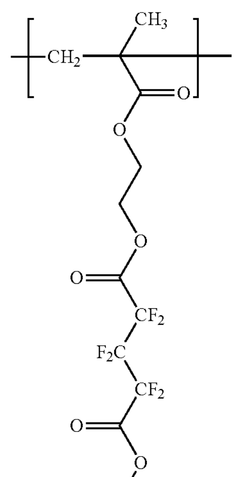
(a4-1′-5)
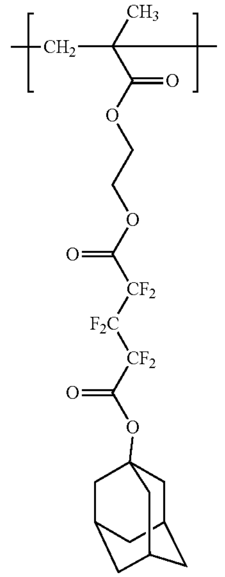

-continued
(a4-1′-6)
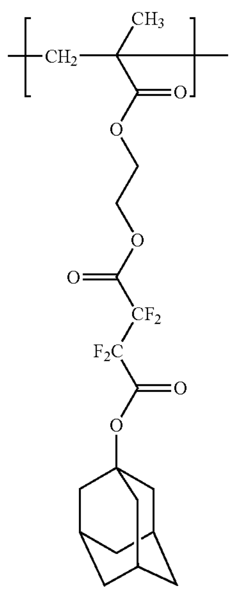
(a4-1′-7)
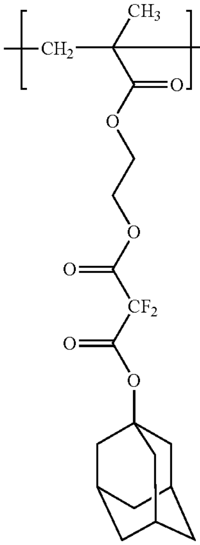
-continued
(a4-1′-8)
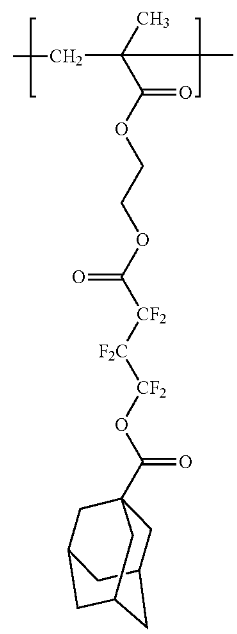
(a4-1′-9)
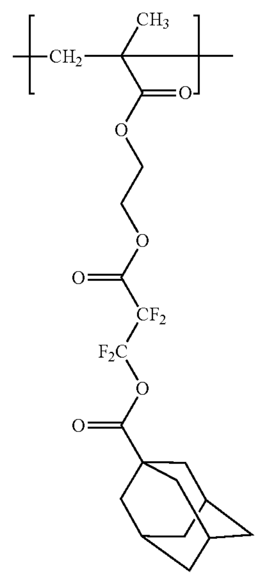

-continued (a4-1'-10)

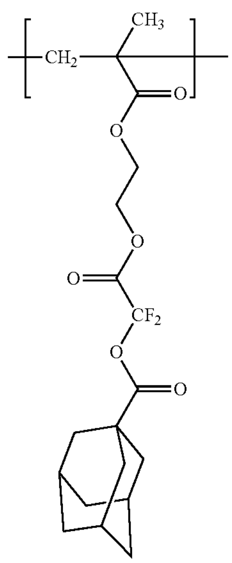

(a4-1'-11)

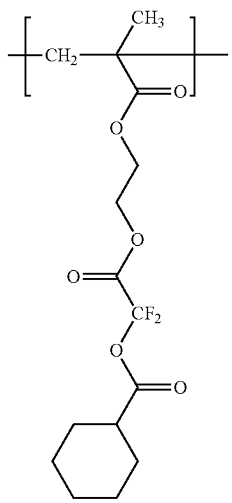

The structural unit represented by formula (a4-1) is preferably a structural unit represented by formula (a4-2):

(a4-2)

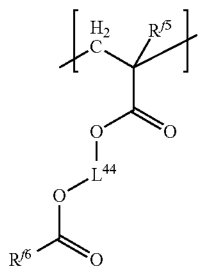

wherein, in formula (a4-2), $R^{f5}$ represents a hydrogen atom or a methyl group, $L^{44}$ represents an alkanediyl group having 1 to 6 carbon atoms, and $—CH_2—$ included in the alkanediyl group may be replaced by —O— or —CO—, $R^{f6}$ represents a saturated hydrocarbon group having 1 to 20 carbon atoms having a fluorine atom, and the upper limit of the total number of carbon atoms of $L^{44}$ and $R^{f6}$ is 21.

Examples of the alkanediyl group having 1 to 6 carbon atoms of $L^{44}$ include the same groups as mentioned for the alkanediyl group in $A^{a41}$.

Examples of the saturated hydrocarbon group of $R^{f6}$ include the same groups as mentioned for $R^{42}$.

The alkanediyl group having 1 to 6 carbon atoms in $L^{44}$ is preferably an alkanediyl group having 2 to 4 carbon atoms, and more preferably an ethylene group.

The structural unit represented by formula (a4-2) includes, for example, structural units represented by formula (a4-1-1) to formula (a4-1-11). A structural unit in which a methyl group corresponding to $R^{f5}$ in the structural unit (a4-2) is substituted with a hydrogen atom is also exemplified as the structural unit represented by formula (a4-2).

Examples of the structural unit (a4) include a structural unit represented by formula (a4-3):

(a4-3)

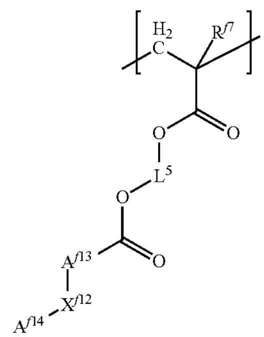

wherein, in formula (a4-3), $R^{f7}$ represents a hydrogen atom or a methyl group, $L^5$ represents an alkanediyl group having 1 to 6 carbon atoms, $A^{f13}$ represents a divalent saturated hydrocarbon group having 1 to 18 carbon atoms which may have a fluorine atom, $X^{f12}$ represents *—O—CO— or *—CO—O— (* represents a bonding site to $A^{f13}$), $A^{f14}$ represents a saturated hydrocarbon group having 1 to 17 carbon atoms which may have a fluorine atom, and at least one of $A^{f13}$ and $A^{f14}$ has a fluorine atom, and the upper limit of the total number of carbon atoms of $L^5$, $A^{f13}$ and $A^{f14}$ is 20.

Examples of the alkanediyl group in $L^5$ include those which are the same as mentioned for the alkanediyl group in $A^{a41}$.

The divalent saturated hydrocarbon group which may have a fluorine atom in $A^{f13}$ is preferably a divalent aliphatic saturated hydrocarbon group which may have a fluorine atom and a divalent alicyclic saturated hydrocarbon group which may have a fluorine atom, and more preferably a perfluoroalkanediyl group.

Examples of the divalent aliphatic saturated hydrocarbon group which may have a fluorine atom include alkanediyl groups such as a methylene group, an ethylene group, a propanediyl group, a butanediyl group and a pentanediyl group; and perfluoroalkanediyl groups such as a difluoromethylene group, a perfluoroethylene group, a perfluoropropanediyl group, a perfluorobutanediyl group and a perfluoropentanediyl group.

The divalent alicyclic hydrocarbon group which may have a fluorine atom may be either monocyclic or polycyclic. Examples of the monocyclic group include a cyclohexanediyl group and a perfluorocyclohexanediyl group. Examples of the polycyclic group include an adamantanediyl group, a norbornanediyl group, a perfluoroadamantanediyl group and the like.

Examples of the saturated hydrocarbon group and the saturated hydrocarbon group which may have a fluorine atom for $A^{f14}$ include the same groups as mentioned for $R^{a42}$. Of these groups, preferred are fluorinated alkyl groups such as a trifluoromethyl group, a difluoromethyl group, a methyl group, a perfluoroethyl group, a 2,2,2-trifluoroethyl group, a 1,1,2,2-tetrafluoroethyl group, an ethyl group, a perfluoropropyl group, a 2,2,3,3,3-pentafluoropropyl group, a propyl group, a perfluorobutyl group, a 1,1,2,2,3,3,4,4-octafluorobutyl group, a butyl group, a perfluoropentyl group, a 2,2,3,3,4,4,5,5,5-nonafluoropentyl group, a pentyl group, a hexyl group, a perfluorohexyl group, a heptyl group, a perfluoroheptyl group, an octyl group and a perfluorooctyl group; a cyclopropylmethyl group, a cyclopropyl group, a cyclobutylmethyl group, a cyclopentyl group, a cyclohexyl group, a perfluorocyclohexyl group, an adamantyl group, an adamantylmethyl group, an adamantyldimethyl group, a norbornyl group, a norbornylmethyl group, a perfluoroadamantyl group, a perfluoroadamantylmethyl group and the like.

In formula (a4-3), $L^5$ is preferably an ethylene group.

The divalent saturated hydrocarbon group of $A^{f13}$ is preferably a group including a chain hydrocarbon group having 1 to 6 carbon atoms and a divalent alicyclic hydrocarbon group having 3 to 12 carbon atoms, and more preferably a divalent chain hydrocarbon group having 2 to 3 carbon atoms.

The saturated hydrocarbon group of $A^{f14}$ is preferably a group including a chain hydrocarbon group having 3 to 12 carbon atoms and an alicyclic hydrocarbon group having 3 to 12 carbon atoms, and more preferably a group including a chain hydrocarbon group having 3 to 10 carbon atoms and an alicyclic hydrocarbon group having 3 to 10 carbon atoms. Of these groups, $A^{f14}$ is preferably a group including an alicyclic hydrocarbon group having 3 to 12 carbon atoms, and more preferably a cyclopropylmethyl group, a cyclopentyl group, a cyclohexyl group, a norbornyl group and an adamantyl group.

The structural unit represented by formula (a4-3) includes, for example, structural units represented by formula (a4-1'-1) to formula (a4-1'-11). A structural unit in which a methyl group corresponding to $R^{f7}$ in the structural unit (a4-3) is substituted with a hydrogen atom is also exemplified as the structural unit represented by formula (a4-3).

It is also possible to exemplify, as the structural unit (a4), a structural unit represented by formula (a4-4):

(a4-4)

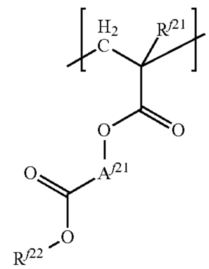

wherein, in formula (a4-4), $R^{f21}$ represents a hydrogen atom or a methyl group, $A^{f21}$ represents $-(CH_2)_{j1}-$, $-(CH_2)_{j2}-O-(CH_2)_{j3}-$ or $-(CH_2)_{j4}-CO-O-(CH_2)_{j5}-$, j1 to j5 each independently represent an integer of 1 to 6, and $R^{f22}$ represents a saturated hydrocarbon group having 1 to 10 carbon atoms having a fluorine atom.

Examples of the saturated hydrocarbon group of $R^{f22}$ include those which are the same as the saturated hydrocarbon group represented by $R^{a42}$. $R^{f22}$ is preferably an alkyl group having 1 to 10 carbon atoms having a fluorine atom or an alicyclic hydrocarbon group having 1 to 10 carbon atoms having a fluorine atom, more preferably an alkyl group having 1 to 10 carbon atoms having a fluorine atom, and still more preferably an alkyl group having 1 to 6 carbon atoms which has a fluorine atom.

In formula (a4-4), $A^{f21}$ is preferably $-(CH_2)_{j1}-$, more preferably an ethylene group or a methylene group, and still more preferably a methylene group.

The structural unit represented by formula (a4-4) includes, for example, the following structural units and structural units in which a methyl group corresponding to $R^{f21}$ in the structural unit (a4-4) is substituted with a hydrogen atom in structural units represented by the following formulas.

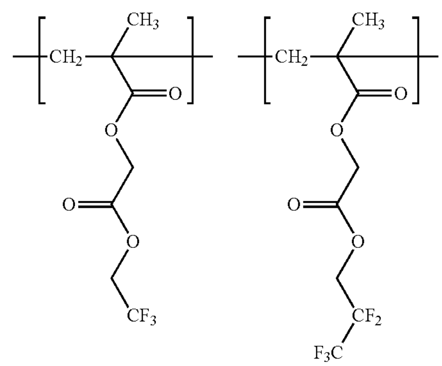

-continued
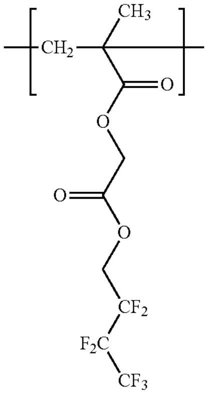 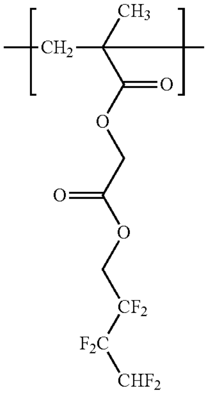
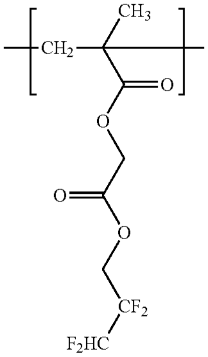 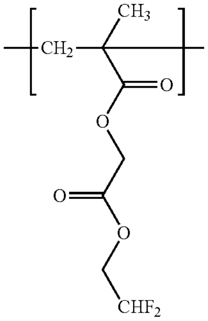
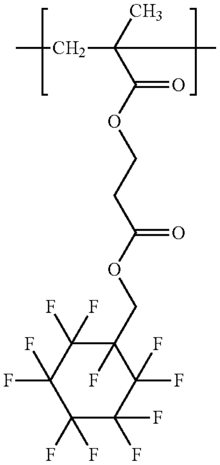 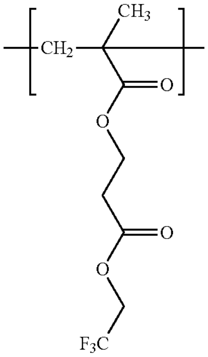
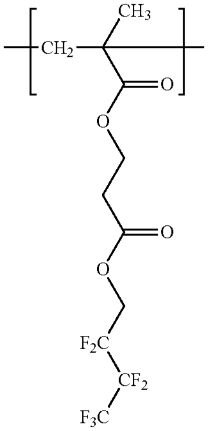 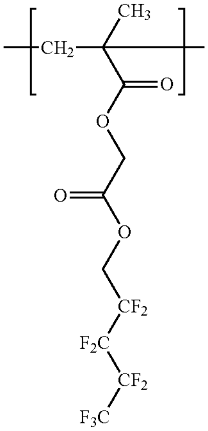
-continued
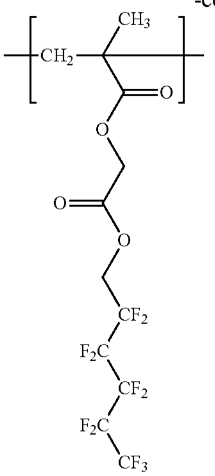 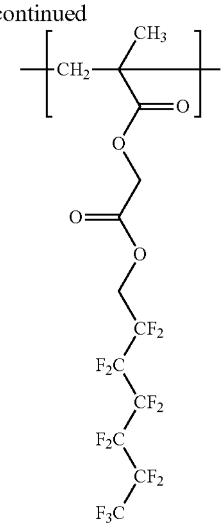
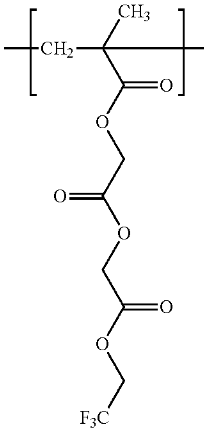 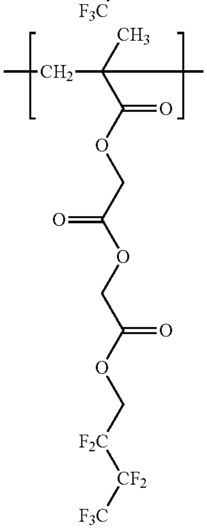
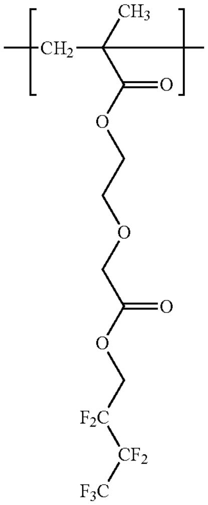
When the resin (A) includes the structural unit (a4), the content is preferably 1 to 20 mol %, more preferably 2 to 15 mol %, and still more preferably 3 to 10 mol %, based on all structural units of the resin (A).
<Structural Unit (a5)>
Examples of a non-leaving hydrocarbon group possessed by the structural unit (a5) include groups having a linear, branched or cyclic hydrocarbon group. Of these, the structural unit (a5) is preferably a group having an alicyclic hydrocarbon group.

The structural unit (a5) includes, for example, a structural unit represented by formula (a5-1):

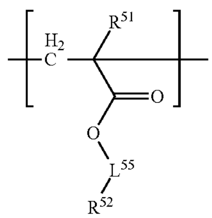

(a5-1)

wherein, in formula (a5-1), $R^{51}$ represents a hydrogen atom or a methyl group, $R^{52}$ represents an alicyclic hydrocarbon group having 3 to 18 carbon atoms, and a hydrogen atom included in the alicyclic hydrocarbon group may be substituted with an aliphatic hydrocarbon group having 1 to 8 carbon atoms, and $L^{55}$ represents a single bond or a divalent saturated hydrocarbon group having 1 to 18 carbon atoms, and —$CH_2$— included in the saturated hydrocarbon group may be replaced by —O— or —CO—.

The alicyclic hydrocarbon group in $R^{52}$ may be either monocyclic or polycyclic. The monocyclic alicyclic hydrocarbon group includes, for example, a cyclopropyl group, a cyclobutyl group, a cyclopentyl group and a cyclohexyl group. The polycyclic alicyclic hydrocarbon group includes, for example, an adamantyl group and a norbornyl group.

The aliphatic hydrocarbon group having 1 to 8 carbon atoms includes, for example, alkyl groups such as a methyl group, an ethyl group, a propyl group, an isopropyl group, a butyl group, a sec-butyl group, a tert-butyl group, a pentyl group, a hexyl group, an octyl group and a 2-ethylhexyl group.

Examples of the alicyclic hydrocarbon group having a substituent includes a 3-methyladamantyl group and the like.

$R^{52}$ is preferably an unsubstituted alicyclic hydrocarbon group having 3 to 18 carbon atoms, and more preferably an adamantyl group, a norbornyl group or a cyclohexyl group.

Examples of the divalent saturated hydrocarbon group in $L^{55}$ include a divalent chain saturated hydrocarbon group and a divalent alicyclic saturated hydrocarbon group, and a divalent chain saturated hydrocarbon group is preferred.

The divalent chain saturated hydrocarbon group includes, for example, alkanediyl groups such as a methylene group, an ethylene group, a propanediyl group, a butanediyl group and a pentanediyl group.

The divalent alicyclic saturated hydrocarbon group may be either monocyclic or polycyclic. Examples of the monocyclic alicyclic saturated hydrocarbon group include cycloalkanediyl groups such as a cyclopentanediyl group and a cyclohexanediyl group. Examples of the polycyclic divalent alicyclic saturated hydrocarbon group include an adamantanediyl group and a norbornanediyl group.

The group in which —$CH_2$— included in the divalent saturated hydrocarbon group represented by $L^{55}$ is replaced by —O— or —CO— includes, for example, groups represented by formula (L1-1) to formula (L1-4). In the following formulas, * and ** each represent a bonding site, and * represents a bonding site to an oxygen atom.

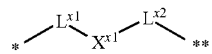

(L1-1)

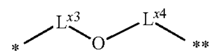

(L1-2)

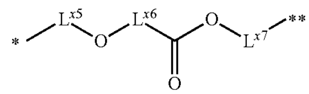

(L1-3)

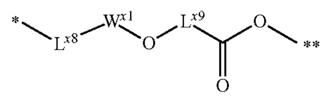

(L1-4)

In formula (L1-1), $X^{x1}$ represents *—O—CO— or *—CO—O— (* represents a bonding site to $L^{x1}$), $L^{x1}$ represents a divalent aliphatic saturated hydrocarbon group having 1 to 16 carbon atoms, $L^{x2}$ represents a single bond or a divalent aliphatic saturated hydrocarbon group having 1 to 15 carbon atoms, and the total number of carbon atoms of $L^{x1}$ and $L^{x2}$ is 16 or less.

In formula (L1-2), $L^{x3}$ represents a divalent aliphatic saturated hydrocarbon group having 1 to 17 carbon atoms, $L^{x4}$ represents a single bond or a divalent aliphatic saturated hydrocarbon group having 1 to 16 carbon atoms, and the total number of carbon atoms of $L^{x3}$ and $L^{x4}$ is 17 or less.

In formula (L1-3), $L^{x5}$ represents a divalent aliphatic saturated hydrocarbon group having 1 to 15 carbon atoms, $L^{x6}$ and $L^{x7}$ each independently represent a single bond or a divalent aliphatic saturated hydrocarbon group having 1 to 14 carbon atoms, and the total number of carbon atoms of $L^{x5}$, $L^{x6}$ and $L^{x7}$ is 15 or less.

In formula (L1-4), $L^{x8}$ and $L^{x9}$ represents a single bond or a divalent aliphatic saturated hydrocarbon group having 1 to 12 carbon atoms, $W^{x1}$ represents a divalent alicyclic saturated hydrocarbon group having 3 to 15 carbon atoms, and the total number of carbon atoms of $L^{x8}$, $L^{x9}$ and $W^{x1}$ is 15 or less.

$L^{x1}$ is preferably a divalent aliphatic saturated hydrocarbon group having 1 to 8 carbon atoms, and more preferably a methylene group or an ethylene group.

$L^{x2}$ is preferably a single bond or a divalent aliphatic saturated hydrocarbon group having 1 to 8 carbon atoms, and more preferably a single bond.

$L^{x3}$ is preferably a divalent aliphatic saturated hydrocarbon group having 1 to 8 carbon atoms.

$L^{x4}$ is preferably a single bond or a divalent aliphatic saturated hydrocarbon group having 1 to 8 carbon atoms.

$L^{x3}$ is preferably a divalent aliphatic saturated hydrocarbon group having 1 to 8 carbon atoms, and more preferably a methylene group or an ethylene group.

$L^{x6}$ is preferably a single bond or a divalent aliphatic saturated hydrocarbon group having 1 to 8 carbon atoms, and more preferably a methylene group or an ethylene group.

$L^{x7}$ is preferably a single bond or a divalent aliphatic saturated hydrocarbon group having 1 to 8 carbon atoms.

$L^{x8}$ is preferably a single bond or a divalent aliphatic saturated hydrocarbon group having 1 to 8 carbon atoms, and more preferably a single bond or a methylene group.

$L^{x9}$ is preferably a single bond or a divalent aliphatic saturated hydrocarbon group having 1 to 8 carbon atoms, and more preferably a single bond or a methylene group.

$W^{x1}$ is preferably a divalent alicyclic saturated hydrocarbon group having 3 to 10 carbon atoms, and more preferably a cyclohexanediyl group or an adamantanediyl group.

The group represented by formula (L1-1) includes, for example, the following divalent groups.

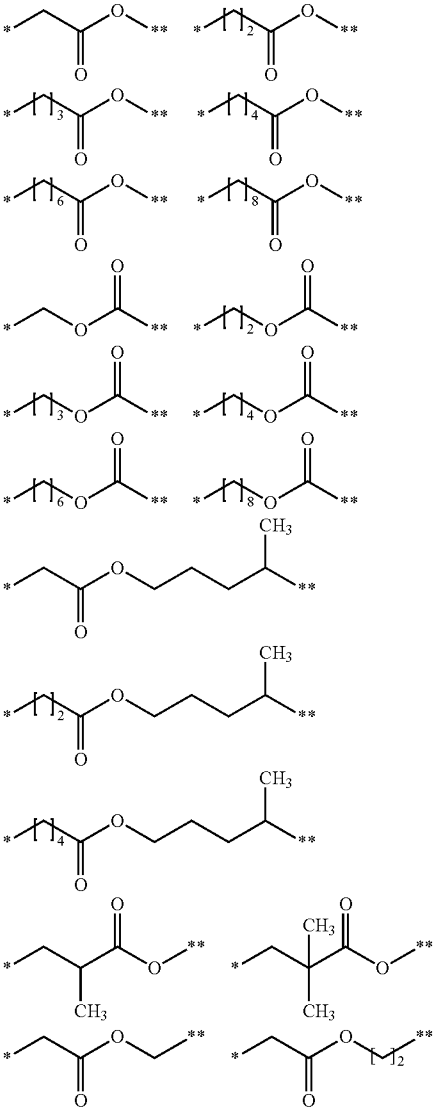

The group represented by formula (L1-2) includes, for example, the following divalent groups.

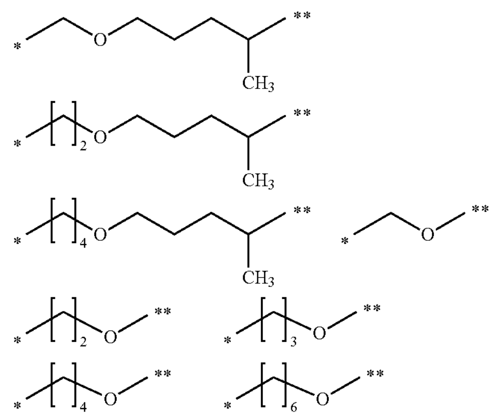

The group represented by formula (L1-3) includes, for example, the following divalent groups.

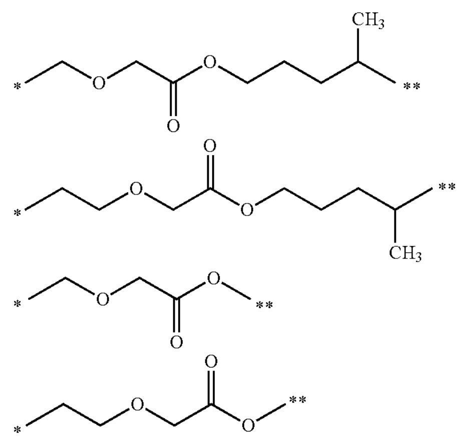

The group represented by formula (L1-4) includes, for example, the following divalent groups.

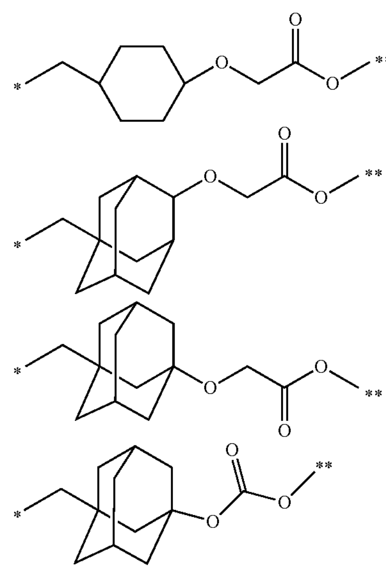

-continued
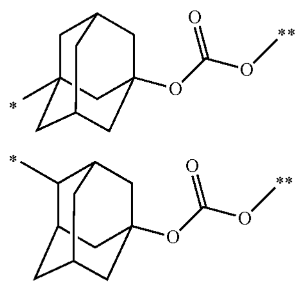
$L^{55}$ is preferably a single bond or a group represented by formula (L1-1).
Examples of the structural unit (a5-1) include the following structural units and structural units in which a methyl group corresponding to $R^{51}$ in the structural unit (a5-1) in the following structural units is substituted with a hydrogen atom.
(a5-1-1)
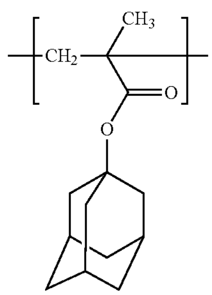
(a5-1-2)
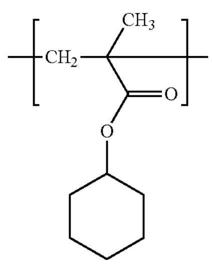
(a5-1-3)
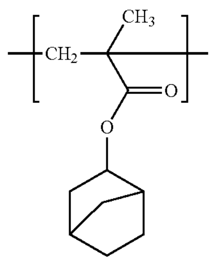
-continued
(a5-1-4)
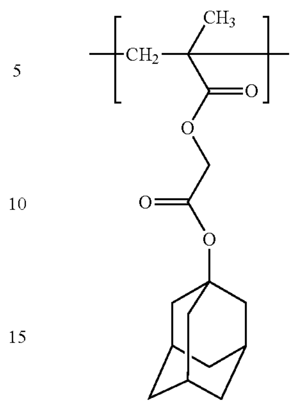
(a5-1-5)
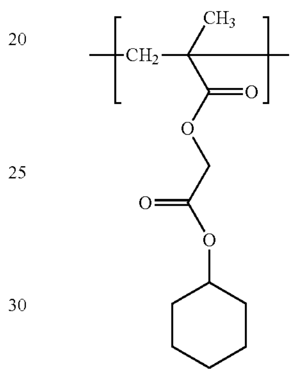
(a5-1-6)
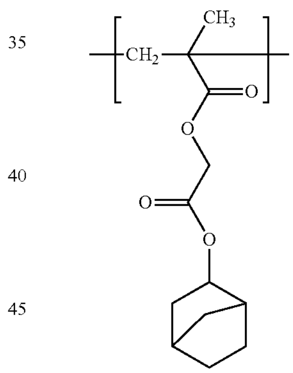
(a5-1-7)
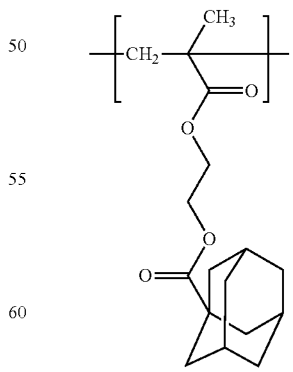

-continued
(a5-1-8)
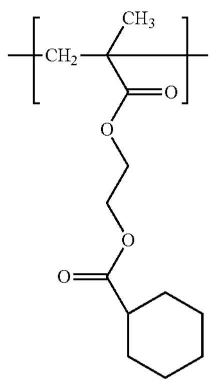
(a5-1-9)
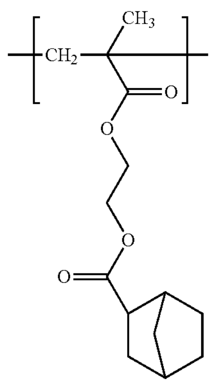
(a5-1-10)
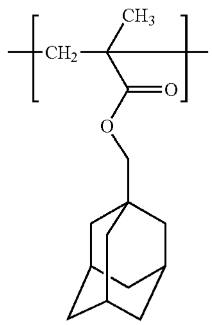
(a5-1-11)
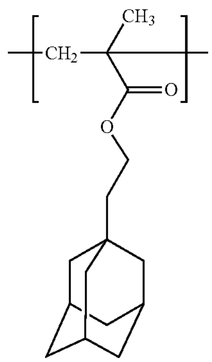
-continued
(a5-1-12)
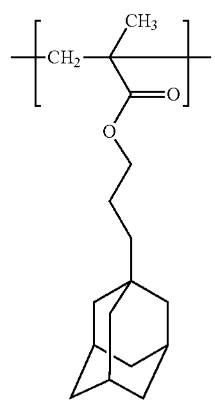
(a5-1-13)
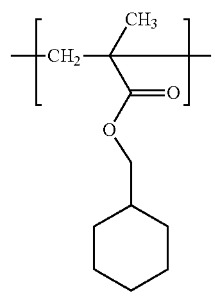
(a5-1-14)
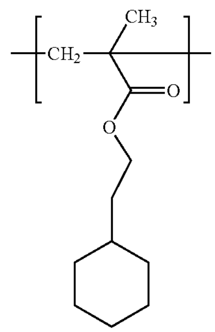
(a5-1-15)
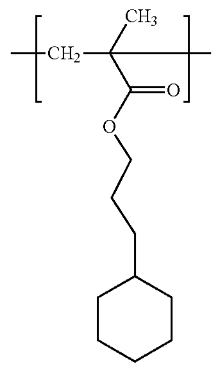

-continued (a5-1-16)

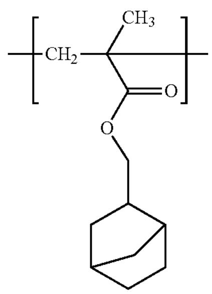

(a5-1-17)

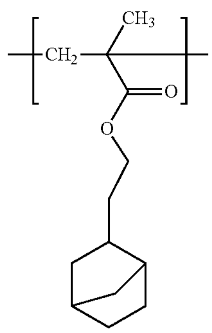

(a5-1-18)

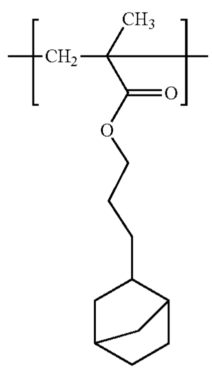

When the resin (A) includes the structural unit (a5), the content is preferably 1 to 30 mol %, more preferably 2 to 20 mol %, and still more preferably 3 to 15 mol %, based on all structural units of the resin (A).

<Structural Unit (II)>

The resin (A) may further include a structural unit which is decomposed upon exposure to radiation to generate an acid (hereinafter sometimes referred to as "structural unit (II)"). Specific examples of the structural unit (II) include the structural units mentioned in JP 2016-79235 A, and a structural unit having a sulfonate group or a carboxylate group and an organic cation in a side chain or a structural unit having a sulfonio group and an organic anion in a side chain are preferred.

The structural unit having a sulfonate group or a carboxylate group in a side chain is preferably a structural unit represented by formula (II-2-A'):

(II-2-A')

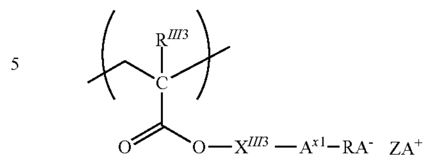

wherein, in formula (II-2-A'), $X^{III3}$ represents a divalent saturated hydrocarbon group having 1 to 18 carbon atoms, —$CH_2$— included in the saturated hydrocarbon group may be replaced by —O—, —S— or —CO—, and a hydrogen atom included in the saturated hydrocarbon group may be substituted with a halogen atom, an alkyl group having 1 to 6 carbon atoms which may have a halogen atom, or a hydroxy group, $A^{x1}$ represents an alkanediyl group having 1 to 8 carbon atoms, and a hydrogen atom included in the alkanediyl group may be substituted with a fluorine atom or a perfluoroalkyl group having 1 to 6 carbon atoms, $RA^-$ represents a sulfonate group or a carboxylate group, $R^{III3}$ represents a hydrogen atom, a halogen atom or an alkyl group having 1 to 6 carbon atoms which may have a halogen atom, and $ZA^+$ represents an organic cation.

Examples of the halogen atom represented by $R^{III3}$ include a fluorine atom, a chlorine atom, a bromine atom and an iodine atom.

Examples of the alkyl group having 1 to 6 carbon atoms which may have a halogen atom represented by $R^{III3}$ include those which are the same as the alkyl group having 1 to 6 carbon atoms which may have a halogen atom represented by $R^{a8}$.

Examples of the alkanediyl group having 1 to 8 carbon atoms represented by $A^{x1}$ include a methylene group, an ethylene group, a propane-1,3-diyl group, a butane-1,4-diyl group, a pentane-1,5-diyl group, a hexane-1,6-diyl group, an ethane-1,1-diyl group, a propane-1,1-diyl group, a propane-1,2-diyl group, a propane-2,2-diyl group, a pentane-2,4-diyl group, a 2-methylpropane-1,3-diyl group, a 2-methylpropane-1,2-diyl group, a pentane-1,4-diyl group, a 2-methylbutane-1,4-diyl group and the like.

Examples of the perfluoroalkyl group having 1 to 6 carbon atoms which may be substituted with $A^{X1}$ include a trifluoromethyl group, a perfluoroethyl group, a perfluoropropyl group, a perfluoroisopropyl group, a perfluorobutyl group, a perfluorosec-butyl group, a perfluorotert-butyl group, a perfluoropentyl group, a perfluorohexyl group and the like.

Examples of the divalent saturated hydrocarbon group having 1 to 18 carbon atoms represented by $X^{III3}$ include a linear or branched alkanediyl group, a monocyclic or a polycyclic divalent alicyclic saturated hydrocarbon group, or a combination thereof.

Specific examples thereof include linear alkanediyl groups such as a methylene group, an ethylene group, a propane-1,3-diyl group, a propane-1,2-diyl group, a butane-1,4-diyl group, a pentane-1,5-diyl group, a hexane-1,6-diyl group, a heptane-1,7-diyl group, an octane-1,8-diyl group, a nonane-1,9-diyl group, a decane-1,10-diyl group, an undecane-1,11-diyl group and a dodecane-1,12-diyl group; branched alkanediyl groups such as a butane-1,3-diyl group, a 2-methylpropane-1,3-diyl group, a 2-methylpropane-1,2-diyl group, a pentane-1,4-diyl group and a 2-methylbutane- 1,4-diyl group; cycloalkanediyl group such as a cyclobutane-1,3-diyl group, a cyclopentane-1,3-diyl group, a cyclohexane-1,4-diyl group and a cyclooctane-1,5-diyl group; and divalent polycyclic alicyclic saturated hydrocarbon groups such as a norbornane-1,4-diyl group, a norbornane-2,5-diyl group, an adamantane-1,5-diyl group and an adamantane-2,6-diyl group.

Those in which —$CH_2$— included in the saturated hydrocarbon group is replaced by —O—, —S— or —CO— include, for example, divalent groups represented by formula (X1) to formula (X53). Before replacing —$CH_2$— included in the saturated hydrocarbon group by —O—, —S— or —CO—, the number of carbon atoms is 17 or less. In the following formulas, * and ** represent a bonding site, and * represents a bonding site to $A^{x1}$.

(X1)

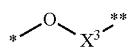

(X2)

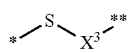

(X3)

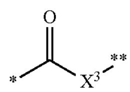

(X4)

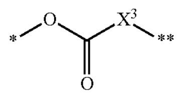

(X5)

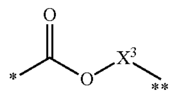

(X6)

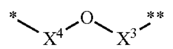

(X7)

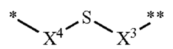

(X8)

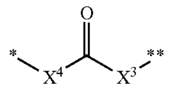

(X9)

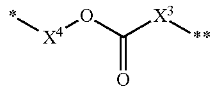

(X10)

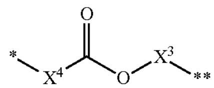

(X11)

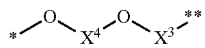

(X12)

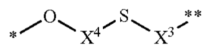

(X13)

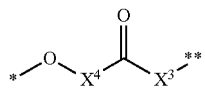

(X14)

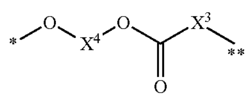

-continued (X15)

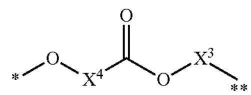

(X16)

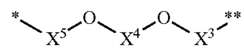

(X17)

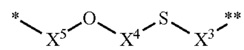

(X18)

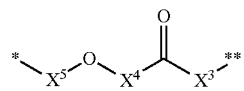

(X19)

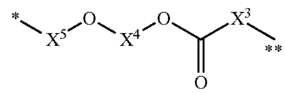

(X20)

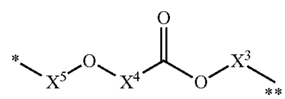

(X21)

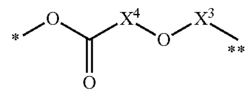

(X22)

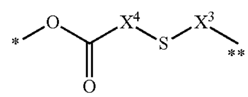

(X23)

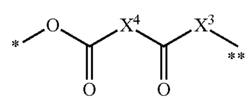

(X24)

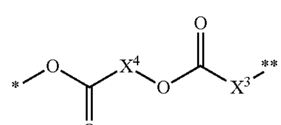

(X25)

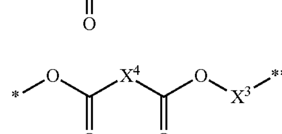

(X26)

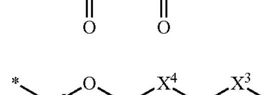

(X27)

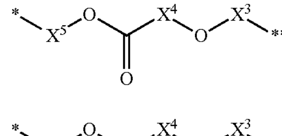

(X28)

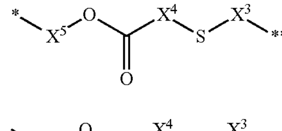

(X29)

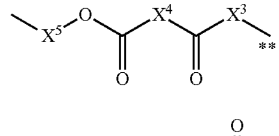

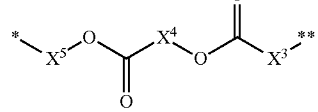

-continued (X30)

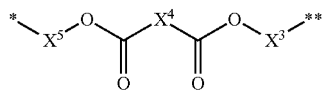

(X31)

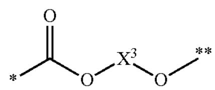

(X32)

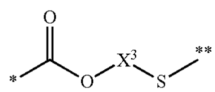

(X33)

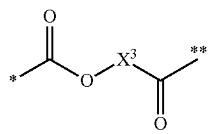

(X34)

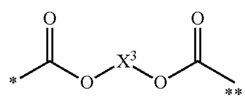

(X35)

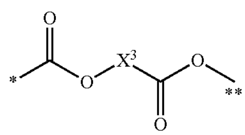

(X36)

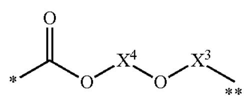

(X37)

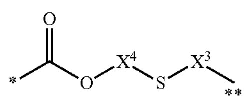

(X38)

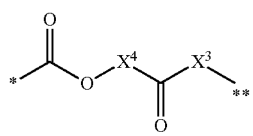

(X39)

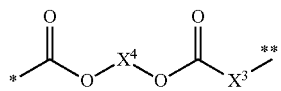

(X40)

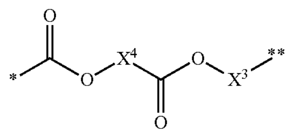

(X41)

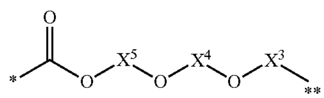

(X42)

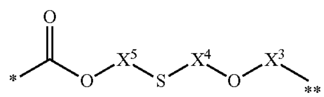

-continued (X43)

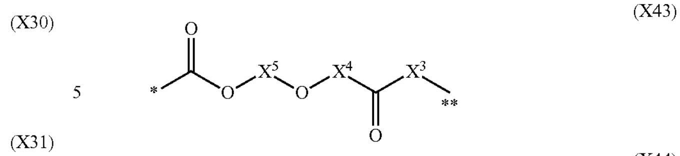

(X44)

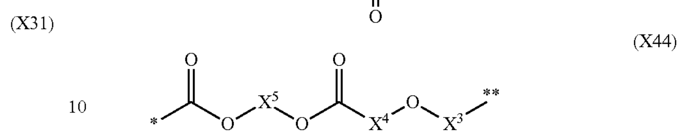

(X45)

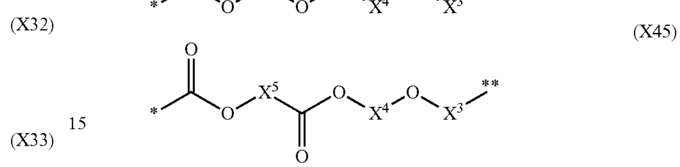

(X46)

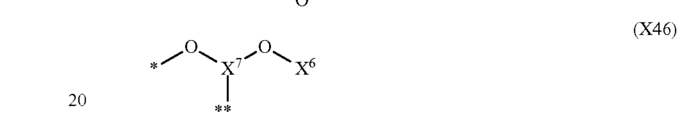

(X47)

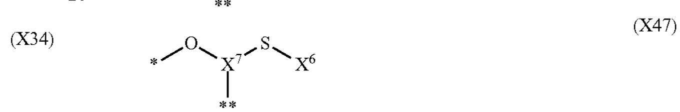

(X48)

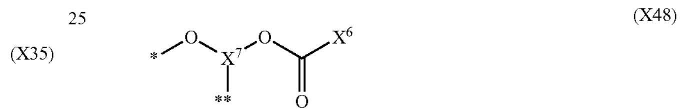

(X49)

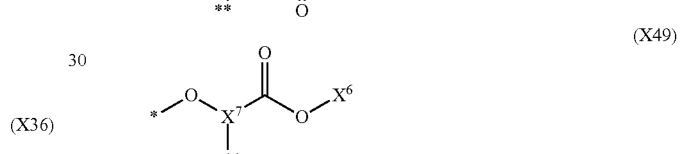

(X50)

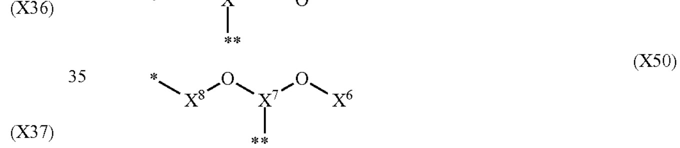

(X51)

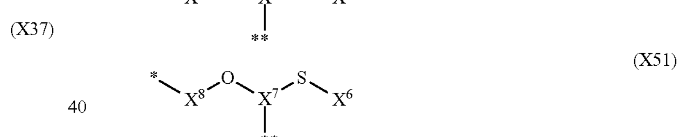

(X52)

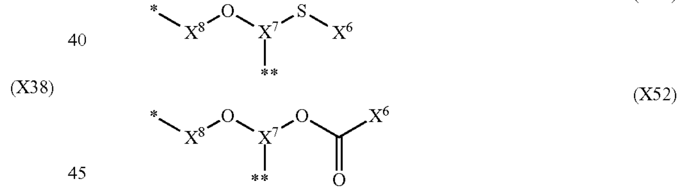

(X53)

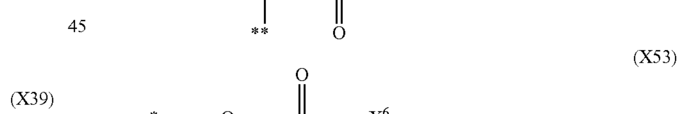

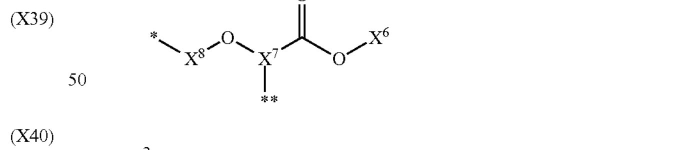

$X^3$ represents a divalent saturated hydrocarbon group having 1 to 16 carbon atoms.

$X^4$ represents a divalent saturated hydrocarbon group having 1 to 15 carbon atoms.

$X^5$ represents a divalent saturated hydrocarbon group having 1 to 13 carbon atoms.

$X^6$ represents a divalent saturated hydrocarbon group having 1 to 14 carbon atoms.

$X^7$ represents a trivalent saturated hydrocarbon group having 1 to 14 carbon atoms.

$X^8$ represents a divalent saturated hydrocarbon group having 1 to 13 carbon atoms.

Examples of the organic cation of $ZA^+$ include an organic onium cation, an organic sulfonium cation, an organic iodonium cation, an organic ammonium cation, a benzothiazolium cation and an organic phosphonium cation. Of these, an organic sulfonium cation and an organic iodonium cation are preferable, and an arylsulfonium cation is more preferable. Specific examples thereof include a cation represented by any one of formula (b2-1) to formula (b2-4) (hereinafter sometimes referred to as "cation (b2-1)" according to the number of formula).

(b2-1)

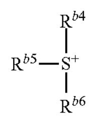

(b2-2)

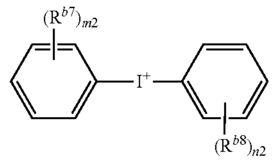

(b2-3)

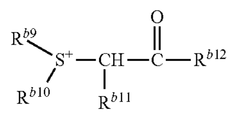

(b2-4)

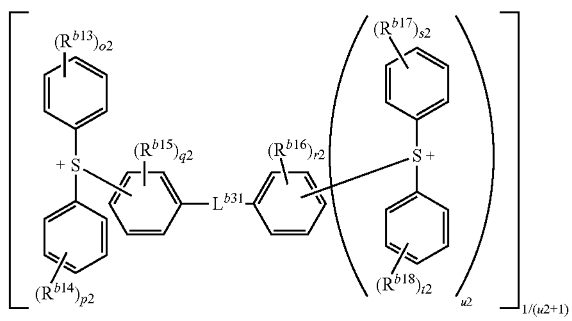

In formula (b2-1) to formula (b2-4), $R^{b4}$ to $R^{b6}$ each independently represent a chain hydrocarbon group having 1 to 30 carbon atoms, an alicyclic hydrocarbon group having 3 to 36 carbon atoms or an aromatic hydrocarbon group having 6 to 36 carbon atoms, a hydrogen atom included in the chain hydrocarbon group may be substituted with a hydroxy group, an alkoxy group having 1 to 12 carbon atoms, an alicyclic hydrocarbon group having 3 to 12 carbon atoms or an aromatic hydrocarbon group having 6 to 18 carbon atoms, a hydrogen atom included in the alicyclic hydrocarbon group may be substituted with a halogen atom, an aliphatic hydrocarbon group having 1 to 18 carbon atoms, an alkylcarbonyl group having 2 to 4 carbon atoms or a glycidyloxy group, and a hydrogen atom included in the aromatic hydrocarbon group may be substituted with a halogen atom, a hydroxy group or an alkoxy group having 1 to 12 carbon atoms, $R^{b4}$ and $R^{b5}$ may be bonded to each other to form a ring together with sulfur atoms to which $R^{b4}$ and $R^{b5}$ are bonded, and $—CH_2—$ included in the ring may be replaced by —O—, —S— or —CO—, $R^{b7}$ and $R^{b8}$ each independently represent a halogen atom, a hydroxy group, an aliphatic hydrocarbon group having 1 to 12 carbon atoms or an alkoxy group having 1 to 12 carbon atoms, m2 and n2 each independently represent an integer of 0 to 5, when m2 is 2 or more, a plurality of $R^{b7}$ may be the same or different, and when n2 is 2 or more, a plurality of $R^{b8}$ may be the same or different, $R^{b9}$ and $R^{b10}$ each independently represent a chain hydrocarbon group having 1 to 36 carbon atoms or an alicyclic hydrocarbon group having 3 to 36 carbon atoms, $R^{b9}$ and $R^{b10}$ may be bonded to each other to form a ring together with sulfur atoms to which $R^{b9}$ and $R^{b10}$ are bonded, and $—CH_2—$ included in the ring may be replaced by —O—, —S— or —CO—, $R^{b11}$ represents a hydrogen atom, a chain hydrocarbon group having 1 to 36 carbon atoms, an alicyclic hydrocarbon group having 3 to 36 carbon atoms or an aromatic hydrocarbon group having 6 to 18 carbon atoms, $R^{b12}$ represents a chain hydrocarbon group having 1 to 12 carbon atoms, an alicyclic hydrocarbon group having 3 to 18 carbon atoms or an aromatic hydrocarbon group having 6 to 18 carbon atoms, a hydrogen atom included in the chain hydrocarbon group may be substituted with an aromatic hydrocarbon group having 6 to 18 carbon atoms, and a hydrogen atom included in the aromatic hydrocarbon group may be substituted with an alkoxy group having 1 to 12 carbon atoms or an alkylcarbonyloxy group having 1 to 12 carbon atoms, $R^{b11}$ and $R^{b12}$ may be bonded to each other to form a ring, including —CH—CO— to which $R^{b11}$ and $R^{b12}$ are bonded, and $—CH_2—$ included in the ring may be replaced by —O—, —S— or —CO—, $R^{b13}$ to $R^{b18}$ each independently represent a hydroxy group, an aliphatic hydrocarbon group having 1 to 12 carbon atoms or an alkoxy group having 1 to 12 carbon atoms, $L^{b31}$ represents a sulfur atom or an oxygen atom, o2, p2, s2 and t2 each independently represent an integer of 0 to 5, q2 and r2 each independently represent an integer of 0 to 4, u2 represents 0 or 1, and when o2 is 2 or more, a plurality of $R^{b13}$ are the same or different from each other, when p2 is 2 or more, a plurality of $R^{b14}$ are the same or different from each other, when q2 is 2 or more, a plurality of $R^{b15}$ are the same or different from each other, when r2 is 2 or more, a plurality of $R^{b16}$ are the same or different from each other, when s2 is 2 or more, a plurality of $R^{b17}$ are the same or different from each other, and when t2 is 2 or more, a plurality of $R^{b18}$ are the same or different from each other.

The aliphatic hydrocarbon group represents a chain hydrocarbon group and an alicyclic hydrocarbon group.

Examples of the chain hydrocarbon group include alkyl groups such as a methyl group, an ethyl group, a propyl group, an isopropyl group, a butyl group, a sec-butyl group, a tert-butyl group, a pentyl group, a hexyl group, an octyl group and a 2-ethylhexyl group.

Particularly, the chain hydrocarbon group of $R^{b9}$ to $R^{b12}$ preferably has 1 to 12 carbon atoms.

The alicyclic hydrocarbon group may be either monocyclic or polycyclic, and examples of the monocyclic alicyclic hydrocarbon group include cycloalkyl groups such as a cyclopropyl group, a cyclobutyl group, a cyclopentyl group, a cyclohexyl group, a cycloheptyl group, a cyclooctyl group and a cyclodecyl group. Examples of the polycyclic alicyclic hydrocarbon group include a decahydronaphthyl group, an adamantyl group, a norbornyl group and the following groups.

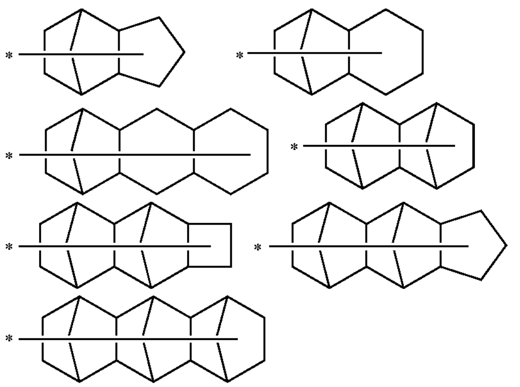

Particularly, the alicyclic hydrocarbon group of $R^{b9}$ to $R^{b12}$ preferably has 3 to 18 carbon atoms, and more preferably 4 to 12 carbon atoms.

Examples of the alicyclic hydrocarbon group in which a hydrogen atom is substituted with an aliphatic hydrocarbon group include a methylcyclohexyl group, a dimethylcyclohexyl group, a 2-methyladamantan-2-yl group, a 2-ethyladamantan-2-yl group, a 2-isopropyladamantan-2-yl group, a methylnorbornyl group, an isobornyl group and the like. In the alicyclic hydrocarbon group in which a hydrogen atom is substituted with an aliphatic hydrocarbon group, the total number of carbon atoms of the alicyclic hydrocarbon group and the aliphatic hydrocarbon group is preferably 20 or less.

Examples of the aromatic hydrocarbon group include aryl groups such as a phenyl group, a biphenyl group, a naphthyl group and a phenanthryl group. The aromatic hydrocarbon group may have a chain hydrocarbon group or an alicyclic hydrocarbon group, and examples of the aromatic hydrocarbon group having a chain hydrocarbon group include a tolyl group, a xylyl group, a cumenyl group, a mesityl group, a p-ethylphenyl group, a p-tert-butylphenyl group, a 2,6-diethylphenyl group, a 2-methyl-6-ethylphenyl group and the like, and examples of the aromatic hydrocarbon group having an alicyclic hydrocarbon group include a p-cyclohexylphenyl group, a p-adamantylphenyl group and the like.

When the aromatic hydrocarbon group has a chain hydrocarbon group or an alicyclic hydrocarbon group, a chain hydrocarbon group having 1 to 18 carbon atoms and an alicyclic hydrocarbon group having 3 to 18 carbon atoms are preferable.

Examples of the aromatic hydrocarbon group in which a hydrogen atom is substituted with an alkoxy group include a p-methoxyphenyl group and the like.

Examples of the chain hydrocarbon group in which a hydrogen atom is substituted with an aromatic hydrocarbon group include aralkyl groups such as a benzyl group, a phenethyl group, a phenylpropyl group, a trityl group, a naphthylmethyl group and a naphthylethyl group.

Examples of the alkoxy group include a methoxy group, an ethoxy group, a propoxy group, a butoxy group, a pentyloxy group, a hexyloxy group, a heptyloxy group, an octyloxy group, a decyloxy group and a dodecyloxy group.

Examples of the alkylcarbonyl group include an acetyl group, a propionyl group and a butyryl group.

Examples of the halogen atom include a fluorine atom, a chlorine atom, a bromine atom and an iodine atom.

Examples of the alkylcarbonyloxy group include a methylcarbonyloxy group, an ethylcarbonyloxy group, a propylcarbonyloxy group, an isopropylcarbonyloxy group, a butylcarbonyloxy group, a sec-butylcarbonyloxy group, a tert-butylcarbonyloxy group, a pentylcarbonyloxy group, a hexylcarbonyloxy group, an octylcarbonyloxy group and a 2-ethylhexylcarbonyloxy group.

The ring formed by bonding $R^{b4}$ and $R^{b5}$ each other, together with sulfur atoms to which $R^{b4}$ and $R^{b5}$ are bonded, may be a monocyclic, polycyclic, aromatic, nonaromatic, saturated or unsaturated ring. This ring includes a ring having 3 to 18 carbon atoms and is preferably a ring having 4 to 18 carbon atoms. The ring containing a sulfur atom includes a 3-membered to 12-membered ring and is preferably a 3-membered to 7-membered ring and includes, for example, the following rings. * represents a bonding site.

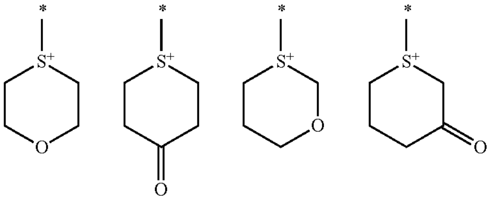

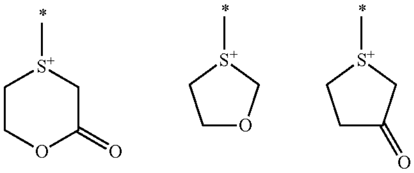

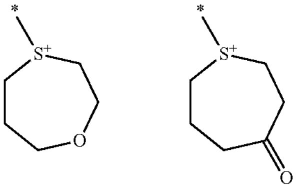

The ring formed by combining $R^{b9}$ and $R^{b10}$ together may be a monocyclic, polycyclic, aromatic, nonaromatic, saturated or unsaturated ring. This ring includes a 3-membered to 12-membered ring and is preferably a 3-membered to 7-membered ring. The ring includes, for example, a thiolan-1-ium ring (tetrahydrothiophenium ring), a thian-1-ium ring, a 1,4-oxathian-4-ium ring and the like.

The ring formed by combining $R^{b11}$ and $R^{b12}$ together may be a monocyclic, polycyclic, aromatic, nonaromatic, saturated or unsaturated ring. This ring includes a 3-membered to 12-membered ring and is preferably a 3-membered to 7-membered ring. Examples thereof include an oxocycloheptane ring, an oxocyclohexane ring, an oxonorbornane ring, an oxoadamantane ring and the like.

Of cation (b2-1) to cation (b2-4), a cation (b2-1) is preferable.

Examples of the cation (b2-1) include the following cations.

-continued
(b2-c-1)
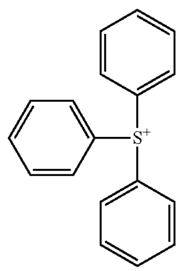
(b2-c-2)
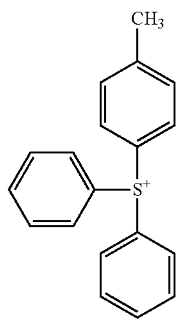
(b2-c-3)
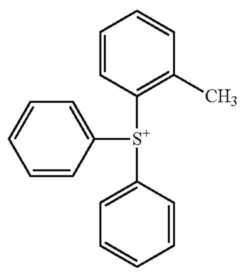
(b2-c-4)
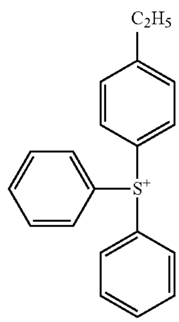
(b2-c-5)
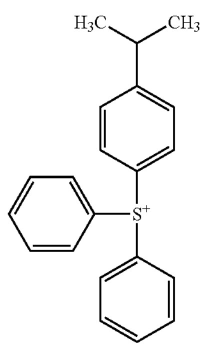
(b2-c-6)
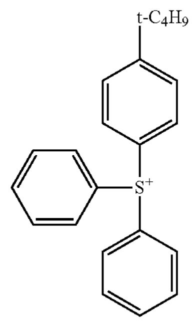
(b2-c-7)
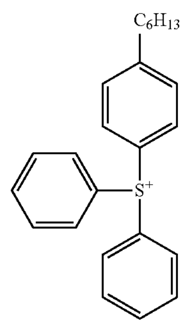
(b2-c-8)
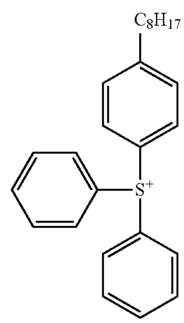
(b2-c-9)
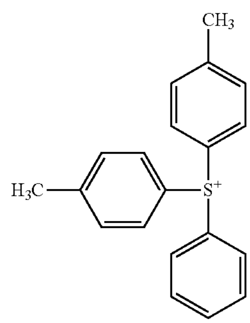

-continued
(b2-c-10)
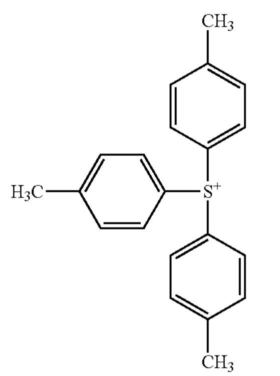
(b2-c-11)
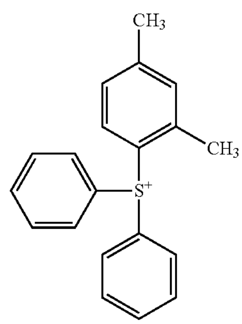
(b2-c-12)
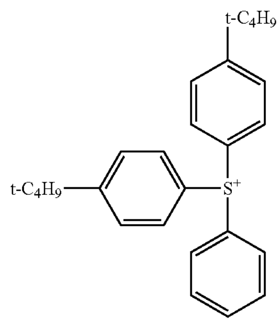
(b2-c-13)
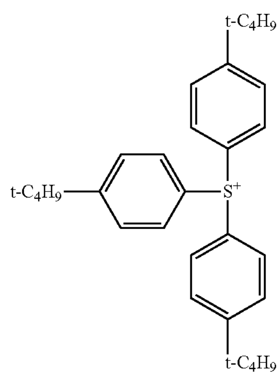
(b2-c-14)
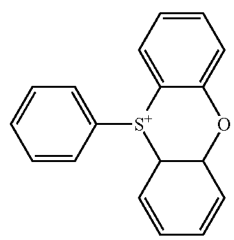
-continued
(b2-c-15)
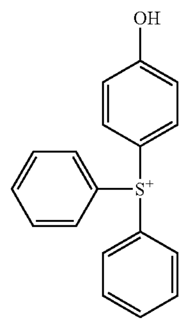
(b2-c-16)
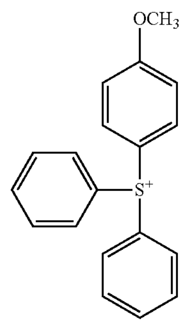
(b2-c-17)
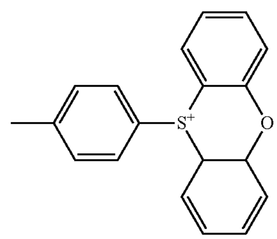
(b2-c-18)
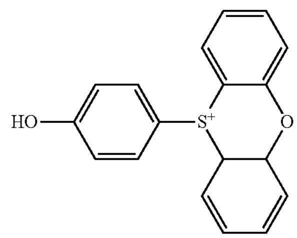
(b2-c-19)
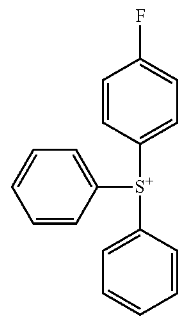

-continued
(b2-c-20)
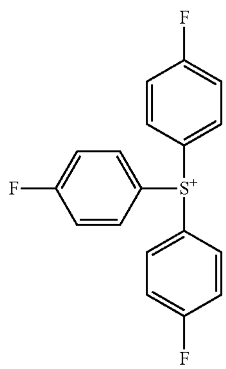
(b2-c-21)
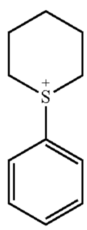
(b2-c-22)
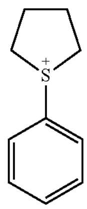
(b2-c-23)
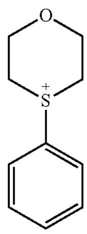
(b2-c-24)
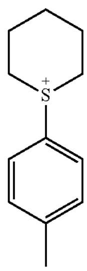
(b2-c-25)
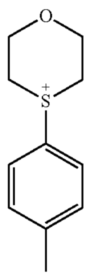
-continued
(b2-c-26)
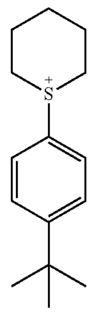
(b2-c-27)
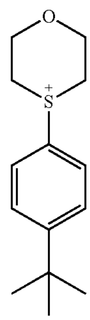
(b2-c-47)
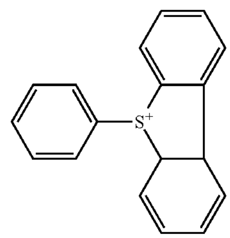
(b2-c-48)
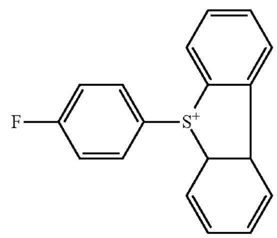
(b2-c-49)
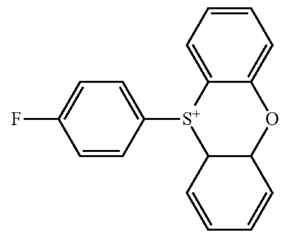
Examples of the cation (b2-2) include the following cations and the like.
(b2-c-28)
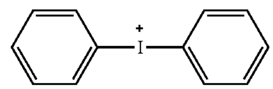

-continued
(b2-c-29)
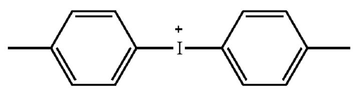
(b2-c-30)
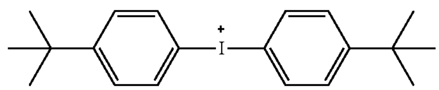
(b2-c-50)
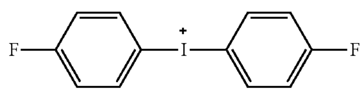
Examples of the cation (b2-3) include the following cations and the like.
(b2-c-31)
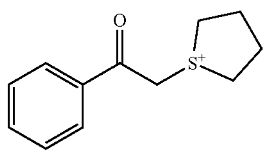
(b2-c-32)
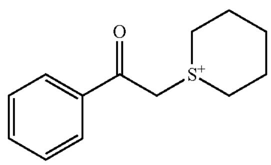
(b2-c-33)
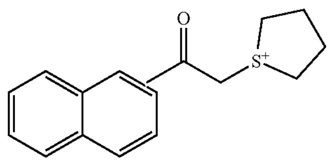
(b2-c-34)
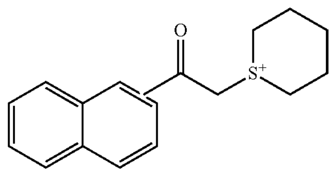
Examples of the cation (b2-4) include the following cations and the like.
(b2-c-35)
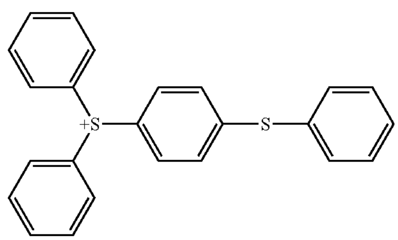
-continued
(b2-c-36)
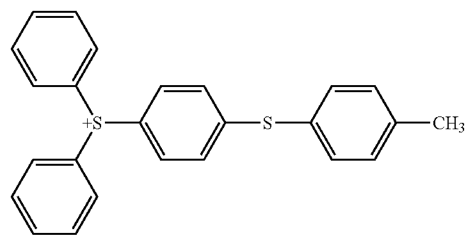
(b2-c-37)
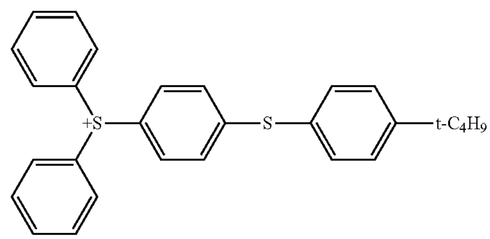
(b2-c-38)
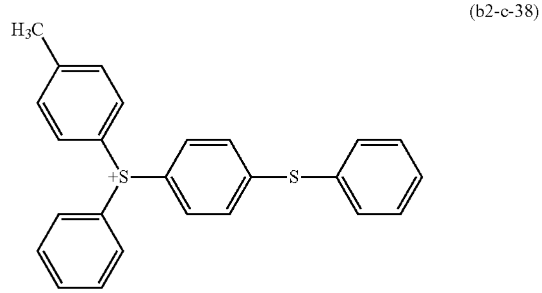
(b2-c-39)
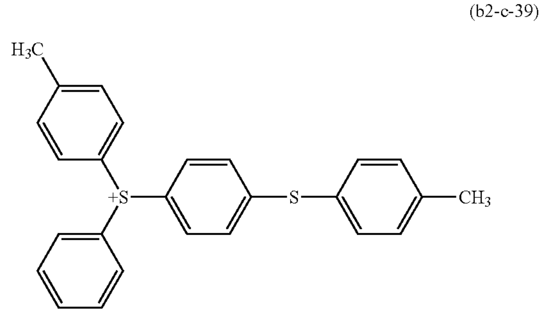
(b2-c-40)
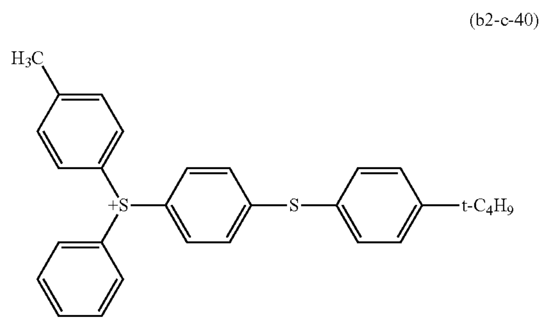

-continued (b2-c-41)

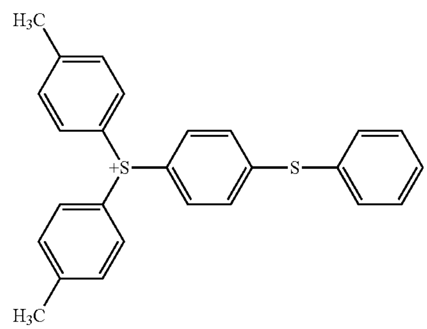

(b2-c-42)

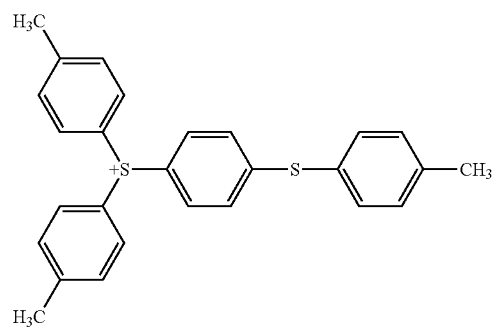

(b2-c-43)

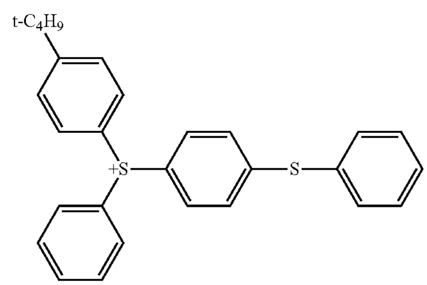

(b2-c-44)

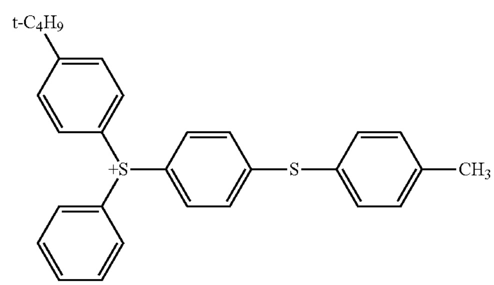

(b2-c-45)

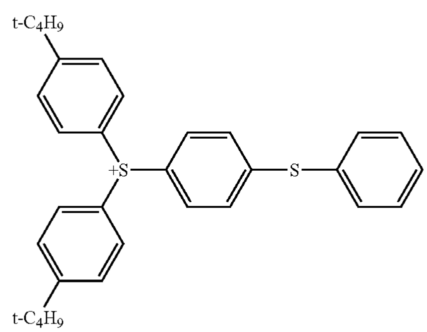

-continued (b2-c-46)

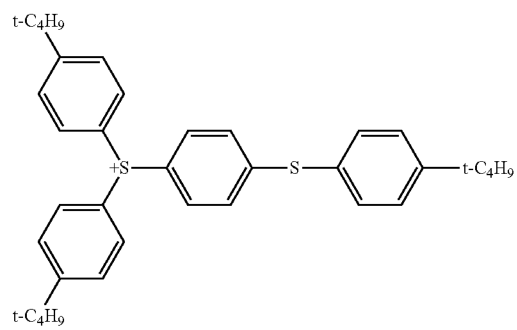

The structural unit represented by formula (II-2-A') is preferably a structural unit represented by formula (II-2-A):

(II-2-A)

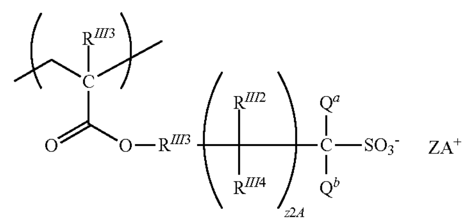

wherein, in formula (II-2-A), $R^{III3}$, $X^{III3}$ and $ZA^+$ are the same as defined above, z2A represents an integer of 0 to 6, $R^{III2}$ and $R^{III4}$ each independently represent a hydrogen atom, a fluorine atom or a perfluoroalkyl group having 1 to 6 carbon atoms, and when z2A is 2 or more, a plurality of $R^{III2}$ and $R^{III4}$ may be the same or different from each other, and $Q^a$ and $Q^b$ each independently represent a fluorine atom or a perfluoroalkyl group having 1 to 6 carbon atoms.

Examples of the perfluoroalkyl group having 1 to 6 carbon atoms represented by $R^{III2}$, $R^{III4}$, $Q^a$ and $Q^b$ include those which are the same as the perfluoroalkyl group having 1 to 6 carbon atoms represented by $Q^{b1}$ mentioned below.

The structural unit represented by formula (II-2-A) is preferably a structural unit represented by formula (II-2-A-1):

(II-2-A-1)

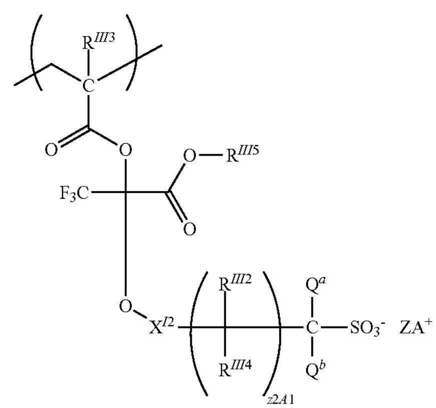

wherein, in formula (II-2-A-1), $R^{III2}$, $R^{III3}$, $R^{III4}$, $Q^a$, $Q^b$ and $ZA^+$ are the same as defined above, $R^{III5}$ represents a saturated hydrocarbon group having 1 to 12 carbon atoms, z2A1 represents an integer of 0 to 6, and $X^{I2}$ represents a divalent saturated hydrocarbon group having 1 to 11 carbon atoms, $—CH_2—$ included in the saturated hydrocarbon group may be replaced by —O—, —S— or —CO—, and a hydrogen atom included in the saturated hydrocarbon group may be substituted with a halogen atom or a hydroxy group.

Examples of the saturated hydrocarbon group having 1 to 12 carbon atoms represented by $R^{III5}$ include linear or branched alkyl groups such as a methyl group, an ethyl group, a propyl group, an isopropyl group, a butyl group, a sec-butyl group, a tert-butyl group, a pentyl group, a hexyl group, a heptyl group, an octyl group, a nonyl group, a decyl group, an undecyl group and a dodecyl group.

Examples of the divalent saturated hydrocarbon group represented by $X^{I2}$ include those which are the same as the divalent saturated hydrocarbon group represented by $X^{III3}$.

The structural unit represented by formula (II-2-A-1) is more preferably a structural unit represented by formula (II-2-A-2):

(II-2-A-2)

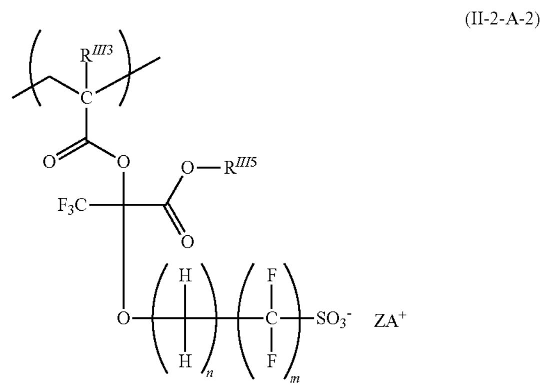

wherein, in formula (II-2-A-2), $R^{III3}$, $R^{III5}$ and $ZA^+$ are the same as defined above, and m and n each independently represent 1 or 2.

The structural unit represented by formula (II-2-A') includes, for example, the following structural units, structural units in which a group corresponding to a methyl group of $R^{III3}$ is substituted with a hydrogen atom, a halogen atom (e.g., fluorine atom) or an alkyl group having 1 to 6 carbon atoms which may have a halogen atom (e.g., trifluoromethyl group, etc.) or the like and the structural units mentioned in WO 2012/050015 A. $ZA^+$ represents an organic cation.

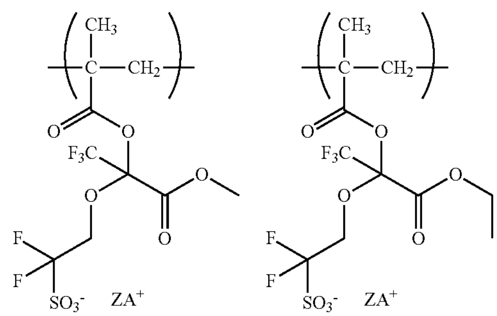

-continued

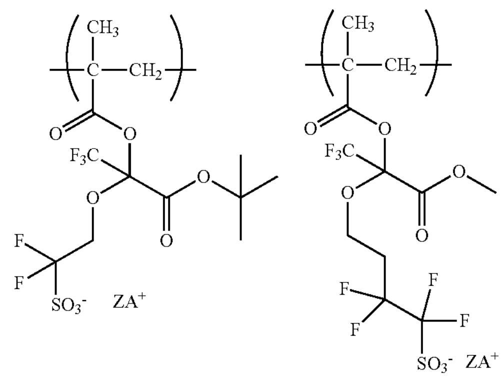

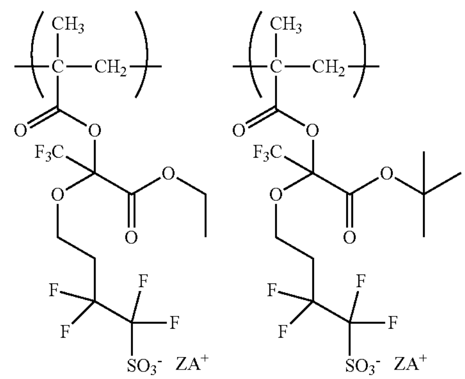

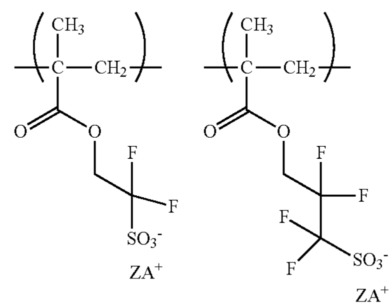

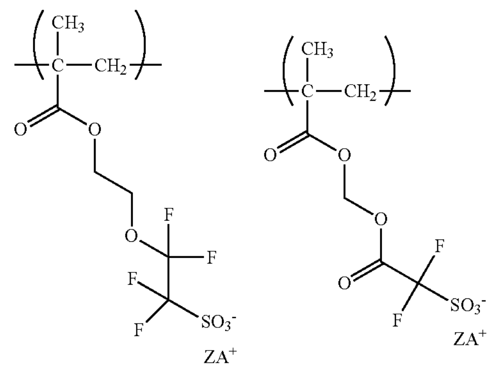

-continued

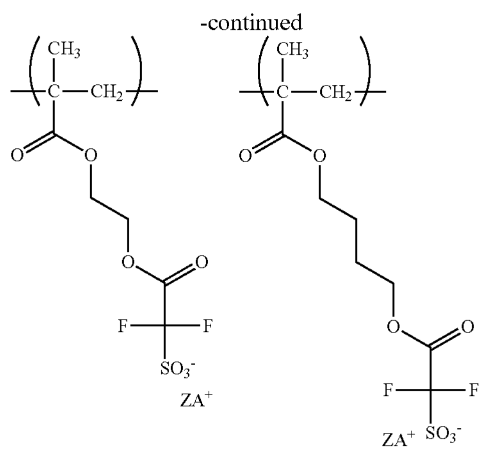

The structural unit having a sulfonio group and an organic anion in a side chain is preferably a structural unit represented by formula (II-1-1):

(II-1-1)

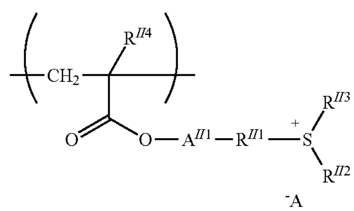

wherein, in formula (II-1-1), $A^{II1}$ represents a single bond or a divalent linking group, $R^{II1}$ represents a divalent aromatic hydrocarbon group having 6 to 18 carbon atoms, $R^{II2}$ and $R^{II3}$ each independently represent a hydrocarbon group having 1 to 18 carbon atoms, and $R^{II2}$ and $R^{II3}$ may be bonded to each other to form a ring together with sulfur atoms to which $R^{II2}$ and $R^{II3}$ are bonded, $R^{II4}$ represents a hydrogen atom, a halogen atom or an alkyl group having 1 to 6 carbon atoms which may have a halogen atom, and $A^-$ represents an organic anion.

Examples of the divalent aromatic hydrocarbon group having 6 to 18 carbon atoms represented by $R^{II1}$ include a phenylene group and a naphthylene group.

Examples of the hydrocarbon group represented by $R^{II2}$ and $R^{II3}$ include an alkyl group, an alicyclic hydrocarbon group, an aromatic hydrocarbon group, and groups formed by combining these groups. Specifically, those which are the same as the hydrocarbon group in $R^{a1'}$, $R^{a2'}$ and $R^{a3'}$ are exemplified.

Examples of the halogen atom represented by $R^{II4}$ include a fluorine atom, a chlorine atom, a bromine atom and an iodine atom.

Examples of the alkyl group having 1 to 6 carbon atoms which may have a halogen atom represented by $R^{II4}$ include those which are the same as the alkyl group having 1 to 6 carbon atoms which may have a halogen atom represented by $R^{a8}$.

Examples of the divalent linking group represented by $A^{II1}$ include a divalent saturated hydrocarbon group having 1 to 18 carbon atoms, and —$CH_2$— included in the divalent saturated hydrocarbon group may be replaced by —O—, —S— or —CO—. Specific examples thereof include those which are the same as the divalent saturated hydrocarbon group having 1 to 18 carbon atoms represented by $X^{III3}$.

Examples of the structural unit including a cation in formula (II-1-1) include the following structural units and structural units in which a group corresponding to $R^{II4}$ is substituted with a hydrogen atom, a fluorine atom, a trifluoromethyl group or the like.

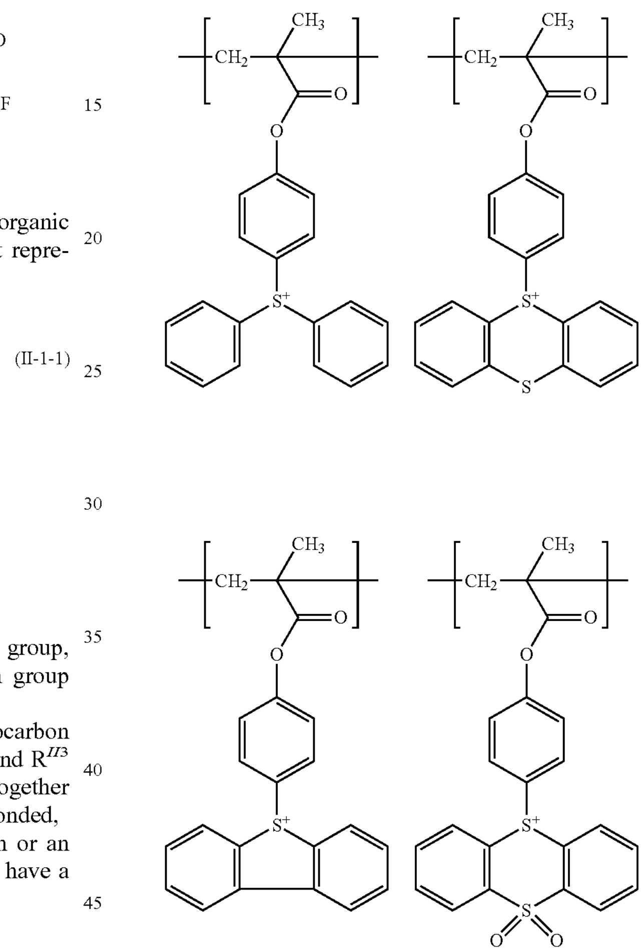

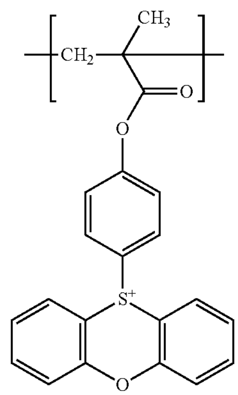

-continued

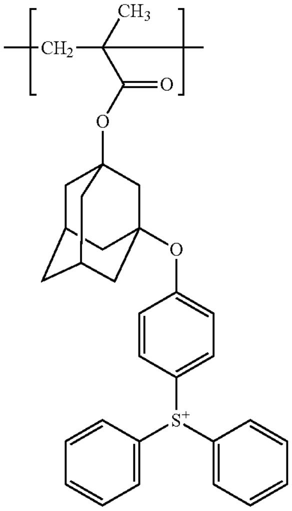

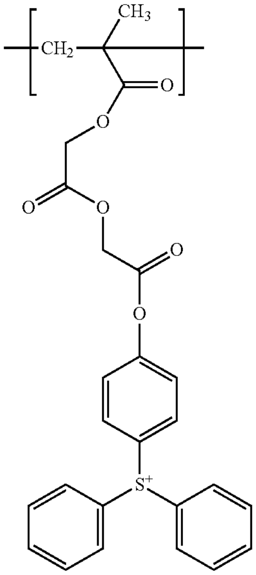

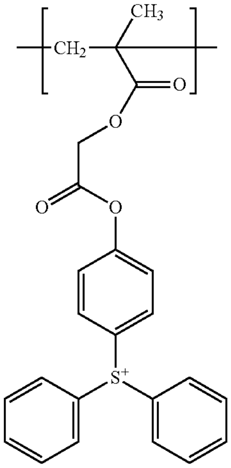

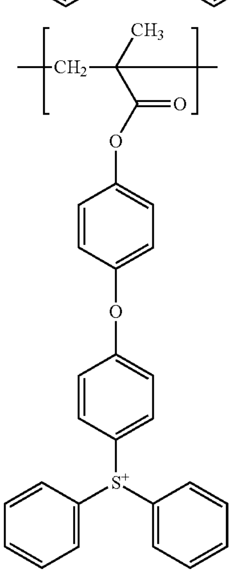

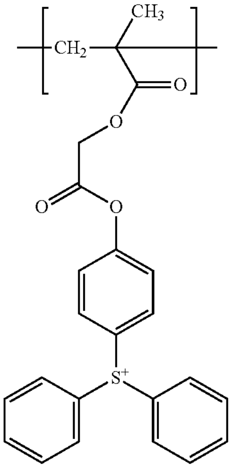

-continued

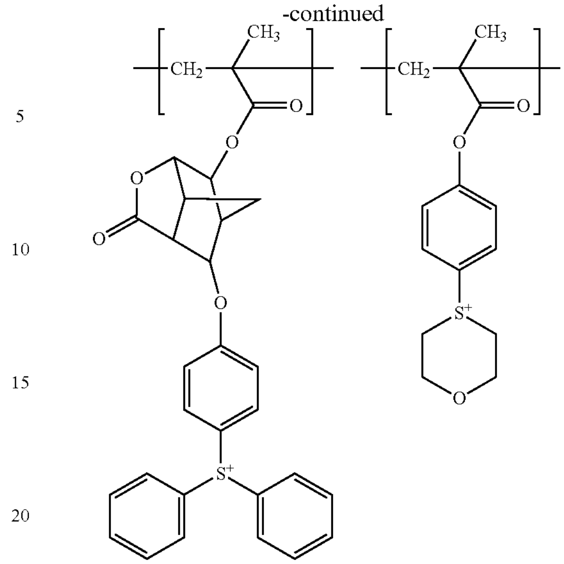

Examples of the organic anion represented by $A^-$ include a sulfonic acid anion, a sulfonylimide anion, a sulfonylmethide anion and a carboxylic acid anion. The organic anion represented by $A^-$ is preferably a sulfonic acid anion, and the sulfonic acid anion is more preferably an anion contained in a salt represented by the below-mentioned formula (B1).

Examples of the sulfonylimide anion represented by $A^-$ include the following.

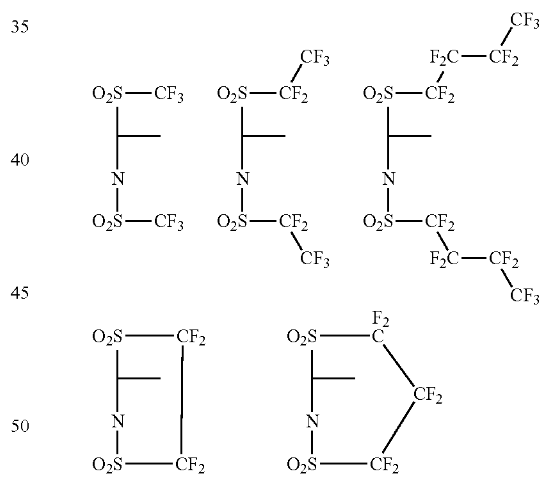

Examples of the sulfonylmethide anion include the following.

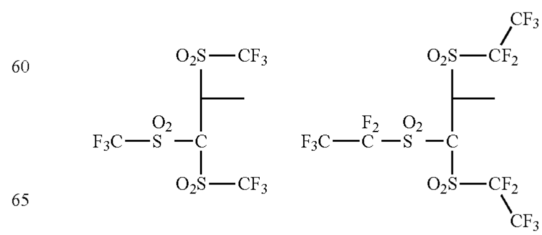

-continued
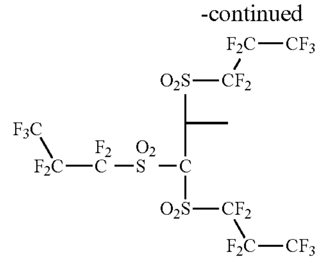
Examples of the carboxylic acid anion include the following.
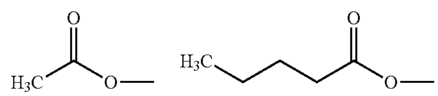
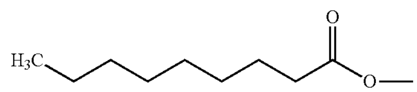
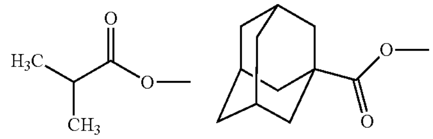
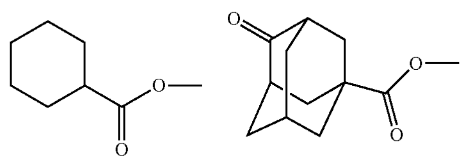
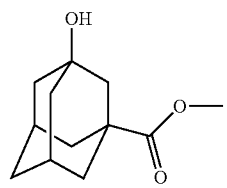
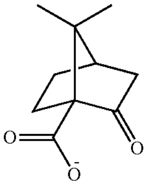
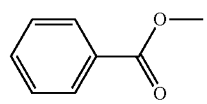
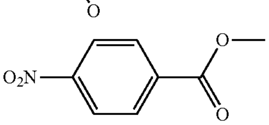
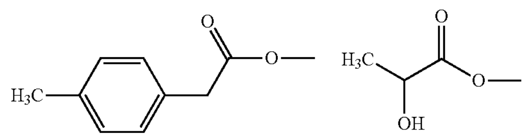
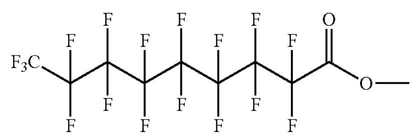
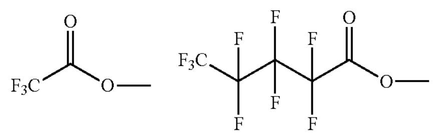
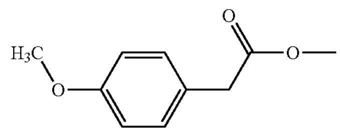
-continued
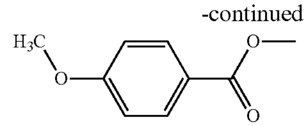
Examples of the structural unit represented by formula (II-1-1) include structural units represented by the following formulas.
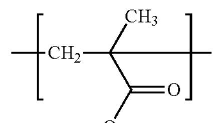
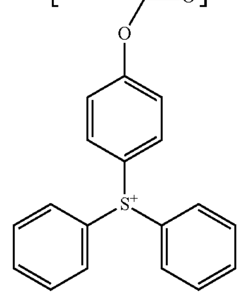
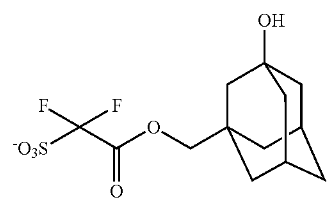
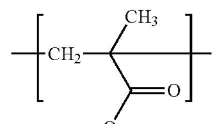
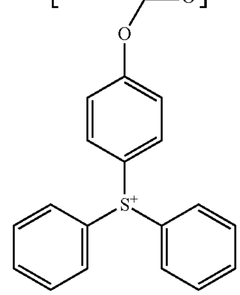
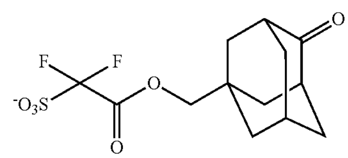

-continued
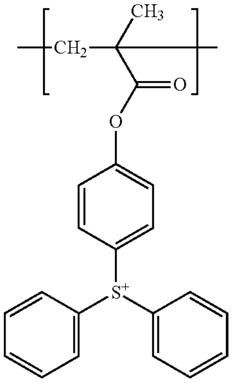
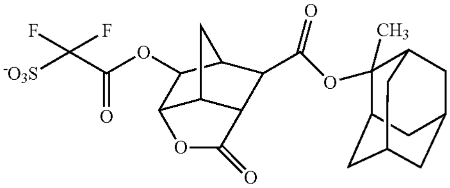
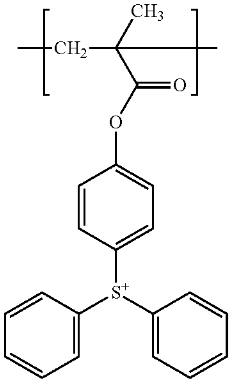
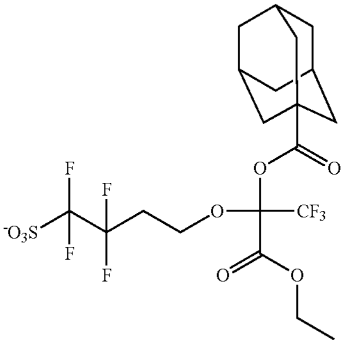
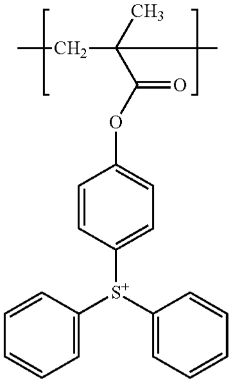
-continued
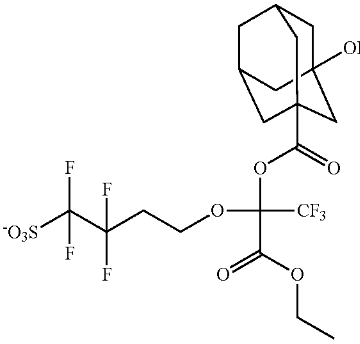
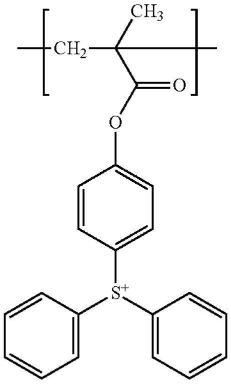
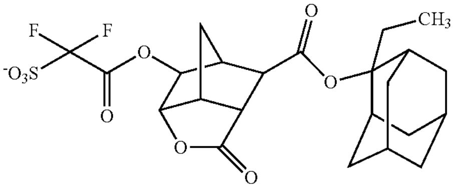
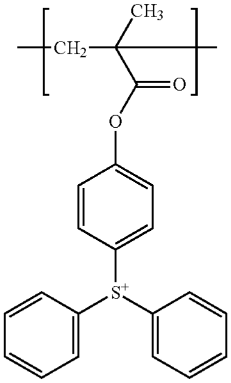
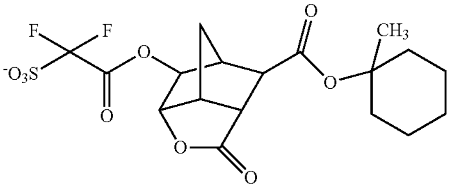

-continued

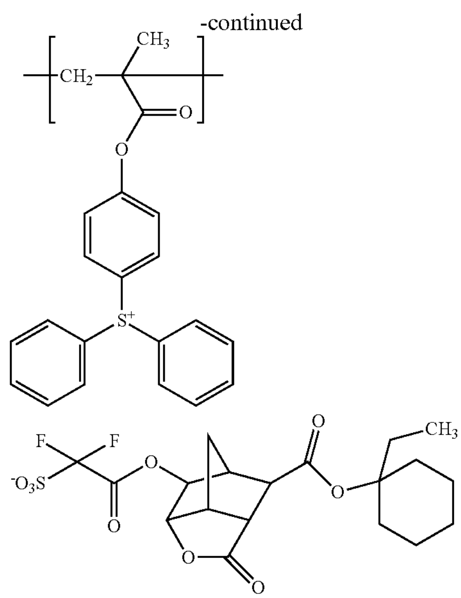

When the structural unit (II) is included in the resin (A), the content of the structural unit (II) is preferably 1 to 20 mol %, more preferably 2 to 15 mol %, and still more preferably 3 to 10 mol %, based on all structural units of the resin (A).

The resin (A) may include structural units other than the structural units mentioned above, and examples of such structural unit include structural units well-known in the art.

The resin (A) is preferably a resin composed of a structural unit (a1) and a structural unit (s), i.e., a copolymer of a monomer (a1) and a monomer (s).

The structural unit (a1) is preferably at least one selected from the group consisting of a structural unit (a1-0), a structural unit (a1-1) and a structural unit (a1-2) (preferably the structural unit having a cyclohexyl group, and a cyclopentyl group), more preferably at least two, and still more preferably at least two selected from the group consisting of a structural unit (a1-1) and a structural unit (a1-2).

The structural unit (s) is preferably at least one selected from the group consisting of a structural unit (a2) and a structural unit (a3). The structural unit (a2) is preferably a structural unit (a2-1) or a structural unit (a2-A). The structural unit (a3) is preferably at least one selected from the group consisting of a structural unit represented by formula (a3-1), a structural unit represented by formula (a3-2) and a structural unit represented by formula (a3-4).

The respective structural units constituting the resin (A) may be used alone, or two or more structural units may be used in combination. Using a monomer from which these structural units are derived, it is possible to produce by a known polymerization method (e.g. radical polymerization method). The content of the respective structural units included in the resin (A) can be adjusted according to the amount of the monomer used in the polymerization.

The weight-average molecular weight of the resin (A) is preferably 2,000 or more (more preferably 2,500 or more, and still more preferably 3,000 or more), and 50,000 or less (more preferably 30,000 or less, and still more preferably 15,000 or less). In the present specification, the weight-average molecular weight is a value determined by gel permeation chromatography under the conditions mentioned in Examples.

<Resin Other than Resin (A)>

In the resist composition of the present invention, resins other than the resin (A) may be used in combination.

The resin other than the resin (A) includes, for example, a resin including a structural unit (a4) or a structural unit (a5) (hereinafter sometimes referred to as resin (X)).

The resin (X) is preferably a resin including a structural unit (a4), particularly.

In the resin (X), the content of the structural unit (a4) is preferably 30 mol % or more, more preferably 40 mol % or more, and still more preferably 45 mol % or more, based on the total of all structural units of the resin (X).

Examples of the structural unit, which may be further included in the resin (X), include a structural unit (a1), a structural unit (a2), a structural unit (a3) and structural units derived from other known monomers. Particularly, the resin (X) is preferably a resin composed only of a structural unit (a4) and/or a structural unit (a5).

The respective structural unit constituting the resin (X) may be used alone, or two or more structural units may be used in combination. Using a monomer from which these structural units are derived, it is possible to produce by a known polymerization method (e.g. radical polymerization method). The content of the respective structural units included in the resin (X) can be adjusted according to the amount of the monomer used in the polymerization.

The weight-average molecular weight of the resin (X) is preferably 6,000 or more (more preferably 7,000 or more) and 80,000 or less (more preferably 60,000 or less). The measurement means of the weight-average molecular weight of the resin (X) is the same as in the case of the resin (A).

When the resist composition of the present invention includes the resin (X), the content is preferably 1 to 60 parts by mass, more preferably 1 to 50 parts by mass, still more preferably 1 to 40 parts by mass, yet more preferably 1 to 30 parts by mass, and particularly preferably 1 to 8 parts by mass, based on 100 parts by mass of the resin (A).

The content of the resin (A) in the resist composition is preferably 80% by mass or more and 99% by mass or less, and more preferably 90% by mass or more and 99% by mass or less, based on the solid component of the resist composition. When including resins other than the resin (A), the total content of the resin (A) and resins other than the resin (A) is preferably 80% by mass or more and 99% by mass or less, and more preferably 90% by mass or more and 99% by mass or less, based on the solid component of the resist composition. The solid component of the resist composition and the content of the resin thereto can be measured by a known analysis means such as liquid chromatography or gas chromatography.

<Acid Generator (B)>

Either nonionic or ionic acid generator may be used as the acid generator (B). Examples of the nonionic acid generator include sulfonate esters (e.g., 2-nitrobenzyl ester, aromatic sulfonate, oxime sulfonate, N-sulfonyloxyimide, sulfonyloxyketone, diazonaphthoquinone 4-sulfonate), sulfones (e.g., disulfone, ketosulfone, sulfonyldiazomethane) and the like. Typical examples of the ionic acid generator include onium salts containing an onium cation (e.g., diazonium salt, phosphonium salt, sulfonium salt, iodonium salt). Examples of the anion of the onium salt include sulfonic acid anion, sulfonylimide anion, sulfonylmethide anion and the like.

Specific examples of the acid generator (B) include compounds generating an acid upon exposure to radiation mentioned in JP 63-26653 A, JP 55-164824 A, JP 62-69263 A, JP 63-146038 A, JP 63-163452 A, JP 62-153853 A, JP 63-146029 A, U.S. Pat. Nos. 3,779,778, 3,849,137, DE Patent No. 3914407 and EP Patent No. 126,712. Compounds produced by a known method may also be used. Two or more acid generators (B) may also be used in combination.

The acid generator (B) is preferably a fluorine-containing acid generator, and more preferably a salt represented by formula (B1) (hereinafter sometimes referred to as "acid generator (B1)"):

(B1)

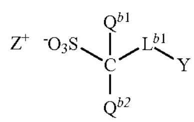

wherein, in formula (B1), $Q^{b1}$ and $Q^{b2}$ each independently represent a fluorine atom or a perfluoroalkyl group having 1 to 6 carbon atoms, $L^{b1}$ represents a divalent saturated hydrocarbon group having 1 to 24 carbon atoms, —$CH_2$— included in the divalent saturated hydrocarbon group may be replaced by —O— or —CO—, and a hydrogen atom included in the divalent saturated hydrocarbon group may be substituted with a fluorine atom or a hydroxy group, Y represents a methyl group which may have a substituent or an alicyclic hydrocarbon group having 3 to 24 carbon atoms which may have a substituent, and —$CH_2$— included in the alicyclic hydrocarbon group may be replaced by —O—, —$S(O)_2$— or —CO—, and $Z^+$ represents an organic cation.

Examples of the perfluoroalkyl group represented by $Q^{b1}$ and $Q^{b2}$ include a trifluoromethyl group, a perfluoroethyl group, a perfluoropropyl group, a perfluoroisopropyl group, a perfluorobutyl group, a perfluorosec-butyl group, a perfluorotert-butyl group, a perfluoropentyl group and a perfluorohexyl group.

Preferably, $Q^{b1}$ and $Q^{b2}$ are each independently a fluorine atom or a trifluoromethyl group, and more preferably, both are fluorine atoms.

Examples of the divalent saturated hydrocarbon group in $L^{b1}$ include a linear alkanediyl group, a branched alkanediyl group, and a monocyclic or polycyclic divalent alicyclic saturated hydrocarbon group, or the divalent saturated hydrocarbon group may be a group formed by combining two or more of these groups.

Examples of the divalent saturated hydrocarbon group in $L^{b1}$ include a linear alkanediyl group, a branched alkanediyl group, and a monocyclic or polycyclic divalent alicyclic saturated hydrocarbon group, or the divalent saturated hydrocarbon group may be a group formed by combining two or more of these groups.

Specific examples thereof include linear alkanediyl groups such as a methylene group, an ethylene group, a propane-1,3-diyl group, a butane-1,4-diyl group, a pentane-1,5-diyl group, a hexane-1,6-diyl group, a heptane-1,7-diyl group, an octane-1,8-diyl group, a nonane-1,9-diyl group, a decane-1,10-diyl group, an undecane-1,11-diyl group, a dodecane-1,12-diyl group, a tridecane-1,13-diyl group, a tetradecane-1,14-diyl group, a pentadecane-1,15-diyl group, a hexadecane-1,16-diyl group and a heptadecane-1,17-diyl group;

branched alkanediyl groups such as an ethane-1,1-diyl group, a propane-1,1-diyl group, a propane-1,2-diyl group, a propane-2,2-diyl group, a pentane-2,4-diyl group, a 2-methylpropane-1,3-diyl group, a 2-methylpropane-1,2-diyl group, a pentane-1,4-diyl group and a 2-methylbutane-1,4-diyl group;

monocyclic divalent alicyclic saturated hydrocarbon groups which are cycloalkanediyl groups such as a cyclobutane-1,3-diyl group, a cyclopentane-1,3-diyl group, a cyclohexane-1,4-diyl group and a cyclooctane-1,5-diyl group; and polycyclic divalent alicyclic saturated hydrocarbon groups such as a norbornane-1,4-diyl group, a norbornane-2,5-diyl group, an adamantane-1,5-diyl group and an adamantane-2,6-diyl group.

The group in which —$CH_2$— included in the divalent saturated hydrocarbon group represented by $L^{b1}$ is replaced by —O— or —CO— includes, for example, a group represented by any one of formula (b1-1) to formula (b1-3). In groups represented by formula (b1-1) to formula (b1-3) and groups represented by formula (b1-4) to formula (b1-11) which are specific examples thereof, * and ** represent a bonding site, and * represents a bonding site to —Y.

(b1-1)

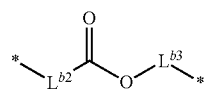

(b1-2)

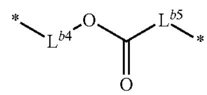

(b1-3)

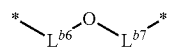

In formula (b1-1), $L^{b2}$ represents a single bond or a divalent saturated hydrocarbon group having 1 to 22 carbon atoms, and a hydrogen atom included in the saturated hydrocarbon group may be substituted with a fluorine atom, $L^{b3}$ represents a single bond or a divalent saturated hydrocarbon group having 1 to 22 carbon atoms, a hydrogen atom included in the saturated hydrocarbon group may be substituted with a fluorine atom or a hydroxy group, and —$CH_2$— included in the saturated hydrocarbon group may be replaced by —O— or —CO—, and the total number of carbon atoms of $L^{b2}$ and $L^{b3}$ is 22 or less.

In formula (b1-2), $L^{b4}$ represents a single bond or a divalent saturated hydrocarbon group having 1 to 22 carbon atoms, and a hydrogen atom included in the saturated hydrocarbon group may be substituted with a fluorine atom, $L^{b5}$ represents a single bond or a divalent saturated hydrocarbon group having 1 to 22 carbon atoms, a hydrogen atom included in the saturated hydrocarbon group may be substituted with a fluorine atom or a hydroxy group, and —$CH_2$— included in the saturated hydrocarbon group may be replaced by —O— or —CO—, and the total number of carbon atoms of $L^{b4}$ and $L^{b5}$ is 22 or less.

In formula (b1-3), $L^{b6}$ represents a single bond or a divalent saturated hydrocarbon group having 1 to 23 carbon atoms, a hydrogen atom included in the saturated hydrocarbon group may be substituted with a fluorine atom or a hydroxy group, $L^{b7}$ represents a single bond or a divalent saturated hydrocarbon group having 1 to 23 carbon atoms, a hydrogen atom included in the saturated hydrocarbon group may be substituted with a fluorine atom or a hydroxy group, and —$CH_2$— included in the saturated hydrocarbon group may be replaced by —O— or —CO—, and the total number of carbon atoms of $L^{b6}$ and $L^{b7}$ is 23 or less.

In groups represented by formula (b1-1) to formula (b1-3), when —$CH_2$— included in the saturated hydrocarbon group is replaced by —O— or —CO—, the number of carbon atoms before replacement is taken as the number of carbon atoms of the saturated hydrocarbon group.

Examples of the divalent saturated hydrocarbon group include those which are the same as the divalent saturated hydrocarbon group of $L^{b1}$.

$L^{b2}$ is preferably a single bond.

$L^{b3}$ is preferably a divalent saturated hydrocarbon group having 1 to 4 carbon atoms.

$L^{b4}$ is preferably a divalent saturated hydrocarbon group having 1 to 8 carbon atoms, and a hydrogen atom included in the divalent saturated hydrocarbon group may be substituted with a fluorine atom.

$L^{b5}$ is preferably a single bond or a divalent saturated hydrocarbon group having 1 to 8 carbon atoms.

$L^{b6}$ is preferably a single bond or a divalent saturated hydrocarbon group having 1 to 4 carbon atoms, and a hydrogen atom included in the saturated hydrocarbon group may be substituted with a fluorine atom.

$L^{b7}$ is preferably a single bond or a divalent saturated hydrocarbon group having 1 to 18 carbon atoms, a hydrogen atom included in the saturated hydrocarbon group may be substituted with a fluorine atom or a hydroxy group, and —$CH_2$— included in the divalent saturated hydrocarbon group may be replaced by —O— or —CO—.

The group in which —$CH_2$— included in the divalent saturated hydrocarbon group represented by $L^{b1}$ is replaced by —O— or —CO— is preferably a group represented by formula (b1-1) or formula (b1-3).

Examples of the group represented by formula (b1-1) include groups represented by formula (b1-4) to formula (b1-8).

(b1-4)

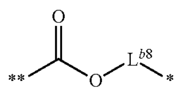

(b1-5)

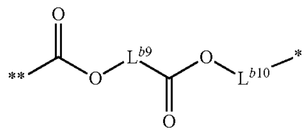

(b1-6)

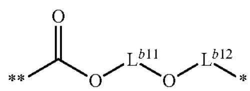

(b1-7)

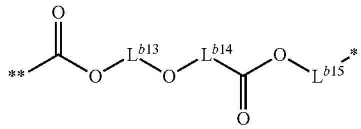

-continued (b1-8)

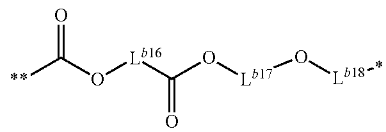

In formula (b1-4), $L^{b8}$ represents a single bond or a divalent saturated hydrocarbon group having 1 to 22 carbon atoms, and a hydrogen atom included in the saturated hydrocarbon group may be substituted with a fluorine atom or a hydroxy group.

In formula (b1-5), $L^{b9}$ represents a divalent saturated hydrocarbon group having 1 to 20 carbon atoms, and —$CH_2$— included in the divalent saturated hydrocarbon group may be replaced by —O— or —CO—.

$L^{b10}$ represents a single bond or a divalent saturated hydrocarbon group having 1 to 19 carbon atoms, and a hydrogen atom included in the divalent saturated hydrocarbon group may be substituted with a fluorine atom or a hydroxy group, and the total number of carbon atoms of $L^{b9}$ and $L^{b10}$ is 20 or less.

In formula (b1-6), $L^{b11}$ represents a divalent saturated hydrocarbon group having 1 to 21 carbon atoms, $L^{b12}$ represents a single bond or a divalent saturated hydrocarbon group having 1 to 20 carbon atoms, and a hydrogen atom included in the divalent saturated hydrocarbon group may be substituted with a fluorine atom or a hydroxy group, and the total number of carbon atoms of $L^{b11}$ and $L^{b12}$ is 21 or less.

In formula (b1-7), $L^{b13}$ represents a divalent saturated hydrocarbon group having 1 to 19 carbon atoms, $L^{b14}$ represents a single bond or a divalent saturated hydrocarbon group having 1 to 18 carbon atoms, and —$CH_2$— included in the divalent saturated hydrocarbon group may be replaced by —O— or —CO—, $L^{b15}$ represents a single bond or a divalent saturated hydrocarbon group having 1 to 18 carbon atoms, and a hydrogen atom included in the divalent saturated hydrocarbon group may be substituted with a fluorine atom or a hydroxy group, and the total number of carbon atoms of $L^{b13}$ to $L^{b15}$ is 19 or less.

In formula (b1-8), $L^{b16}$ represents a divalent saturated hydrocarbon group having 1 to 18 carbon atoms, and —$CH_2$— included in the divalent saturated hydrocarbon group may be replaced by —O— or —CO—, $L^{b17}$ represents a divalent saturated hydrocarbon group having 1 to 18 carbon atoms, $L^{b18}$ represents a single bond or a divalent saturated hydrocarbon group having 1 to 17 carbon atoms, and a hydrogen atom included in the divalent saturated hydrocarbon group may be substituted with a fluorine atom or a hydroxy group, and the total number of carbon atoms of $L^{b16}$ to $L^{b18}$ is 19 or less.

$L^{b8}$ is preferably a divalent saturated hydrocarbon group having 1 to 4 carbon atoms.

$L^{b9}$ is preferably a divalent saturated hydrocarbon group having 1 to 8 carbon atoms.

$L^{b10}$ is preferably a single bond or a divalent saturated hydrocarbon group having 1 to 19 carbon atoms, and more preferably a single bond or a divalent saturated hydrocarbon group having 1 to 8 carbon atoms.

$L^{b11}$ is preferably a divalent saturated hydrocarbon group having 1 to 8 carbon atoms.

$L^{b12}$ is preferably a single bond or a divalent saturated hydrocarbon group having 1 to 8 carbon atoms.

$L^{b13}$ is preferably a divalent saturated hydrocarbon group having 1 to 12 carbon atoms.

$L^{b14}$ is preferably a single bond or a divalent saturated hydrocarbon group having 1 to 6 carbon atoms.

$L^{b15}$ is preferably a single bond or a divalent saturated hydrocarbon group having 1 to 18 carbon atoms, and more preferably a single bond or a divalent saturated hydrocarbon group having 1 to 8 carbon atoms.

$L^{b16}$ is preferably a divalent saturated hydrocarbon group having 1 to 12 carbon atoms.

$L^{b17}$ is preferably a divalent saturated hydrocarbon group having 1 to 6 carbon atoms.

$L^{b18}$ is preferably a single bond or a divalent saturated hydrocarbon group having 1 to 17 carbon atoms, and more preferably a single bond or a divalent saturated hydrocarbon group having 1 to 4 carbon atoms.

Examples of the group represented by formula (b1-3) include groups represented by formula (b1-9) to formula (b1-11).

(b1-9)

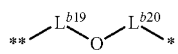

(b1-10)

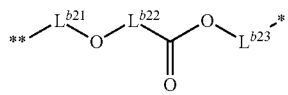

(b1-11)

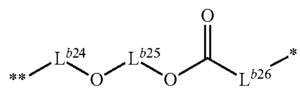

In formula (b1-9), $L^{b19}$ represents a single bond or a divalent saturated hydrocarbon group having 1 to 23 carbon atoms, and a hydrogen atom included in the saturated hydrocarbon group may be substituted with a fluorine atom, $L^{b20}$ represents a single bond or a divalent saturated hydrocarbon group having 1 to 23 carbon atoms, and a hydrogen atom included in the saturated hydrocarbon group may be substituted with a fluorine atom, a hydroxy group or an alkylcarbonyloxy group, —$CH_2$— included in the alkylcarbonyloxy group may be replaced by —O— or —CO—, and a hydrogen atom included in the alkylcarbonyloxy group may be substituted with a hydroxy group, and the total number of carbon atoms of $L^{b19}$ and $L^{b20}$ is 23 or less.

In formula (b1-10), $L^{b21}$ represents a single bond or a divalent saturated hydrocarbon group having 1 to 21 carbon atoms, and a hydrogen atom included in the saturated hydrocarbon group may be substituted with a fluorine atom, $L^{b22}$ represents a single bond or a divalent saturated hydrocarbon group having 1 to 21 carbon atoms, $L^{b23}$ represents a single bond or a divalent saturated hydrocarbon group having 1 to 21 carbon atoms, and a hydrogen atom included in the saturated hydrocarbon group may be substituted with a fluorine atom, a hydroxy group or an alkylcarbonyloxy group, —$CH_2$— included in the alkylcarbonyloxy group may be replaced by —O— or —CO—, and a hydrogen atom included in the alkylcarbonyloxy group may be substituted with a hydroxy group, and the total number of carbon atoms of $L^{b21}$, $L^{b22}$ and $L^{b23}$ is 21 or less.

In formula (b1-11), $L^{b24}$ represents a single bond or a divalent saturated hydrocarbon group having 1 to 20 carbon atoms, and a hydrogen atom included in the saturated hydrocarbon group may be substituted with a fluorine atom, $L^{b25}$ represents a divalent saturated hydrocarbon group having 1 to 21 carbon atoms, $L^{b26}$ represents a single bond or a divalent saturated hydrocarbon group having 1 to 20 carbon atoms, a hydrogen atom included in the saturated hydrocarbon group may be substituted with a fluorine atom, a hydroxy group or an alkylcarbonyloxy group, —$CH_2$— included in the alkylcarbonyloxy group may be replaced by —O— or —CO—, and a hydrogen atom included in the alkylcarbonyloxy group may be substituted with a hydroxy group, and the total number of carbon atoms of $L^{b24}$, $L^{b25}$ and $L^{b26}$ is 21 or less.

In groups represented by formula (b1-9) to formula (b1-11), when a hydrogen atom included in the saturated hydrocarbon group is substituted with an alkylcarbonyloxy group, the number of carbon atoms before substitution is taken as the number of carbon atoms of the saturated hydrocarbon group.

Examples of the alkylcarbonyloxy group include an acetyloxy group, a propionyloxy group, a butyryloxy group, a cyclohexylcarbonyloxy group, an adamantylcarbonyloxy group and the like.

Examples of the group represented by formula (b1-4) include the followings.

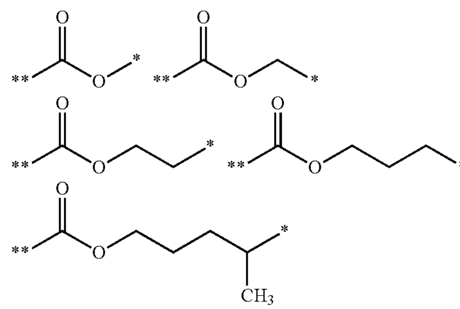

Examples of the group represented by formula (b1-5) include the followings.

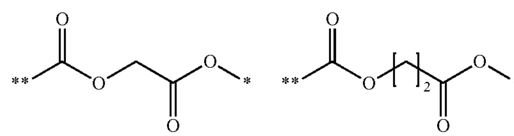

-continued
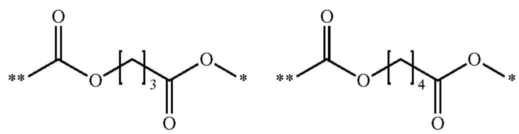
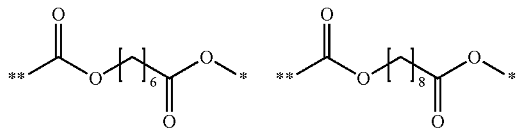
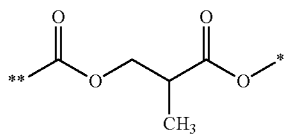
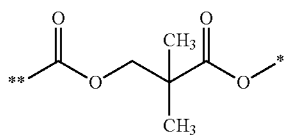
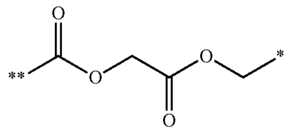
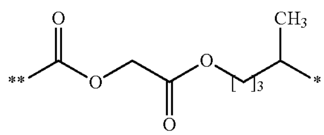
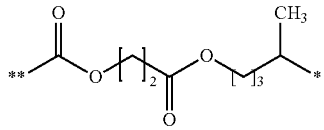
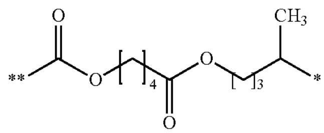
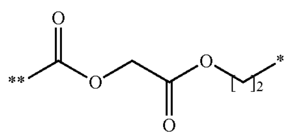
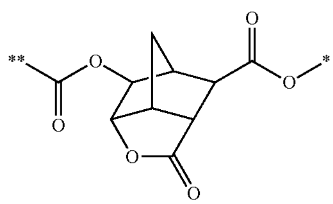
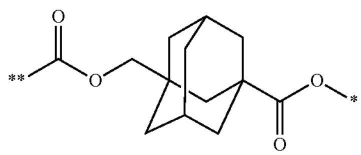
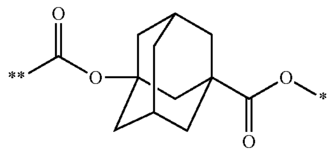
-continued
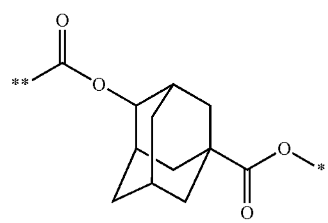
Examples of the group represented by formula (b1-6) include the followings.
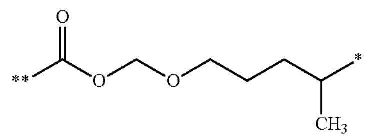
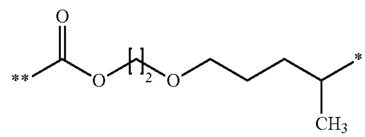
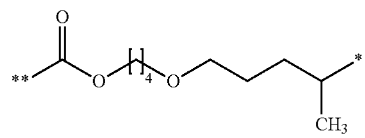
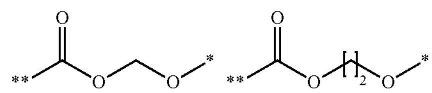
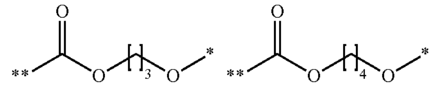
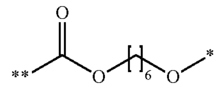
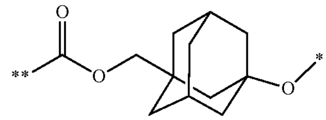
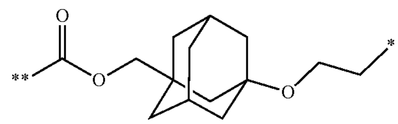
Examples of the group represented by formula (b1-7) include the followings.
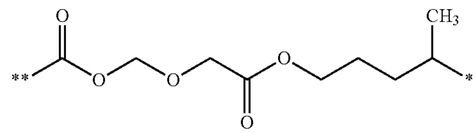
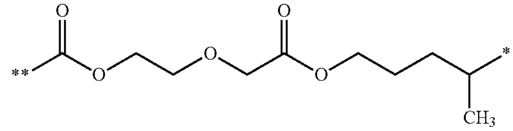

-continued
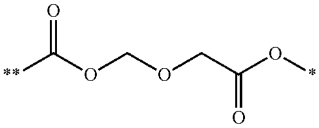
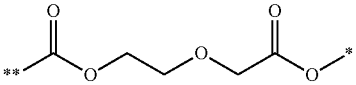
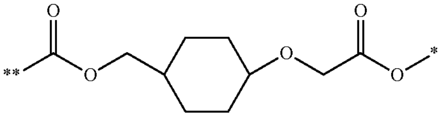
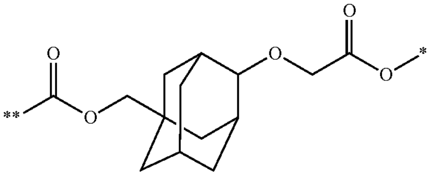
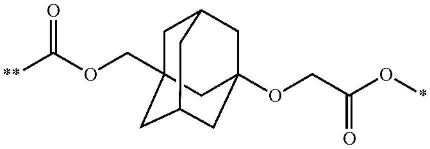
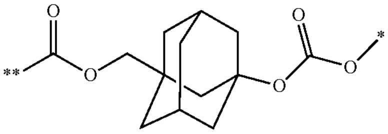
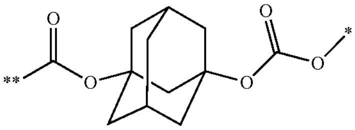
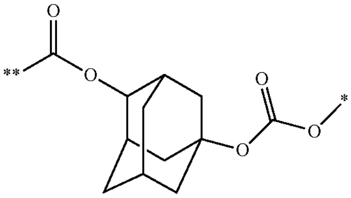
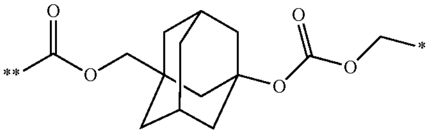
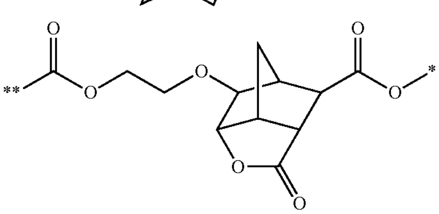
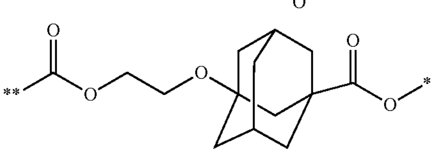
Examples of the group represented by formula (b1-8) include the followings.
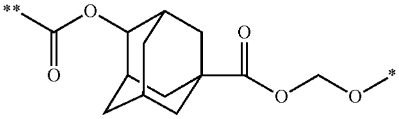
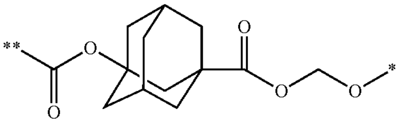
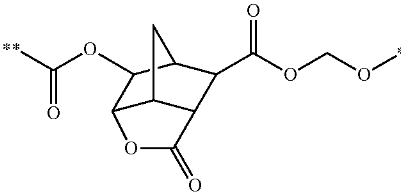
Examples of the group represented by formula (b1-2) include the followings.
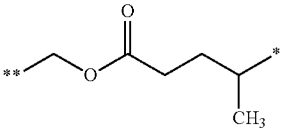
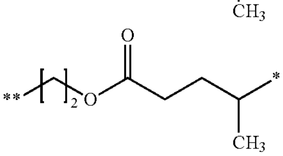
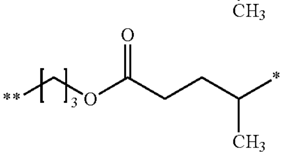
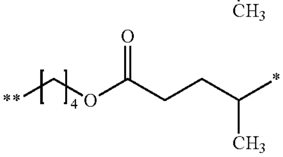
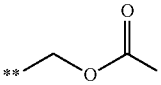
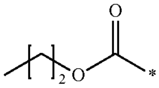
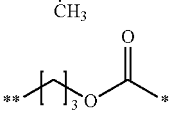
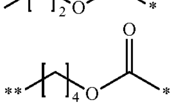
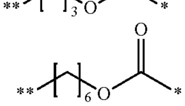
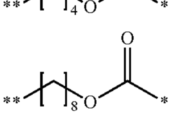
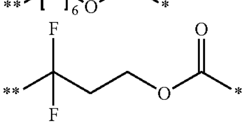
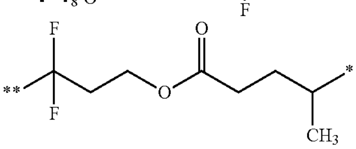
Examples of the group represented by formula (b1-9) include the followings.
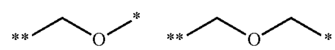

-continued
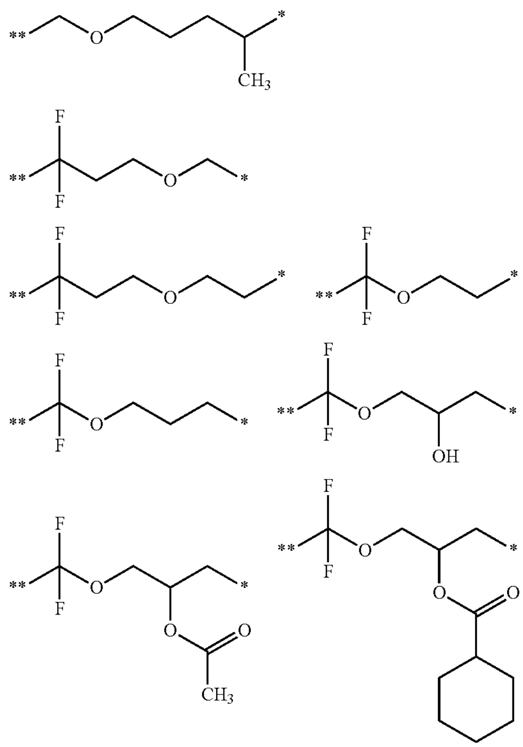
Examples of the group represented by formula (b1-10) include the followings.
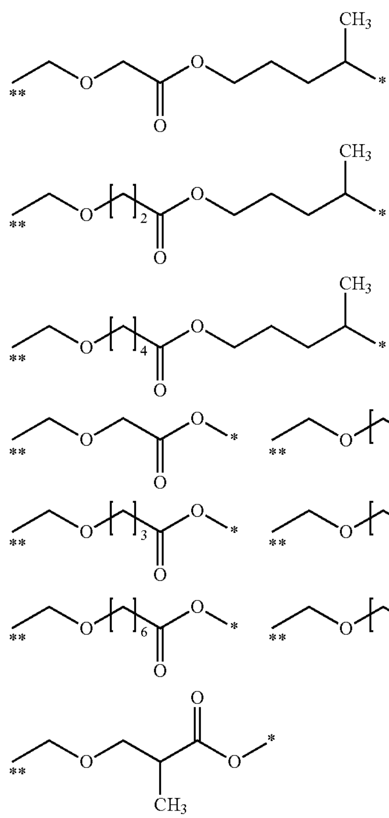
-continued
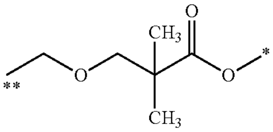
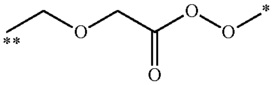
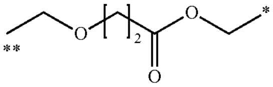
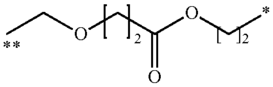
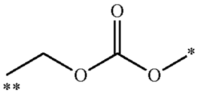
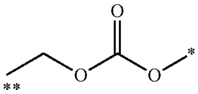
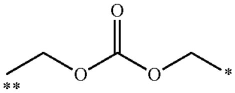
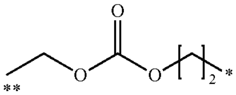
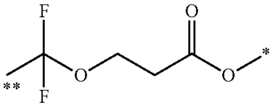
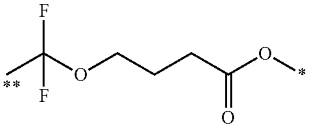
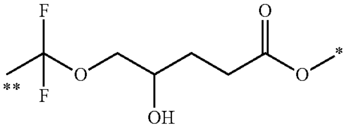
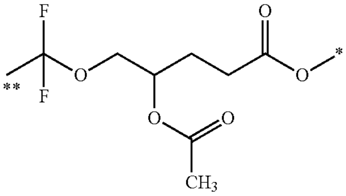
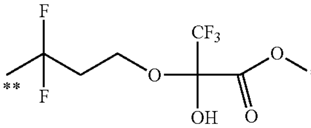
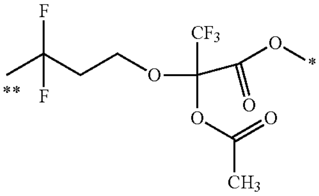

-continued
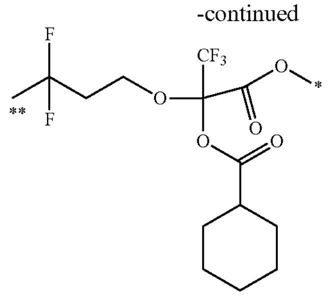
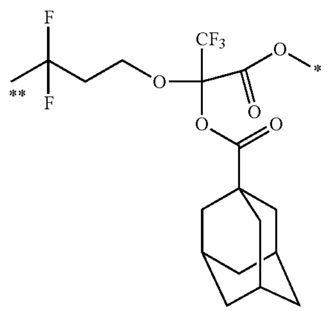
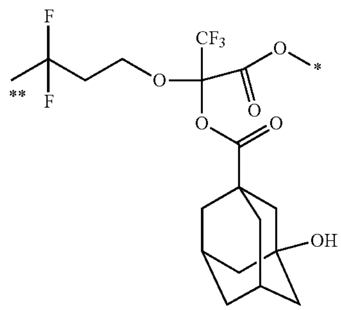
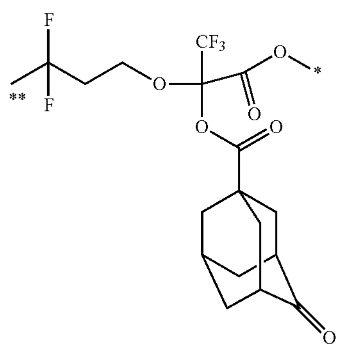
Examples of the group represented by formula (b1-11) include the followings.
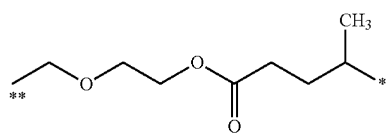
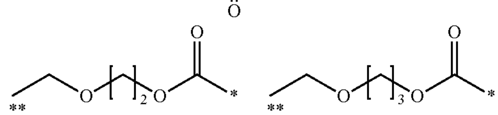
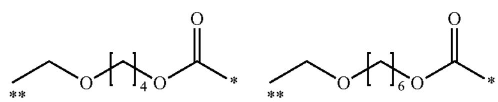
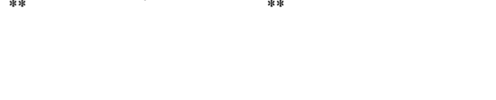
-continued
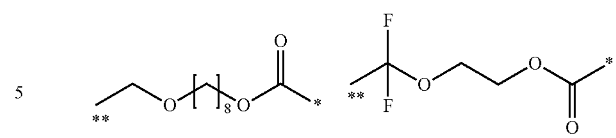
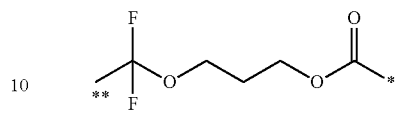
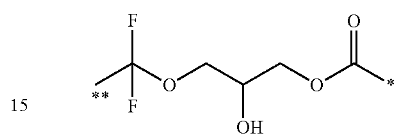
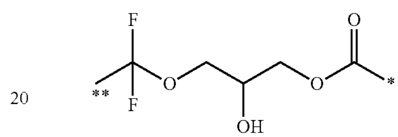
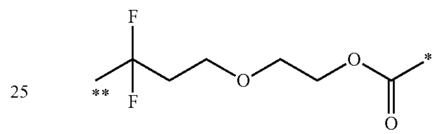
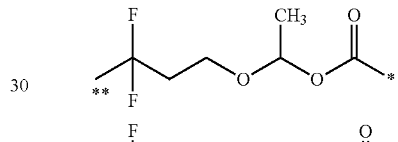
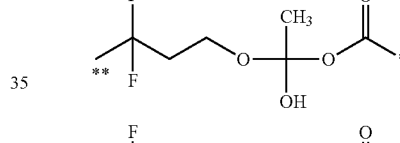
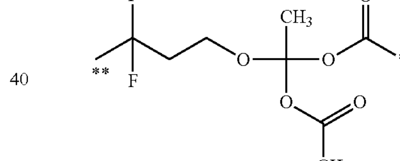
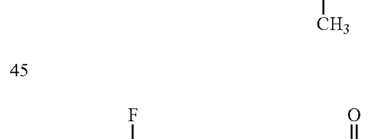
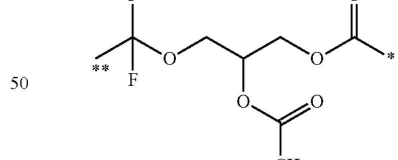
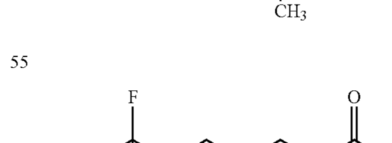
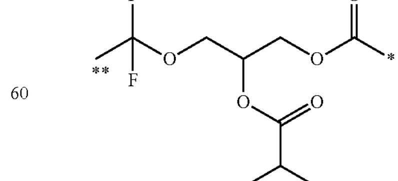
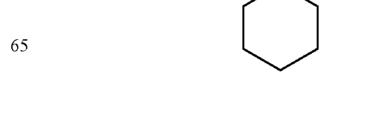
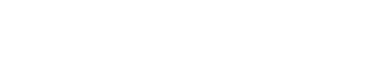

-continued

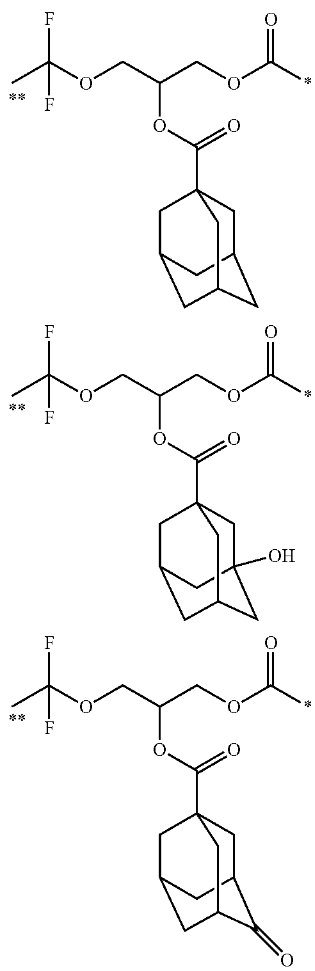

Examples of the alicyclic hydrocarbon group represented by Y include groups represented by formula (Y1) to formula (Y11) and formula (Y36) to formula (Y38).

When —$CH_2$— included in the alicyclic hydrocarbon group represented by Y is replaced by —O—, —$S(O)_2$— or —CO—, the number may be 1, or 2 or more. Examples of such group include formula (Y12) to formula (Y35) and formula (Y39) to formula (Y43). * represents a bonding site to $L^{b1}$.

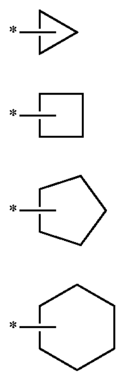

(Y1)

(Y2)

(Y3)

(Y4)

-continued (Y5)

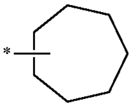

(Y6)

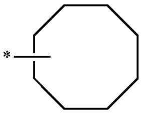

(Y7)

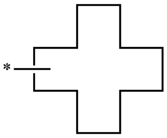

(Y8)

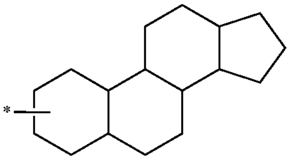

(Y9)

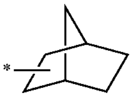

(Y10)

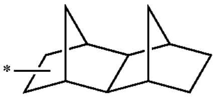

(Y11)

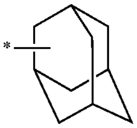

(Y12)

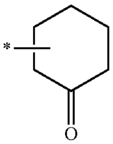

(Y13)

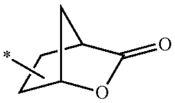

(Y14)

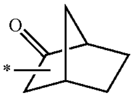

(Y15)

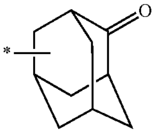

(Y16)

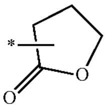

-continued
(Y17)
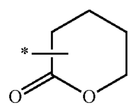
(Y18)
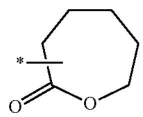
(Y19)
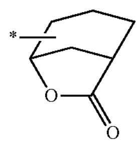
(Y20)
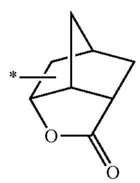
(Y21)
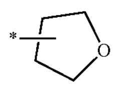
(Y22)
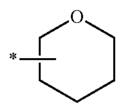
(Y23)
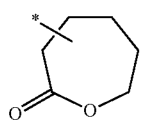
(Y24)
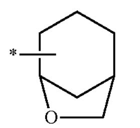
(Y25)
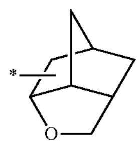
(Y26)
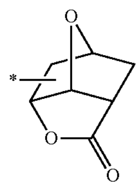
(Y27)
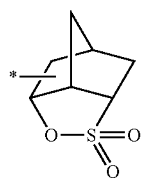
-continued
(Y28)
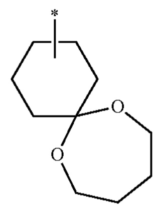
(Y29)
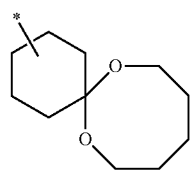
(Y30)
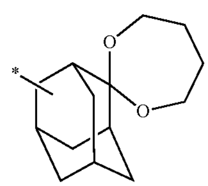
(Y31)
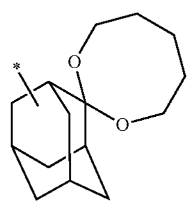
(Y32)
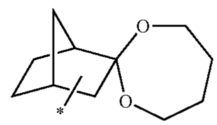
(Y33)
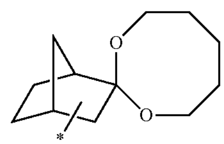
(Y34)
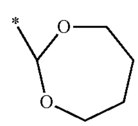
(Y35)
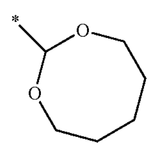
(Y36)
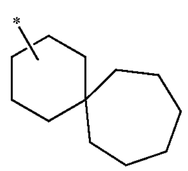

-continued (Y37)

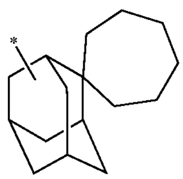

(Y38)

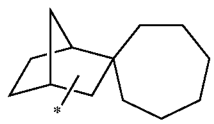

(Y39)

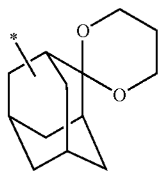

(Y40)

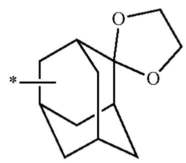

(Y41)

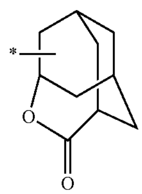

(Y42)

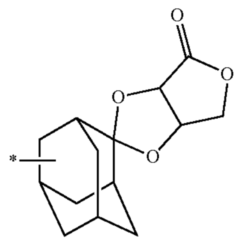

(Y43)

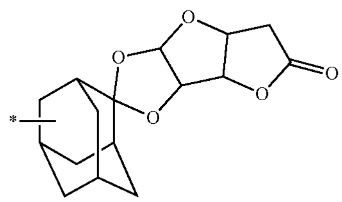

The alicyclic hydrocarbon group represented by Y is preferably a group represented by any one of formula (Y1) to formula (Y20), formula (Y26), formula (Y27), formula (Y30), formula (Y31) and formula (Y39) to formula (Y43), more preferably a group represented by formula (Y11), formula (Y15), formula (Y16), formula (Y20), formula (Y26), formula (Y27), formula (Y30), formula (Y31), formula (Y39), formula (Y40), formula (Y42) or formula (Y43), and still more preferably a group represented by formula (Y11), formula (Y15), formula (Y20), formula (Y26), formula (Y27), formula (Y30), formula (Y31), formula (Y39), formula (Y40), formula (Y42) or formula (Y43).

When the alicyclic hydrocarbon group represented by Y is a spiro ring including an oxygen atom, such as formulas (Y28) to formula (Y35), formula (Y39), formula (Y40), formula (Y42) or formula (Y43), the alkanediyl group between two oxygen atoms preferably has one or more fluorine atoms. Of alkanediyl groups included in a ketal structure, it is preferable that a methylene group adjacent to the oxygen atom is not substituted with a fluorine atom.

Examples of the substituent of the methyl group represented by Y include a halogen atom, a hydroxy group, an alicyclic hydrocarbon group having 3 to 16 carbon atoms, an aromatic hydrocarbon group having 6 to 18 carbon atoms, a glycidyloxy group, a $-(CH_2)_{ja}-CO-O-R^{b1}$ group or a $-(CH_2)_{ja}-O-CO-R^{b1}$ group (wherein $R^{b1}$ represents an alkyl group having 1 to 16 carbon atoms, an alicyclic hydrocarbon group having 3 to 16 carbon atoms, an aromatic hydrocarbon group having 6 to 18 carbon atoms, or groups obtained by combining these groups, $-CH_2-$ included in the alkyl group and the alicyclic hydrocarbon group may be replaced by $-O-$, $-SO_2-$ or $-CO-$, a hydrogen atom included in the alkyl group, the alicyclic hydrocarbon group and the aromatic hydrocarbon group may be substituted with a hydroxy group or a fluorine atom, and ja represents an integer of 0 to 4) and the like.

Examples of the substituent of the alicyclic hydrocarbon group represented by Y include a halogen atom, a hydroxy group, an alkyl group having 1 to 16 carbon atoms which may be substituted with a hydroxy group ($-CH_2-$ included in the alkyl group may be replaced by $-O-$ or $-CO-$), an alicyclic hydrocarbon group having 3 to 16 carbon atoms, an aromatic hydrocarbon group having 6 to 18 carbon atoms, an aralkyl group having 7 to 21 carbon atoms, a glycidyloxy group, a $-(CH_2)_{ja}-CO-O-R^{b1}$ group or a $-(CH_2)_{ja}-O-CO-R^{b1}$ group (wherein $R^{b1}$ represents an alkyl group having 1 to 16 carbon atoms, an alicyclic hydrocarbon group having 3 to 16 carbon atoms, an aromatic hydrocarbon group having 6 to 18 carbon atoms, or groups obtained by combining these groups, $-CH_2-$ included in the alkyl group and the alicyclic hydrocarbon group may be replaced by $-O-$, $-SO_2-$ or $-CO-$, a hydrogen atom included in the alkyl group, the alicyclic hydrocarbon group and the aromatic hydrocarbon group may be substituted with a hydroxy group or a fluorine atom, and ja represents an integer of 0 to 4) and the like.

Examples of the halogen atom include a fluorine atom, a chlorine atom, a bromine atom and an iodine atom.

The alicyclic hydrocarbon group includes, for example, a cyclopentyl group, a cyclohexyl group, a methylcyclohexyl group, a dimethylcyclohexyl group, a cycloheptyl group, a cyclooctyl group, a norbornyl group, an adamantyl group and the like. The alicyclic hydrocarbon group may have a chain hydrocarbon group, and examples thereof include a methylcyclohexyl group, a dimethylcyclohexyl group and the like. The number of carbon atoms of the alicyclic hydrocarbon group is preferably 3 to 12, and more preferably 3 to 10.

Examples of the aromatic hydrocarbon group include aryl groups such as a phenyl group, a naphthyl group, an anthryl group, a biphenyl group and a phenanthryl group. The aromatic hydrocarbon group may have a chain hydrocarbon group or an alicyclic hydrocarbon group, examples of the aromatic hydrocarbon group having a chain hydrocarbon group having 1 to 18 carbon atoms include a tolyl group, a xylyl group, a cumenyl group, a mesityl group, a p-ethylphenyl group, a p-tert-butylphenyl group, a 2,6-diethylphenyl group, a 2-methyl-6-ethylphenyl group and the like, and examples of the aromatic hydrocarbon group having an alicyclic hydrocarbon group having 1 to 18 carbon atoms include a p-cyclohexylphenyl group, a p-adamantylphenyl group and the like. The number of carbon atoms of the aromatic hydrocarbon group is preferably 6 to 14, and more preferably 6 to 10.

Examples of the alkyl group include a methyl group, an ethyl group, a propyl group, an isopropyl group, a butyl group, a sec-butyl group, a tert-butyl group, a pentyl group, a hexyl group, a heptyl group, a 2-ethylhexyl group, an octyl group, a nonyl group, a decyl group, an undecyl group, a dodecyl group and the like. The number of carbon atoms of the alkyl group is preferably 1 to 12, more preferably 1 to 9, still more preferably 1 to 6, and yet more preferably 1 to 4.

Examples of the alkyl group substituted with a hydroxy group include hydroxyalkyl groups such as a hydroxymethyl group and a hydroxyethyl group.

Examples of the aralkyl group include a benzyl group, a phenethyl group, a phenylpropyl group, a naphthylmethyl group and a naphthylethyl group.

Examples of the group in which $—CH_2—$ included in the alkyl group is replaced by —O—, $—S(O)_2—$ or —CO— include an alkoxy group, an alkoxycarbonyl group, an alkylcarbonyl group, an alkylcarbonyloxy group, or groups obtained by combining these groups.

Examples of the alkoxy group include a methoxy group, an ethoxy group, a propoxy group, a butoxy group, a pentyloxy group, a hexyloxy group, a heptyloxy group, an octyloxy group, a decyloxy group and a dodecyloxy group. The number of carbon atoms of the alkoxy group is preferably 1 to 12, more preferably 1 to 6, and still more preferably 1 to 4.

Examples of the alkoxycarbonyl group include a methoxycarbonyl group, an ethoxycarbonyl group, a butoxycarbonyl group and the like. The number of carbon atoms of the alkoxycarbonyl group is preferably 2 to 12, more preferably 2 to 6, and still more preferably 2 to 4.

Examples of the alkylcarbonyl group include an acetyl group, a propionyl group and a butyryl group. The number of carbon atoms of the alkylcarbonyl group is preferably 2 to 12, more preferably 2 to 6, and still more preferably 2 to 4.

Examples of the alkylcarbonyloxy group include an acetyloxy group, a propionyloxy group, a butyryloxy group and the like. The number of carbon atoms of the alkylcarbonyloxy group is preferably 2 to 12, more preferably 2 to 6, and still more preferably 2 to 4.

Examples of the combined group include a group obtained by combining an alkoxy group with an alkyl group, a group obtained by combining an alkoxy group with an alkoxy group, a group obtained by combining an alkoxy group with an alkylcarbonyl group, a group obtained by combining an alkoxy group with an alkylcarbonyloxy group and the like.

Examples of the group obtained by combining an alkoxy group with an alkyl group include alkoxyalkyl groups such as a methoxymethyl group, a methoxyethyl group, an ethoxyethyl group, an ethoxymethyl group and the like. The number of carbon atoms of the alkoxyalkyl group is preferably 2 to 12, more preferably 2 to 6, and still more preferably 2 to 4.

Examples of the group obtained by combining an alkoxy group with an alkoxy group include an alkoxyalkoxy group such as a methoxymethoxy group, a methoxyethoxy group, an ethoxymethoxy group, an ethoxyethoxy group and the like. The number of carbon atoms of the alkoxyalkoxy group is preferably 2 to 12, more preferably 2 to 6, and still more preferably 2 to 4.

Examples of the group obtained by combining an alkoxy group with an alkylcarbonyl group include alkoxyalkylcarbonyl groups such as a methoxyacetyl group, a methoxypropionyl group, an ethoxyacetyl group, an ethoxypropionyl group and the like. The number of carbon atoms of the alkoxyalkylcarbonyl group is preferably 3 to 13, more preferably 3 to 7, and still more preferably 3 to 5.

Examples of the group obtained by combining an alkoxy group with an alkylcarbonyloxy group include alkoxyalkylcarbonyloxy groups such as a methoxyacetyloxy group, a methoxypropionyloxy group, an ethoxyacetyloxy group, an ethoxypropionyloxy group and the like. The number of carbon atoms of the alkoxyalkylcarbonyloxy group is preferably 3 to 13, more preferably 3 to 7, and still more preferably 3 to 5.

Examples of the group in which $—CH_2—$ included in the alicyclic hydrocarbon group is replaced by —O—, $—S(O)_2—$ or —CO— include groups represented by formula (Y12) to formula (Y35), formula (Y39) to formula (Y43) and the like.

Examples of Y include the followings.

(Y100)

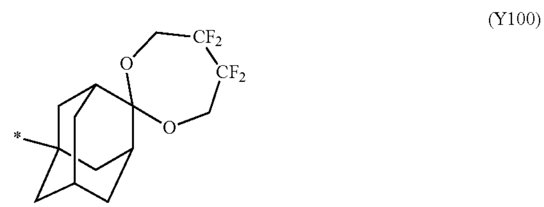

(Y101)

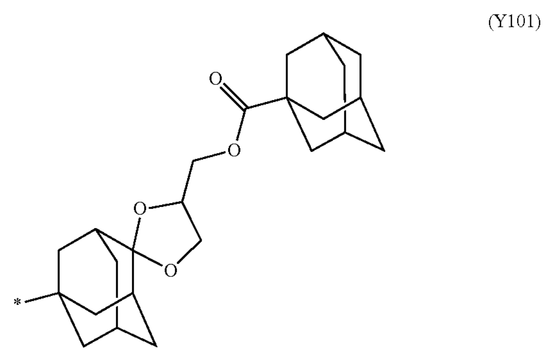

(Y102)

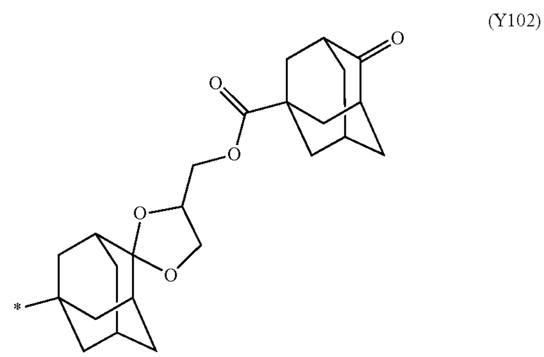

-continued
(Y103)
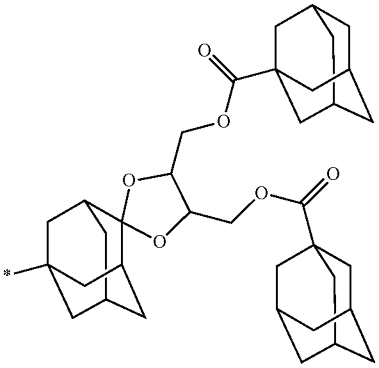
(Y104)
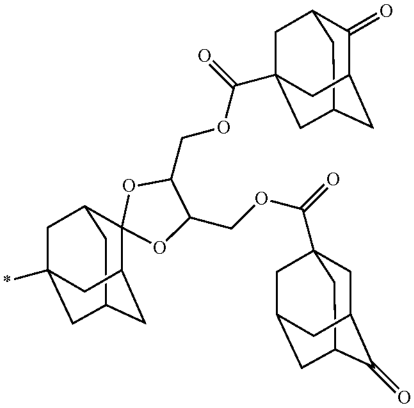
(Y105)
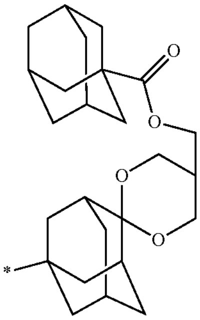
(Y106)
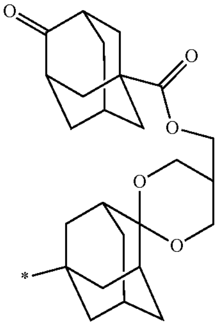
-continued
(Y107)
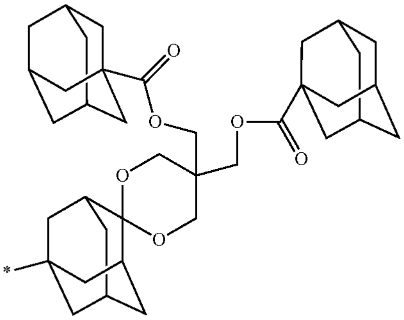
(Y108)
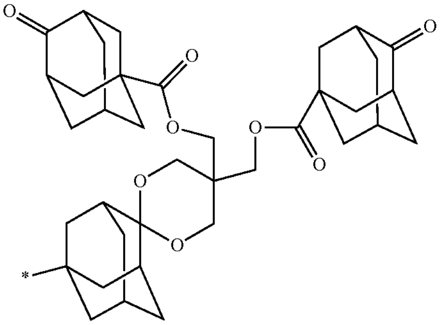
(Y109)
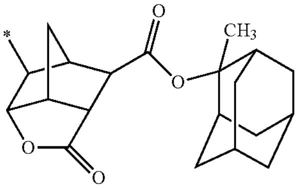
(Y110)
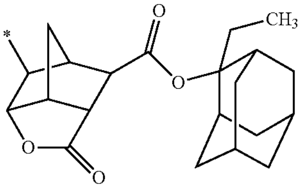
(Y111)
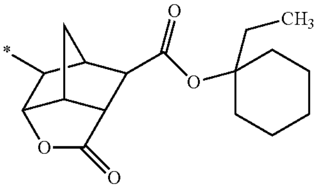
(Y42)
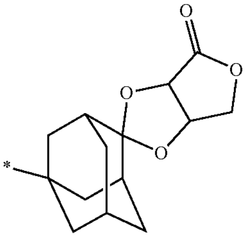

-continued
(Y112)
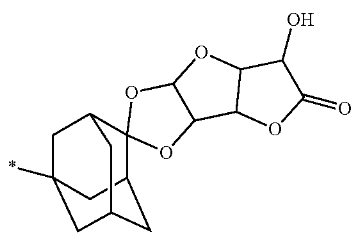
(Y113)
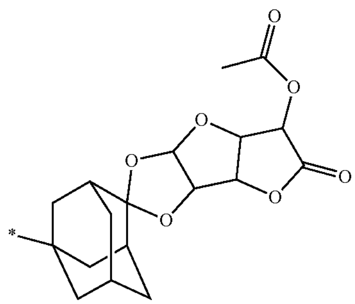
(Y114)
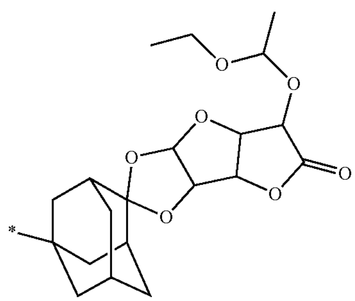
(Y115)
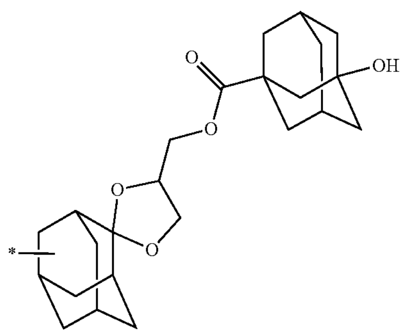
(Y116)
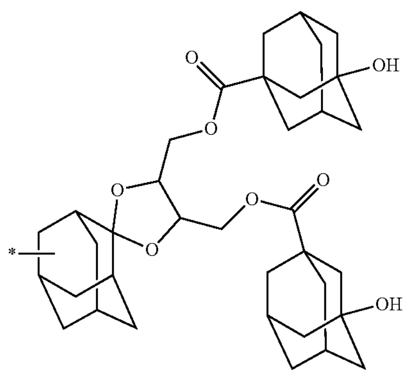
-continued
(Y11)
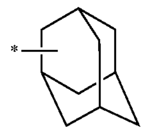
(Y4)
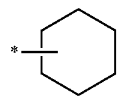
(Y117)
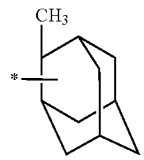
(Y118)
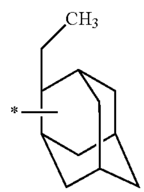
(Y119)
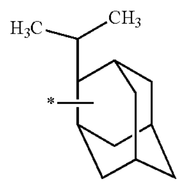
(Y120)
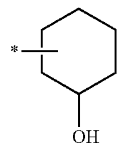
(Y121)
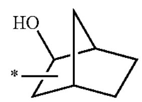
(Y122)
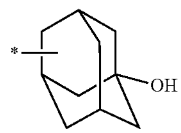
(Y123)
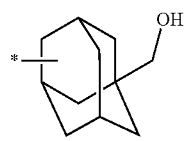
(Y15)
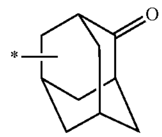

-continued
(Y124)
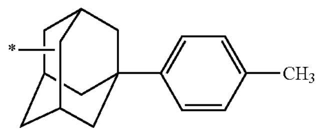
(Y125)
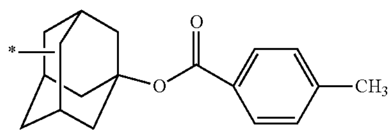
(Y126)
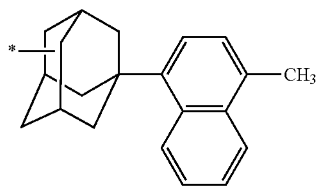
(Y127)
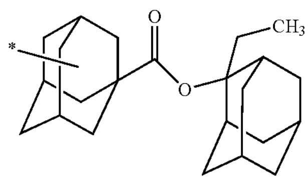
(Y128)
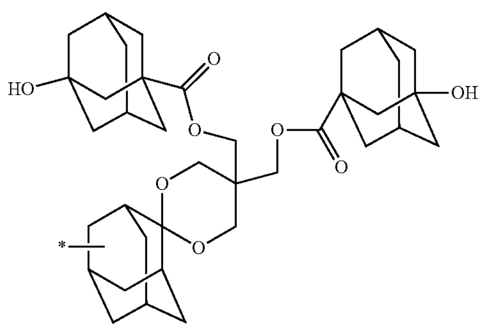
(Y129)
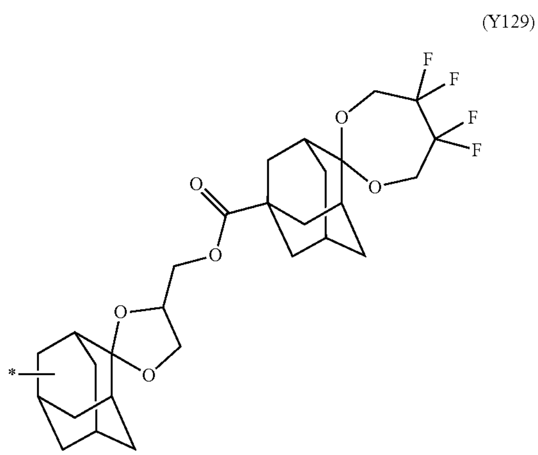
-continued
(Y130)
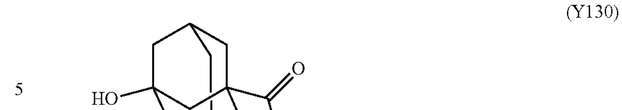
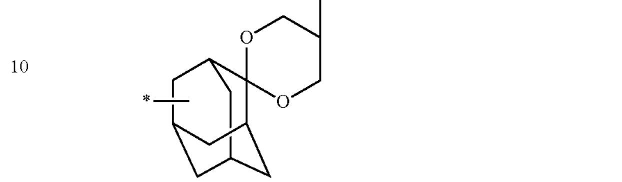
(Y131)
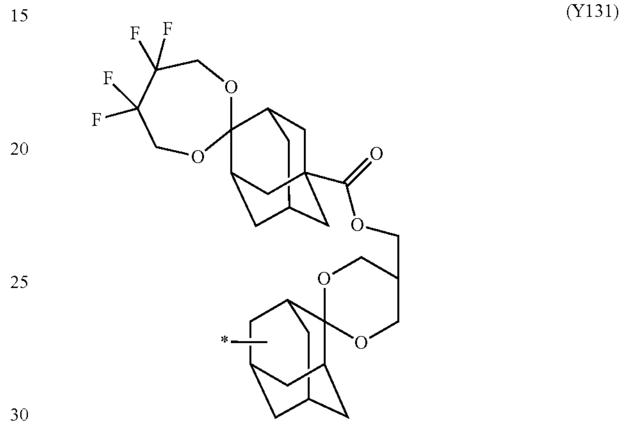
(Y132)
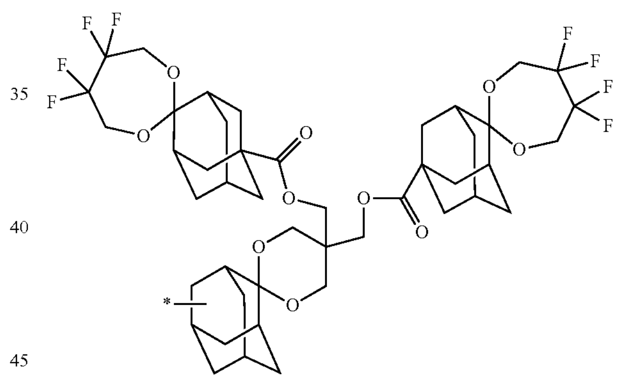
(Y133)
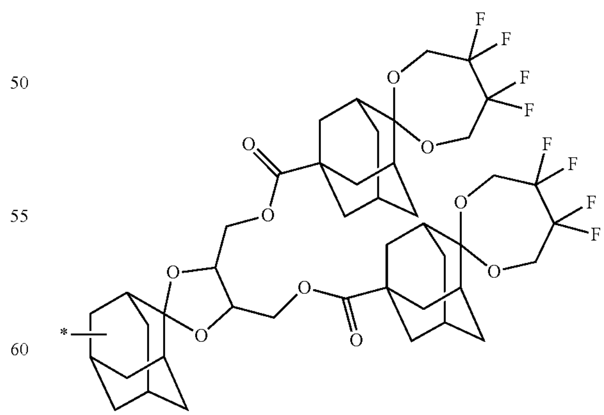
Y is preferably an alicyclic hydrocarbon group having 3 to 24 carbon atoms which may have a substituent, more preferably an alicyclic hydrocarbon group having 3 to 20 carbon atoms which may have a substituent, still more preferably an alicyclic hydrocarbon group having 3 to 18 carbon atoms which may have a substituent, and yet more preferably an adamantyl group which may have a substituent, and —$CH_2$— constituting the alicyclic hydrocarbon group or the adamantyl group may be replaced by —CO—, —$S(O)_2$— or —CO—. Specifically, Y is preferably an adamantyl group, a hydroxyadamantyl group, an oxoadamantyl group, or groups represented by formula (Y42) and formula (Y100) to formula (Y114).

The anion in the salt represented by formula (B1) is preferably anions represented by formula (B1-A-1) to formula (B1-A-59) [hereinafter sometimes referred to as "anion (B1-A-1)" according to the number of formula], and more preferably an anion represented by any one of formula (B1-A-1) to formula (B1-A-4), formula (B1-A-9), formula (B1-A-10), formula (B1-A-24) to formula (B1-A-33), formula (B1-A-36) to formula (B1-A-40) and formula (B1-A-47) to formula (B1-A-59).

(B1-A-1)

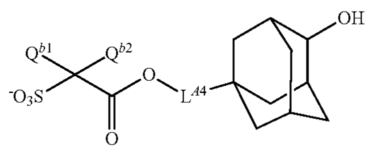

(B1-A-2)

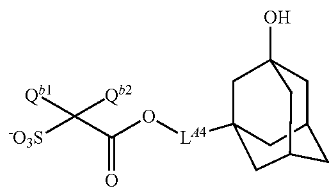

(B1-A-3)

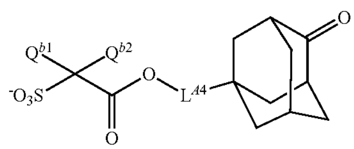

(B1-A-4)

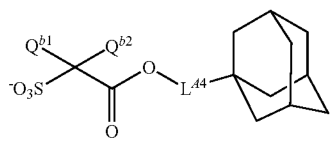

(B1-A-5)

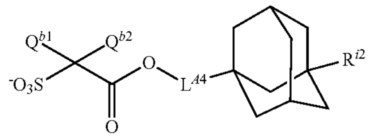

(B1-A-6)

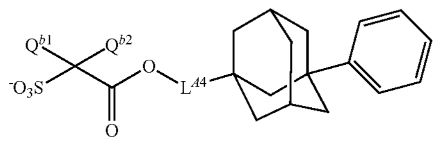

(B1-A-7)

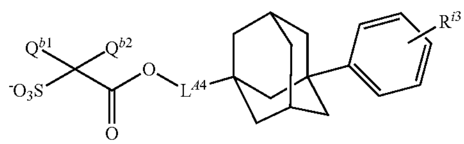

-continued (B1-A-8)

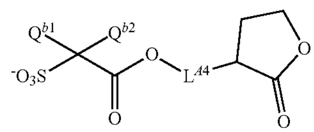

(B1-A-9)

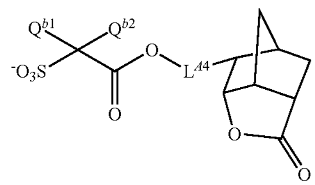

(B1-A-10)

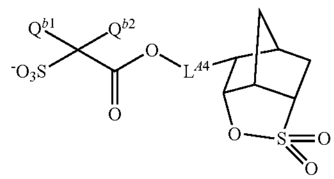

(B1-A-11)

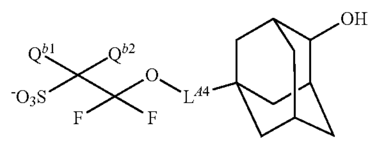

(B1-A-12)

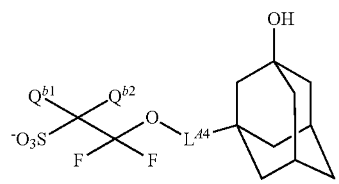

(B1-A-13)

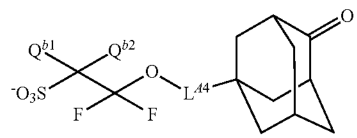

(B1-A-14)

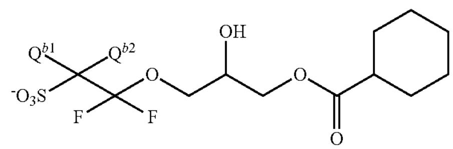

(B1-A-15)

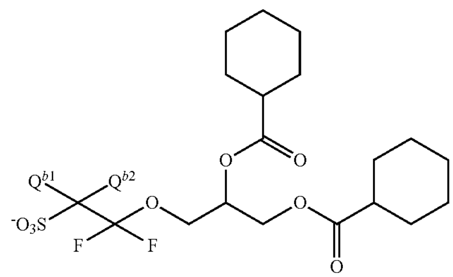

-continued
(B1-A-16)
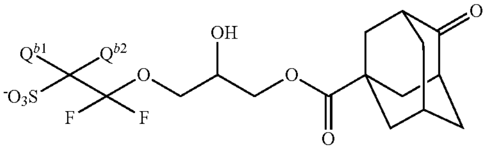
(B1-A-17)
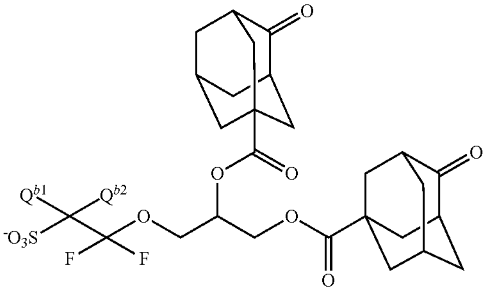
(B1-A-18)
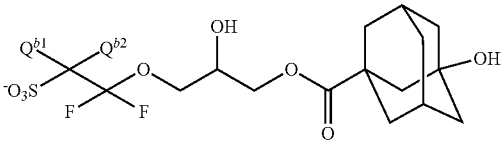
(B1-A-19)
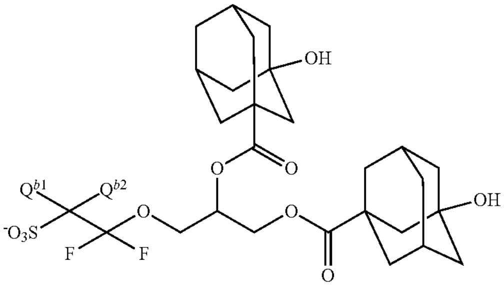
(B1-A-20)
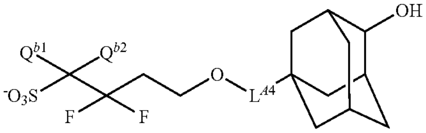
(B1-A-21)
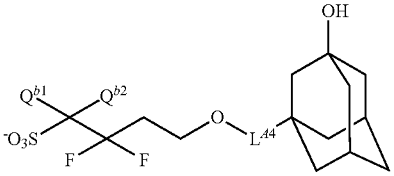
(B1-A-22)
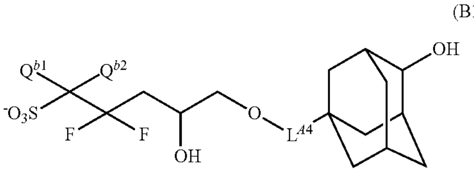
-continued
(B1-A-23)
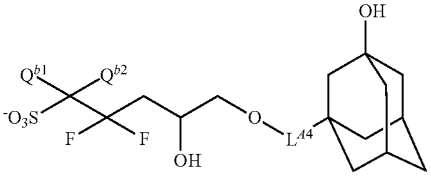
(B1-A-24)
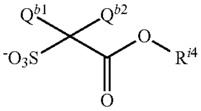
(B1-A-25)
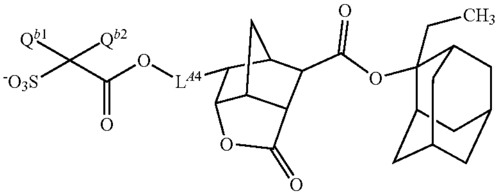
(B1-A-26)
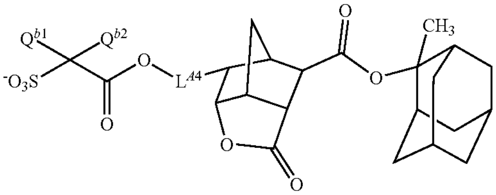
(B1-A-27)
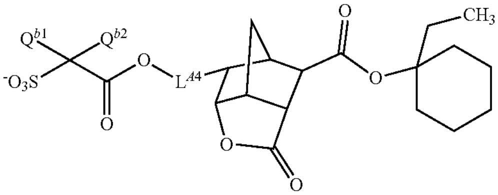
(B1-A-28)
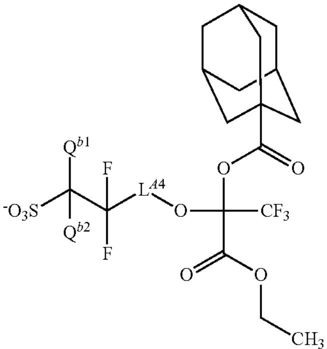

-continued
(B1-A-29)
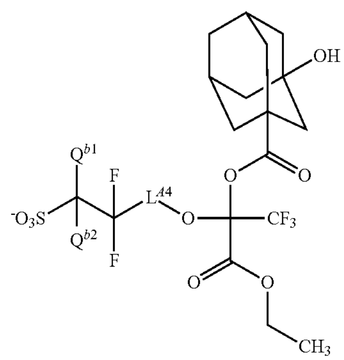
(B1-A-30)
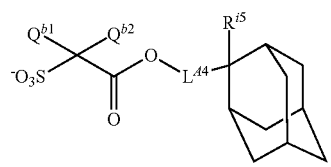
(B1-A-31)
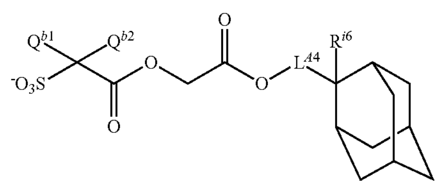
(B1-A-32)
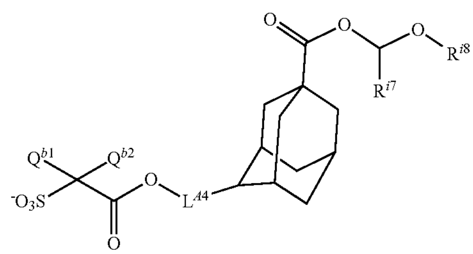
(B1-A-33)
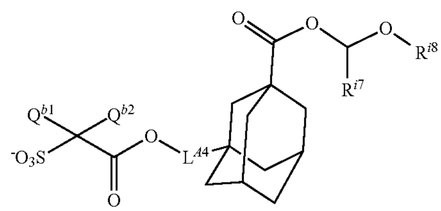
(B1-A-34)
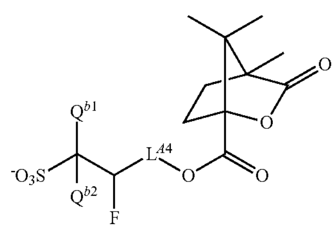
-continued
(B1-A-35)
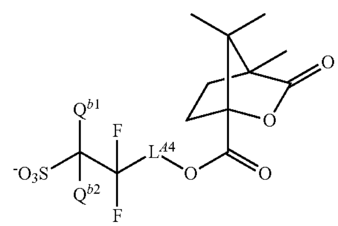
(B1-A-36)
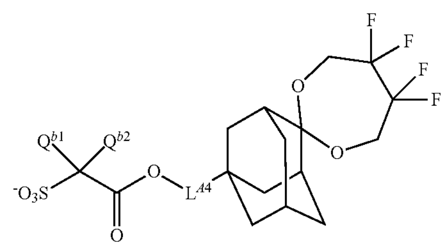
(B1-A-37)
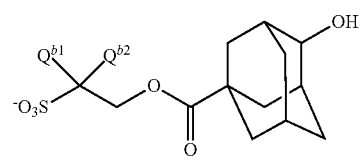
(B1-A-38)
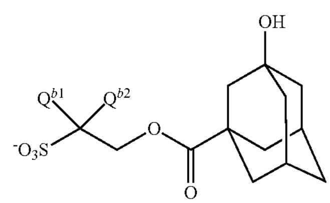
(B1-A-39)
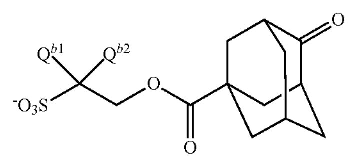
(B1-A-40)
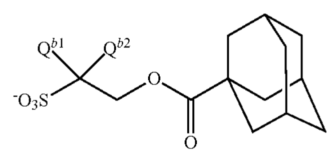
(B1-A-41)
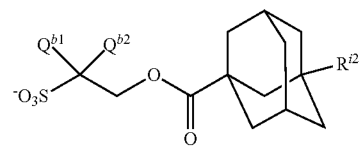
(B1-A-42)
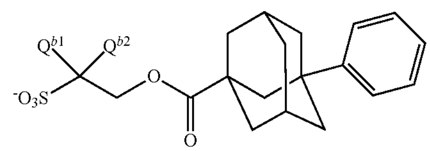

-continued
(B1-A-43)
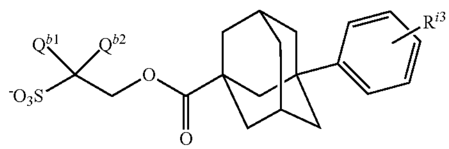
(B1-A-44)
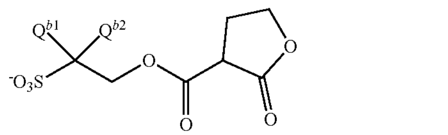
(B1-A-45)
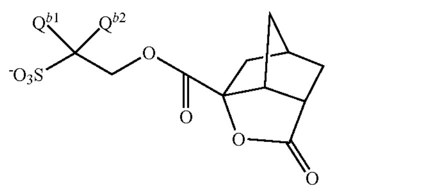
(B1-A-46)
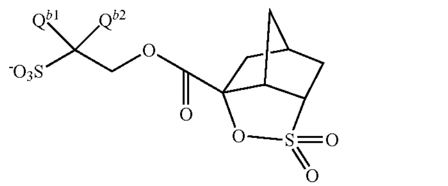
(B1-A-47)
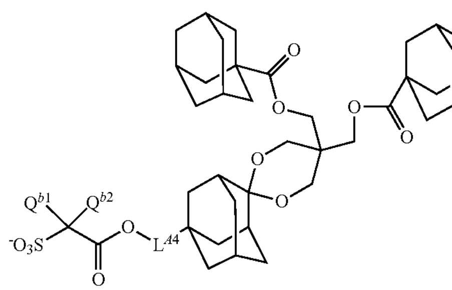
(B1-A-48)
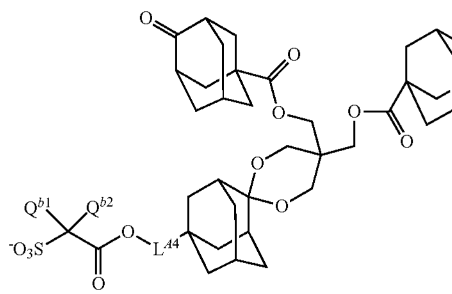
(B1-A-49)
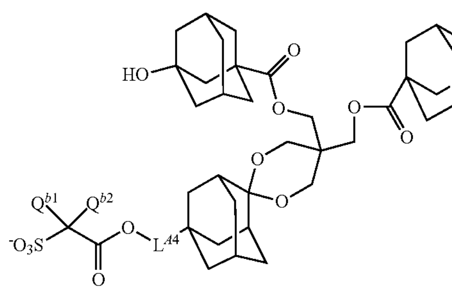
-continued
(B1-A-50)
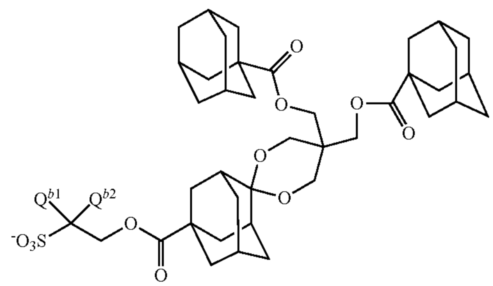
(B1-A-51)
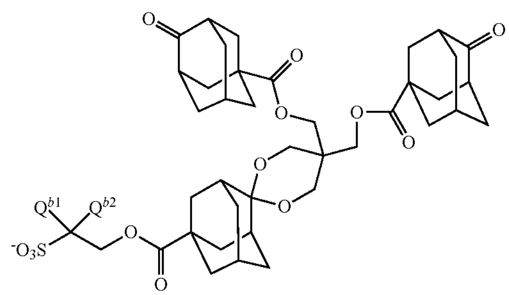
(B1-A-52)
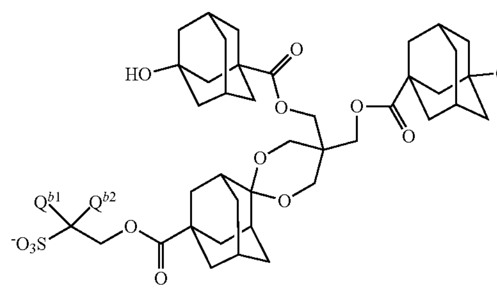
(B1-A-53)
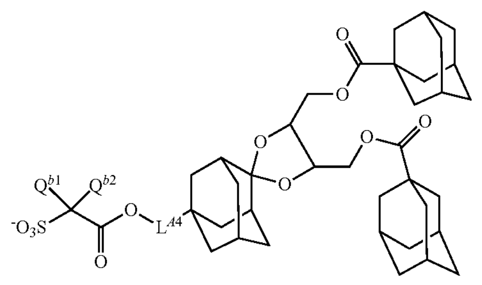
(B1-A-54)
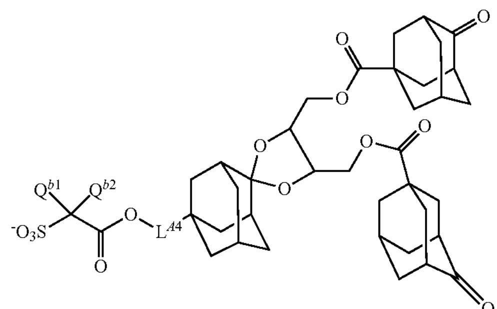

-continued (B1-A-55)

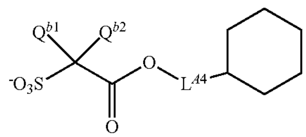

(B1-A-56)

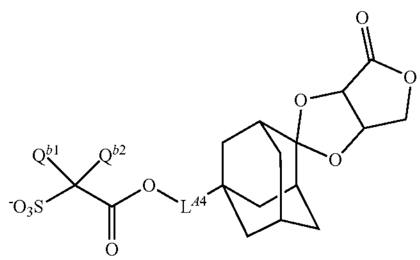

(B1-A-57)

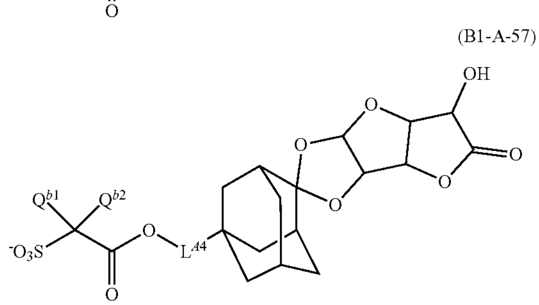

(B1-A-58)

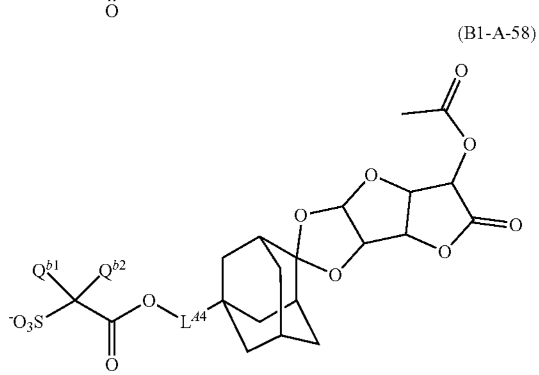

(B1-A-59)

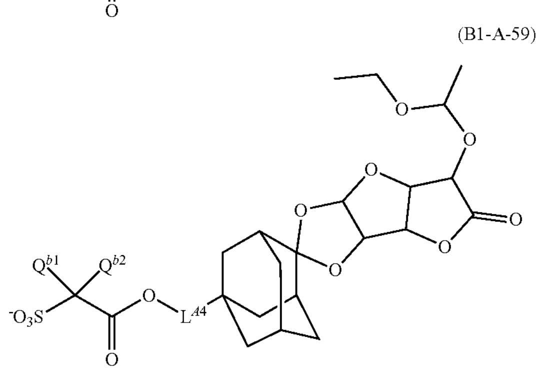

$R^{i2}$ to $R^{i7}$ each independently represent, for example, an alkyl group having 1 to 4 carbon atoms, and preferably a methyl group or an ethyl group. $R^{i8}$ is, for example, an aliphatic hydrocarbon group having 1 to 12 carbon atoms, preferably an alkyl group having 1 to 4 carbon atoms, an alicyclic hydrocarbon group having 5 to 12 carbon atoms or groups formed by combining these groups, and more preferably a methyl group, an ethyl group, a cyclohexyl group or an adamantyl group. $L^{A4}$ is a single bond or an alkanediyl group having 1 to 4 carbon atoms.

$Q^{b1}$ and $Q^{b2}$ are the same as defined above.

Specific examples of the anion in the salt represented by formula (B1) include anions mentioned in JP 2010-204646 A.

Preferable anions in the salt represented by formula (B1) are anions represented by formula (B1a-1) to formula (B1a-38).

(B1a-1)

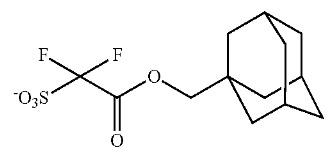

(B1a-2)

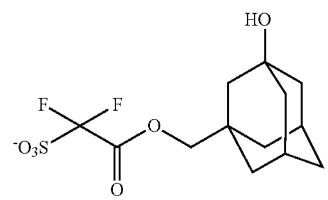

(B1a-3)

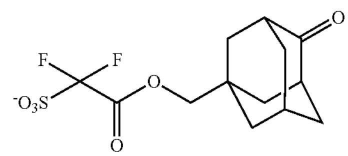

(B1a-4)

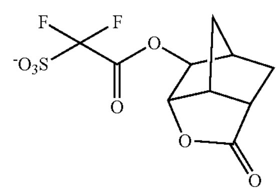

(B1a-5)

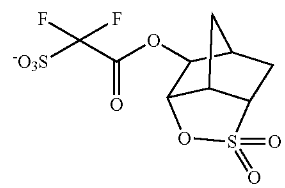

(B1a-6)

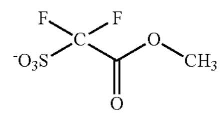

(B1a-7)

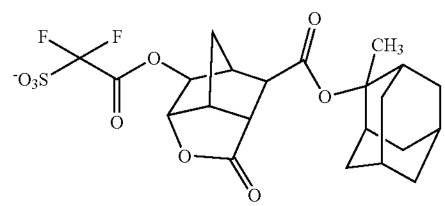

(B1a-8)

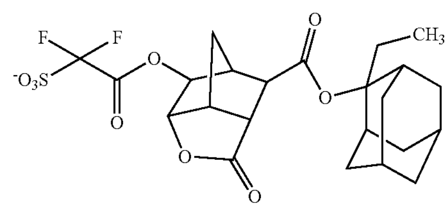

-continued
(B1a-9)
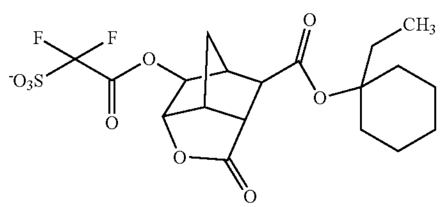
(B1a-10)
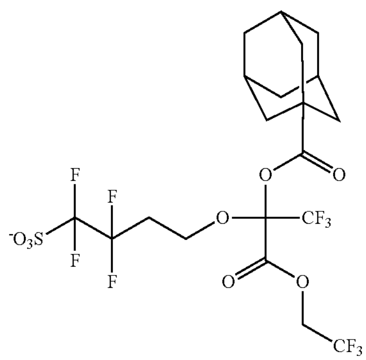
(B1a-11)
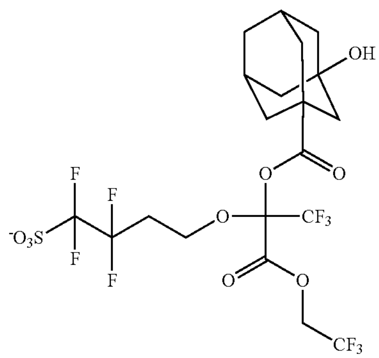
(B1a-12)
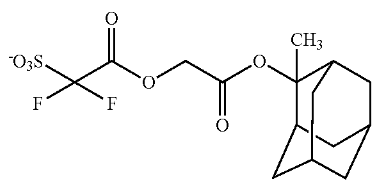
(B1a-13)
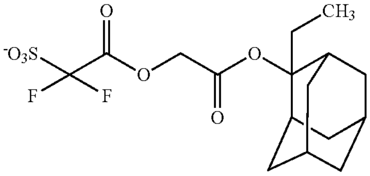
(B1a-14)
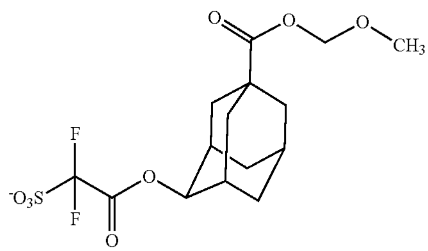
-continued
(B1a-15)
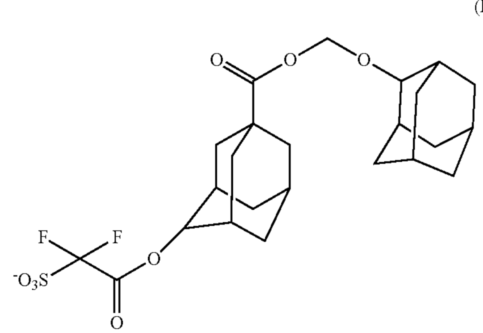
(B1a-16)
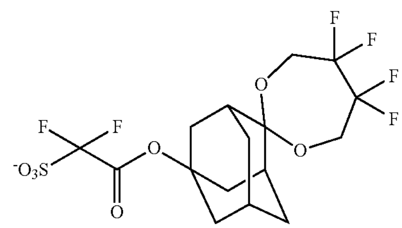
(B1a-17)
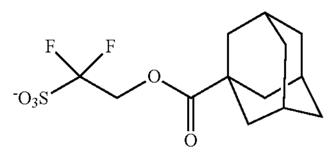
(B1a-18)
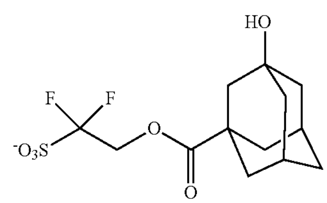
(B1a-19)
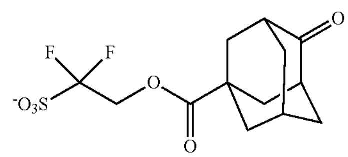
(B1a-20)
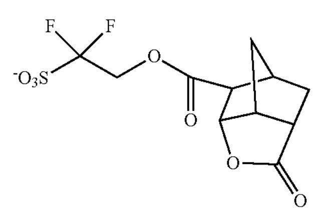
(B1a-21)
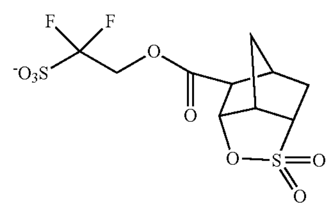

-continued
(B1a-22)
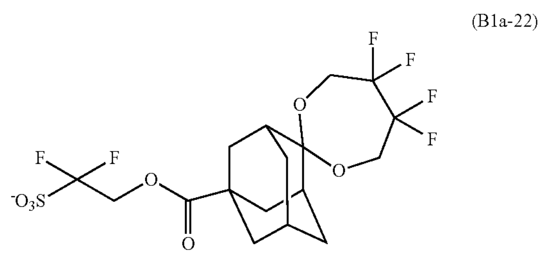
(B1a-23)
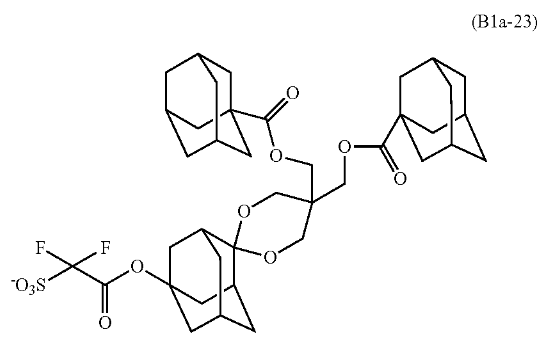
(B1a-24)
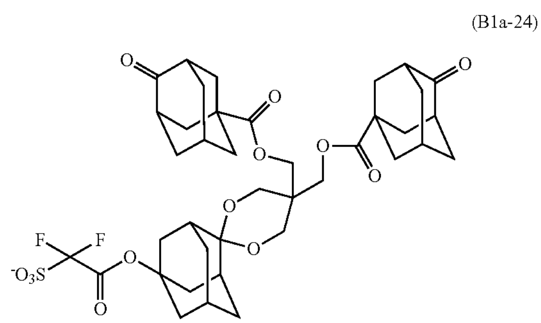
(B1a-25)
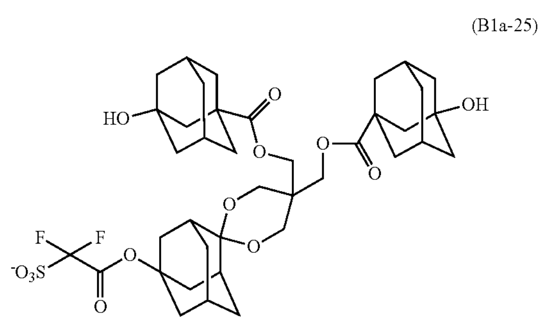
(B1a-26)
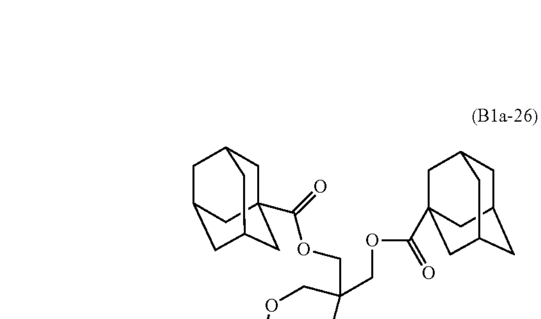
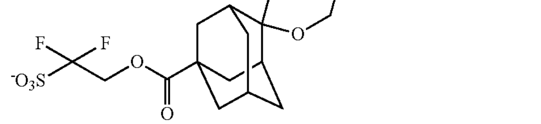
-continued
(B1a-27)
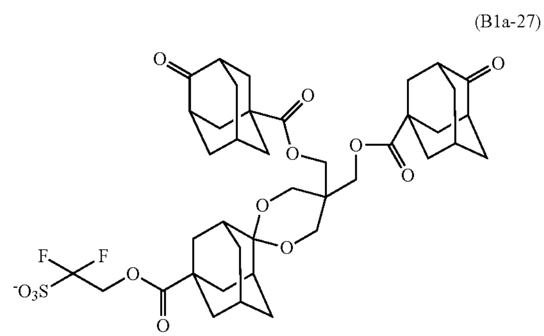
(B1a-28)
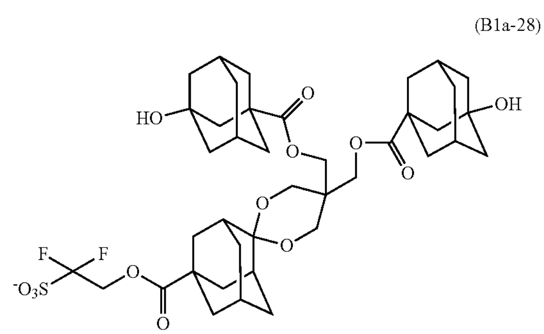
(B1a-29)
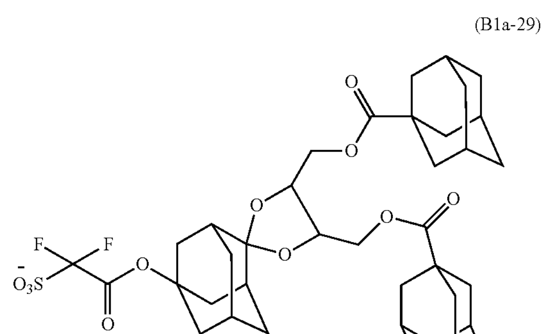
(B1a-30)
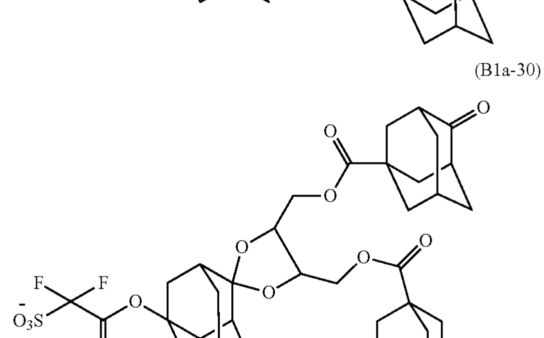
(B1a-31)
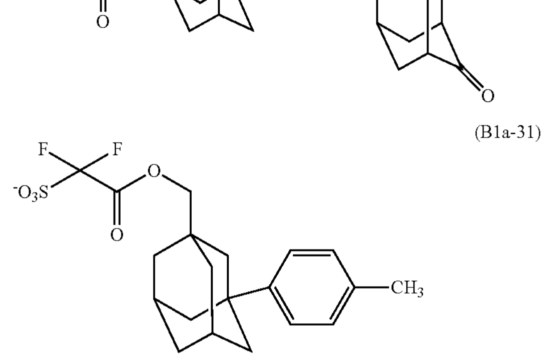

-continued (B1a-32)

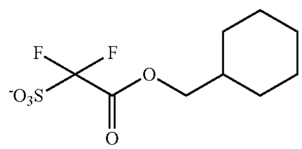

(B1a-33)

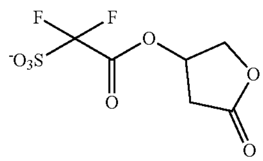

(B1a-34)

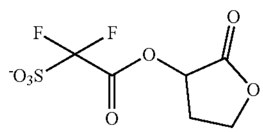

(B1a-35)

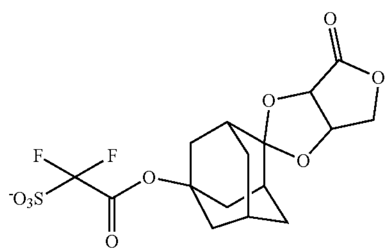

(B1a-36)

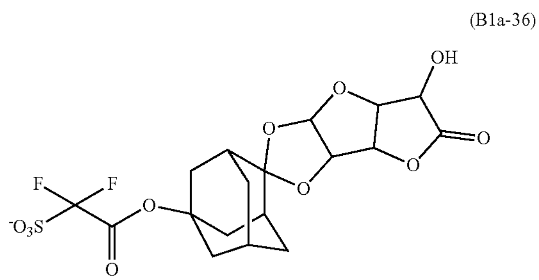

(B1a-37)

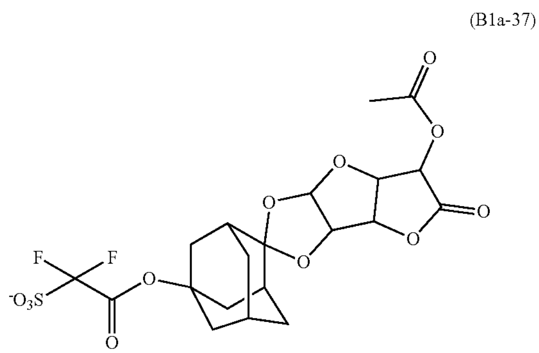

-continued (B1a-38)

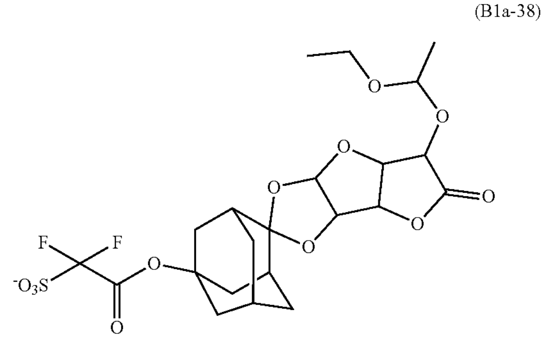

Of these, an anion represented by any one of formula (B1a-1) to formula (B1a-3), formula (B1a-7) to formula (B1a-16), formula (B1a-18), formula (B1a-19) and formula (B1a-22) to formula (B1a-38) is preferable.

Examples of the organic cation of $Z^+$ include an organic onium cation, an organic sulfonium cation, an organic iodonium cation, an organic ammonium cation, a benzothiazolium cation and an organic phosphonium cation, and include those which are the same as the organic cation $ZA^+$ in the structural unit represented by formula (II-2-A'). Of these, an organic sulfonium cation and an organic iodonium cation are preferable, and an arylsulfonium cation is more preferable.

The acid generator (B) is a combination of the anion mentioned above and the organic cation mentioned above, and these can be optionally combined. The acid generator (B) preferably includes a combination of an anion represented by any one of formula (B1a-1) to formula (B1a-3), formula (B1a-7) to formula (B1a-16), formula (B1a-18), formula (B1a-19) and formula (B1a-22) to formula (B1a-38) with a cation (b2-1) or a cation (b2-3).

The acid generator (B) preferably includes those represented by formula (B1-1) to formula (B1-56). Of these acid generators, those containing an arylsulfonium cation are preferable and those represented by formula (B1-1) to formula (B1-3), formula (B1-5) to formula (B1-7), formula (B1-11) to formula (B1-14), formula (B1-20) to formula (B1-26), formula (B1-29) and formula (B1-31) to formula (B1-56) are particularly preferable.

(B1-1)

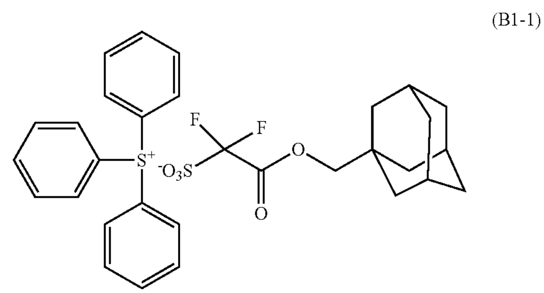

-continued
(B1-2)
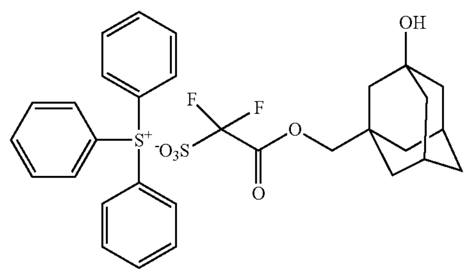
(B1-3)
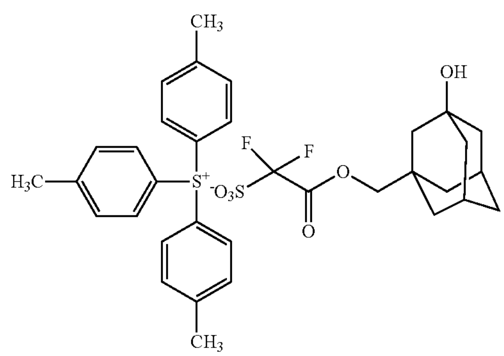
(B1-4)
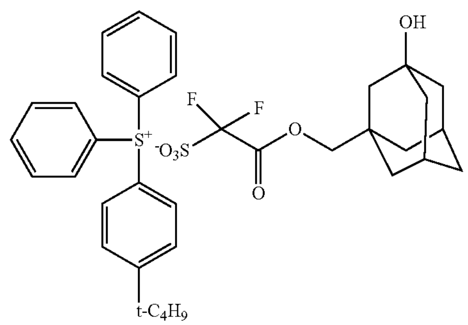
(B1-5)
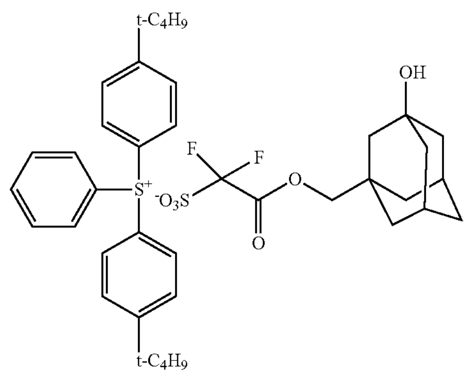
(B1-6)
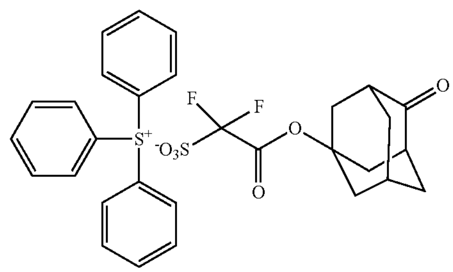
-continued
(B1-7)
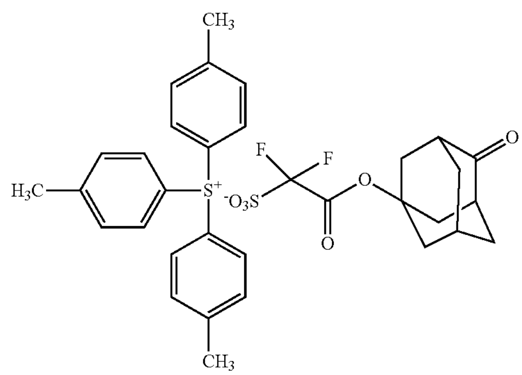
(B1-8)
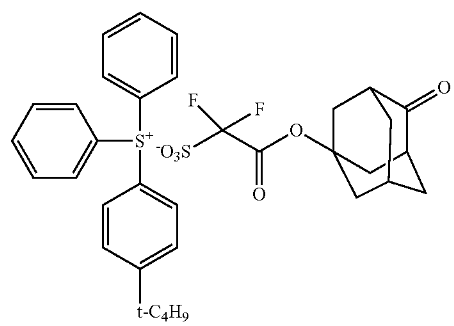
(B1-9)
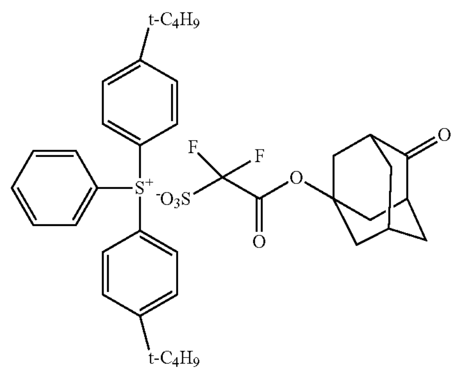
(B1-10)
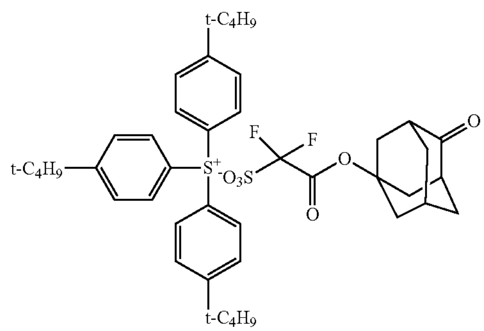

-continued
(B1-11)
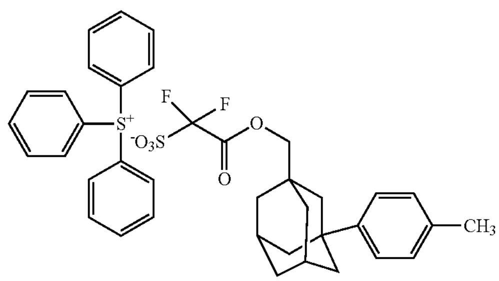
(B1-12)
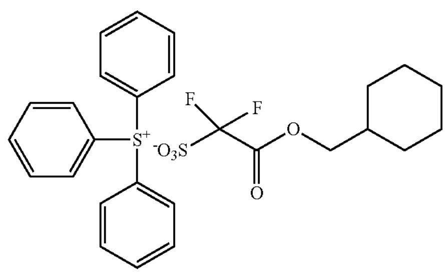
(B1-13)
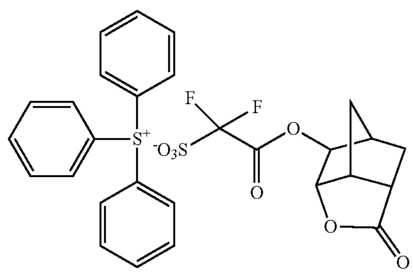
(B1-14)
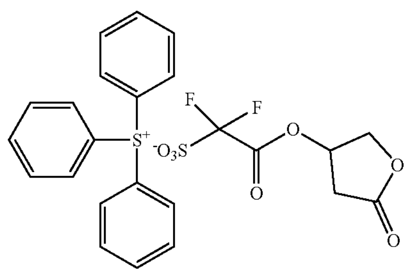
(B1-15)
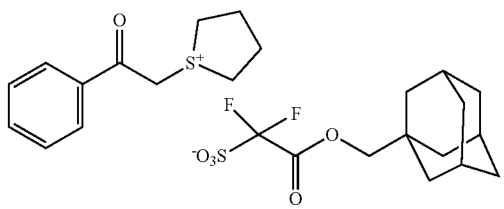
(B1-16)
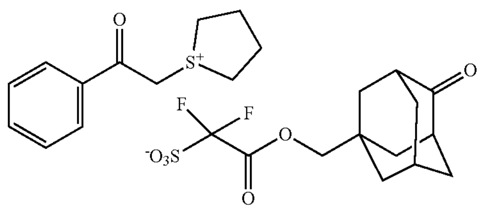
-continued
(B1-17)
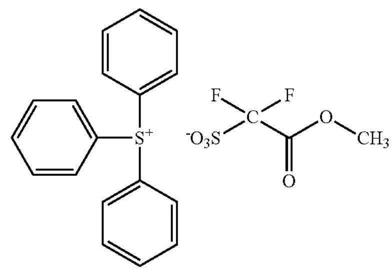
(B1-18)
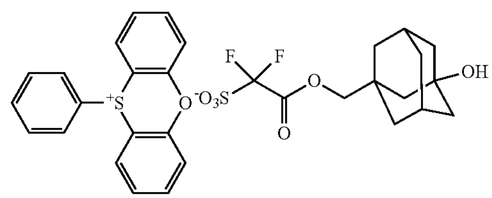
(B1-19)
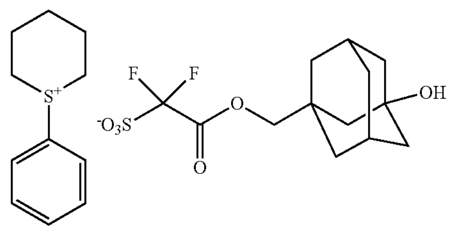
(B1-20)
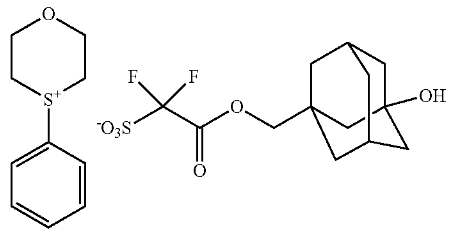
(B1-21)
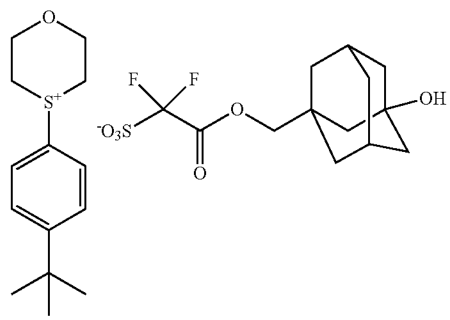
(B1-22)
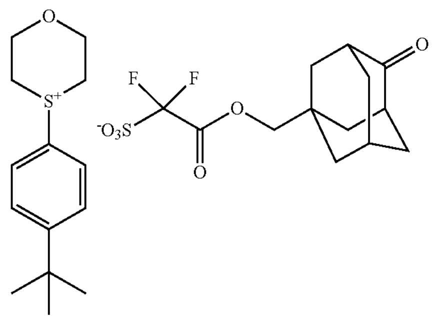

-continued
(B1-23)
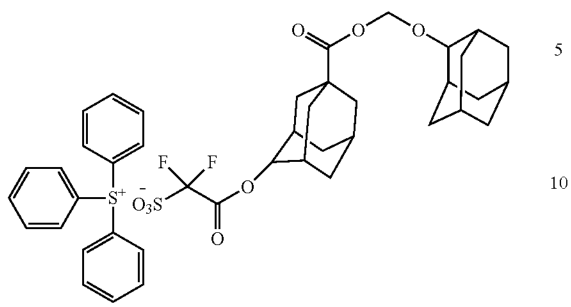
(B1-24)
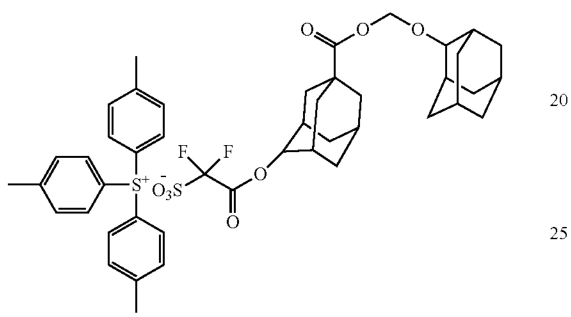
(B1-25)
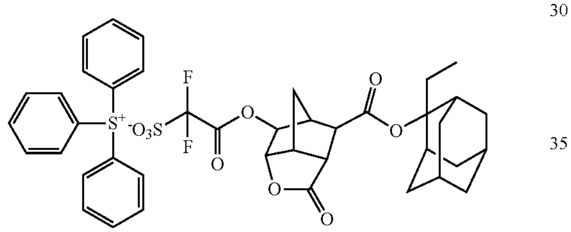
(B1-26)
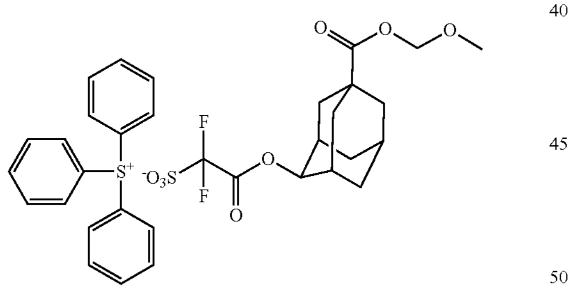
(B1-27)
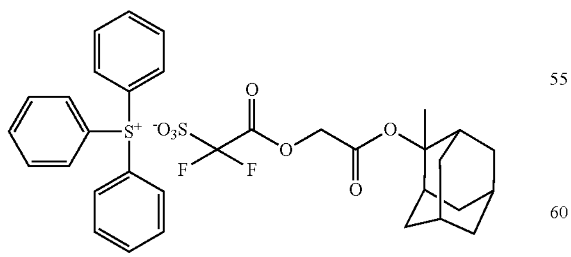
-continued
(B1-28)
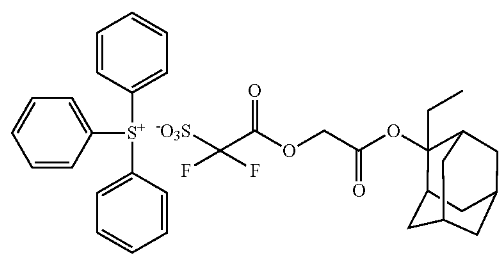
(B1-29)
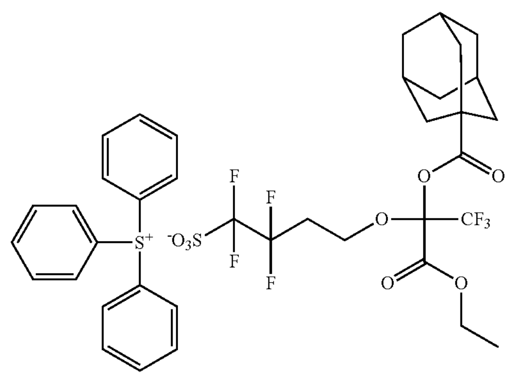
(B1-30)
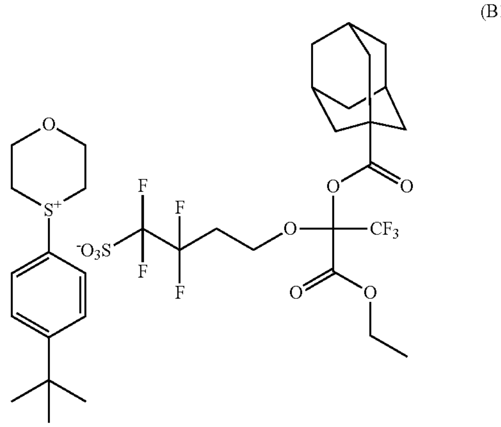
(B1-31)
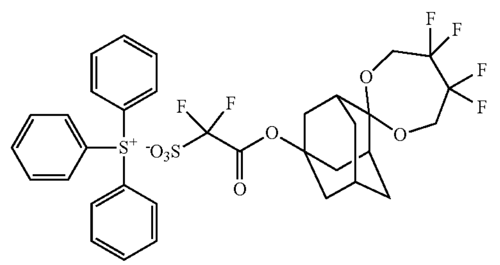

-continued
(B1-32)
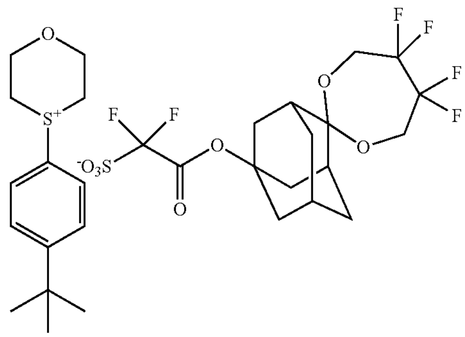
(B1-33)
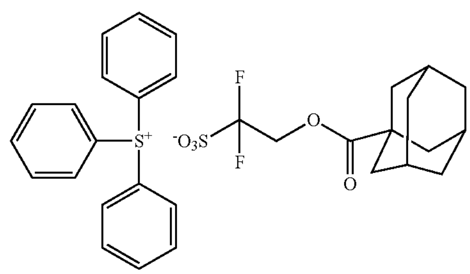
(B1-34)
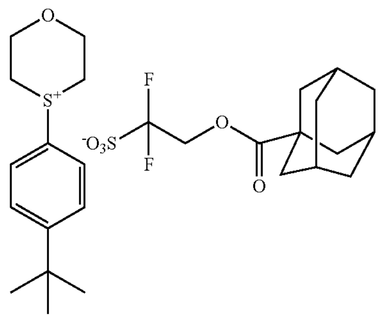
(B1-35)
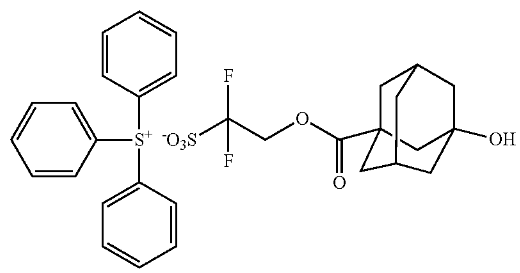
(B1-36)
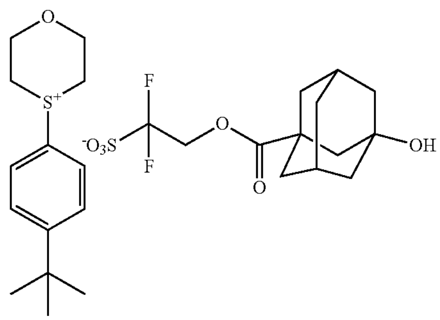
-continued
(B1-37)
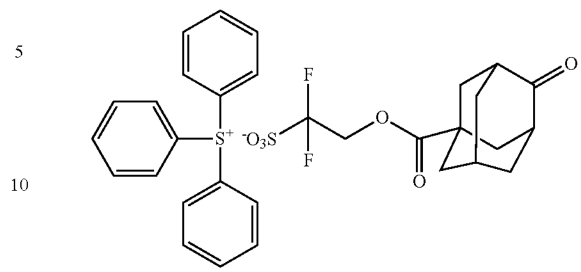
(B1-38)
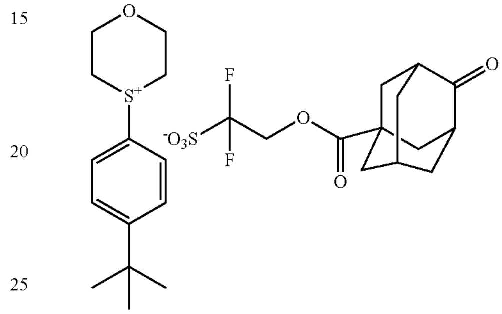
(B1-39)
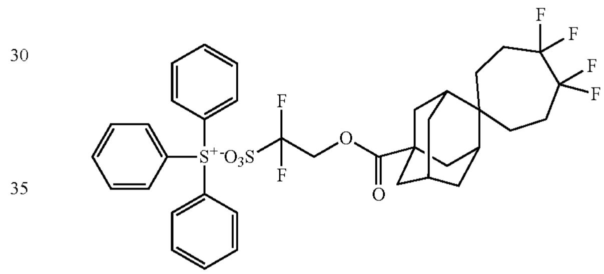
(B1-40)
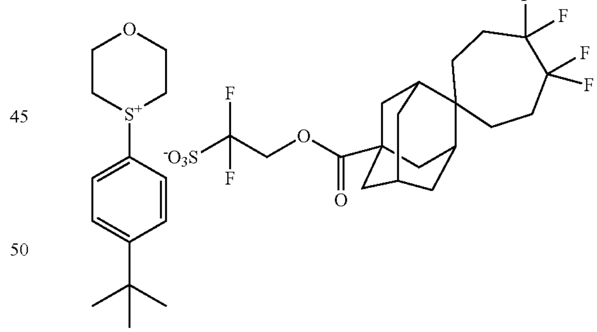
(B1-41)
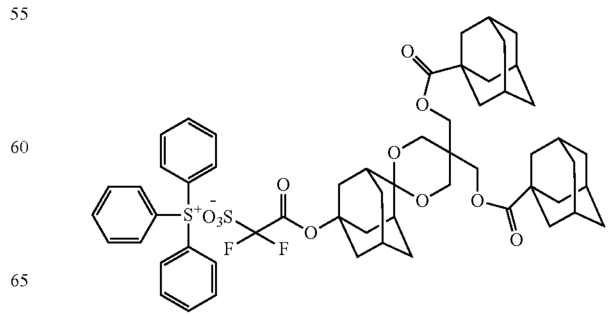

-continued
(B1-42)
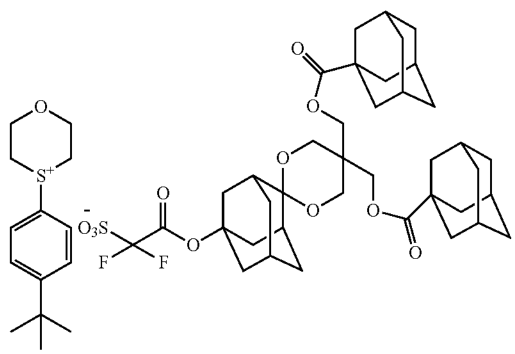
(B1-43)
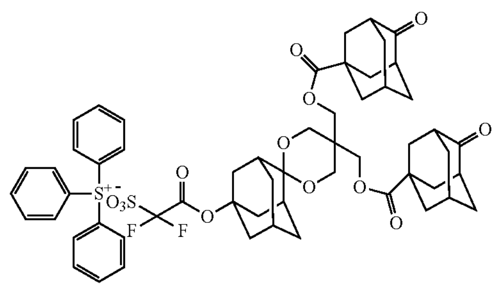
(B1-44)
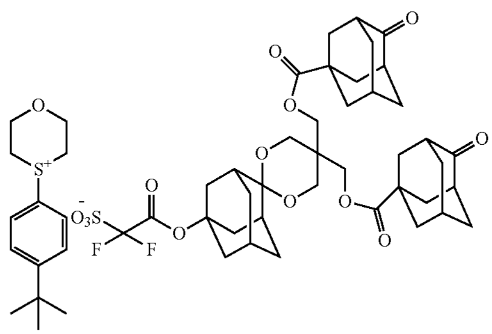
(B1-45)
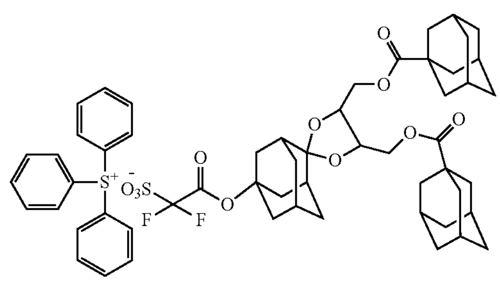
(B1-46)
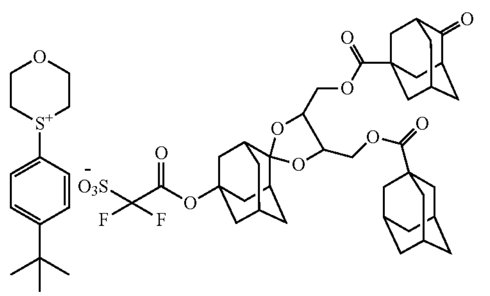
-continued
(B1-47)
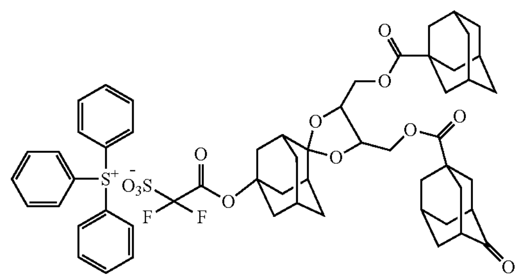
(B1-48)
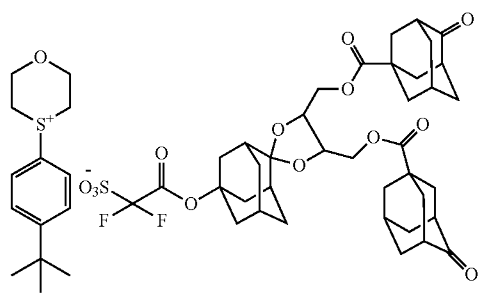
(B1-49)
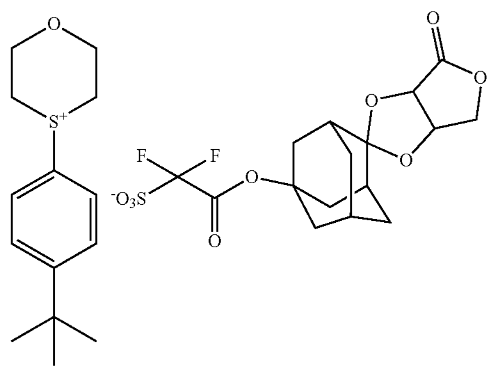
(B1-50)
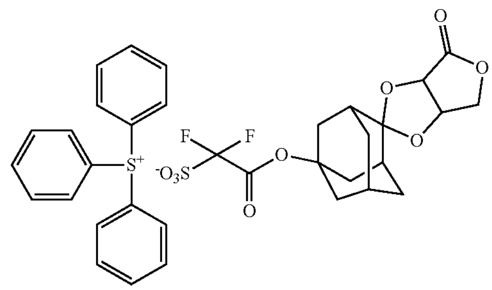
(B1-51)
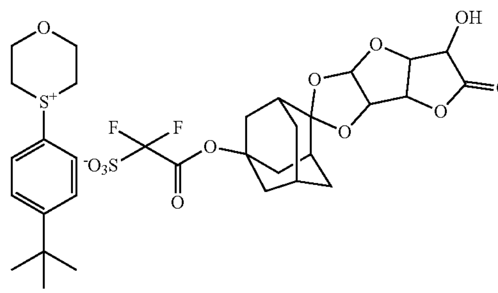

-continued (B1-52)

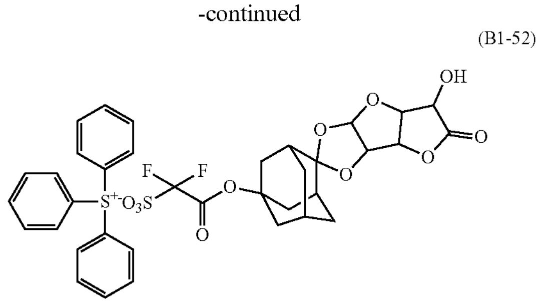

(B1-53)

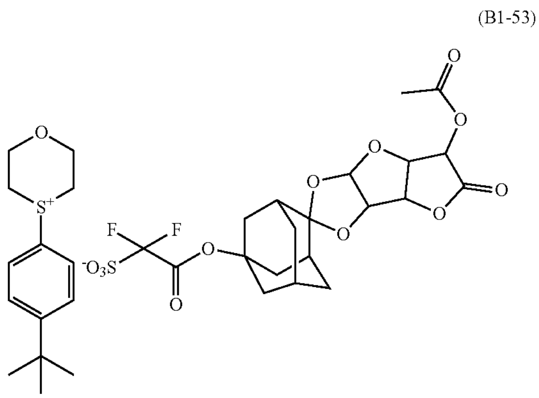

(B1-54)

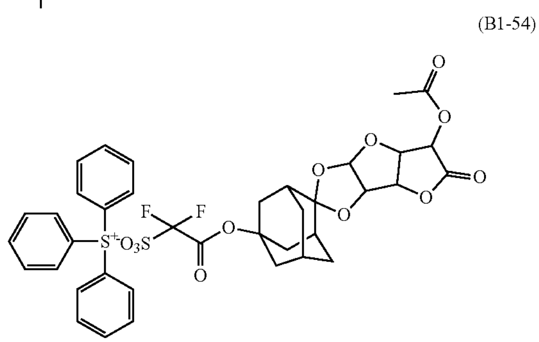

(B1-55)

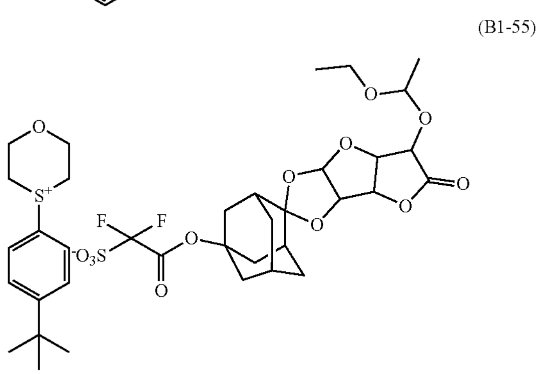

(B1-56)

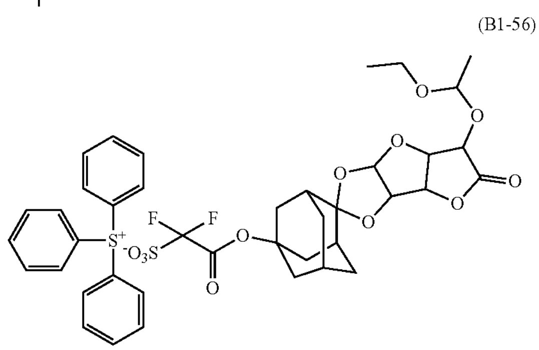

In the resist composition of the present invention, the content of the acid generator is preferably 1 part by mass or more and 45 parts by mass or less, more preferably 1 part by mass or more and 40 parts by mass or less, and still more preferably 3 parts by mass or more and 35 parts by mass or less, based on 100 parts by mass of the resin (A). The resist composition of the present invention may include one acid generator (B) or a plurality of acid generators.

<Solvent (E)>

The content of the solvent (E) in the resist composition is usually 90% by mass or more and 99.9% by mass or less, preferably 92% by mass or more and 99% by mass or less, and more preferably 94% by mass or more and 99% by mass or less. The content of the solvent (E) can be measured, for example, by a known analysis means such as liquid chromatography or gas chromatography.

Examples of the solvent (E) include glycol ether esters such as ethylcellosolve acetate, methylcellosolve acetate and propylene glycol monomethyl ether acetate; glycol ethers such as propylene glycol monomethyl ether; esters such as ethyl lactate, butyl acetate, amyl acetate and ethyl pyruvate; ketones such as acetone, methyl isobutyl ketone, 2-heptanone and cyclohexanone; and cyclic esters such as γ-butyrolactone. The solvent (E) may be used alone, or two or more solvents may be used.

<Other Components>

The resist composition of the present invention may also include components other than the components mentioned above (hereinafter sometimes referred to as "other components (F)"), if necessary. The other components (F) are not particularly limited and it is possible to use various additives known in the resist field, for example, sensitizers, dissolution inhibitors, surfactants, stabilizers and dyes.

<Preparation of Resist Composition>

The resist composition of the present invention can be prepared by mixing a salt (I), a resin (A) and an acid generator (B), and if necessary, resins other than the resin (A) used, a solvent (E), a quencher (C) and other components (F). The order of mixing these components is any order and is not particularly limited. It is possible to select, as the temperature during mixing, appropriate temperature from 10 to 40° C., according to the type of the resin, the solubility in the solvent (E) of the resin and the like. It is possible to select, as the mixing time, appropriate time from 0.5 to 24 hours according to the mixing temperature. The mixing means is not particularly limited and it is possible to use mixing with stirring.

After mixing the respective components, the mixture is preferably filtered through a filter having a pore diameter of about 0.003 to 0.2 μm.

(Method for Producing Resist Pattern)

The method for producing a resist pattern of the present invention include:

(1) a step of applying the resist composition of the present invention on a substrate, (2) a step of drying the applied composition to form a composition layer, (3) a step of exposing the composition layer, (4) a step of heating the exposed composition layer, and (5) a step of developing the heated composition layer.

The resist composition can be usually applied on a substrate using a conventionally used apparatus, such as a spin coater. Examples of the substrate include inorganic substrates such as a silicon wafer. Before applying the resist composition, the substrate may be washed, and an organic antireflection film may be formed on the substrate.

The solvent is removed by drying the applied composition to form a composition layer. Drying is performed by evaporating the solvent using a heating device such as a hot plate (so-called "prebake"), or a decompression device. The heating temperature is preferably 50 to 200° C. and the heating time is preferably 10 to 180 seconds. The pressure during drying under reduced pressure is preferably about 1 to $1.0\times10^5$ Pa.

The composition layer thus obtained is usually exposed using an aligner. The aligner may be a liquid immersion aligner. It is possible to use, as an exposure source, various exposure sources, for example, exposure sources capable of emitting laser beam in an ultraviolet region such as KrF excimer laser (wavelength of 248 nm), ArF excimer laser (wavelength of 193 nm) and $F_2$ excimer laser (wavelength of 157 nm), an exposure source capable of emitting harmonic laser beam in a far-ultraviolet or vacuum ultra violet region by wavelength-converting laser beam from a solid-state laser source (YAG or semiconductor laser), an exposure source capable of emitting electron beam or EUV and the like. In the present specification, such exposure to radiation is sometimes collectively referred to as "exposure". The exposure is usually performed through a mask corresponding to a pattern to be required. When electron beam is used as the exposure source, exposure may be performed by direct writing without using the mask.

The exposed composition layer is subjected to a heat treatment (so-called "post-exposure bake") to promote the deprotection reaction in an acid-labile group. The heating temperature is usually about 50 to 200° C., and preferably about 70 to 150° C.

The heated composition layer is usually developed with a developing solution using a development apparatus. Examples of the developing method include a dipping method, a paddle method, a spraying method, a dynamic dispensing method and the like. The developing temperature is preferably, for example, 5 to 60° C. and the developing time is preferably, for example, 5 to 300 seconds. It is possible to produce a positive resist pattern or negative resist pattern by selecting the type of the developing solution as follows.

When the positive resist pattern is produced from the resist composition of the present invention, an alkaline developing solution is used as the developing solution. The alkaline developing solution may be various aqueous alkaline solutions used in this field. Examples thereof include aqueous solutions of tetramethylammonium hydroxide and (2-hydroxyethyl)trimethylammonium hydroxide (commonly known as choline). The surfactant may be contained in the alkaline developing solution.

It is preferred that the developed resist pattern is washed with ultrapure water and then water remaining on the substrate and the pattern is removed.

When the negative resist pattern is produced from the resist composition of the present invention, a developing solution containing an organic solvent (hereinafter sometimes referred to as "organic developing solution") is used as the developing solution.

Examples of the organic solvent contained in the organic developing solution include ketone solvents such as 2-hexanone and 2-heptanone; glycol ether ester solvents such as propylene glycol monomethyl ether acetate; ester solvents such as butyl acetate; glycol ether solvents such as propylene glycol monomethyl ether; amide solvents such as N,N-dimethylacetamide; and aromatic hydrocarbon solvents such as anisole.

The content of the organic solvent in the organic developing solution is preferably 90% by mass or more and 100% by mass or less, more preferably 95% by mass or more and 100% by mass or less, and still more preferably the organic developing solution is substantially composed of the organic solvent.

Particularly, the organic developing solution is preferably a developing solution containing butyl acetate and/or 2-heptanone. The total content of butyl acetate and 2-heptanone in the organic developing solution is preferably 50% by mass or more and 100% by mass or less, more preferably 90% by mass or more and 100% by mass or less, and still more preferably the organic developing solution is substantially composed of butyl acetate and/or 2-heptanone.

The surfactant may be contained in the organic developing solution. A trace amount of water may be contained in the organic developing solution.

During development, the development may be stopped by replacing by a solvent with the type different from that of the organic developing solution.

The developed resist pattern is preferably washed with a rinsing solution. The rinsing solution is not particularly limited as long as it does not dissolve the resist pattern, and it is possible to use a solution containing an ordinary organic solvent which is preferably an alcohol solvent or an ester solvent.

After washing, the rinsing solution remaining on the substrate and the pattern is preferably removed.

(Application)

The resist composition of the present invention is suitable as a resist composition for exposure of KrF excimer laser, a resist composition for exposure of ArF excimer laser, a resist composition for exposure of electron beam (EB) or a resist composition for exposure of EUV, particularly a resist composition for exposure of ArF excimer laser, a resist composition for exposure of electron beam (EB) or a resist composition for exposure of EUV, and the resist composition is useful for fine processing of semiconductors.

EXAMPLES

The present invention will be described more specifically by way of Examples. Percentages and parts expressing the contents or amounts used in the Examples are by mass unless otherwise specified.

The weight-average molecular weight is a value determined by gel permeation chromatography under the following conditions.

Apparatus: Model HLC-8120GPC (manufactured by TOSOH CORPORATION)

Column: TSKgel Multipore IIXL-M×3+ guard column (manufactured by TOSOH CORPORATION)

Eluent: tetrahydrofuran

Flow rate: 1.0 mL/min

Detector: RI detector

Column temperature: 40° C.

Injection amount: 100 μl

Molecular weight standards: polystyrene standard (manufactured by TOSOH CORPORATION)

Structures of compounds were confirmed by measuring a molecular ion peak using mass spectrometry (Liquid Chromatography: Model 1100, manufactured by Agilent Technologies, Inc., Mass Spectrometry: Model LC/MSD, manufactured by Agilent Technologies, Inc.). The value of this molecular ion peak in the following Examples is indicated by "MASS".

Example 1: Synthesis of Salt Represented by Formula (I-1)

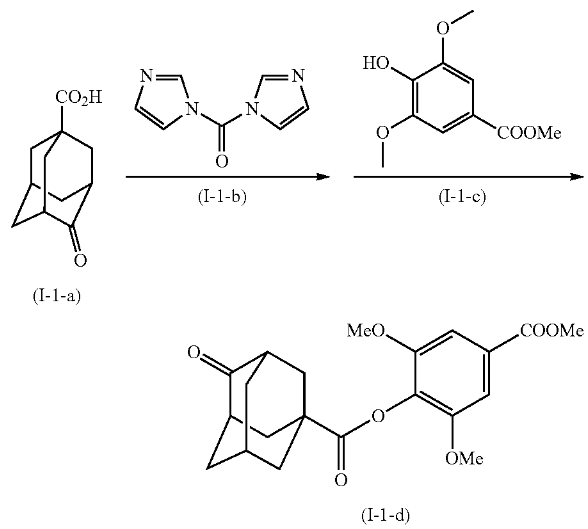

(I-1-b)

(I-1-c)

(I-1-a)

(I-1-d)

10 Part of a compound represented by formula (I-1-a) and 40 parts of chloroform were mixed and, after stirring at 23° C. for 30 minutes, 7.51 parts of a compound represented by formula (I-1-b) was added and the temperature was raised to 50° C., followed by stirring at 50° C. for 2 hours. To the mixture thus obtained, 8.74 parts of a compound represented by formula (I-1-c) was added, followed by stirring at 50° C. for 3 hours. The mixture thus obtained was cooled to 23° C. and then 40 parts of ion-exchanged water and, after stirring at 23° C. for 30 minutes, the organic layer was isolated through separation. To the organic layer thus obtained, 40 parts of an aqueous 5% oxalic acid solution was added and, after stirring at 23° C. for 30 minutes, the organic layer was isolated through separation. The organic layer thus obtained was concentrated to obtain 15.65 parts of a compound represented by formula (I-1-d).

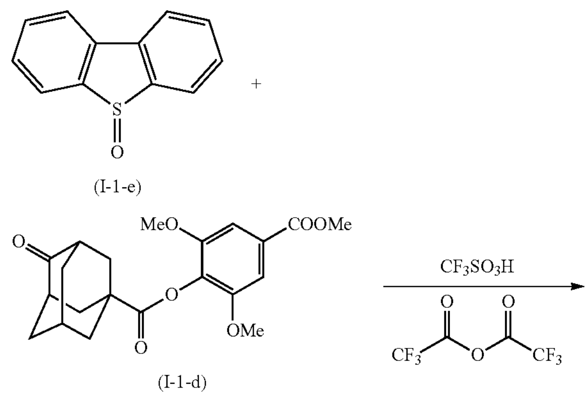

(I-1-e)

(I-1-d)

-continued

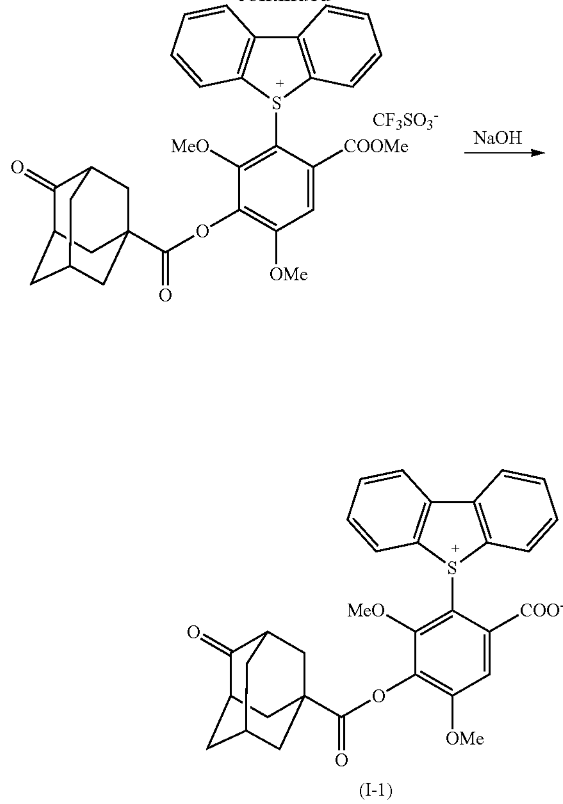

(I-1)

2.92 parts of a compound represented by formula (I-1-e), 30 parts of chloroform, 5.66 parts of a compound represented by formula (I-1-d) and 4.37 parts of trifluoromethanesulfonic acid were mixed, followed by stirring at 23° C. for 30 minutes and further cooling to 5° C. To the mixture thus obtained, 6.12 parts of trifluoroacetic anhydride was added dropwise over 15 minutes, followed by further stirring at 23° C. for 2 hours. To the mixture thus obtained, 40 parts of ion-exchanged water was added and, after stirring at 23° C. for 30 minutes, an organic layer was isolated through separation. To the organic layer thus obtained, 35 parts of an aqueous 10% sodium hydroxide solution was added and, after stirring at 23° C. for 30 minutes, an organic layer was isolated through separation. This operation was performed twice. To the organic layer thus obtained, 40 parts of an aqueous 5% oxalic acid solution was added and, after stirring at 23° C. for 30 minutes, an organic layer was isolated through separation. To the organic layer thus obtained, 40 parts of ion-exchanged water was added and, after stirring at 23° C. for 30 minutes, an organic layer was isolated through separation. This water washing operation was performed five times. The organic layer thus obtained was concentrated and then 30 parts of t-butyl methyl ether was added to the residue, followed by stirring at 23° C. for 30 minutes and further filtration to obtain 4.28 parts of a salt represented by formula (I-1).

MASS (ESI (+) Spectrum): 557.2 $[M+H]^+$

Example 2: Synthesis of Salt Represented by Formula (I-8)

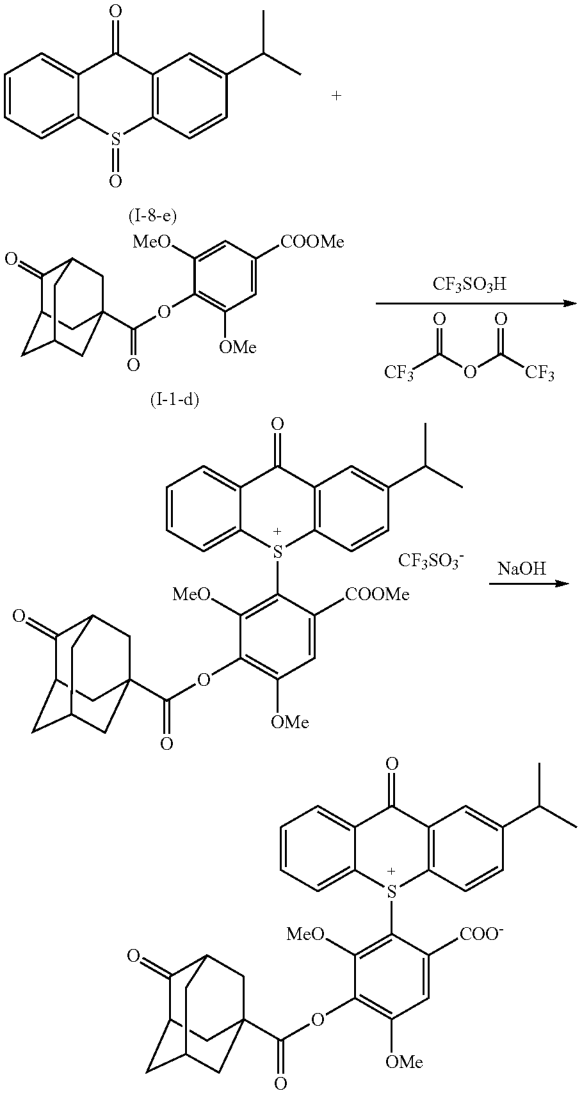

(I-8-e)

(I-1-d)

(I-8)

3.94 Parts of a compound represented by formula (I-8-e), 30 parts of chloroform, 5.66 parts of a compound represented by formula (I-1-d) and 4.37 parts of trifluoromethanesulfonic acid were mixed, followed by stirring at 23° C. for 30 minutes and further cooling to 5° C. To the mixture thus obtained, 6.12 parts of trifluoroacetic anhydride was added dropwise over 15 minutes, followed by further stirring at 23° C. for 2 hours. To the mixture thus obtained, 40 parts of ion-exchanged water was added and, after stirring at 23° C. for 30 minutes, an organic layer was isolated through separation. To the organic layer thus obtained, 35 parts of an aqueous 10% sodium hydroxide solution was added and, after stirring at 23° C. for 30 minutes, an organic layer was isolated through separation. This operation was performed twice. To the organic layer thus obtained, 40 parts of an aqueous 5% oxalic acid solution was added and, after stirring at 23° C. for 30 minutes, an organic layer was isolated through separation. To the organic layer thus obtained, 40 parts of ion-exchanged water was added and, after stirring at 23° C. for 30 minutes, an organic layer was isolated through separation. This water washing operation was performed five times. The organic layer thus obtained was concentrated and then 30 parts of t-butyl methyl ether was added to the residue, followed by stirring at 23° C. for 30 minutes and further filtration to obtain 3.96 parts of a salt represented by formula (I-8).

MASS (ESI (+) Spectrum): 627.2 $[M+H]^+$

Example 3: Synthesis of Salt Represented by Formula (I-2)

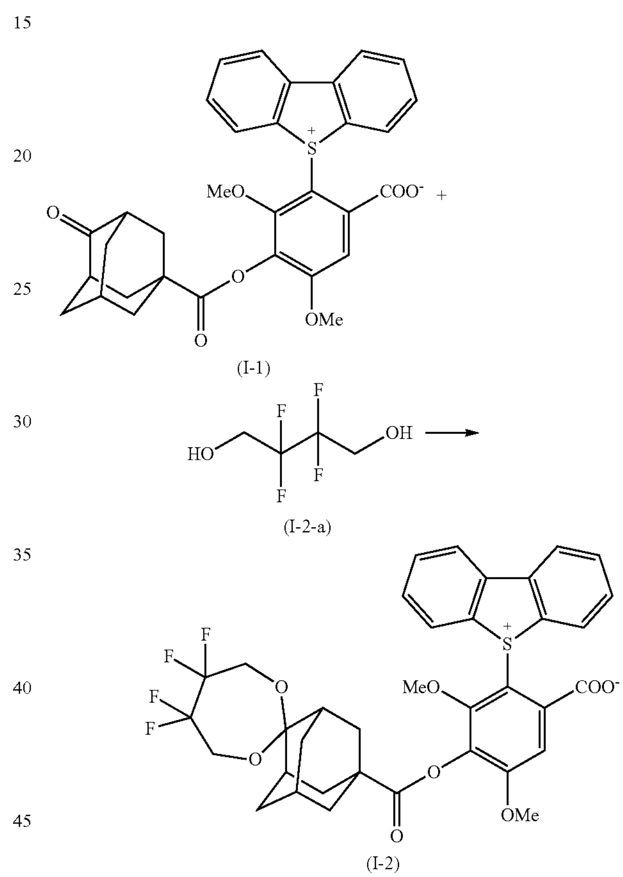

(I-1)

(I-2-a)

(I-2)

1.00 part of a salt represented by formula (I-1) and 20 parts of 1,2-dichloroethane were charged and, after stirring at 23° C. for 30 minutes, 0.58 part of a compound represented by formula (I-2-a) and 0.03 part of p-toluenesulfonic acid were added, followed by stirring at reflux at 100° C. for 3 hours. The reaction product thus obtained was cooled to 23° C. and then 50 parts of chloroform and 25 parts of an aqueous 5% sodium hydrogen carbonate were added, followed by stirring at 23° C. for 30 minutes. After stirring, standing and isolation through separation were performed. To the organic layer thus recovered, 25 parts of ion-exchanged water was charged and, after stirring at 23° C. for 30 minutes, the organic layer was recovered by isolation through separation. This water washing operation was performed five times. The organic layer thus obtained was concentrated and then 20 parts of tert-butyl methyl ether was added to the concentrate thus obtained, followed by stirring, stirring at 23° C. for 1 hour and further filtration to obtain 0.58 part of a salt represented by formula (I-2).

MASS (ESI (+) Spectrum): 701.2 $[M+H]^+$

Example 4: Synthesis of Salt Represented by Formula (I-39)

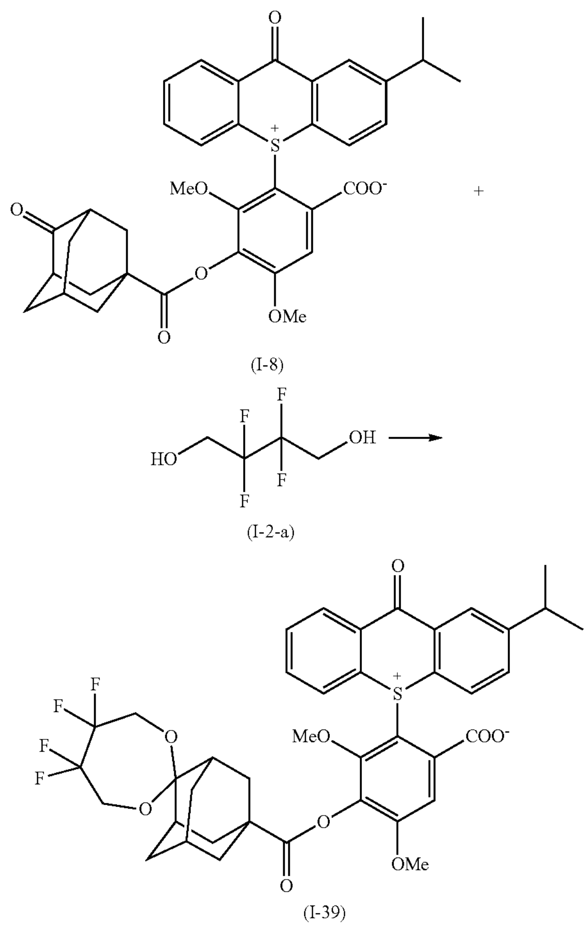

(I-8)

(I-2-a)

(I-39)

1.13 Parts of a salt represented by formula (I-8) and 20 parts of 1,2-dichloroethane were charged and, after stirring at 23° C. for 30 minutes, 0.58 part of a compound represented by formula (I-2-a) and 0.03 part of p-toluenesulfonic acid were added, followed by stirring at reflux at 100° C. for 3 hours. The reaction product thus obtained was cooled to 23° C. and then 50 parts of chloroform and 25 parts of an aqueous 5% sodium hydrogen carbonate were added, followed by stirring at 23° C. for 30 minutes. After stirring, standing and isolation through separation were performed. To the organic layer thus recovered, 25 parts of ion-exchanged water was charged and, after stirring at 23° C. for 30 minutes, the organic layer was recovered by isolation through separation. This water washing operation was performed five times. The organic layer thus obtained was concentrated and then 20 parts of tert-butyl methyl ether was added to the concentrate thus obtained, followed by stirring. After stirring at 23° C. for 1 hour, filtration was performed to obtain 0.39 part of a salt represented by formula (I-39).

MASS (ESI (+) Spectrum): 771.2 $[M+H]^+$

Example 5: Synthesis of Salt Represented by Formula (I-38)

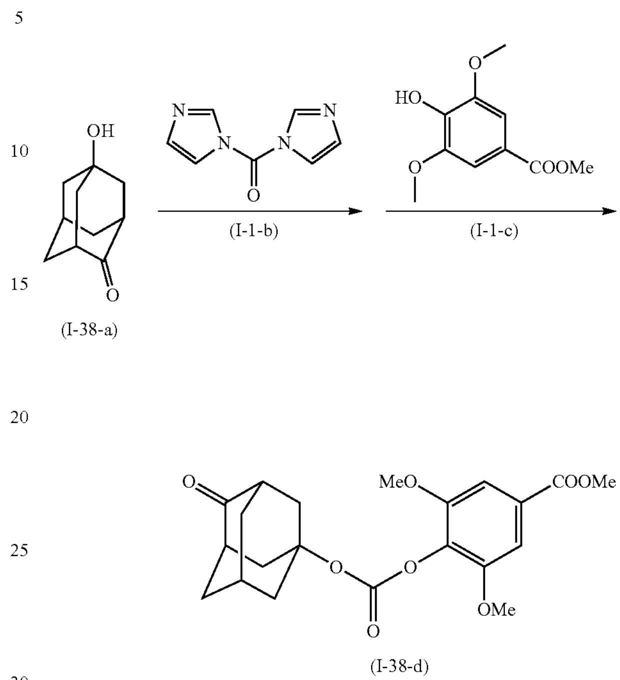

(I-38-a)

(I-38-d)

8.56 Parts of a compound represented by formula (I-38-a) and 40 parts of chloroform were mixed and, after stirring at 23° C. for 30 minutes, 7.51 parts of a compound represented by formula (I-1-b) was added and the temperature was raised to 50° C., followed by stirring at 50° C. for 2 hours. To the mixture thus obtained, 8.74 parts of a compound represented by formula (I-1-c) was added, followed by stirring at 50° C. for 3 hours. The mixture thus obtained was cooled to 23° C. and then 40 parts of ion-exchanged water was added and, after stirring at 23° C. for 30 minutes, the organic layer was isolated through separation. To the organic layer thus obtained, 40 parts of an aqueous 5% oxalic acid solution was added and, after stirring at 23° C. for 30 minutes, the organic layer was isolated through separation. The organic layer thus obtained was concentrated to obtain 16.42 parts of a compound represented by formula (I-38-d).

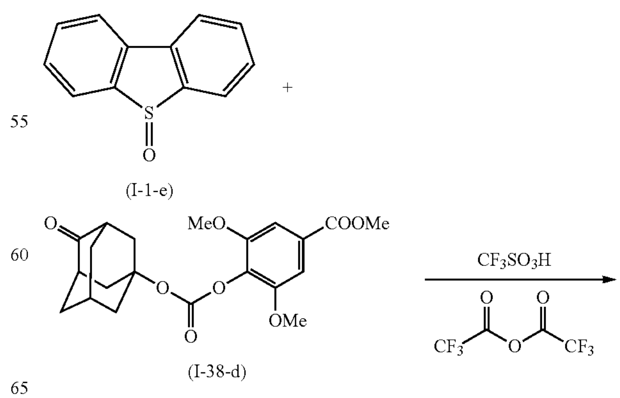

(I-1-e)

(I-38-d)

-continued

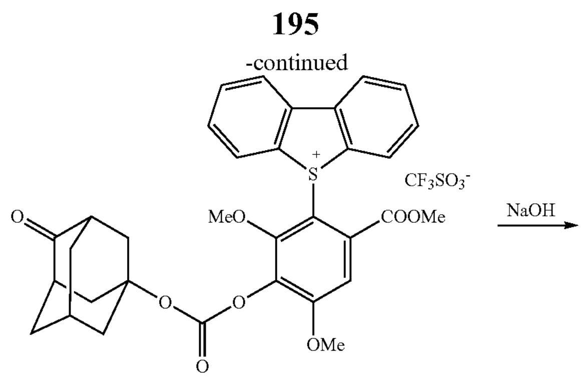

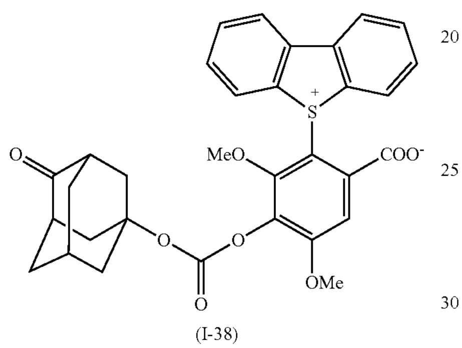

(I-38)

2.92 Parts of a compound represented by formula (I-1-e), 30 parts of chloroform, 5.89 parts of a compound represented by formula (I-38-d) and 4.37 parts of trifluoromethanesulfonic acid were mixed, followed by stirring at 23° C. for 30 minutes and further cooling to 5° C. To the mixture thus obtained, 6.12 parts of trifluoroacetic anhydride was added dropwise over 15 minutes, followed by further stirring at 23° C. for 2 hours. To the mixture thus obtained, 40 parts of ion-exchanged water was added and, after stirring at 23° C. for 30 minutes, an organic layer was isolated through separation. To the organic layer thus obtained, 35 parts of an aqueous 10% sodium hydroxide solution was added and, after stirring at 23° C. for 30 minutes, an organic layer was isolated through separation. This operation was performed twice. To the organic layer thus obtained, 40 parts of an aqueous 5% oxalic acid solution was added and, after stirring at 23° C. for 30 minutes, an organic layer was isolated through separation. To the organic layer thus obtained, 40 parts of ion-exchanged water was added and, after stirring at 23° C. for 30 minutes, an organic layer was isolated through separation. This water washing operation was performed five times. The organic layer thus obtained was concentrated and then 30 parts of t-butyl methyl ether was added to the residue, followed by stirring at 23° C. for 30 minutes and further filtration to obtain 4.28 parts of a salt represented by formula (I-38).

MASS (ESI (+) Spectrum): 573.2 $[M+H]^+$

Example 6: Synthesis of Salt Represented by Formula (I-40)

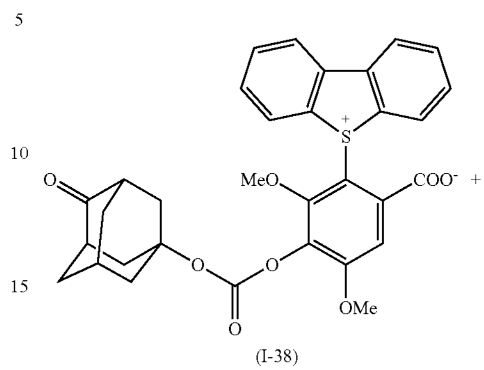

(I-38)

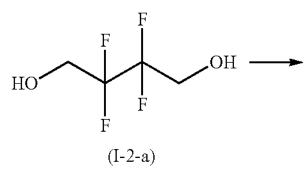

(I-2-a)

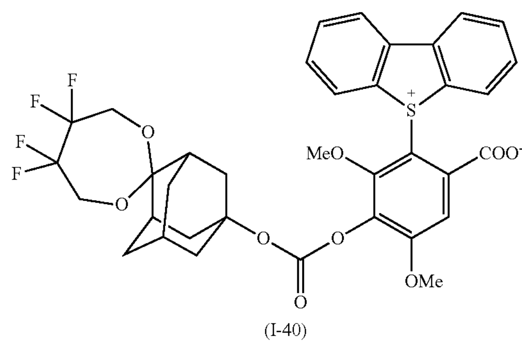

(I-40)

1.03 Parts of a salt represented by formula (I-38) and 20 parts of 1,2-dichloroethane were charged and, after stirring at 23° C. for 30 minutes, 0.58 part of a compound represented by formula (I-2-a) and 0.03 part of p-toluenesulfonic acid were added, followed by stirring at reflux at 100° C. for 3 hours. The reaction product thus obtained was cooled to 23° C. and then 50 parts of chloroform and 25 parts of an aqueous 5% sodium hydrogen carbonate were added, followed by stirring at 23° C. for 30 minutes. After stirring, standing and isolation through separation were performed. To the organic layer thus recovered, 25 parts of ion-exchanged water was charged and, after stirring at 23° C. for 30 minutes, the organic layer was recovered by isolation through separation. This water washing operation was performed five times. The organic layer thus obtained was concentrated and then 20 parts of tert-butyl methyl ether was added to the concentrate thus obtained, followed by stirring at 23° C. for 1 hour and further filtration to obtain 0.62 part of a salt represented by formula (I-40).

MASS (ESI (+) Spectrum): 717.2 $[M+H]^+$

Example 7: Synthesis of Salt Represented by Formula (I-35)

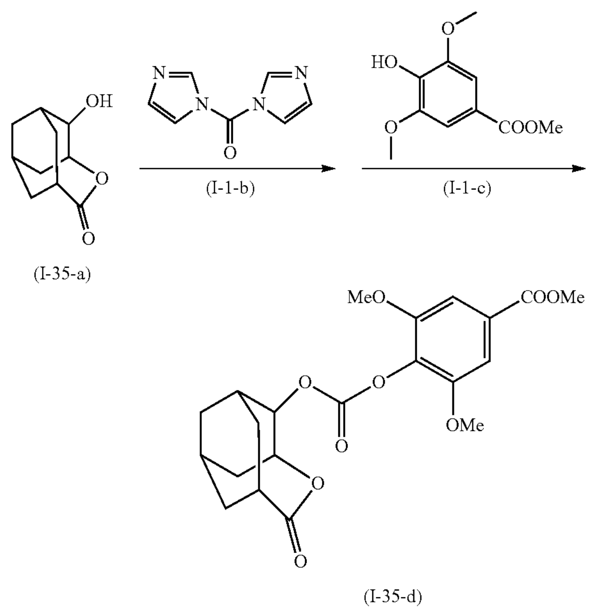

(I-1-b)

(I-1-c)

(I-35-a)

(I-35-d)

9.38 Parts of a compound represented by formula (I-35-a) and 40 parts of chloroform were mixed and, after stirring at 23° C. for 30 minutes, 7.51 parts of a compound represented by formula (I-1-b) was added and the temperature was raised to 50° C., followed by stirring at 50° C. for 2 hours. To the mixture thus obtained, 8.74 parts of a compound represented by formula (I-1-c) was added, followed by stirring at 50° C. for 3 hours. The mixture thus obtained was cooled to 23° C. and then 40 parts of ion-exchanged water was added and, after stirring at 23° C. for 30 minutes, the organic layer was isolated through separation. To the organic layer thus obtained, 40 parts of an aqueous 5% oxalic acid solution was added and, after stirring at 23° C. for 30 minutes, the organic layer was isolated through separation. The organic layer thus obtained was concentrated to obtain 16.11 parts of a compound represented by formula (I-35-d).

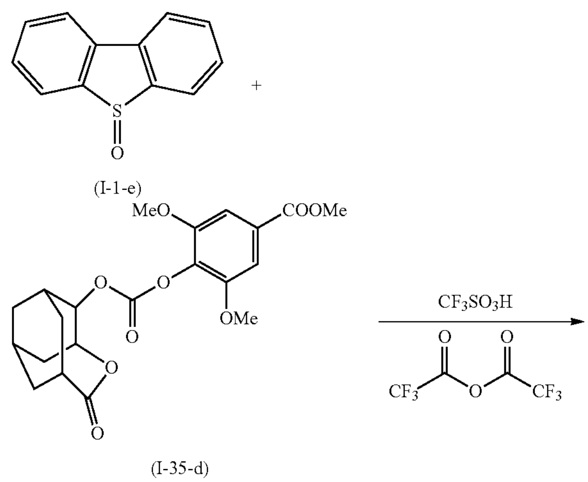

(I-1-e)

(I-35-d)

-continued

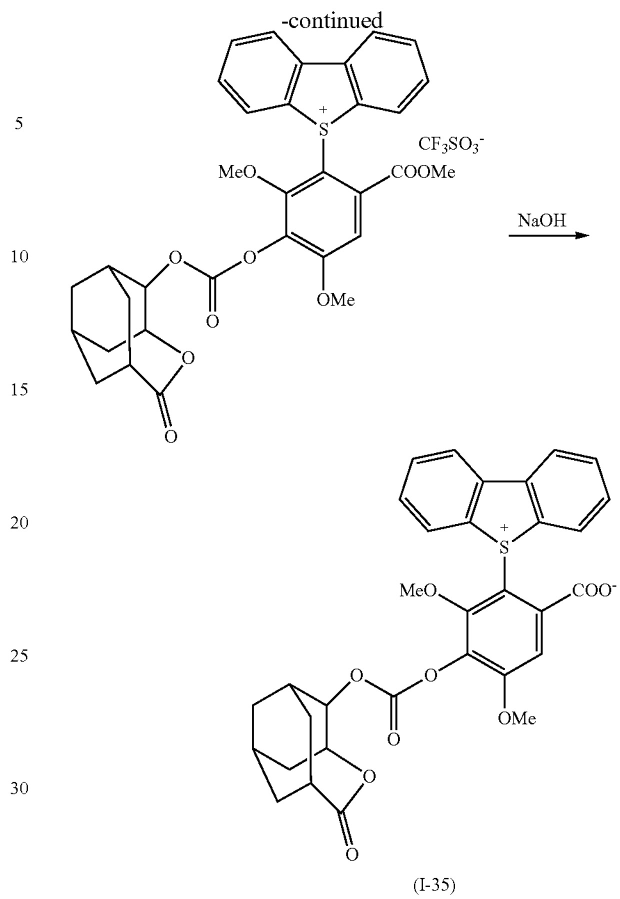

(I-35)

2.92 Parts of a compound represented by formula (I-1-e), 30 parts of chloroform, 6.12 parts of a compound represented by formula (I-35-d) and 4.37 parts of trifluoromethanesulfonic acid were mixed, followed by stirring at 23° C. for 30 minutes and further cooling to 5° C. To the mixture thus obtained, 6.12 parts of trifluoroacetic anhydride was added dropwise over 15 minutes, followed by stirring at 23° C. for 2 hours. To the mixture thus obtained, 40 parts of ion-exchanged water was added and, after stirring at 23° C. for 30 minutes, an organic layer was isolated through separation. To the organic layer thus obtained, 35 parts of an aqueous 10% sodium hydroxide solution was added and, after stirring at 23° C. for 30 minutes, an organic layer was isolated through separation. This operation was performed twice. To the organic layer thus obtained, 40 parts of an aqueous 5% oxalic acid solution was added and, after stirring at 23° C. for 30 minutes, an organic layer was isolated through separation. To the organic layer thus obtained, 40 parts of ion-exchanged water was added and, after stirring at 23° C. for 30 minutes, an organic layer was isolated through separation. This water washing operation was performed five times. The organic layer thus obtained was concentrated and then 30 parts of t-butyl methyl ether was added to the residue, followed by stirring at 23° C. for 30 minutes and further filtration to obtain 4.44 parts of a salt represented by formula (I-35).

MASS (ESI (+) Spectrum): 589.2 $[M+H]^+$

Synthesis of Resin

Compounds (monomers) used in the synthesis of the resin (A) are shown below. Hereinafter, these compounds are referred to as "monomer (a1-1-3)" according to the number of formula.

-continued (a1-1-3)

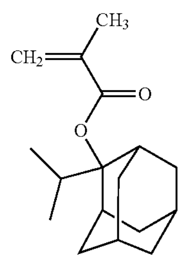

(a1-2-5)

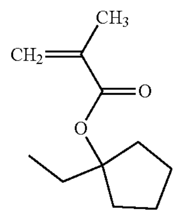

(a2-1-3)

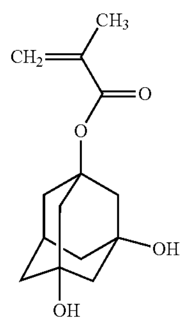

(a3-4-2)

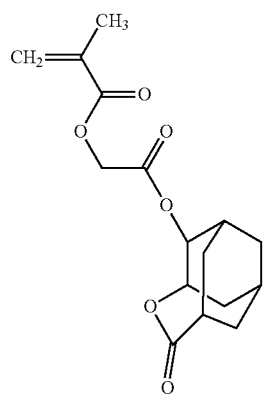

(a4-0-12)

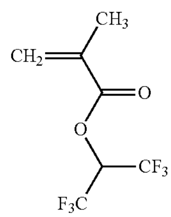

(a5-1-1)

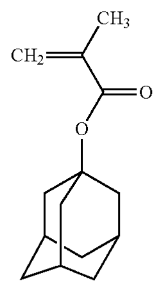

Synthesis Example 1: Synthesis of Resin A1

Using a monomer (a1-1-3), a monomer (a1-2-5), a monomer (a2-1-3) and a monomer (a3-4-2) as monomers, these monomers were mixed in a molar ratio of 45:14:2.5:38.5 [monomer (a1-1-3):monomer (a1-2-5):monomer (a2-1-3):monomer (a3-4-2)], and propylene glycol monomethyl ether acetate was added to this monomer mixture in the amount of 1.5 mass times the total mass of all monomers to obtain a solution. To the solution thus obtained, azobisisobutyronitrile and azobis(2,4-dimethylvaleronitrile) as initiators were added in the amounts of 1 mol % and 3 mol % based on the amount of all monomers, and then the mixture was heated at 73° C. for about 5 hours. The reaction mixture thus obtained was poured into a large amount of methanol/water mixed solvent to precipitate a resin, and this resin was filtered. A reprecipitation operation of dissolving the resin thus obtained again in propylene glycol monomethyl ether acetate to obtain a solution, pouring the solution into a methanol/water mixed solvent to precipitate the resin, and filtering the resin was performed twice to obtain a resin A1 having a weight-average molecular weight of $7.6\times10^3$ in a yield of 68%. This resin A1 has the following structural units.

A1

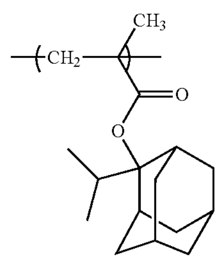

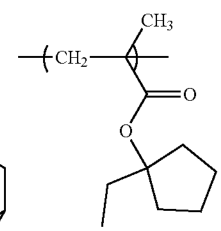

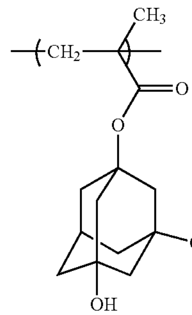

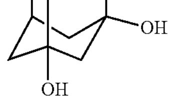

-continued

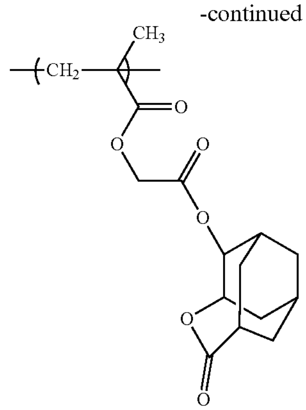

Synthesis Example 2: Synthesis of Resin X1

Using a monomer (a5-1-1) and a monomer (a4-0-12) as monomers, these monomers were mixed in a molar ratio of 50:50 [monomer (a5-1-1):monomer (a4-0-12)], and methyl isobutyl ketone was added to this monomer mixture in the amount of 1.2 mass times the amount of all monomers to obtain a solution. To the solution thus obtained, azobis(2,4-dimethylvaleronitrile) as an initiator was added in the amount of 3 mol % based on the amount of all monomers, and then the mixture was heated at 70° C. for about 5 hours. The reaction mixture thus obtained was poured into a large amount of methanol/water mixed solvent to precipitate a resin, and this resin was filtered to obtain a resin X1 having a weight-average molecular weight of $1.0\times10^4$ in a yield of 91%. This resin X1 has the following structural units.

X1

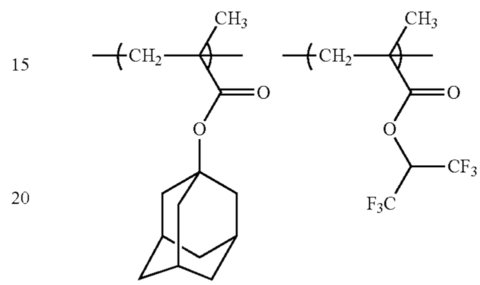

<Preparation of Resist Compositions>

As shown in Table 1, the following respective components were mixed, and the mixtures thus obtained were filtered through a fluorine resin filter having a pore diameter of 0.2 μm to prepare resist compositions.

TABLE 1

| Resist composition | Resin | Acid generator | Salt (I) | Quencher (C) | PB/PEB |
|---|---|---|---|---|---|
| Composition 1 | X1/A1 = 0.2/10 parts | B1-21/B1-22 = 0.90/0.45 parts | I-1 = 0.8 parts | — | 90° C./85° C. |
| Composition 2 | X1/A1 = 0.2/10 parts | B1-21/B1-22 = 0.90/0.45 parts | I-8 = 0.8 parts | — | 90° C./85° C. |
| Composition 3 | X1/A1 = 0.2/10 parts | B1-21/B1-22 = 0.90/0.45 parts | 1-2 = 0.8 parts | — | 90° C./85° C. |
| Composition 4 | X1/A1 = 0.2/10 parts | B1-21/B1-22 = 0.90/0.45 parts | I-35 = 0.8 parts | — | 90° C./85° C. |
| Composition 5 | X1/A1 = 0.2/10 parts | B1-21/B1-22 = 0.90/0.45 parts | I-38 = 0.8 parts | — | 90° C./85° C. |
| Composition 6 | X1/A1 = 0.2/10 parts | B1-21/B1-22 = 0.90/0.45 parts | I-39 = 0.8 parts | — | 90° C./85° C. |
| Composition 7 | X1/A1 = 0.2/10 parts | B1-21/B1-22 = 0.90/0.45 parts | I-40 = 0.8 parts | — | 90° C./85° C. |
| Comparative Composition 1 | X1/A1 = 0.2/10 parts | B1-21/B1-22 = 0.90/0.45 parts | — | IX-1 = 0.8 parts | 90° C./85° C. |
| Comparative Composition 2 | X1/A1 = 0.2/10 parts | B1-21/B1-22 = 0.90/0.45 parts | — | IX-2 = 0.8 parts | 90° C./85° C. |

<Resin>

A1, X1: Resin A1, Resin X1

<Acid Generator (B)>

B1-21: Salt represented by formula (B1-21)

B1-22: Salt represented by formula (B1-22)

(B1-21)

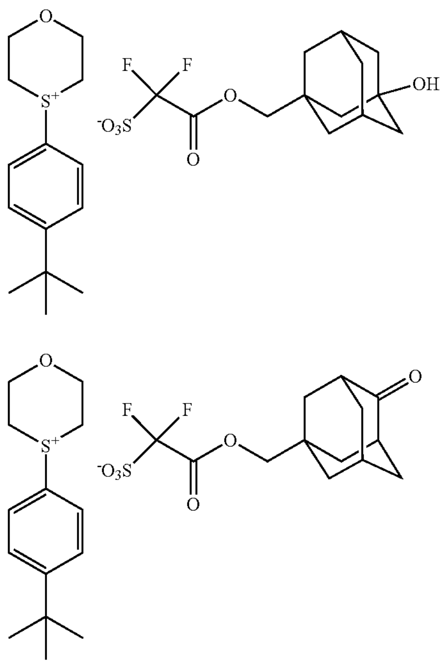

(B1-22)

<Salt (I)>

I-1: Salt represented by formula (I-1)

I-2: Salt represented by formula (I-2)

I-8: Salt represented by formula (I-8)

I-35: Salt represented by formula (I-35)

I-38: Salt represented by formula (I-38)

I-39: Salt represented by formula (I-39)

I-40: Salt represented by formula (I-40)

<Quencher (C)>

IX-1:

IX-2:

(IX-1)

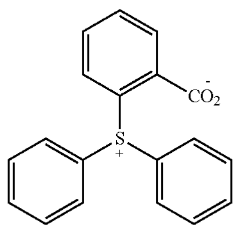

-continued (IX-2)

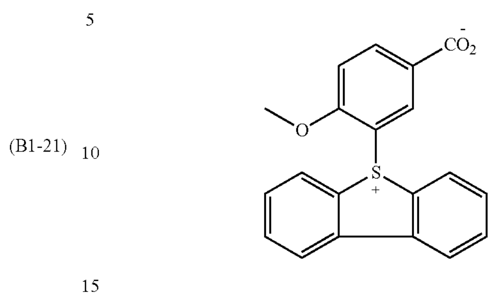

<Solvent>

| | |
|---|---|
| Propylene glycol monomethyl ether acetate | 265 parts |
| propylene glycol monomethyl ether | 20 parts |
| 2-Heptanone | 20 parts |
| γ-Butyrolactone | 3.5 parts |

(Production of Resist Pattern and Evaluation Thereof)

A composition for an organic antireflective film (ARC-29, manufactured by Nissan Chemical Co. Ltd.) was applied onto a silicon wafer and baked under the conditions at 205° C. for 60 seconds to form a 78 nm thick organic antireflective film on the silicon wafer. Then, the above resist composition was applied on the organic antireflective film by coating (spin coating) in such a manner that the thickness of the film after drying became 85 nm. The silicon wafer coated with the resist composition was pre-baked for 60 seconds on a direct hot plate at the temperature mentioned in the "PB" column in Table 1 to form a composition layer. The silicon wafer with the composition layer thus formed thereon was exposed through a mask for forming a contact hole pattern (hole pitch of 90 nm/hole diameter of 55 nm) stepwise with changing exposure dose using an ArF excimer laser stepper for immersion lithography (XT: 1900Gi, manufactured by ASML Ltd.: NA=1.35, 3/4 Annular, XY-polarization). Ultrapure water was used for medium of immersion.

After exposure, post-exposure baking was performed on a hot plate for 60 seconds at the temperature mentioned in the "PEB" column in Table 1. Then, the composition layer on the silicon wafer was subjected to development at 23° C. for 20 seconds by a dynamic dispense method using butyl acetate (manufactured by Tokyo Chemical Industry Co., Ltd.) as a developing solution to obtain a negative resist pattern.

Effective sensitivity was represented as the exposure dose at which the hole diameter formed using the mask became 45 nm in the resist pattern obtained after development.

<Evaluation of Mask Error Factor (MFF)>

Using masks each having a hole diameter (hole dimeter of the translucent part of the mask) of 57 nm, 56 nm, 55 nm, 54 nm and 53 nm (hole pitch is 90 nm in any case), resist patterns were produced at the effective sensitivity. When mask hole dimeters are plotted on the abscissa axis, while diameters of holes of the photoresist patterns formed (transferred) on the substrate by exposure are plotted on the ordinate axis, the slope of a plotted regression line was determined as the MEF value.

The results are shown in Table 2. The numerical value in the Table indicates the MEF value.

TABLE 2

| | Resist composition | MEF |
|---|---|---|
| Example 8 | Composition 1 | 3.99 |
| Example 9 | Composition 2 | 3.96 |
| Example 10 | Composition 3 | 3.84 |
| Example 11 | Composition 4 | 3.85 |
| Example 12 | Composition 5 | 3.92 |
| Example 13 | Composition 6 | 3.79 |
| Example 14 | Composition 7 | 3.80 |
| Comparative Example 1 | Comparative Composition 1 | 4.28 |
| Comparative Example 2 | Comparative Composition 2 | 4.32 |

As compared with Comparative compositions 1 and 2, Compositions 1 to 7 exhibited smaller slope of the plotted regression line, leading to satisfactory mask error factor (MEF).

INDUSTRIAL APPLICABILITY

A salt and a resist composition including the salt of the present invention are capable of obtaining a resist pattern with satisfactory mask error factor (MEF) and are therefore extremely useful for fine processing of semiconductors.

The invention claimed is:

1. A salt represented by formula (I):

(I)

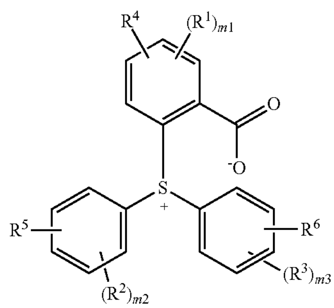

wherein, in formula (I), $R^1$ represents a halogen atom, an alkyl fluoride group having 1 to 6 carbon atoms or a hydrocarbon group having 1 to 18 carbon atoms, and —$CH_2$-included in the hydrocarbon group may be replaced by —O—or —CO—, provided that at least two $R^1$ are a chain hydrocarbon group, and at least one-$CH_2$-included in the chain hydrocarbon group is replaced by —O—or —CO—, $R^2$ and $R^3$ each independently represent a halogen atom, an alkyl fluoride group having 1 to 6 carbon atoms or a hydrocarbon group having 1 to 18 carbon atoms, —$CH_2$-included in the hydrocarbon group may be replaced by —O—or —CO—, or $R^2$ and $R^3$ may be bonded to each other to form a single bond or an alkanediyl bridge having 1 to 6 carbon atoms together with carbon atoms to which $R^2$ and $R^3$ are bonded, and —$CH_2$-included in the alkanediyl bridge may be replaced by —O—, —S—, —CO—, —SO—or —$SO_2$—, m1 represents an integer of 2 to 3, and when m1 is 2 or more, a plurality of $R^1$ may be the same or different from each other, m2 represents an integer of 0 to 4, and when m2 is 2 or more, a plurality of $R^2$ may be the same or different from each other, m3 represents an integer of 0 to 4, and when m3 is 2 or more, a plurality of $R^3$ may be the same or different from each other, $R^4$ represents-$X^2$—$R^7$, $R^4$ is bonded at a meta-position with respect to a bonding site of $S^+$ on the benzene ring, $R^5$ and $R^6$ each independently represent a hydrogen atom or —$X^2$—$R^7$, $X^2$ represents *—CO—O—, *—O—CO—or *—O—CO—O—, and * represents a bonding site to the benzene ring, and $R^7$ represents a hydrocarbon group including a cyclic hydrocarbon group having 3 to 18 carbon atoms and the cyclic hydrocarbon group may have a substituent, and —$CH_2$-included in the hydrocarbon group may be replaced by —O—, —S—, —$SO_2$—or —CO—, provided that the cyclic hydrocarbon group for $R^7$ has at least one substituent, or at least one-$CH_2$-included in the hydrocarbon group for $R^7$ is replaced by —O—, —S—, —$SO_2$—or —CO—.

2. A quencher comprising the salt according to claim 1.

3. A resist composition comprising the quencher according to claim 2, a resin including a structural unit having an acid-labile group, and an acid generator.

4. The resist composition according to claim 3, wherein the resin including a structural unit having an acid-labile group includes at least one selected from the group consisting of a structural unit represented by formula (a1-1) and a structural unit represented by formula (a1-2):

(a1-1)

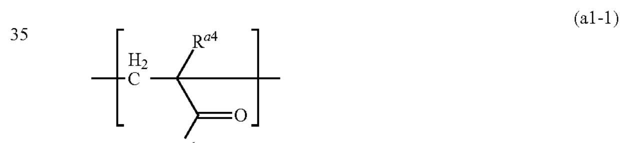

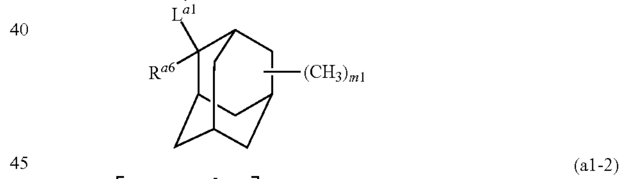

(a1-2)

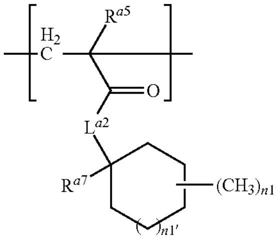

wherein, in formula (a1-1) and formula (a1-2), $L^{a1}$ and $L^{a2}$ each independently represent —O—or *—O—$(CH_2)_{k1}$—CO—O—, k1 represents an integer of 1 to 7, and * represents a bonding site to—CO—, $R^{a4}$ and $R^{a5}$ each independently represent a hydrogen atom or a methyl group, $R^{a6}$ and $R^{a7}$ each independently represent an alkyl group having 1 to 8 carbon atoms, an alicyclic hydrocarbon group having 3 to 18 carbon atoms, or a group obtained by combining these groups, m1 represents an integer of 0 to 14, n1 represents an integer of 0 to 10, and n1' represents an integer of 0 to 3.

5. The resist composition according to claim 3, wherein the acid generator includes a salt represented by formula (B1):

(B1)

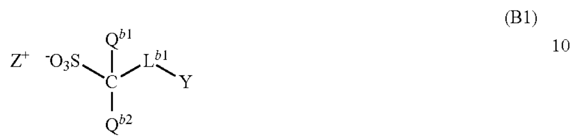

wherein, in formula (B1), $Q^{b1}$ and $Q^{b2}$ each independently represent a fluorine atom or a perfluoroalkyl group having 1 to 6 carbon atoms, $L^{b1}$ represents a divalent saturated hydrocarbon group having 1 to 24 carbon atoms, —$CH_2$-included in the divalent saturated hydrocarbon group may be replaced by —O—or —CO—, and the hydrogen atom included in the divalent saturated hydrocarbon group may be substituted with a fluorine atom or a hydroxy group, Y represents a methyl group which may have a substituent or an alicyclic hydrocarbon group having 3 to 24 carbon atoms which may have a substituent, and —$CH_2$-included in the alicyclic hydrocarbon group may be replaced by —O—, —S(O) 2- or —CO—, and $Z^+$ represents an organic cation.

6. The resist composition according to claim 3, further comprising a salt generating an acid having an acidity lower than that of an acid generated from the acid generator.

7. The resist composition according to claim 3, further comprising a resin including a structural unit having a fluorine atom.

8. A method for producing a resist pattern, which comprises:

(1) a step of applying the resist composition according to claim 4 on a substrate, (2) a step of drying the applied composition to form a composition layer, (3) a step of exposing the composition layer, (4) a step of heating the exposed composition layer, and (5) a step of developing the heated composition layer.

9. A salt represented by formula (I):

(I)

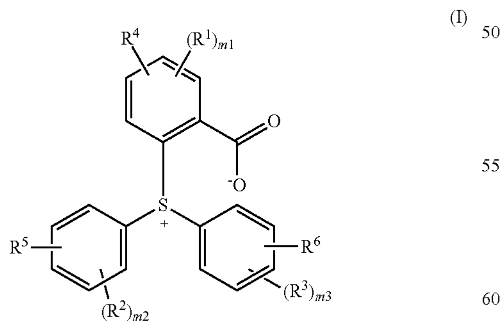

wherein, in formula (I), $R^1$ represents a halogen atom, an alkyl fluoride group having 1 to 6 carbon atoms or a hydrocarbon group having 1 to 18 carbon atoms, and —$CH_2$-included in the hydrocarbon group may be replaced by —O—or —CO—, provided that at least two $R^1$ are a chain hydrocarbon group, and at least one-$CH_2$-included in the chain hydrocarbon group is replaced by —O—or —CO—, $R^2$ and $R^3$ each independently represent a halogen atom, an alkyl fluoride group having 1 to 6 carbon atoms or a hydrocarbon group having 1 to 18 carbon atoms, —$CH_2$-included in the hydrocarbon group may be replaced by —O—or —CO—, or $R^2$ and $R^3$ may be bonded to each other to form a single bond or an alkanediyl bridge having 1 to 6 carbon atoms together with carbon atoms to which $R^2$ and $R^3$ are bonded, and —$CH_2$-included in the alkanediyl bridge may be replaced by —O—, —S—, —CO—, —SO—or —$SO_2$—, m1 represents an integer of 2 to 3, and when m1 is 2 or more, a plurality of $R^1$ may be the same or different from each other, m2 represents an integer of 1 to 4, and when m2 is 2 or more, a plurality of $R^2$ may be the same or different from each other, m3 represents an integer of 1 to 4, and when m3 is 2 or more, a plurality of $R^3$ may be the same or different from each other, $R^4$ represents-$X^2$—$R^7$, $R^4$ is bonded at a meta-position with respect to a bonding site of $S^+$ on the benzene ring, $R^5$ and $R^6$ each independently represent a hydrogen atom or —$X^2$—$R^7$, $X^2$ represents *—CO—O—, *—O—CO—or *—O—CO—O—, and * represents a bonding site to the benzene ring, and $R^7$ represents a hydrocarbon group including a cyclic hydrocarbon group having 3 to 18 carbon atoms and the cyclic hydrocarbon group may have a substituent, and —$CH_2$-included in the hydrocarbon group may be replaced by —O—, —S—, —$SO_2$—or —CO—, wherein one of $R^2$ and one of $R^3$ are bonded to each other to form a single bond or an alkanediyl bridge having 1 to 6 carbon atoms together with carbon atoms to which $R^2$ and $R^3$ are bonded, and —$CH_2$-included in the alkanediyl bridge may be replaced by —O—, —S—, —CO—, —SO—or —$SO_2$—.

10. The salt according to claim 1, wherein $R^1$ represents a fluorine atom, an alkyl fluoride group having 1 to 4 carbon atoms, an alkyl group having 1 to 6 carbon atoms or an alicyclic hydrocarbon group having 3 to 10 carbon atoms, and —$CH_2$-included in the alkyl group and the alicyclic hydrocarbon group may be replaced by —O—or —CO—, provided that at least two $R^1$ are an alkyl group, and at least one-$CH_2$-included in the alkyl group is replaced by —O—or —CO—, and $R^2$ and $R^3$ each independently represent a fluorine atom, an alkyl fluoride group having 1 to 4 carbon atoms, an alkyl group having 1 to 6 carbon atoms or an alicyclic hydrocarbon group having 3 to 10 carbon atoms, and —$CH_2$-included in the alkyl group and the alicyclic hydrocarbon group may be replaced by —O—or —CO—, or $R^2$ and $R^3$ may be bonded to each other to form a single bond or an alkanediyl bridge having 1 to 6 carbon atoms together with carbon atoms to which $R^2$ and $R^3$ are bonded, and —$CH_2$-included in the alkanediyl bridge may be replaced by —O—, —S—, —CO—, —SO—or —$SO_2$—.

11. The salt according to claim 1, wherein m1 represents an integer of 2 to 3, m2 represents an integer of 0 to 3, and m3 represents an integer of 0 to 3.

12. The salt according to claim 1, wherein when m1 is an integer of 2 or more, at least one of $R^1$ is bonded at the ortho-position or the para-position with respect to the bonding site of $S^+$ on the benzene ring, when m2 is an integer of 1 or more, at least one of $R^2$ is bonded at the meta-position or the para-position with respect to the bonding site of $S^+$ on the benzene ring, and when m3 is an integer of 1 or more, at least one of $R^3$ is bonded at the meta-position or the para-position with respect to the bonding site of $S^+$ on the benzene ring.

13. The salt according to claim 1, wherein $R^5$ is bonded at the meta-position or the para-position with respect to the bonding site of $S^+$ on the benzene ring, and $R^6$ is bonded at the meta-position or the para-position with respect to the bonding site of $S^+$ on the benzene ring.

14. The salt according to claim 1, wherein $R^7$ represents an alicyclic hydrocarbon group having 3 to 18 carbon atoms, the alicyclic hydrocarbon group may have at least one selected from the group consisting of an alkyl group having 1 to 4 carbon atoms, a hydroxy group and a fluorine atom, and $—CH_2$-included in the alicyclic hydrocarbon group may be replaced by —O—, —S—, $—SO_2—$or —CO—, a group obtained by combining an alicyclic hydrocarbon group having 3 to 18 carbon atoms with a chain hydrocarbon group having 1 to 6 carbon atoms, the alicyclic hydrocarbon group may have at least one selected from the group consisting of an alkyl group having 1 to 4 carbon atoms, a hydroxy group and a fluorine atom, and $—CH_2$-included in the combined group may be replaced by —O—, —S—, $—SO_2—$or —CO—, an aromatic hydrocarbon group having 6 to 18 carbon atoms, the aromatic hydrocarbon group may have at least one selected from the group consisting of an alkyl group having 1 to 4 carbon atoms, a hydroxy group and a fluorine atom, or a group obtained by combining an aromatic hydrocarbon group having 6 to 18 carbon atoms with a chain hydrocarbon group having 1 to 6 carbon atoms, the aromatic hydrocarbon group may have at least one selected from the group consisting of an alkyl group having 1 to 4 carbon atoms, a hydroxy group and a fluorine atom, and $—CH_2$-included in the combined group may be replaced by —O—, —S—, $—SO_2—$or —CO—.

15. The salt according to claim 1, wherein at least one of $R^5$ and $R^6$ is-$X^2—R^7$.

16. The salt according to claim 1, wherein the salt represents a salt represented by formula (IB):

(IB)

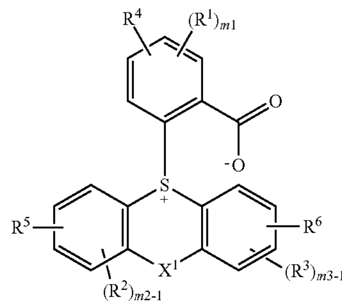

wherein, in formula (IB), $R^1$, $R^2$, $R^3$, m1, $R^4$, $R^5$, $R^6$, $X^2$ and $R^7$ are as defined in formula (I), m2 and m3 each independently represent an integer of 1 to 4, and $X^1$ represents a single bond, $—CH_2—$, —O—, —S—, —CO—, —SO—or $—SO_2—$.

17. The salt according to claim 1, wherein m1 represents an integer of 2 to 3, and $R^1$ represents a hydrocarbon group having 1 to 18 carbon atoms, and $—CH_2$-included in the hydrocarbon group and bonded to the benzene ring is replaced by —O—, provided that at least two $R^1$ are a chain hydrocarbon group, and $—CH_2$-included in the chain hydrocarbon group and bonded to the benzene ring is replaced by —O—.

18. The salt according to claim 9, wherein one of $R^2$ and one of $R^3$ are bonded to each other to form a single bond or —CO—.

19. The salt according to claim 1, wherein $X^2$ represents *—O—CO—O—.

* * * * *